(12) United States Patent
Ochi

(10) Patent No.: US 10,583,182 B2
(45) Date of Patent: Mar. 10, 2020

(54) RECOMBINANT MULTIPLE DOMAIN FUSION PROTEIN MITOGENS AND USE THEREOF FOR INDUCING ENHANCEMENT OR REPRESSION OF ANTIGEN-SPECIFIC IMMUNITY

(71) Applicant: Atsuo Ochi, Fair Lawn, NJ (US)

(72) Inventor: Atsuo Ochi, Fair Lawn, NJ (US)

( * ) Notice: Subject to any disclaimer, the term of this patent is extended or adjusted under 35 U.S.C. 154(b) by 201 days.

(21) Appl. No.: 15/893,648

(22) Filed: Feb. 11, 2018

(65) Prior Publication Data

US 2018/0200352 A1    Jul. 19, 2018

Related U.S. Application Data

(63) Continuation of application No. 12/483,876, filed on Jun. 12, 2009, now Pat. No. 9,931,386.

(60) Provisional application No. 61/073,010, filed on Jun. 16, 2008.

(51) Int. Cl.

| | |
|---|---|
| *C12N 5/00* | (2006.01) |
| *C12N 15/09* | (2006.01) |
| *C12N 15/63* | (2006.01) |
| *C07K 14/48* | (2006.01) |
| *C07K 14/525* | (2006.01) |
| *C07K 16/18* | (2006.01) |
| *C07K 19/00* | (2006.01) |
| *A61K 39/00* | (2006.01) |
| *C07K 14/705* | (2006.01) |
| *A61K 39/145* | (2006.01) |
| *A61K 39/39* | (2006.01) |
| *C07K 14/715* | (2006.01) |
| *A61K 39/12* | (2006.01) |
| *A61K 38/18* | (2006.01) |
| *A61K 38/19* | (2006.01) |
| *A61K 39/395* | (2006.01) |
| *A61K 38/17* | (2006.01) |

(52) U.S. Cl.
CPC .......... *A61K 39/0008* (2013.01); *A61K 39/12* (2013.01); *A61K 39/145* (2013.01); *A61K 39/39* (2013.01); *C07K 14/48* (2013.01); *C07K 14/525* (2013.01); *C07K 14/705* (2013.01); *C07K 14/70532* (2013.01); *C07K 14/7151* (2013.01); *C07K 16/18* (2013.01); *C07K 19/00* (2013.01); *C12N 15/09* (2013.01); *C12N 15/63* (2013.01); *A61K 38/177* (2013.01); *A61K 38/179* (2013.01); *A61K 38/1774* (2013.01); *A61K 38/1793* (2013.01); *A61K 38/185* (2013.01); *A61K 38/191* (2013.01); *A61K 39/3955* (2013.01); *A61K 2039/53* (2013.01); *A61K 2039/55533* (2013.01); *A61K 2039/6031* (2013.01); *A61K 2039/70* (2013.01); *C07K 14/70503* (2013.01); *C07K 2319/30* (2013.01); *C12N 5/00* (2013.01); *C12N 2760/16134* (2013.01); *C12N 2760/16234* (2013.01)

(58) Field of Classification Search
CPC .... C07K 14/435; C07K 14/475; C07K 14/52; C07K 14/705; C07K 14/70503; C07K 14/71; C07K 14/715; C07K 19/00; C07K 5/00; C07K 15/09; C07K 14/48; C07K 14/525; C07K 16/18; A61K 38/17; A61K 38/177; A61K 38/1774; A61K 38/179; A61K 38/1793; A61K 38/18; A61K 38/19; A61K 38/20; A61K 39/395

See application file for complete search history.

(56) References Cited

U.S. PATENT DOCUMENTS

| | | | | |
|---|---|---|---|---|
| 2005/0152872 | A1* | 7/2005 | Gaide | C07K 14/70578 424/85.1 |
| 2005/0244370 | A1* | 11/2005 | Pfizenmaier | C07K 14/475 424/85.1 |
| 2009/0232808 | A1* | 9/2009 | Priest | A61K 38/191 424/134.1 |

FOREIGN PATENT DOCUMENTS

WO    WO-200149318 A1 *  7/2001

OTHER PUBLICATIONS

Assohou-Luty et al. A CD40-CD95L fusion protein interferes with CD40L-induced prosurvival signaling and allows membrane CD40L-restricted activation of CD95. J Mol Med 84: 785-797, 2006.*
Economides et al. Cytokine traps: multi-component, high-affinity blockers of cytokine action. Nature Med 9(1): 47-52, 2003.*
Jazayeri et al. Fc-based cytokines. Biodrugs 22(1): 11-26, 2008.*
MacEwan et al. TNF ligands and receptors—a matter of life and death. Brit J Pharmacol 135: 855-875, 2002.*

* cited by examiner

*Primary Examiner* — Bridget E Bunner

(57) ABSTRACT

The invention relates to cell stimulatory fusion proteins and DNA sequences, vectors comprising at least two agonists of TNF/TNFR super family, immunoglobulin super family, cytokine family proteins and optional antigen combination. Instructions for use of these proteins and DNA constructs as immune adjuvants and vaccines for treatment of various chronic diseases such as viral infection are also provided. Additionally, the use of these protein and DNA constructs as immune suppressant for treatment of various chronic diseases, such as autoimmunity and organ transplant rejection, is also illustrated.

6 Claims, 94 Drawing Sheets

Specification includes a Sequence Listing.

Schematic diagram of the presumed structure of the multi-ligand fusion protein and the interaction with target cells to induce cell activation.

Figure 2A. Registered sequence of CD40 ligand of human origin (SEQ ID NO: 1).

```
actttgacag tcttctcatg ctgcctctgc caccttctct gccagaagat accatttcaa        60
ctttaacaca gc atg atc gaa aca tac aac caa act tct ccc cga tct gcg       111
          Met Ile Glu Thr Tyr Asn Gln Thr Ser Pro Arg Ser Ala
           1           5                      10 gcc act gga ctg ccc atc agc atg aaa att ttt atg tat tta ctt act         159
Ala Thr Gly Leu Pro Ile Ser Met Lys Ile Phe Met Tyr Leu Leu Thr
         15              20              25 gtt ttt ctt atc acc cag atg att ggg tca gca ctt ttt gct gtg tat         207
Val Phe Leu Ile Thr Gln Met Ile Gly Ser Ala Leu Phe Ala Val Tyr
 30              35              40                   45 ctt cat aga agg ttg gac aag ata gaa gat gaa agg aat ctt cat gaa         255
Leu His Arg Arg Leu Asp Lys Ile Glu Asp Glu Arg Asn Leu His Glu
                 50              55              60 gat ttt gta ttc atg aaa acg ata cag aga tgc aac aca gga gaa aga         303
Asp Phe Val Phe Met Lys Thr Ile Gln Arg Cys Asn Thr Gly Glu Arg
             65              70              75 tcc tta tcc tta ctg aac tgt gag gag att aaa agc cag ttt gaa ggc         351
Ser Leu Ser Leu Leu Asn Cys Glu Glu Ile Lys Ser Gln Phe Glu Gly
         80              85              90 ttt gtg aag gat ata atg tta aac aaa gag gag acg aag aaa gaa aac         399
Phe Val Lys Asp Ile Met Leu Asn Lys Glu Glu Thr Lys Lys Glu Asn
         95             100             105 agc ttt gaa atg caa aaa ggt gat cag aat cct caa att gcg gca cat         447
Ser Phe Glu Met Gln Lys Gly Asp Gln Asn Pro Gln Ile Ala Ala His
110             115             120             125 gtc ata agt gag gcc agc agt aaa aca aca tct gtg tta cag tgg gct         495
Val Ile Ser Glu Ala Ser Ser Lys Thr Thr Ser Val Leu Gln Trp Ala
                130             135             140 gaa aaa gga tac tac acc atg agc aac aac ttg gta acc ctg gaa aat         543
Glu Lys Gly Tyr Tyr Thr Met Ser Asn Asn Leu Val Thr Leu Glu Asn
             145             150             155 ggg aaa cag ctg acc gtt aaa aga caa gga ctc tat tat atc tat gcc         591
Gly Lys Gln Leu Thr Val Lys Arg Gln Gly Leu Tyr Tyr Ile Tyr Ala
         160             165             170
```

Figure 2B. Registered sequence of CD40 ligand of human origin (SEQ ID NO: 1).

| | | | | | | | | | | | | | |
|---|---|---|---|---|---|---|---|---|---|---|---|---|---|
| caa | gtc | acc | ttc | tgt | tcc | aat | cgg | gaa | gct | tcg | agt | caa | gct | cca | ttt | 639 |
| Gln | Val | Thr | Phe | Cys | Ser | Asn | Arg | Glu | Ala | Ser | Ser | Gln | Ala | Pro | Phe |
| 175 | | | | | 180 | | | | | 185 | | | | | | ata gcc agc ctc tgc cta aag tcc ccc ggt aga ttc gag aga atc tta 687
Ile Ala Ser Leu Cys Leu Lys Ser Pro Gly Arg Phe Glu Arg Ile Leu
190                 195                 200                 205 ctc aga gct gca aat acc cac agt tcc gcc aaa cct tgc ggg caa caa 735
Leu Arg Ala Ala Asn Thr His Ser Ser Ala Lys Pro Cys Gly Gln Gln
                210                 215                 220 tcc att cac ttg gga gga gta ttt gaa ttg caa cca ggt gct tcg gtg 783
Ser Ile His Leu Gly Gly Val Phe Glu Leu Gln Pro Gly Ala Ser Val
            225                 230                 235 ttt gtc aat gtg act gat cca agc caa gtg agc cat ggc act ggc ttc 831
Phe Val Asn Val Thr Asp Pro Ser Gln Val Ser His Gly Thr Gly Phe
        240                 245                 250 acg tcc ttt ggc tta ctc aaa ctc tgaacagtgt caccttgcag gctgtggtgg   885
Thr Ser Phe Gly Leu Leu Lys Leu
255                 260 agctgacgct gggagtcttc ataatacagc acagcggtta agcccacccc ctgttaactg   945
cctatttata accctaggat cctccttatg gagaactatt tattatacac tccaaggcat  1005
gtagaactgt aataagtgaa ttacaggtca catgaaacca aaacgggccc tgctccataa  1065
gagcttatat atctgaagca gcaaccccac tgatgcagac atccagagag tcctatgaaa  1125
agacaaggcc attatgcaca ggttgaattc tgagtaaaca gcagataact tgccaagttc  1185
agttttgttt ctttgcgtgc agtgtctttc catggataat gcatttgatt tatcagtgaa  1245
gatgcagaag ggaaatgggg agcctcagct cacattcagt tatggttgac tctgggttcc  1305
tatggccttg ttggaggggg ccaggctcta gaacgtctaa cacagtggag aaccgaaacc  1365
cccccccccc ccccgccacc ctctcggaca gttattcatt ctctttcaat ctctctctct  1425
ccatctctct ctttcagtct ctctctctca acctctttct tccaatctct ctttctcaat  1485
ctctctgttt cccctttgtca gtctcttccc tcccccagtc tctcttctca atccccctttt  1545 ctaacacaca cacacacaca cacacacaca cacacacaca cacacacaca cacacagagt  1605

Figure 2C. Registered sequence of CD40 ligand of human origin (SEQ ID NO: 1).

```
caggccgttg ctagtcagtt ctcttctttc caccctgtcc ctatctctac cactatagat      1665
gagggtgagg agtagggagt gcagccctga gcctgcccac tcctcattac gaaatgactg      1725
tatttaaagg aaatctattg tatctacctg cagtctccat tgtttccaga gtgaacttgt      1785
aattatcttg ttatttattt tttgaataat aaagacctct taacattaa                  1834
```

Figure 3A. Registered sequence of oncostatin M of human origin (SEQ ID NO: 3).

```
agccgagagg tgtcaccccc agcgggcgcg ggccggagca cgggcaccca gc atg ggg         58
                                                         Met Gly
                                                         -25 gta ctg ctc aca cag agg acg ctg ctc agt ctg gtc ctt gca ctc ctg          106
Val Leu Leu Thr Gln Arg Thr Leu Leu Ser Leu Val Leu Ala Leu Leu
            -20                     -15                 -10 ttt cca agc atg gcg agc atg gcg gct ata ggc agc tgc tcg aaa gag          154
Phe Pro Ser Met Ala Ser Met Ala Ala Ile Gly Ser Cys Ser Lys Glu
        -5              -1  1                   5 tac cgc gtg ctc ctt ggc cag ctc cag aag cag aca gat ctc atg cag          202
Tyr Arg Val Leu Leu Gly Gln Leu Gln Lys Gln Thr Asp Leu Met Gln
10                      15              20                  25 gac acc agc aga ctc ctg gac ccc tat ata cgt atc caa ggc ctg gat          250
Asp Thr Ser Arg Leu Leu Asp Pro Tyr Ile Arg Ile Gln Gly Leu Asp
                30              35                  40 gtt cct aaa ctg aga gag cac tgc agg gag cgc ccc ggg gcc ttc ccc          298
Val Pro Lys Leu Arg Glu His Cys Arg Glu Arg Pro Gly Ala Phe Pro
            45                  50                  55 agt gag gag acc ctg agg ggg ctg ggc agg cgg ggc ttc ctg cag acc          346
Ser Glu Glu Thr Leu Arg Gly Leu Gly Arg Arg Gly Phe Leu Gln Thr
        60                  65                  70 ctc aat gcc aca ctg ggc tgc gtc ctg cac aga ctg gcc gac tta gag          394
Leu Asn Ala Thr Leu Gly Cys Val Leu His Arg Leu Ala Asp Leu Glu
        75                  80                  85 cag cgc ctc ccc aag gcc cag gat ttg gag agg tct ggg ctg aac atc          442
Gln Arg Leu Pro Lys Ala Gln Asp Leu Glu Arg Ser Gly Leu Asn Ile
90              95                  100                 105 gag gac ttg gag aag ctg cag atg gcg agg ccg aac atc ctc ggg ctc          490
Glu Asp Leu Glu Lys Leu Gln Met Ala Arg Pro Asn Ile Leu Gly Leu
                110                 115                 120 agg aac aac atc tac tgc atg gcc cag ctg ctg gac aac tca gac acg          538
Arg Asn Asn Ile Tyr Cys Met Ala Gln Leu Leu Asp Asn Ser Asp Thr
                125                 130                 135 gct gag ccc acg aag gct ggc cgg ggg gcc tct cag ccg ccc acc ccc          586
Ala Glu Pro Thr Lys Ala Gly Arg Gly Ala Ser Gln Pro Pro Thr Pro
            140                 145                 150
```

Figure 3B. Registered sequence of oncostatin M of human origin (SEQ ID NO: 3).

```
acc cct gcc tcg gat gct ttt cag cgc aag ctg gag ggc tgc agg ttc           634
Thr Pro Ala Ser Asp Ala Phe Gln Arg Lys Leu Glu Gly Cys Arg Phe
    155             160                 165 ctg cat ggc tac cat cgc ttc atg cac tca gtg ggg cgg gtc ttc agc           682
Leu His Gly Tyr His Arg Phe Met His Ser Val Gly Arg Val Phe Ser
170             175                 180                 185 aag tgg ggg gag agc ccg aac cgg agc cgg aga cac agc ccc cac cag           730
Lys Trp Gly Glu Ser Pro Asn Arg Ser Arg Arg His Ser Pro His Gln
                190                 195                 200 gcc ctg agg aag ggg gtg cgc agg acc aga ccc tcc agg aaa ggc aag           778
Ala Leu Arg Lys Gly Val Arg Arg Thr Arg Pro Ser Arg Lys Gly Lys
            205                 210                 215 aga ctc atg acc agg gga cag ctg ccc cgg tagcctcgag agcacccctt             828
Arg Leu Met Thr Arg Gly Gln Leu Pro Arg
            220                 225 gccggtgaag dbatgcggcag gtgctctgtg gatgagagga accatcgcag gatgacagct        888
cccgggtccc caaacctgtt cccctctgct actagccact gagaagtgca ctttaagagg        948
tgggagctgg gcagacccct ctacctcctc caggctggga gacagagtca ggctgttgcg        1008
ctcccacctc agccccaagt tccccaggcc cagtggggtg gccgggcggg ccacgcggga        1068
ccgactttcc attgattcag gggtctgatg acacaggctg actcatggcc gggctgactg        1128
cccccctgcc ttgctccccg aggcctgccg gtccttccct ctcatgactt gcagggccgt        1188
tgcccccaga cttcctcctt tccgtgtttc tgaaggggag gtcacagcct gagctggcct        1248
cctatgcctc atcatgtccc aaaccagaca cctggatgtc tgggtgacct cactttaggc        1308
agctgtaaca gcggcagggt gtcccaggag ccctgatccg ggggtccagg gaatggagct        1368
caggtcccag gccagccccg aagtcgccac gtggcctggg gcaggtcact ttacctctgt        1428
ggacctgttt tctctttgtg aagctaggga gttagaggct gtacaaggcc cccactgcct        1488
gtcggttgct tggattccct gacgtaaggt ggatattaaa aatctgtaaa tcaggacagg        1548
tggtgcaaat ggcgctggga ggtgtacacg gaggtctctg taaaagcaga cccacctccc        1608
agcgccggga agcccgtctt gggtcctcgc tgctggctgc tcccctggt ggtggatcct         1668
```

Figure 3C. Registered sequence of oncostatin M of human origin (SEQ ID NO: 3).

```
ggaattttct cacgcaggag ccattgctct cctagagggg gtctcagaaa ctgcgaggcc      1728
agttccttgg agggacatga ctaatttatc gatttttatc aatttttatc agttttatat      1788
ttataagcct tatttatgat gtatatttaa tgttaatatt gtgcaaactt atatttaaaa      1848
cttgcctggt ttctaaaaaa aaaaaaaaaa aa                                    1880
```

Figure 4A. Registered sequence of IgG1 Fc of human origin (SEQ ID NO: 5).

```
atg aaa aag aca gct atc gcg att gca gtg gca ctg gct ggt ttc gct        48
Met Lys Lys Thr Ala Ile Ala Ile Ala Val Ala Leu Ala Gly Phe Ala
1             5                 10                  15 acc gta gcg cag gcc gac gtc gag tcc aaa tct tgt gac aaa act cac        96
Thr Val Ala Gln Ala Asp Val Glu Ser Lys Ser Cys Asp Lys Thr His
                20                  25                  30 aca tgc cca ccg tgc cca gca cct gaa ctc ctg ggg gga ccg tca gtc       144
Thr Cys Pro Pro Cys Pro Ala Pro Glu Leu Leu Gly Gly Pro Ser Val
        35                  40                  45 ttc ctc ttc ccc cca aaa ccc aag gac acc ctc atg atc tcc cgg acc       192
Phe Leu Phe Pro Pro Lys Pro Lys Asp Thr Leu Met Ile Ser Arg Thr
    50                  55                  60 cct gag gtc aca tgc gtg gtg gtg gac gtg agc cac gaa gac cct gag       240
Pro Glu Val Thr Cys Val Val Val Asp Val Ser His Glu Asp Pro Glu
65              70                  75                  80 gtc aag ttc aac tgg tac gtg gac ggc gtg gag gtg cat aat gcc aag       288
Val Lys Phe Asn Trp Tyr Val Asp Gly Val Glu Val His Asn Ala Lys
                85                  90                  95 aca aag ccg cgg gag gag cag tac aac agc acg tac cgt gtg gtc agc       336
Thr Lys Pro Arg Glu Glu Gln Tyr Asn Ser Thr Tyr Arg Val Val Ser
            100                 105                 110 gtc ctc acc gtc ctg cac cag gac tgg ctg aat ggc aag gag tac aag       384
Val Leu Thr Val Leu His Gln Asp Trp Leu Asn Gly Lys Glu Tyr Lys
        115                 120                 125 tgc aag gtc tcc aac aaa gcc ctc cca gcc ccc atc gag aaa acc atc       432
Cys Lys Val Ser Asn Lys Ala Leu Pro Ala Pro Ile Glu Lys Thr Ile
    130                 135                 140 tcc aaa gcc aaa ggg cag ccc cga gag cca cag gtg tac acc ctg ccc       480
Ser Lys Ala Lys Gly Gln Pro Arg Glu Pro Gln Val Tyr Thr Leu Pro
145                 150                 155                 160 cca tcc cgg gat gag ctg acc aag aac cag gtc agc ctg acc tgc ctg       528
Pro Ser Arg Asp Glu Leu Thr Lys Asn Gln Val Ser Leu Thr Cys Leu
                165                 170                 175 gtc aaa ggc ttc tat ccc agc gac atc gcc gtg gag tgg gag agc aat       576
Val Lys Gly Phe Tyr Pro Ser Asp Ile Ala Val Glu Trp Glu Ser Asn
            180                 185                 190
```

Figure 4B. Registered sequence of IgG1 Fc of human origin (SEQ ID NO: 5).

| ggg | cag | ccg | gag | aac | aac | tac | aag | acc | acg | cct | ccc | gtg | ctg | gac | tcc | 624 |
|---|---|---|---|---|---|---|---|---|---|---|---|---|---|---|---|---|
| Gly | Gln | Pro | Glu | Asn | Asn | Tyr | Lys | Thr | Thr | Pro | Pro | Val | Leu | Asp | Ser | |
| | | 195 | | | | | 200 | | | | | 205 | | | | |

| gac | ggc | tcc | ttc | ttc | ctc | tac | agc | aag | ctc | acc | gtg | gac | aag | agc | agg | 672 |
|---|---|---|---|---|---|---|---|---|---|---|---|---|---|---|---|---|
| Asp | Gly | Ser | Phe | Phe | Leu | Tyr | Ser | Lys | Leu | Thr | Val | Asp | Lys | Ser | Arg | |
| | 210 | | | | | 215 | | | | | 220 | | | | | |

| tgg | cag | cag | ggg | aac | gtc | ttc | tca | tgc | tcc | gtg | atg | cat | gag | gct | ctg | 720 |
|---|---|---|---|---|---|---|---|---|---|---|---|---|---|---|---|---|
| Trp | Gln | Gln | Gly | Asn | Val | Phe | Ser | Cys | Ser | Val | Met | His | Glu | Ala | Leu | |
| 225 | | | | | 230 | | | | | 235 | | | | | 240 | |

| cac | aac | cac | tac | acg | cag | aag | agc | ctc | tcc | ctg | tct | ccg | ggt | aaa | tga | 768 |
|---|---|---|---|---|---|---|---|---|---|---|---|---|---|---|---|---|
| His | Asn | His | Tyr | Thr | Gln | Lys | Ser | Leu | Ser | Leu | Ser | Pro | Gly | Lys | | |
| | | | | 245 | | | | 250 | | | | | 255 | | | |

Figure 5A. Nucleotide sequence and amino acid sequence of the CD40L-IgFc fusion protein (SEQ ID NO: 7).

```
gctagc atg ggg gta ctg ctc aca cag agg acg ctg ctc agt ctg gtc        48
       Met Gly Val Leu Leu Thr Gln Arg Thr Leu Leu Ser Leu Val
       -25                 -20                 -15 ctt gca ctc ctg ttt cca agc atg gcg agc atg ctt cat aga agg ttg       96
Leu Ala Leu Leu Phe Pro Ser Met Ala Ser Met Leu His Arg Arg Leu
    -10                 -5              -1  1                5 gac aag ata gaa gat gaa agg aat ctt cat gaa gat ttt gta ttc atg      144
Asp Lys Ile Glu Asp Glu Arg Asn Leu His Glu Asp Phe Val Phe Met
            10                  15                  20 aaa acg ata cag aga tgc aac aca gga gaa aga tcc tta tcc tta ctg      192
Lys Thr Ile Gln Arg Cys Asn Thr Gly Glu Arg Ser Leu Ser Leu Leu
            25                  30                  35 aac tgt gag gag att aaa agc cag ttt gaa ggc ttt gtg aag gat ata      240
Asn Cys Glu Glu Ile Lys Ser Gln Phe Glu Gly Phe Val Lys Asp Ile
            40                  45                  50 atg tta aac aaa gag gag acg aag aaa gaa aac agc ttt gaa atg caa      288
Met Leu Asn Lys Glu Glu Thr Lys Lys Glu Asn Ser Phe Glu Met Gln
    55                  60                  65 aaa ggt gat cag aat cct caa att gcg gca cat gtc ata agt gag gcc      336
Lys Gly Asp Gln Asn Pro Gln Ile Ala Ala His Val Ile Ser Glu Ala
70                  75                  80                  85 agc agt aaa aca aca tct gtg tta cag tgg gct gaa aaa gga tac tac      384
Ser Ser Lys Thr Thr Ser Val Leu Gln Trp Ala Glu Lys Gly Tyr Tyr
            90                  95                  100 acc atg agc aac aac ttg gta acc ctg gaa aat ggg aaa cag ctg acc      432
Thr Met Ser Asn Asn Leu Val Thr Leu Glu Asn Gly Lys Gln Leu Thr
            105                 110                 115 gtt aaa aga caa gga ctc tat tat atc tat gcc caa gtc acc ttc tgt      480
Val Lys Arg Gln Gly Leu Tyr Tyr Ile Tyr Ala Gln Val Thr Phe Cys
        120                 125                 130 tcc aat cgg gaa gct tcg agt caa gct cca ttt ata gcc agc ctc tgc      528
Ser Asn Arg Glu Ala Ser Ser Gln Ala Pro Phe Ile Ala Ser Leu Cys
        135                 140                 145 cta aag tcc ccc ggt aga ttc gag aga atc tta ctc aga gct gca aat      576
Leu Lys Ser Pro Gly Arg Phe Glu Arg Ile Leu Leu Arg Ala Ala Asn
150                 155                 160                 165
```

Figure 5B. Nucleotide sequence and amino acid sequence of the CD40L-IgFc fusion protein (SEQ ID NO: 7).

```
acc cac agt tcc gcc aaa cct tgc ggg caa caa tcc att cac ttg gga         624
Thr His Ser Ser Ala Lys Pro Cys Gly Gln Gln Ser Ile His Leu Gly
            170                 175                 180 gga gta ttt gaa ttg caa cca ggt gct tcg gtg ttt gtc aat gtg act         672
Gly Val Phe Glu Leu Gln Pro Gly Ala Ser Val Phe Val Asn Val Thr
            185                 190                 195 gat cca agc caa gtg agc cat ggc act ggc ttc acg tcc ttt ggc tta         720
Asp Pro Ser Gln Val Ser His Gly Thr Gly Phe Thr Ser Phe Gly Leu
            200                 205                 210 ctc aaa ctc gag ccc aaa tct tgt gac aaa act cac aca tgc cca ccg         768
Leu Lys Leu Glu Pro Lys Ser Cys Asp Lys Thr His Thr Cys Pro Pro
            215                 220                 225 tgc cca gca cct gaa ctc ctg ggg gga ccg tca gtc ttc ctc ttc ccc         816
Cys Pro Ala Pro Glu Leu Leu Gly Gly Pro Ser Val Phe Leu Phe Pro
230                 235                 240                 245 cca aaa ccc aag gac acc ctc atg atc tcc cgg acc cct gag gtc aca         864
Pro Lys Pro Lys Asp Thr Leu Met Ile Ser Arg Thr Pro Glu Val Thr
                250                 255                 260 tgc gtg gtg gtg gac gtg agc cac gaa gac cct gag gtc aag ttc aac         912
Cys Val Val Val Asp Val Ser His Glu Asp Pro Glu Val Lys Phe Asn
                265                 270                 275 tgg tac gtg gac ggc gtg gag gtg cat aat gcc aag aca aag ccg cgg         960
Trp Tyr Val Asp Gly Val Glu Val His Asn Ala Lys Thr Lys Pro Arg
                280                 285                 290 gag gag cag tac aac agc acg tac cgt gtg gtc agc gtc ctc acc gtc        1008
Glu Glu Gln Tyr Asn Ser Thr Tyr Arg Val Val Ser Val Leu Thr Val
            295                 300                 305 ctg cac cag gac tgg ctg aat ggc aag gag tac aag tgc aag gtc tcc        1056
Leu His Gln Asp Trp Leu Asn Gly Lys Glu Tyr Lys Cys Lys Val Ser
310                 315                 320                 325 aac aaa gcc ctc cca gcc ccc atc gag aaa acc atc tcc aaa gcc aaa        1104
Asn Lys Ala Leu Pro Ala Pro Ile Glu Lys Thr Ile Ser Lys Ala Lys
                330                 335                 340
```

Figure 5C. Nucleotide sequence and amino acid sequence of the CD40L-IgFc fusion protein (SEQ ID NO: 7).

```
ggg cag ccc cga gaa cca cag gtg tac acc ctg ccc cca tcc cgg gat           1152
Gly Gln Pro Arg Glu Pro Gln Val Tyr Thr Leu Pro Pro Ser Arg Asp
            345             350             355 gag ctg acc aag aac cag gtc agc ctg acc tgc ctg gtc aaa ggc ttc           1200
Glu Leu Thr Lys Asn Gln Val Ser Leu Thr Cys Leu Val Lys Gly Phe
            360             365             370 tat ccc agc gac atc gcc gtg gag tgg gag agc aat ggg cag ccg gag           1248
Tyr Pro Ser Asp Ile Ala Val Glu Trp Glu Ser Asn Gly Gln Pro Glu
    375             380             385 aac aac tac aag acc acg cct ccc gtg ctg gac tcc gac ggc tcc ttc           1296
Asn Asn Tyr Lys Thr Thr Pro Pro Val Leu Asp Ser Asp Gly Ser Phe
390             395             400             405 ttc ctc tac agc aag ctc acc gtg gac aag agc agg tgg cag cag ggg           1344
Phe Leu Tyr Ser Lys Leu Thr Val Asp Lys Ser Arg Trp Gln Gln Gly
            410             415             420 aac gtc ttc tca tgc tcc gtg atg cat gag gct ctg cac aac cac tac           1392
Asn Val Phe Ser Cys Ser Val Met His Glu Ala Leu His Asn His Tyr
            425             430             435 acg cag aag agc ctc tcc ctg tct ccg ggt aaa tgatctaga                     1434
Thr Gln Lys Ser Leu Ser Leu Ser Pro Gly Lys
            440             445
```

Figure 6A. Registered sequence of Fas ligand of human origin (SEQ ID NO: 9).

```
gaggtgtttc ccttagctat ggaaactcta taagagagat ccagcttgcc tcctcttgag        60
cagtcagcaa cagggtcccg tccttgacac ctcagcctct acaggactga gaagaagtaa       120
aaccgtttgc tggggctggc ctgactcacc agctgcc atg cag cag ccc ttc aat        175
                                          Met Gln Gln Pro Phe Asn
                                           1                   5 tac cca tat ccc cag atc tac tgg gtg gac agc agt gcc agc tct ccc        223
Tyr Pro Tyr Pro Gln Ile Tyr Trp Val Asp Ser Ser Ala Ser Ser Pro
         10                  15                  20 tgg gcc cct cca ggc aca gtt ctt ccc tgt cca acc tct gtg ccc aga        271
Trp Ala Pro Pro Gly Thr Val Leu Pro Cys Pro Thr Ser Val Pro Arg
         25                  30                  35 agg cct ggt caa agg agg cca cca cca ccg cca ccg cca cca cta            319
Arg Pro Gly Gln Arg Arg Pro Pro Pro Pro Pro Pro Pro Pro Leu
         40                  45                  50 cca cct ccg ccg ccg ccg cca cca ctg cct cca cta ccg ctg cca ccc        367
Pro Pro Pro Pro Pro Pro Pro Pro Leu Pro Pro Leu Pro Leu Pro Pro
55                  60                  65                  70 ctg aag aag aga ggg aac cac agc aca ggc ctg tgt ctc ctt gtg atg        415
Leu Lys Lys Arg Gly Asn His Ser Thr Gly Leu Cys Leu Leu Val Met
                     75                  80                  85 ttt ttc atg gtt ctg gtt gcc ttg gta gga ttg ggc ctg ggg atg ttt        463
Phe Phe Met Val Leu Val Ala Leu Val Gly Leu Gly Leu Gly Met Phe
                 90                  95                 100 cag ctc ttc cac cta cag aag gag ctg gca gaa ctc cga gag tct acc        511
Gln Leu Phe His Leu Gln Lys Glu Leu Ala Glu Leu Arg Glu Ser Thr
             105                 110                 115 agc cag atg cac aca gca tca tct ttg gag aag caa ata ggc cac ccc        559
Ser Gln Met His Thr Ala Ser Ser Leu Glu Lys Gln Ile Gly His Pro
         120                 125                 130 agt cca ccc cct gaa aaa aag gag ctg agg aaa gtg gcc cat tta aca        607
Ser Pro Pro Pro Glu Lys Lys Glu Leu Arg Lys Val Ala His Leu Thr
135                 140                 145                 150 ggc aag tcc aac tca agg tcc atg cct ctg gaa tgg gaa gac act tat        655
Gly Lys Ser Asn Ser Arg Ser Met Pro Leu Glu Trp Glu Asp Thr Tyr
                 155                 160                 165
```

Figure 6B. Registered sequence of Fas ligand of human origin (SEQ ID NO: 9).

| | | | | | | | | | | | | | | |
|---|---|---|---|---|---|---|---|---|---|---|---|---|---|---|
| gga | att | gtc | ctg | ctt | tct | gga | gtg | aag | tat | aag | aag | ggt | ggc | ctt | gtg | 703
| Gly | Ile | Val | Leu | Leu | Ser | Gly | Val | Lys | Tyr | Lys | Lys | Gly | Gly | Leu | Val |
| | | | 170 | | | | | 175 | | | | | 180 | | |

| atc | aat | gaa | act | ggg | ctg | tac | ttt | gta | tat | tcc | aaa | gta | tac | ttc | cgg | 751
| Ile | Asn | Glu | Thr | Gly | Leu | Tyr | Phe | Val | Tyr | Ser | Lys | Val | Tyr | Phe | Arg |
| | | | 185 | | | | | 190 | | | | | 195 | | |

| ggt | caa | tct | tgc | aac | aac | ctg | ccc | ctg | agc | cac | aag | gtc | tac | atg | agg | 799
| Gly | Gln | Ser | Cys | Asn | Asn | Leu | Pro | Leu | Ser | His | Lys | Val | Tyr | Met | Arg |
| | | | 200 | | | | | 205 | | | | | 210 | | |

| aac | tct | aag | tat | ccc | cag | gat | ctg | gtg | atg | atg | gag | ggg | aag | atg | atg | 847
| Asn | Ser | Lys | Tyr | Pro | Gln | Asp | Leu | Val | Met | Met | Glu | Gly | Lys | Met | Met |
| 215 | | | | | 220 | | | | | 225 | | | | | 230 |

| agc | tac | tgc | act | act | ggg | cag | atg | tgg | gcc | cgc | agc | agc | tac | ctg | ggg | 895
| Ser | Tyr | Cys | Thr | Thr | Gly | Gln | Met | Trp | Ala | Arg | Ser | Ser | Tyr | Leu | Gly |
| | | | | 235 | | | | | 240 | | | | | 245 | |

| gca | gtg | ttc | aat | ctt | acc | agt | gct | gat | cat | tta | tat | gtc | aac | gta | tct | 943
| Ala | Val | Phe | Asn | Leu | Thr | Ser | Ala | Asp | His | Leu | Tyr | Val | Asn | Val | Ser |
| | | | | 250 | | | | | 255 | | | | | 260 | |

| gag | ctc | tct | ctg | gtc | aat | ttt | gag | gaa | tct | cag | acg | ttt | ttc | ggc | tta | 991
| Glu | Leu | Ser | Leu | Val | Asn | Phe | Glu | Glu | Ser | Gln | Thr | Phe | Phe | Gly | Leu |
| | | | | 265 | | | | | 270 | | | | | 275 | |

| tat | aag | ctc | taagagaagc | actttgggat | tctttccatt | atgattcttt | 1040
| Tyr | Lys | Leu |
| | | 280 |

| gttacaggca | ccgagaatgt | tgtattcagt | gagggtcttc | ttacatgcat | ttgaggtcaa | 1100 |
| gtaagaagac | atgaaccaag | tggaccttga | gaccacaggg | ttcaaaatgt | ctgtagctcc | 1160 |
| tcaactcacc | taatgtttat | gagccagaca | aatggaggaa | tatgacggaa | gaacatagaa | 1220 |
| ctctgggctg | ccatgtgaag | agggagaagc | atgaaaaagc | agctaccagg | tgttctacac | 1280 |
| tcatcttagt | gcctgagagt | atttaggcag | attgaaaagg | acaccttta | actcacctct | 1340 |
| caaggtgggc | cttgctacct | caaggggggac | tgtctttcag | atacatggtt | gtgacctgag | 1400 |
| gatttaaggg | atggaaaagg | aagactagag | gcttgcataa | taagctaaag | aggctgaaag | 1460 |
| aggccaatgc | cccactggca | gcatcttcac | ttctaaatgc | atatcctgag | ccatcggtga | 1520 |

Figure 6C. Registered sequence of Fas ligand of human origin (SEQ ID NO: 9).

```
aactaacaga taagcaagag agatgttttg gggactcatt tcattcctaa cacagcatgt    1580
gtatttccag tgcaattgta ggggtgtgtg tgtgtgtgtg tgtgtgtgtg tgtgtatgac    1640
taaagagaga atgtagatat tgtgaagtac atattaggaa aatatgggtt gcatttggtc    1700
aagattttga atgcttcctg acaatcaact ctaatagtgc ttaaaaatca ttgattgtca    1760
gctactaatg atgttttcct ataatataat aaatatttat gtagatgtgc atttttgtga    1820
aatgaaaaca tgtaataaaa agtatatgtt aggatacaaa aaaaaaaaaa aaaaaaaaa    1880 aaaaaaaaaa aaaaaaaaaa aaaaaaaa                                      1909
```

Figure 7A. Nucleotide sequence and amino acid sequence of the FasL-IgFc fusion protein (SEQ ID NO: 11).

```
gctagc atg ggg gta ctg ctc aca cag agg acg ctg ctc agt ctg gtc            48
       Met Gly Val Leu Leu Thr Gln Arg Thr Leu Leu Ser Leu Val
       -25                 -20                 -15 ctt gca ctc ctg ttt cca agc atg gcg agc atg ctc gag cag ctc ttc            96
Leu Ala Leu Leu Phe Pro Ser Met Ala Ser Met Leu Glu Gln Leu Phe
    -10                 -5              -1  1               5 cac cta cag aag gag ctg gca gaa ctc cga gag tct acc agc cag atg           144
His Leu Gln Lys Glu Leu Ala Glu Leu Arg Glu Ser Thr Ser Gln Met
                10                  15                  20 cac aca gca tca tct ttg gag aag caa ata ggc cac ccc agt cca ccc           192
His Thr Ala Ser Ser Leu Glu Lys Gln Ile Gly His Pro Ser Pro Pro
                25                  30                  35 cct gaa aaa aag gag ctg agg aaa gtg gcc cat tta aca ggc aag tcc           240
Pro Glu Lys Lys Glu Leu Arg Lys Val Ala His Leu Thr Gly Lys Ser
            40                  45                  50 aac tca agg tcc atg cct ctg gaa tgg gaa gac acc tat gga att gtc           288
Asn Ser Arg Ser Met Pro Leu Glu Trp Glu Asp Thr Tyr Gly Ile Val
    55                  60                  65 ctg ctt tct gga gtg aag tat aag aag ggt ggc ctt gtg atc aat gaa           336
Leu Leu Ser Gly Val Lys Tyr Lys Lys Gly Gly Leu Val Ile Asn Glu
70                  75                  80                  85 act ggg ctg tac ttt gta tat tcc aaa gta tac ttc cgg ggt caa tct           384
Thr Gly Leu Tyr Phe Val Tyr Ser Lys Val Tyr Phe Arg Gly Gln Ser
                90                  95                  100 tgc aac aac ctg ccc ctg agc cac aag gtc tac atg agg aac tct aag           432
Cys Asn Asn Leu Pro Leu Ser His Lys Val Tyr Met Arg Asn Ser Lys
            105                 110                 115 tat ccc cag gat ctg gtg atg atg gag ggg aag atg atg agc tac tgc           480
Tyr Pro Gln Asp Leu Val Met Met Glu Gly Lys Met Met Ser Tyr Cys
        120                 125                 130 act act ggg cag atg tgg gcc cgc agc agc tac ctg ggg gca gtg ttc           528
Thr Thr Gly Gln Met Trp Ala Arg Ser Ser Tyr Leu Gly Ala Val Phe
        135                 140                 145 aat ctt acc agt gct gat cat tta tat gtc aac gta tct gag ctc tct           576
Asn Leu Thr Ser Ala Asp His Leu Tyr Val Asn Val Ser Glu Leu Ser
150                 155                 160                 165
```

Figure 7B. Nucleotide sequence and amino acid sequence of the FasL-IgFc fusion protein (SEQ ID NO: 11).

| | | | | | | | | | | | | | | | | |
|---|---|---|---|---|---|---|---|---|---|---|---|---|---|---|---|---|
| ctg | gtc | aat | ttt | gag | gaa | tct | cag | acg | ttt | ttc | ggc | tta | tat | aag | ctc | 624 |
| Leu | Val | Asn | Phe | Glu | Glu | Ser | Gln | Thr | Phe | Phe | Gly | Leu | Tyr | Lys | Leu | |
| | | | | 170 | | | | | 175 | | | | | 180 | | |
| gag | ccc | aaa | tct | tgt | gac | aaa | act | cac | aca | tgc | cca | ccg | tgc | cca | gca | 672 |
| Glu | Pro | Lys | Ser | Cys | Asp | Lys | Thr | His | Thr | Cys | Pro | Pro | Cys | Pro | Ala | |
| | | | 185 | | | | | 190 | | | | | 195 | | | |
| cct | gaa | ctc | ctg | ggg | gga | ccg | tca | gtc | ttc | ctc | ttc | ccc | cca | aaa | ccc | 720 |
| Pro | Glu | Leu | Leu | Gly | Gly | Pro | Ser | Val | Phe | Leu | Phe | Pro | Pro | Lys | Pro | |
| | | | 200 | | | | | 205 | | | | | 210 | | | |
| aag | gac | acc | ctc | atg | atc | tcc | cgg | acc | cct | gag | gtc | aca | tgc | gtg | gtg | 768 |
| Lys | Asp | Thr | Leu | Met | Ile | Ser | Arg | Thr | Pro | Glu | Val | Thr | Cys | Val | Val | |
| | | 215 | | | | | 220 | | | | | 225 | | | | |
| gtg | gac | gtg | agc | cac | gaa | gac | cct | gag | gtc | aag | ttc | aac | tgg | tac | gtg | 816 |
| Val | Asp | Val | Ser | His | Glu | Asp | Pro | Glu | Val | Lys | Phe | Asn | Trp | Tyr | Val | |
| 230 | | | | | 235 | | | | | 240 | | | | | 245 | |
| gac | ggc | gtg | gag | gtg | cat | aat | gcc | aag | aca | aag | ccg | cgg | gag | gag | cag | 864 |
| Asp | Gly | Val | Glu | Val | His | Asn | Ala | Lys | Thr | Lys | Pro | Arg | Glu | Glu | Gln | |
| | | | | 250 | | | | | 255 | | | | | 260 | | |
| tac | aac | agc | acg | tac | cgt | gtg | gtc | agc | gtc | ctc | acc | gtc | ctg | cac | cag | 912 |
| Tyr | Asn | Ser | Thr | Tyr | Arg | Val | Val | Ser | Val | Leu | Thr | Val | Leu | His | Gln | |
| | | | 265 | | | | | 270 | | | | | 275 | | | |
| gac | tgg | ctg | aat | ggc | aag | gag | tac | aag | tgc | aag | gtc | tcc | aac | aaa | gcc | 960 |
| Asp | Trp | Leu | Asn | Gly | Lys | Glu | Tyr | Lys | Cys | Lys | Val | Ser | Asn | Lys | Ala | |
| | | | 280 | | | | | 285 | | | | | 290 | | | |
| ctc | cca | gcc | ccc | atc | gag | aaa | acc | atc | tcc | aaa | gcc | aaa | ggg | cag | ccc | 1008 |
| Leu | Pro | Ala | Pro | Ile | Glu | Lys | Thr | Ile | Ser | Lys | Ala | Lys | Gly | Gln | Pro | |
| | | | 295 | | | | | 300 | | | | | 305 | | | |
| cga | gaa | cca | cag | gtg | tac | acc | ctg | ccc | cca | tcc | cgg | gat | gag | ctg | acc | 1056 |
| Arg | Glu | Pro | Gln | Val | Tyr | Thr | Leu | Pro | Pro | Ser | Arg | Asp | Glu | Leu | Thr | |
| 310 | | | | | 315 | | | | | 320 | | | | | 325 | |
| aag | aac | cag | gtc | agc | ctg | acc | tgc | ctg | gtc | aaa | ggc | ttc | tat | ccc | agc | 1104 |
| Lys | Asn | Gln | Val | Ser | Leu | Thr | Cys | Leu | Val | Lys | Gly | Phe | Tyr | Pro | Ser | |
| | | | | 330 | | | | | 335 | | | | | 340 | | |

Figure 7C. Nucleotide sequence and amino acid sequence of the FasL-IgFc fusion protein (SEQ ID NO: 11).

```
gac atc gcc gtg gag tgg gag agc aat ggg cag ccg gag aac aac tac       1152
Asp Ile Ala Val Glu Trp Glu Ser Asn Gly Gln Pro Glu Asn Asn Tyr
            345                 350                 355 aag acc acg cct ccc gtg ctg gac tcc gac ggc tcc ttc ttc ctc tac       1200
Lys Thr Thr Pro Pro Val Leu Asp Ser Asp Gly Ser Phe Phe Leu Tyr
            360                 365                 370 agc aag ctc acc gtg gac aag agc agg tgg cag cag ggg aac gtc ttc       1248
Ser Lys Leu Thr Val Asp Lys Ser Arg Trp Gln Gln Gly Asn Val Phe
    375                 380                 385 tca tgc tcc gtg atg cat gag gct ctg cac aac cac tac acg cag aag       1296
Ser Cys Ser Val Met His Glu Ala Leu His Asn His Tyr Thr Gln Lys
390                 395                 400                 405 agc ctc tcc ctg tct ccg ggt aaa tgatctaga                             1329
Ser Leu Ser Leu Ser Pro Gly Lys
                410
```

Figure 8A. Nucleotide sequence and amino acid sequence of the CD40L-FasL-IgFc fusion protein (SEQ ID NO: 13).

```
gctagc atg ggg gta ctg ctc aca cag agg acg ctg ctc agt ctg gtc              48
       Met Gly Val Leu Leu Thr Gln Arg Thr Leu Leu Ser Leu Val
        1           5                  10 ctt gca ctc ctg ttt cca agc atg gcg agc atg ctt cat aga agg ttg             96
Leu Ala Leu Leu Phe Pro Ser Met Ala Ser Met Leu His Arg Arg Leu
15              20                  25                  30 gac aag ata gaa gat gaa agg aat ctt cat gaa gat ttt gta ttc atg            144
Asp Lys Ile Glu Asp Glu Arg Asn Leu His Glu Asp Phe Val Phe Met
                35                  40                  45 aaa acg ata cag aga tgc aac aca gga gaa aga tcc tta tcc tta ctg            192
Lys Thr Ile Gln Arg Cys Asn Thr Gly Glu Arg Ser Leu Ser Leu Leu
                50                  55                  60 aac tgt gag gag att aaa agc cag ttt gaa ggc ttt gtg aag gat ata            240
Asn Cys Glu Glu Ile Lys Ser Gln Phe Glu Gly Phe Val Lys Asp Ile
            65                  70                  75 atg tta aac aaa gag gag acg aag aaa gaa aac agc ttt gaa atg caa            288
Met Leu Asn Lys Glu Glu Thr Lys Lys Glu Asn Ser Phe Glu Met Gln
        80                  85                  90 aaa ggt gat cag aat cct caa att gcg gca cat gtc ata agt gag gcc            336
Lys Gly Asp Gln Asn Pro Gln Ile Ala Ala His Val Ile Ser Glu Ala
95                  100                 105                 110 agc agt aaa aca aca tct gtg tta cag tgg gct gaa aaa gga tac tac            384
Ser Ser Lys Thr Thr Ser Val Leu Gln Trp Ala Glu Lys Gly Tyr Tyr
                115                 120                 125 acc atg agc aac aac ttg gta acc ctg gaa aat ggg aaa cag ctg acc            432
Thr Met Ser Asn Asn Leu Val Thr Leu Glu Asn Gly Lys Gln Leu Thr
                130                 135                 140 gtt aaa aga caa gga ctc tat tat atc tat gcc caa gtc acc ttc tgt            480
Val Lys Arg Gln Gly Leu Tyr Tyr Ile Tyr Ala Gln Val Thr Phe Cys
        145                 150                 155 tcc aat cgg gaa gct tcg agt caa gct cca ttt ata gcc agc ctc tgc            528
Ser Asn Arg Glu Ala Ser Ser Gln Ala Pro Phe Ile Ala Ser Leu Cys
        160                 165                 170 cta aag tcc ccc ggt aga ttc gag aga atc tta ctc aga gct gca aat            576
Leu Lys Ser Pro Gly Arg Phe Glu Arg Ile Leu Leu Arg Ala Ala Asn
175                 180                 185                 190
```

Figure 8B. Nucleotide sequence and amino acid sequence of the CD40L-FasL-IgFc fusion protein (SEQ ID NO: 13).

```
acc cac agt tcc gcc aaa cct tgc ggg caa caa tcc att cac ttg gga          624
Thr His Ser Ser Ala Lys Pro Cys Gly Gln Gln Ser Ile His Leu Gly
            195                 200                 205 gga gta ttt gaa ttg caa cca ggt gct tcg gtg ttt gtc aat gtg act          672
Gly Val Phe Glu Leu Gln Pro Gly Ala Ser Val Phe Val Asn Val Thr
            210                 215                 220 gat cca agc caa gtg agc cat ggc act ggc ttc acg tcc ttt ggc tta          720
Asp Pro Ser Gln Val Ser His Gly Thr Gly Phe Thr Ser Phe Gly Leu
            225                 230                 235 ctc aaa ctc gag cag ctc ttc cac cta cag aag gag ctg gca gaa ctc          768
Leu Lys Leu Glu Gln Leu Phe His Leu Gln Lys Glu Leu Ala Glu Leu
            240                 245                 250 cga gag tct acc agc cag atg cac aca gca tca tct ttg gag aag caa          816
Arg Glu Ser Thr Ser Gln Met His Thr Ala Ser Ser Leu Glu Lys Gln
255                 260                 265                 270 ata ggc cac ccc agt cca ccc cct gaa aaa aag gag ctg agg aaa gtg          864
Ile Gly His Pro Ser Pro Pro Pro Glu Lys Lys Glu Leu Arg Lys Val
            275                 280                 285 gcc cat tta aca ggc aag tcc aac tca agg tcc atg cct ctg gaa tgg          912
Ala His Leu Thr Gly Lys Ser Asn Ser Arg Ser Met Pro Leu Glu Trp
            290                 295                 300 gaa gac acc tat gga att gtc ctg ctt tct gga gtg aag tat aag aag          960
Glu Asp Thr Tyr Gly Ile Val Leu Leu Ser Gly Val Lys Tyr Lys Lys
            305                 310                 315 ggt ggc ctt gtg atc aat gaa act ggg ctg tac ttt gta tat tcc aaa         1008
Gly Gly Leu Val Ile Asn Glu Thr Gly Leu Tyr Phe Val Tyr Ser Lys
            320                 325                 330 gta tac ttc cgg ggt caa tct tgc aac aac ctg ccc ctg agc cac aag         1056
Val Tyr Phe Arg Gly Gln Ser Cys Asn Asn Leu Pro Leu Ser His Lys
335                 340                 345                 350 gtc tac atg agg aac tct aag tat ccc cag gat ctg gtg atg atg gag         1104
Val Tyr Met Arg Asn Ser Lys Tyr Pro Gln Asp Leu Val Met Met Glu
            355                 360                 365 ggg aag atg atg agc tac tgc act act ggg cag atg tgg gcc cgc agc         1152
Gly Lys Met Met Ser Tyr Cys Thr Thr Gly Gln Met Trp Ala Arg Ser
            370                 375                 380
```

Figure 8C. Nucleotide sequence and amino acid sequence of the CD40L-FasL-IgFc fusion protein (SEQ ID NO: 13).

```
agc tac ctg ggg gca gtg ttc aat ctt acc agt gct gat cat tta tat    1200
Ser Tyr Leu Gly Ala Val Phe Asn Leu Thr Ser Ala Asp His Leu Tyr
        385                 390                 395 gtc aac gta tct gag ctc tct ctg gtc aat ttt gag gaa tct cag acg    1248
Val Asn Val Ser Glu Leu Ser Leu Val Asn Phe Glu Glu Ser Gln Thr
        400                 405                 410 ttt ttc ggc tta tat aag ctc gag ccc aaa tct tgt gac aaa act cac    1296
Phe Phe Gly Leu Tyr Lys Leu Glu Pro Lys Ser Cys Asp Lys Thr His
415                 420                 425                 430 aca tgc cca ccg tgc cca gca cct gaa ctc ctg ggg gga ccg tca gtc    1344
Thr Cys Pro Pro Cys Pro Ala Pro Glu Leu Leu Gly Gly Pro Ser Val
                435                 440                 445 ttc ctc ttc ccc cca aaa ccc aag gac acc ctc atg atc tcc cgg acc    1392
Phe Leu Phe Pro Pro Lys Pro Lys Asp Thr Leu Met Ile Ser Arg Thr
                450                 455                 460 cct gag gtc aca tgc gtg gtg gtg gac gtg agc cac gaa gac cct gag    1440
Pro Glu Val Thr Cys Val Val Val Asp Val Ser His Glu Asp Pro Glu
            465                 470                 475 gtc aag ttc aac tgg tac gtg gac ggc gtg gag gtg cat aat gcc aag    1488
Val Lys Phe Asn Trp Tyr Val Asp Gly Val Glu Val His Asn Ala Lys
            480                 485                 490 aca aag ccg cgg gag gag cag tac aac agc acg tac cgt gtg gtc agc    1536
Thr Lys Pro Arg Glu Glu Gln Tyr Asn Ser Thr Tyr Arg Val Val Ser
495                 500                 505                 510 gtc ctc acc gtc ctg cac cag gac tgg ctg aat ggc aag gag tac aag    1584
Val Leu Thr Val Leu His Gln Asp Trp Leu Asn Gly Lys Glu Tyr Lys
                515                 520                 525 tgc aag gtc tcc aac aaa gcc ctc cca gcc ccc atc gag aaa acc atc    1632
Cys Lys Val Ser Asn Lys Ala Leu Pro Ala Pro Ile Glu Lys Thr Ile
                530                 535                 540 tcc aaa gcc aaa ggg cag ccc cga gaa cca cag gtg tac acc ctg ccc    1680
Ser Lys Ala Lys Gly Gln Pro Arg Glu Pro Gln Val Tyr Thr Leu Pro
            545                 550                 555 cca tcc cgg gat gag ctg acc aag aac cag gtc agc ctg acc tgc ctg    1728
Pro Ser Arg Asp Glu Leu Thr Lys Asn Gln Val Ser Leu Thr Cys Leu
        560                 565                 570
```

Figure 8D. Nucleotide sequence and amino acid sequence of the CD40L-FasL-IgFc fusion protein (SEQ ID NO: 13).

```
gtc aaa ggc ttc tat ccc agc gac atc gcc gtg gag tgg gag agc aat     1776
Val Lys Gly Phe Tyr Pro Ser Asp Ile Ala Val Glu Trp Glu Ser Asn
575             580             585             590 ggg cag ccg gag aac aac tac aag acc acg cct ccc gtg ctg gac tcc     1824
Gly Gln Pro Glu Asn Asn Tyr Lys Thr Thr Pro Pro Val Leu Asp Ser
            595             600             605 gac ggc tcc ttc ttc ctc tac agc aag ctc acc gtg gac aag agc agg     1872
Asp Gly Ser Phe Phe Leu Tyr Ser Lys Leu Thr Val Asp Lys Ser Arg
        610             615             620 tgg cag cag ggg aac gtc ttc tca tgc tcc gtg atg cat gag gct ctg     1920
Trp Gln Gln Gly Asn Val Phe Ser Cys Ser Val Met His Glu Ala Leu
        625             630             635 cac aac cac tac acg cag aag agc ctc tcc ctg tct ccg ggt aaa         1965
His Asn His Tyr Thr Gln Lys Ser Leu Ser Leu Ser Pro Gly Lys
        640             645             650 tgatctaga                                                           1974
```

Figure 9. Western blotting analysis of CD40L-FasL-IgFc.
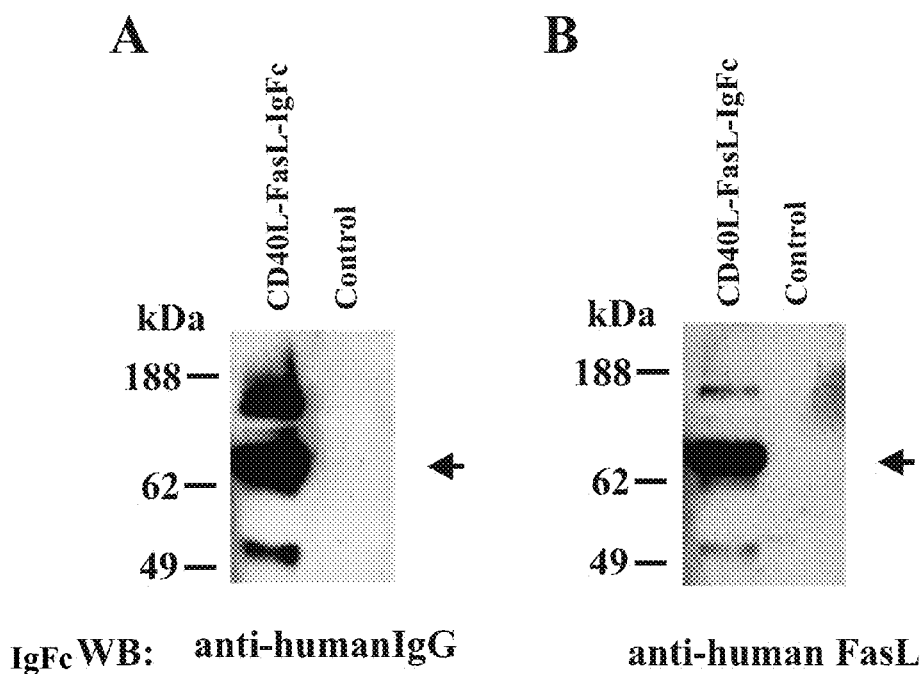
Figure 10. Study of Fas binding by CD40L-FasL-IgFc.
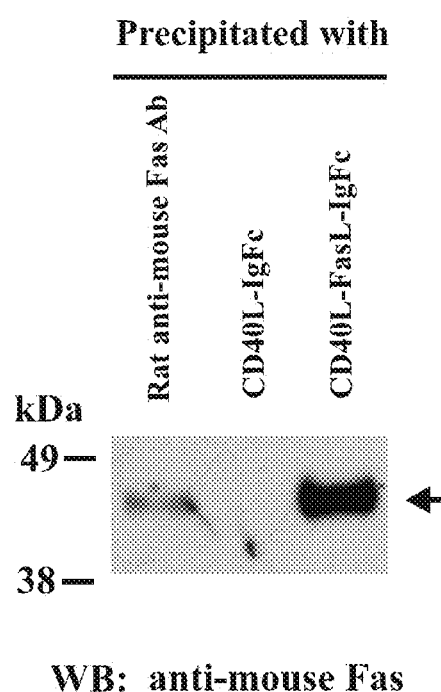

Figure 11. Proliferation of human PBMC induced with CD40L-FasL-IgFc.
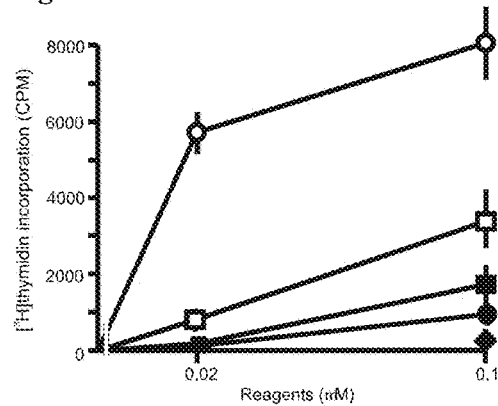
Figure 12. Non-T cell-specific stimulation by CD40L-FasL-IgFc.
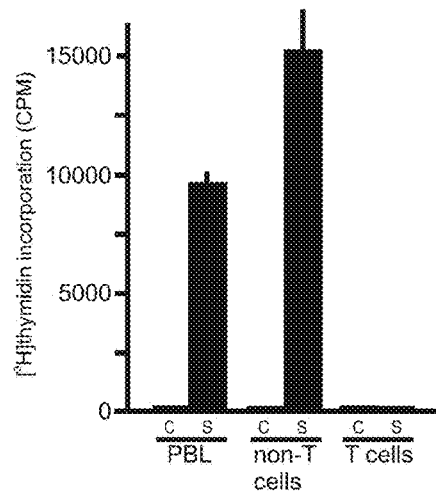
Figure 13. Effects of Polymixin B pre-absorption on the stimulation by CD40L-FasL-IgFc.
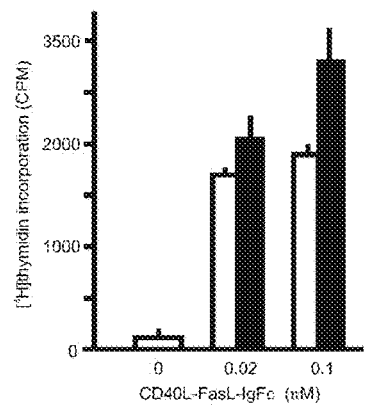

Figure 14. Reduction of CD40L-FasL-IgFc-induced activation by signaling inhibitors.
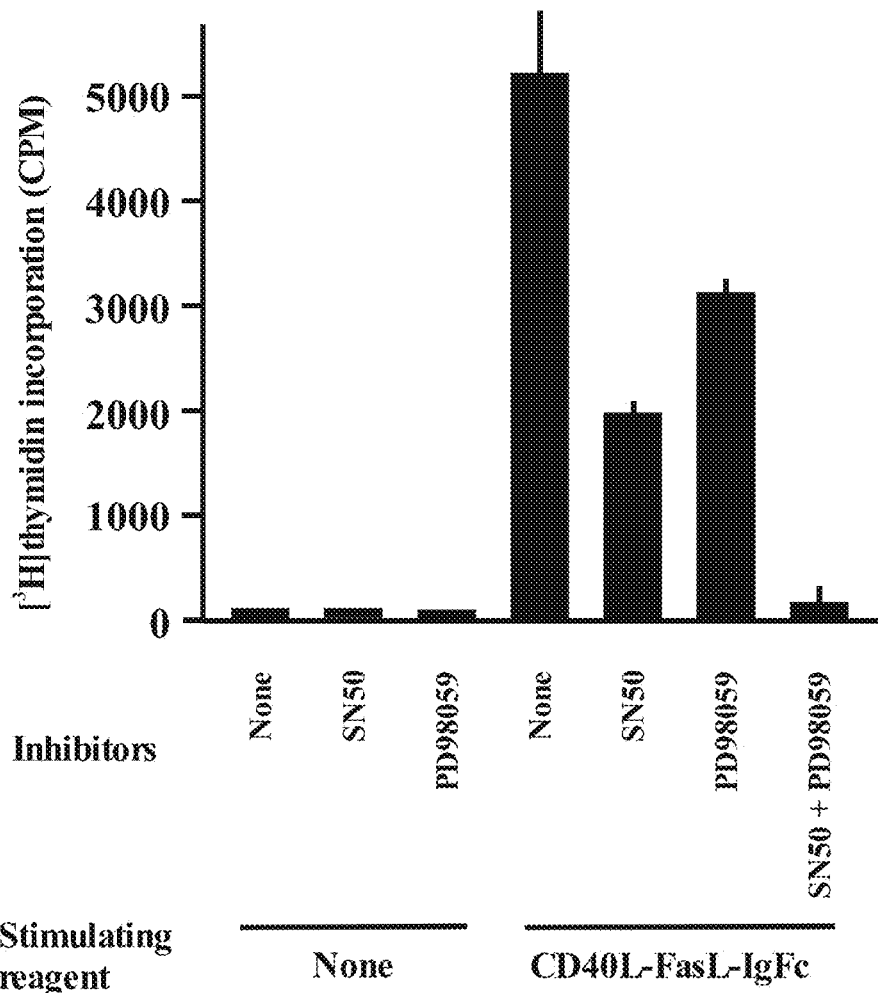
Figure 15. Induction of IgG secretion in PBL cells stimulated with CD40L-FasL-IgFc.
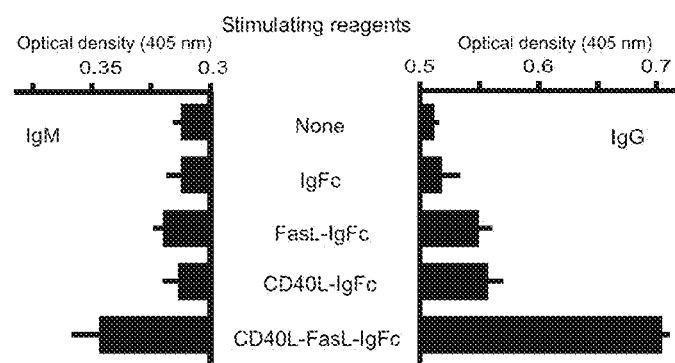

Figure 16. The expression of PRDI-BF1 in response to CD40L-FasL-IgFc stimulation.
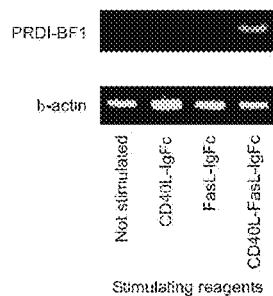
Figure 17. Adjuvant activity of CD40L-FasL-IgFc in mice against OVA.
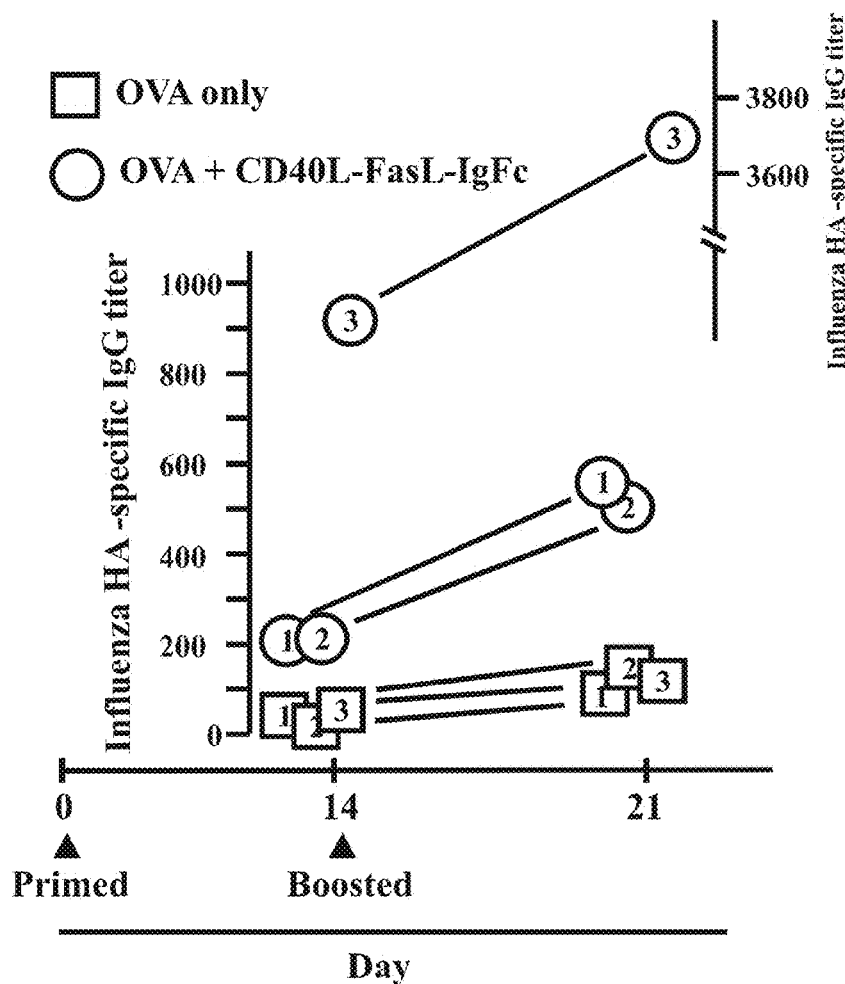

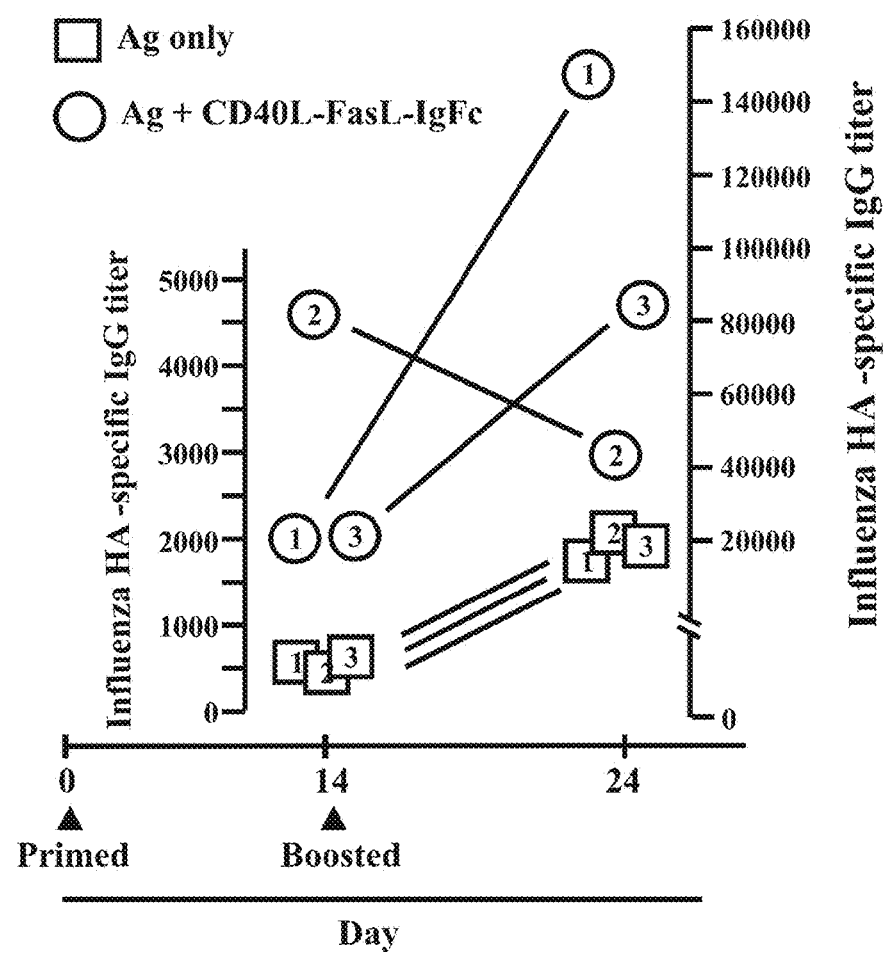
Figure 18. Adjuvant activity of CD40L-FasL-IgFc in mice against Influenza hemaglutinin.

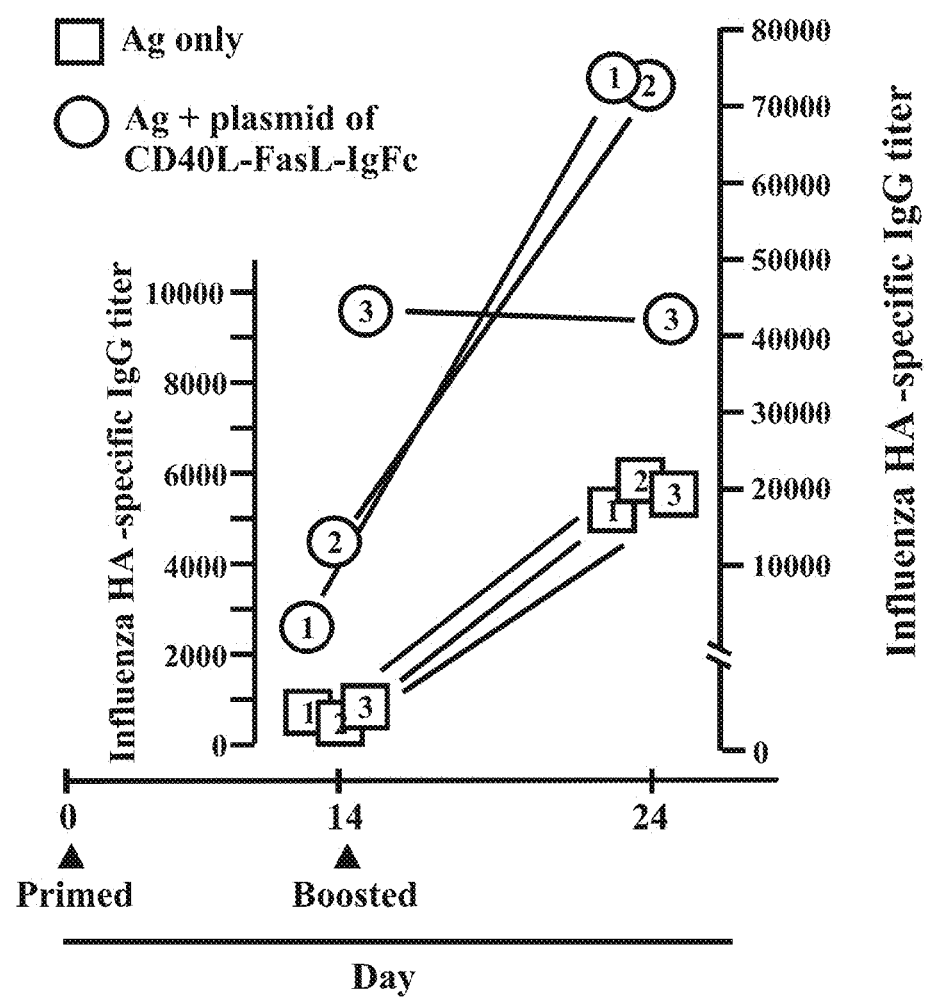
Figure 19. Adjuvant activity of Plasmid DNA of CD40L-FasL-IgFc in mice against Influenza hemaglutinin.

Figure 20. Adjuvant activity of CD40L-FasL-IgFc in mice against Influenza hemaglutinin-spec Figure 21A. Registered sequence of B7-2 of human origin (SEQ ID NO: 15).

```
aggagcctta ggaggtacgg ggagctcgca aatactcctt ttggtttatt cttaccacct        60
tgcttctgtg ttccttggga atgctgctgt gcttatgcat ctggtctctt tttggagcta       120
cagtggacag gcatttgtga cagcact atg gga ctg agt aac att ctc ttt gtg       174
                               Met Gly Leu Ser Asn Ile Leu Phe Val
                                   -15                     -10 atg gcc ttc ctg ctc tct ggt gct gct cct ctg aag att caa gct tat         222
Met Ala Phe Leu Leu Ser Gly Ala Ala Pro Leu Lys Ile Gln Ala Tyr
    -5                  -1  1                 5 ttc aat gag act gca gac ctg cca tgc caa ttt gca aac tct caa aac         270
Phe Asn Glu Thr Ala Asp Leu Pro Cys Gln Phe Ala Asn Ser Gln Asn
10                      15                  20                  25 caa agc ctg agt gag cta gta gta ttt tgg cag gac cag gaa aac ttg         318
Gln Ser Leu Ser Glu Leu Val Val Phe Trp Gln Asp Gln Glu Asn Leu
                    30                  35                  40 gtt ctg aat gag gta tac tta ggc aaa gag aaa ttt gac agt gtt cat         366
Val Leu Asn Glu Val Tyr Leu Gly Lys Glu Lys Phe Asp Ser Val His
            45                  50                  55 tcc aag tat atg ggc cgc aca agt ttt gat tcg gac agt tgg acc ctg         414
Ser Lys Tyr Met Gly Arg Thr Ser Phe Asp Ser Asp Ser Trp Thr Leu
                60                  65                  70 aga ctt cac aat ctt cag atc aag gac aag ggc ttg tat caa tgt atc         462
Arg Leu His Asn Leu Gln Ile Lys Asp Lys Gly Leu Tyr Gln Cys Ile
        75                  80                  85 atc cat cac aaa aag ccc aca gga atg att cgc atc cac cag atg aat         510
Ile His His Lys Lys Pro Thr Gly Met Ile Arg Ile His Gln Met Asn
90                  95                  100                 105 tct gaa ctg tca gtg ctt gct aac ttc agt caa cct gaa ata gta cca         558
Ser Glu Leu Ser Val Leu Ala Asn Phe Ser Gln Pro Glu Ile Val Pro
                    110                 115                 120 att tct aat ata aca gaa aat gtg tac ata aat ttg acc tgc tca tct         606
Ile Ser Asn Ile Thr Glu Asn Val Tyr Ile Asn Leu Thr Cys Ser Ser
            125                 130                 135 ata cac ggt tac cca gaa cct aag aag atg agt gtt ttg cta aga acc         654
Ile His Gly Tyr Pro Glu Pro Lys Lys Met Ser Val Leu Leu Arg Thr
                140                 145                 150
```

Figure 21B. Registered sequence of B7-2 of human origin (SEQ ID NO: 15).

| | | | | | | | | | | | | | | | |
|---|---|---|---|---|---|---|---|---|---|---|---|---|---|---|---|
| aag | aat | tca | act | atc | gag | tat | gat | ggt | gtt | atg | cag | aaa | tct | caa | gat | 702 |
| Lys | Asn | Ser | Thr | Ile | Glu | Tyr | Asp | Gly | Val | Met | Gln | Lys | Ser | Gln | Asp | |
| | 155 | | | | | 160 | | | | | 165 | | | | | |

| aat | gtc | aca | gaa | ctg | tac | gac | gtt | tcc | atc | agc | ttg | tct | gtt | tca | gac | 750 |
| Asn | Val | Thr | Glu | Leu | Tyr | Asp | Val | Ser | Ile | Ser | Leu | Ser | Val | Ser | Asp | |
| 170 | | | | | 175 | | | | | 180 | | | | | 185 | |

| aag | acg | cgg | ctt | tta | tct | tca | cct | ttc | tct | ata | gag | ctt | gag | ttc | cct | 798 |
| Lys | Thr | Arg | Leu | Leu | Ser | Ser | Pro | Phe | Ser | Ile | Glu | Leu | Glu | Phe | Pro | |
| | | | | | 190 | | | | | 195 | | | | | 200 | |

| gat | gtt | acg | agc | aat | atg | acc | atc | ttc | tgt | att | ctg | gaa | act | gac | cct | 846 |
| Asp | Val | Thr | Ser | Asn | Met | Thr | Ile | Phe | Cys | Ile | Leu | Glu | Thr | Asp | Pro | |
| | | | 205 | | | | | 210 | | | | | 215 | | | |

| cag | cct | ccc | cca | gac | cac | att | cct | tgg | att | aca | gct | gta | ctt | cca | aca | 894 |
| Gln | Pro | Pro | Pro | Asp | His | Ile | Pro | Trp | Ile | Thr | Ala | Val | Leu | Pro | Thr | |
| | | 220 | | | | | 225 | | | | | 230 | | | | |

| gtt | att | ata | tgt | gtg | atg | gtt | ttc | tgt | cta | att | cta | tgg | aaa | tgg | aag | 942 |
| Val | Ile | Ile | Cys | Val | Met | Val | Phe | Cys | Leu | Ile | Leu | Trp | Lys | Trp | Lys | |
| | 235 | | | | | 240 | | | | | 245 | | | | | |

| aag | aag | aag | cgg | cct | cgc | aac | tct | tat | aaa | tgt | gga | acc | aac | aca | atg | 990 |
| Lys | Lys | Lys | Arg | Pro | Arg | Asn | Ser | Tyr | Lys | Cys | Gly | Thr | Asn | Thr | Met | |
| 250 | | | | | 255 | | | | | 260 | | | | | 265 | |

| gag | agg | gaa | gag | agt | gaa | cag | acc | aag | aaa | aga | gaa | aaa | atc | cat | ata | 1038 |
| Glu | Arg | Glu | Glu | Ser | Glu | Gln | Thr | Lys | Lys | Arg | Glu | Lys | Ile | His | Ile | |
| | | | | 270 | | | | | 275 | | | | | 280 | | |

| cct | gaa | aga | tct | gat | gaa | gcc | cag | cgt | gtt | ttt | aaa | agt | tcg | aag | aca | 1086 |
| Pro | Glu | Arg | Ser | Asp | Glu | Ala | Gln | Arg | Val | Phe | Lys | Ser | Ser | Lys | Thr | |
| | | | 285 | | | | | 290 | | | | | 295 | | | |

| tct | tca | tgc | gac | aaa | agt | gat | aca | tgt | ttt | taaataaaga | gtaaagccca | | | | | 1136 |
| Ser | Ser | Cys | Asp | Lys | Ser | Asp | Thr | Cys | Phe | | | | | | | |
| | | 300 | | | | | 305 | | | | | | | | | |

| tacaagtatt | catttttttct | acccttttcct | ttgtaagttc | ctgggcaacc | tttttgattt | 1196 |
| cttccagaag | gcaaaaagac | attaccatga | gtaataaggg | ggctccagga | ctccctctaa | 1256 |
| gtggaatagc | ctccctgtaa | ctccagctct | gctccgtatg | ccaagaggag | actttaattc | 1316 |
| tcttactgct | tcttttcact | tcagagcaca | cttatgggcc | aagcccagct | taatggctca | 1376 |

Figure 21C. Registered sequence of B7-2 of human origin (SEQ ID NO: 15).

```
tgacctggaa ataaaattta ggaccaatac ctcctccaga tcagattctt ctcttaattt      1436
catagattgt gttttttttt taaatagacc tctcaatttc tggaaaactg cctttatct       1496
gcccagaatt ctaagctggt gccccactga attttgtgtg tacctgtgac taaacaacta     1556
cctcctcagt ctgggtggga cttatgtatt tatgaccttta tagtgttaat atcttgaaac    1616
atagagatct atgtactgta atagtgtgat tactatgctc tagagaaaag tctacccctg     1676
ctaaggagtt ctcatccctc tgtcagggtc agtaaggaaa acggtggcct agggtacagg     1736
caacaatgag cagaccaacc taaatttggg gaaattagga gaggcagaga tagaacctgg     1796
agccacttct atctgggctg ttgctaatat tgaggaggct tgccccaccc aacaagccat     1856
agtggagaga actgaataaa caggaaaatg ccagagcttg tgaaccctgt ttctcttgaa     1916
gaactgacta gtgagatggc ctggggaagc tgtgaaagaa ccaaaagaga tcacaatact     1976
caaaagagag agagagagaa aaaagagaga tcttgatcca cagaaataca tgaaatgtct     2036
ggtctgtcca ccccatcaac aagtcttgaa acaagcaaca gatggatagt ctgtccaaat    2096
ggacataaga cagacagcag tttccctggt ggtcagggag gggttttggt gatacccaag    2156
ttattgggat gtcatcttcc tggaagcaga gctggggagg gagagccatc accttgataa    2216
tgggatgaat ggaaggaggc ttaggacttt ccactcctgg ctgagagagg aagagctgca    2276
acggaattag gaagaccaag acacagatca cccggggctt acttagccta cagatgtcct    2336
acgggaacgt gggctggccc agcatagggc tagcaaattt gagttggatg attgttttg     2396
ctcaaggcaa ccagaggaaa cttgcataca gagacagata tactgggaga aatgactttg    2456
aaaacctggc tctaaggtgg gatcactaag ggatggggca gtctctgccc aaacataaag    2516
agaactctgg ggagcctgag ccacaaaaat gttcctttat tttatgtaaa ccctcaaggg    2576
ttatagactg ccatgctaga caagcttgtc catgtaatat tcccatgttt ttaccctgcc    2636
cctgccttga ttagactcct agcacctggc tagtttctaa catgttttgt gcagcacagt    2696
ttttaataaa tgcttgttac attcaaaaaa aaaaaaaaaa aaaaaaaaaa aaaaaaaaaa    2756
aaaaaaaaaa aaaaaaaaaa aaaaaaaaaa aaaaaaaaaa aaaaaaaaaa a             2807
```

Figure 22A. Nucleotide sequence and amino acid sequence of the B7-2-FasL-IgFc fusion protein (SEQ ID NO: 17).

```
gctagc atg ggg gta ctg ctc aca cag agg acg ctg ctc agt ctg gtc        48
       Met Gly Val Leu Leu Thr Gln Arg Thr Leu Leu Ser Leu Val
       -25             -20                 -15 ctt gca ctc ctg ttt cca agc atg gcg agc atg gaa ttc acg cgt gct       96
Leu Ala Leu Leu Phe Pro Ser Met Ala Ser Met Glu Phe Thr Arg Ala
-10                 -5              -1  1               5 cct ctg aag att caa gct tat ttc aat gag act gca gac ctg cca tgc      144
Pro Leu Lys Ile Gln Ala Tyr Phe Asn Glu Thr Ala Asp Leu Pro Cys
                10              15              20 caa ttt gca aac tct caa aac caa agc ctg agt gag cta gta gta ttt      192
Gln Phe Ala Asn Ser Gln Asn Gln Ser Leu Ser Glu Leu Val Val Phe
            25              30              35 tgg cag gac cag gaa aac ttg gtt ctg aat gag gta tac tta ggc aaa      240
Trp Gln Asp Gln Glu Asn Leu Val Leu Asn Glu Val Tyr Leu Gly Lys
            40              45              50 gag aaa ttt gac agt gtt cat tcc aag tat atg ggc cgc aca agt ttt      288
Glu Lys Phe Asp Ser Val His Ser Lys Tyr Met Gly Arg Thr Ser Phe
55              60              65 gat tcg gac agt tgg acc ctg aga ctt cac aat ctt cag atc aag gac      336
Asp Ser Asp Ser Trp Thr Leu Arg Leu His Asn Leu Gln Ile Lys Asp
70              75              80              85 aag ggc ttg tat caa tgt atc atc cat cac aaa aag ccc aca gga atg      384
Lys Gly Leu Tyr Gln Cys Ile Ile His His Lys Lys Pro Thr Gly Met
            90              95              100 att cgc atc cac cag atg aat tct gaa ctg tca gtg ctt gct aac ttc      432
Ile Arg Ile His Gln Met Asn Ser Glu Leu Ser Val Leu Ala Asn Phe
        105             110             115 agt caa cct gaa ata gta cca att tct aat ata aca gaa aat gtg tac      480
Ser Gln Pro Glu Ile Val Pro Ile Ser Asn Ile Thr Glu Asn Val Tyr
        120             125             130 ata aat ttg acc tgc tca tct ata cac ggt tac cca gaa cct aag aag      528
Ile Asn Leu Thr Cys Ser Ser Ile His Gly Tyr Pro Glu Pro Lys Lys
        135             140             145 atg agt gtt ttg cta aga acc aag aat tca act atc gag tat gat ggt      576
Met Ser Val Leu Leu Arg Thr Lys Asn Ser Thr Ile Glu Tyr Asp Gly
150             155             160             165
```

Figure 22B. Nucleotide sequence and amino acid sequence of the B7-2-FasL-IgFc fusion protein (SEQ ID NO: 17).

```
gtt atg cag aaa tct caa gat aat gtc aca gaa ctg tac gac gtt tcc      624
Val Met Gln Lys Ser Gln Asp Asn Val Thr Glu Leu Tyr Asp Val Ser
            170                 175                 180 atc agc ttg tct gtt tca ttc cct gat gtt acg agc aat atg acc atc      672
Ile Ser Leu Ser Val Ser Phe Pro Asp Val Thr Ser Asn Met Thr Ile
            185                 190                 195 ttc tgt att ctg gaa act gac aag acg cgg ctt tta tct tca cct ttc      720
Phe Cys Ile Leu Glu Thr Asp Lys Thr Arg Leu Leu Ser Ser Pro Phe
            200                 205                 210 tct ata gag ctt gag gac cct cag cct ccc cca gac cac att cct acg      768
Ser Ile Glu Leu Glu Asp Pro Gln Pro Pro Pro Asp His Ile Pro Thr
            215                 220                 225 cgt ggt acc cag ctc ttc cac cta cag aag gag ctg gca gaa ctc cga      816
Arg Gly Thr Gln Leu Phe His Leu Gln Lys Glu Leu Ala Glu Leu Arg
230                 235                 240                 245 gag tct acc agc cag atg cac aca gca tca tct ttg gag aag caa ata      864
Glu Ser Thr Ser Gln Met His Thr Ala Ser Ser Leu Glu Lys Gln Ile
            250                 255                 260 ggc cac ccc agt cca ccc cct gaa aaa aag gag ctg agg aaa gtg gcc      912
Gly His Pro Ser Pro Pro Pro Glu Lys Lys Glu Leu Arg Lys Val Ala
            265                 270                 275 cat tta aca ggc aag tcc aac tca agg tcc atg cct ctg gaa tgg gaa      960
His Leu Thr Gly Lys Ser Asn Ser Arg Ser Met Pro Leu Glu Trp Glu
            280                 285                 290 gac acc tat gga att gtc ctg ctt tct gga gtg aag tat aag aag ggt     1008
Asp Thr Tyr Gly Ile Val Leu Leu Ser Gly Val Lys Tyr Lys Lys Gly
            295                 300                 305 ggc ctt gtg atc aat gaa act ggg ctg tac ttt gta tat tcc aaa gta     1056
Gly Leu Val Ile Asn Glu Thr Gly Leu Tyr Phe Val Tyr Ser Lys Val
310                 315                 320                 325 tac ttc cgg ggt caa tct tgc aac aac ctg ccc ctg agc cac aag gtc     1104
Tyr Phe Arg Gly Gln Ser Cys Asn Asn Leu Pro Leu Ser His Lys Val
            330                 335                 340 tac atg agg aac tct aag tat ccc cag gat ctg gtg atg atg gag ggg     1152
Tyr Met Arg Asn Ser Lys Tyr Pro Gln Asp Leu Val Met Met Glu Gly
            345                 350                 355
```

Figure 22C. Nucleotide sequence and amino acid sequence of the B7-2-FasL-IgFc fusion protein (SEQ ID NO: 17).

```
aag atg atg agc tac tgc act act ggg cag atg tgg gcc cgc agc agc    1200
Lys Met Met Ser Tyr Cys Thr Thr Gly Gln Met Trp Ala Arg Ser Ser
        360             365             370 tac ctg ggg gca gtg ttc aat ctt acc agt gct gat cat tta tat gtc    1248
Tyr Leu Gly Ala Val Phe Asn Leu Thr Ser Ala Asp His Leu Tyr Val
        375             380             385 aac gta tct gag ctc tct ctg gtc aat ttt gag gaa tct cag acg ttt    1296
Asn Val Ser Glu Leu Ser Leu Val Asn Phe Glu Glu Ser Gln Thr Phe
390             395             400             405 ttc ggc tta tat aag ctc gag ccc aaa tct tgt gac aaa act cac aca    1344
Phe Gly Leu Tyr Lys Leu Glu Pro Lys Ser Cys Asp Lys Thr His Thr
                410             415             420 tgc cca ccg tgc cca gca cct gaa ctc ctg ggg gga ccg tca gtc ttc    1392
Cys Pro Pro Cys Pro Ala Pro Glu Leu Leu Gly Gly Pro Ser Val Phe
        425             430             435 ctc ttc ccc cca aaa ccc aag gac acc ctc atg atc tcc cgg acc cct    1440
Leu Phe Pro Pro Lys Pro Lys Asp Thr Leu Met Ile Ser Arg Thr Pro
        440             445             450 gag gtc aca tgc gtg gtg gtg gac gtg agc cac gaa gac cct gag gtc    1488
Glu Val Thr Cys Val Val Val Asp Val Ser His Glu Asp Pro Glu Val
        455             460             465 aag ttc aac tgg tac gtg gac ggc gtg gag gtg cat aat gcc aag aca    1536
Lys Phe Asn Trp Tyr Val Asp Gly Val Glu Val His Asn Ala Lys Thr
470             475             480             485 aag ccg cgg gag gag cag tac aac agc acg tac cgt gtg gtc agc gtc    1584
Lys Pro Arg Glu Glu Gln Tyr Asn Ser Thr Tyr Arg Val Val Ser Val
        490             495             500 ctc acc gtc ctg cac cag gac tgg ctg aat ggc aag gag tac aag tgc    1632
Leu Thr Val Leu His Gln Asp Trp Leu Asn Gly Lys Glu Tyr Lys Cys
        505             510             515 aag gtc tcc aac aaa gcc ctc cca gcc ccc atc gag aaa acc atc tcc    1680
Lys Val Ser Asn Lys Ala Leu Pro Ala Pro Ile Glu Lys Thr Ile Ser
        520             525             530 aaa gcc aaa ggg cag ccc cga gaa cca cag gtg tac acc ctg ccc cca    1728
Lys Ala Lys Gly Gln Pro Arg Glu Pro Gln Val Tyr Thr Leu Pro Pro
535             540             545
```

Figure 22D. Nucleotide sequence and amino acid sequence of the B7-2-FasL-IgFc fusion protein (SEQ ID NO: 17).

```
tcc cgg gat gag ctg acc aag aac cag gtc agc ctg acc tgc ctg gtc      1776
Ser Arg Asp Glu Leu Thr Lys Asn Gln Val Ser Leu Thr Cys Leu Val
550             555             560             565 aaa ggc ttc tat ccc agc gac atc gcc gtg gag tgg gag agc aat ggg      1824
Lys Gly Phe Tyr Pro Ser Asp Ile Ala Val Glu Trp Glu Ser Asn Gly
                570             575             580 cag ccg gag aac aac tac aag acc acg cct ccc gtg ctg gac tcc gac      1872
Gln Pro Glu Asn Asn Tyr Lys Thr Thr Pro Pro Val Leu Asp Ser Asp
            585             590             595 ggc tcc ttc ttc ctc tac agc aag ctc acc gtg gac aag agc agg tgg      1920
Gly Ser Phe Phe Leu Tyr Ser Lys Leu Thr Val Asp Lys Ser Arg Trp
            600             605             610 cag cag ggg aac gtc ttc tca tgc tcc gtg atg cat gag gct ctg cac      1968
Gln Gln Gly Asn Val Phe Ser Cys Ser Val Met His Glu Ala Leu His
        615             620             625 aac cac tac acg cag aag agc ctc tcc ctg tct ccg ggt aaa tgatctaga   2019
Asn His Tyr Thr Gln Lys Ser Leu Ser Leu Ser Pro Gly Lys
630             635             640
```

Figure 23A. Nucleotide sequence and amino acid sequence of the B7-2- IgFc fusion protein (SEQ ID NO: 19).

```
gctagc atg ggg gta ctg ctc aca cag agg acg ctg ctc agt ctg gtc            48
       Met Gly Val Leu Leu Thr Gln Arg Thr Leu Leu Ser Leu Val
       -25              -20                  -15 ctt gca ctc ctg ttt cca agc atg gcg agc atg ctc gag gct cct ctg           96
Leu Ala Leu Leu Phe Pro Ser Met Ala Ser Met Leu Glu Ala Pro Leu
    -10              -5               -1  1               5 aag att caa gct tat ttc aat gag act gca gac ctg cca tgc caa ttt          144
Lys Ile Gln Ala Tyr Phe Asn Glu Thr Ala Asp Leu Pro Cys Gln Phe
                 10              15                  20 gca aac tct caa aac caa agc ctg agt gag cta gta gta ttt tgg cag          192
Ala Asn Ser Gln Asn Gln Ser Leu Ser Glu Leu Val Val Phe Trp Gln
             25                  30                  35 gac cag gaa aac ttg gtt ctg aat gag gta tac tta ggc aaa gag aaa          240
Asp Gln Glu Asn Leu Val Leu Asn Glu Val Tyr Leu Gly Lys Glu Lys
         40                  45                  50 ttt gac agt gtt cat tcc aag tat atg ggc cgc aca agt ttt gat tcg          288
Phe Asp Ser Val His Ser Lys Tyr Met Gly Arg Thr Ser Phe Asp Ser
    55                  60                  65 gac agt tgg acc ctg aga ctt cgc aat ctt cag atc aag gac aag ggc          336
Asp Ser Trp Thr Leu Arg Leu Arg Asn Leu Gln Ile Lys Asp Lys Gly
70                  75                  80                  85 ttg tat caa tgt atc atc cat cac aaa aag ccc aca gga atg att cgc          384
Leu Tyr Gln Cys Ile Ile His His Lys Lys Pro Thr Gly Met Ile Arg
                 90                  95                  100 atc cac cag atg aat tct gaa ctg tca gtg ctt gct aac ttc agt caa          432
Ile His Gln Met Asn Ser Glu Leu Ser Val Leu Ala Asn Phe Ser Gln
                 105                 110                 115 cct gaa ata gta cca att tct aat ata aca gaa aat gtg tac ata aat          480
Pro Glu Ile Val Pro Ile Ser Asn Ile Thr Glu Asn Val Tyr Ile Asn
             120                 125                 130 ttg acc tgc tca tct ata cac ggt tac cca gaa cct aag aag atg agt          528
Leu Thr Cys Ser Ser Ile His Gly Tyr Pro Glu Pro Lys Lys Met Ser
             135                 140                 145 gtt ttg cta aga acc aag aat tca act atc gag tat gat ggt gtt atg          576
Val Leu Leu Arg Thr Lys Asn Ser Thr Ile Glu Tyr Asp Gly Val Met
150                 155                 160                 165
```

Figure 23B. Nucleotide sequence and amino acid sequence of the B7-2- IgFc fusion protein (SEQ ID NO: 19).

```
cag aaa tct caa gat aat gtc aca gaa ctg tac gac gtt tcc atc agc          624
Gln Lys Ser Gln Asp Asn Val Thr Glu Leu Tyr Asp Val Ser Ile Ser
                170                 175                 180 ttg tct gtt tca ttc cct gat gtt acg agc aat atg acc atc ttc tgt          672
Leu Ser Val Ser Phe Pro Asp Val Thr Ser Asn Met Thr Ile Phe Cys
                185                 190                 195 att ctg gaa act gac aag acg cgg ctt tta tct tca cct ttc tct ata          720
Ile Leu Glu Thr Asp Lys Thr Arg Leu Leu Ser Ser Pro Phe Ser Ile
            200                 205                 210 gag ctt gag gac cct cag cct ccc cca gac cac att cct tct aga ccc          768
Glu Leu Glu Asp Pro Gln Pro Pro Pro Asp His Ile Pro Ser Arg Pro
        215                 220                 225 aaa tct tgt gac aaa act cac aca tgc cca ccg tgc cca gca cct gaa          816
Lys Ser Cys Asp Lys Thr His Thr Cys Pro Pro Cys Pro Ala Pro Glu
230                 235                 240                 245 ctc ctg ggg gga ccg tca gtc ttc ctc ttc ccc cca aaa ccc aag gac          864
Leu Leu Gly Gly Pro Ser Val Phe Leu Phe Pro Pro Lys Pro Lys Asp
                250                 255                 260 acc ctc atg atc tcc cgg acc cct gag gtc aca tgc gtg gtg gtg gac          912
Thr Leu Met Ile Ser Arg Thr Pro Glu Val Thr Cys Val Val Val Asp
                265                 270                 275 gtg agc cac gaa gac cct gag gtc aag ttc aac tgg tac gtg gac ggc          960
Val Ser His Glu Asp Pro Glu Val Lys Phe Asn Trp Tyr Val Asp Gly
            280                 285                 290 gtg gag gtg cat aat gcc aag aca aag ccg cgg gag gag cag tac aac         1008
Val Glu Val His Asn Ala Lys Thr Lys Pro Arg Glu Glu Gln Tyr Asn
        295                 300                 305 agc acg tac cgt gtg gtc agc gtc ctc acc gtc ctg cac cag gac tgg         1056
Ser Thr Tyr Arg Val Val Ser Val Leu Thr Val Leu His Gln Asp Trp
310                 315                 320                 325 ctg aat ggc aag gag tac aag tgc aag gtc tcc aac aaa gcc ctc cca         1104
Leu Asn Gly Lys Glu Tyr Lys Cys Lys Val Ser Asn Lys Ala Leu Pro
                330                 335                 340 gcc ccc atc gag aaa acc atc tcc aaa gcc aaa ggg cag ccc cga gaa         1152
Ala Pro Ile Glu Lys Thr Ile Ser Lys Ala Lys Gly Gln Pro Arg Glu
                345                 350                 355
```

Figure 23C. Nucleotide sequence and amino acid sequence of the B7-2- IgFc fusion protein (SEQ ID NO: 19).

```
cca cag gtg tac acc ctg ccc cca tcc cgg gat gag ctg acc aag aac     1200
Pro Gln Val Tyr Thr Leu Pro Pro Ser Arg Asp Glu Leu Thr Lys Asn
        360                 365                 370 cag gtc agc ctg acc tgc ctg gtc aaa ggc ttc tat ccc agc gac atc     1248
Gln Val Ser Leu Thr Cys Leu Val Lys Gly Phe Tyr Pro Ser Asp Ile
    375                 380                 385 gcc gtg gag tgg gag agc aat ggg cag ccg gag aac aac tac aag acc     1296
Ala Val Glu Trp Glu Ser Asn Gly Gln Pro Glu Asn Asn Tyr Lys Thr
390                 395                 400                 405 acg cct ccc gtg ctg gac tcc gac ggc tcc ttc ttc ctc tac agc aag     1344
Thr Pro Pro Val Leu Asp Ser Asp Gly Ser Phe Phe Leu Tyr Ser Lys
                410                 415                 420 ctc acc gtg gac aag agc agg tgg cag cag ggg aac gtc ttc tca tgc     1392
Leu Thr Val Asp Lys Ser Arg Trp Gln Gln Gly Asn Val Phe Ser Cys
            425                 430                 435 tcc gtg atg cat gag gct ctg cac aac cac tac acg cag aag agc ctc     1440
Ser Val Met His Glu Ala Leu His Asn His Tyr Thr Gln Lys Ser Leu
        440                 445                 450 tcc ctg tct ccg ggt aaa tgagcggccg c                                1469
Ser Leu Ser Pro Gly Lys
    455
```

Figure 24. Western blotting analysis of B7-2-FasL-IgFc.
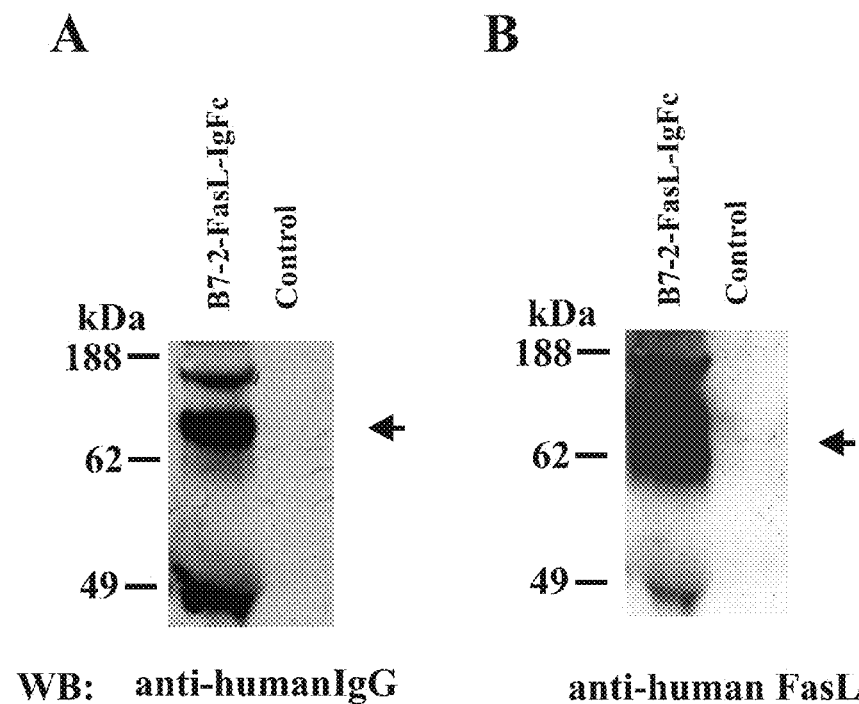
Figure 25. Study of Fas binding by B7-2-FasL-IgFc.
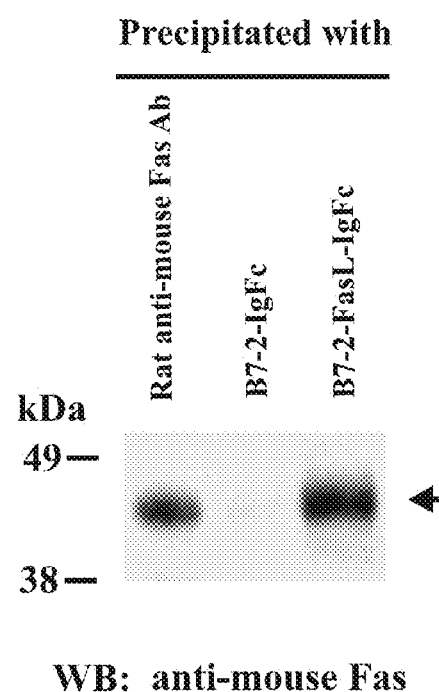

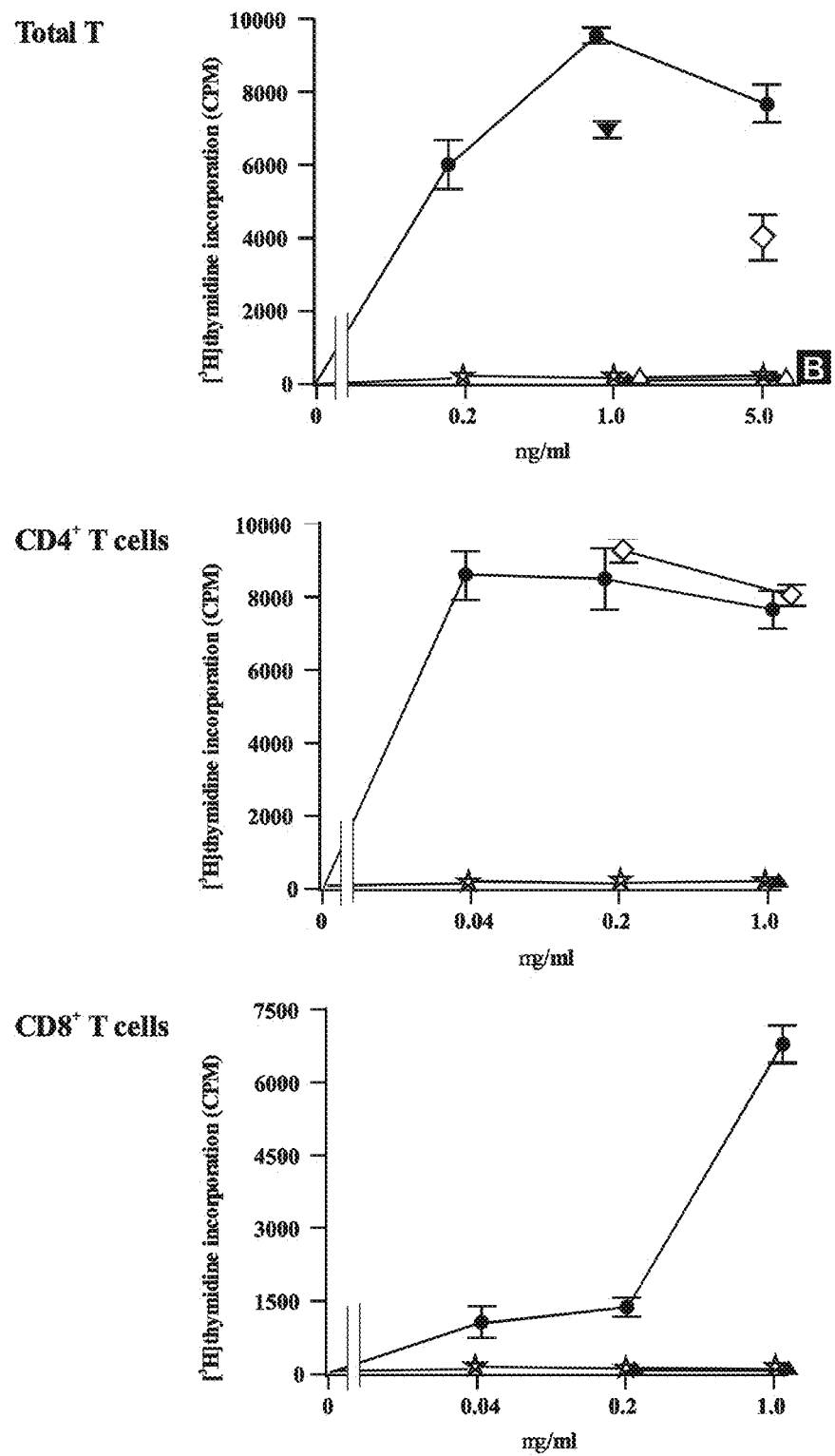
Figure 26. Activation of $CD4^+$ and $CD8^+$ T cells by B7-1-FasL-IgFc.

Figure 27. B7-2-FasL-IgFc stimulates IL-2 production of T cells.
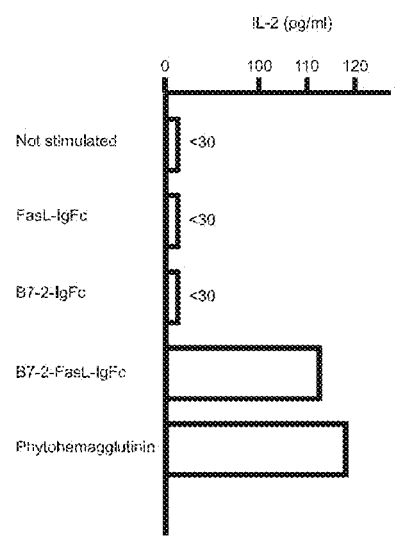
Figure 28. Induction of T-bet by B7-2-FasL-IgFc activation.
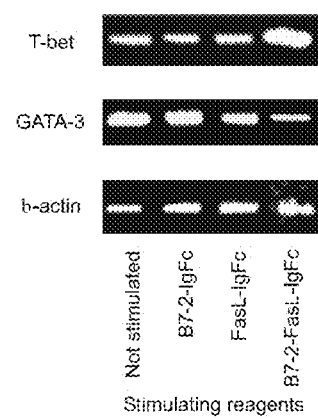

Figure 29. Reduction of B7-2-FasL-IgFc-induced activation by signaling inhibitors.
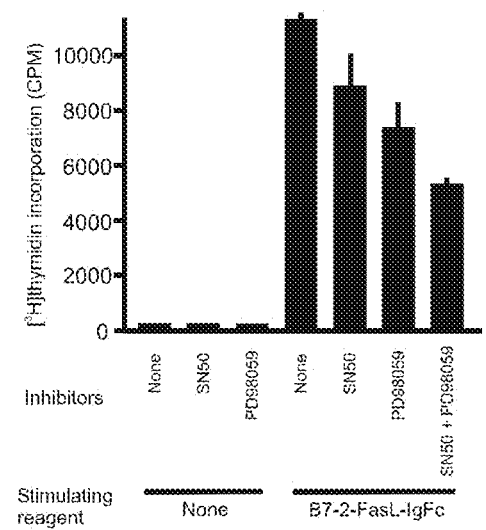

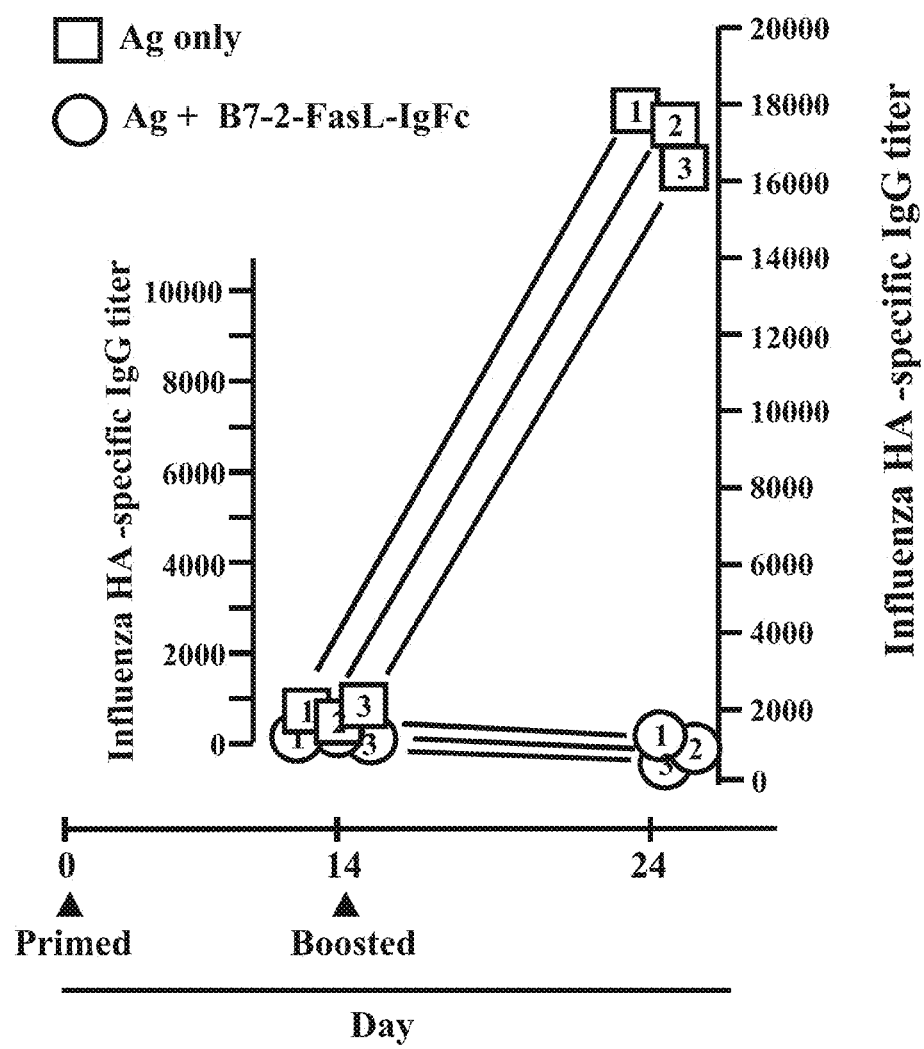
Figure 30. Immunosuppressant activity of B7-2-FasL-IgFc in mice against Influenza hemaglutinin.

Figure 31. Suppressant activity of plasmid DNA of B7-2-FasL-IgFc in mice against Influenza hemaglutinin.

Figure 32. Immunosuppressant activity of B7-2-FasL-IgFc in mice against Influenza hemaglutinin-specific T cell response.

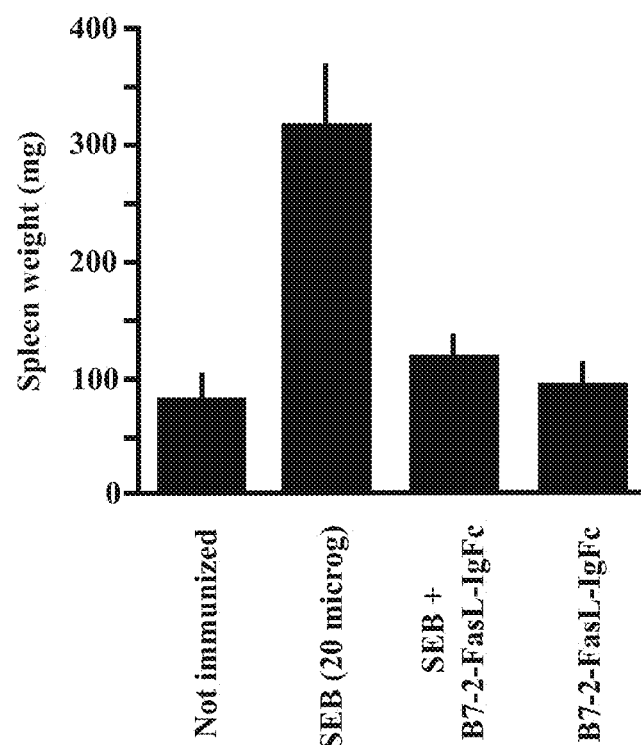
Figure 33. The repression of SEB-induced splenomegaly by co-administrated Plasmid DNA of B7-2-FasL-IgFc.

Figure 34A. Registered sequence of the OX40 ligand of human origin (SEQ ID NO: 21).

```
ccatatcttc atcttccctc tacccagatt gtgaag atg gaa agg gtc caa ccc         54
                                         Met Glu Arg Val Gln Pro
                                         1           5 ctg gaa gag aat gtg gga aat gca gcc agg cca aga ttc gag agg aac        102
Leu Glu Glu Asn Val Gly Asn Ala Ala Arg Pro Arg Phe Glu Arg Asn
            10              15                  20 aag cta ttg ctg gtg gcc tct gta att cag gga ctg ggg ctg ctc ctg        150
Lys Leu Leu Leu Val Ala Ser Val Ile Gln Gly Leu Gly Leu Leu Leu
        25              30                  35 tgc ttc acc tac atc tgc ctg cac ttc tct gct ctt cag gta tca cat        198
Cys Phe Thr Tyr Ile Cys Leu His Phe Ser Ala Leu Gln Val Ser His
    40                  45                  50 cgg tat cct cga att caa agt atc aaa gta caa ttt acc gaa tat aag        246
Arg Tyr Pro Arg Ile Gln Ser Ile Lys Val Gln Phe Thr Glu Tyr Lys
55                  60                  65                  70 aag gag aaa ggt ttc atc ctc act tcc caa aag gag gat gaa atc atg        294
Lys Glu Lys Gly Phe Ile Leu Thr Ser Gln Lys Glu Asp Glu Ile Met
                75                  80                  85 aag gtg cag aac aac tca gtc atc atc aac tgt gat ggg ttt tat ctc        342
Lys Val Gln Asn Asn Ser Val Ile Ile Asn Cys Asp Gly Phe Tyr Leu
                90                  95                  100 atc tcc ctg aag ggc tac ttc tcc cag gaa gtc aac att agc ctt cat        390
Ile Ser Leu Lys Gly Tyr Phe Ser Gln Glu Val Asn Ile Ser Leu His
            105                 110                 115 tac cag aag gat gag gag ccc ctc ttc caa ctg aag aag gtc agg tct        438
Tyr Gln Lys Asp Glu Glu Pro Leu Phe Gln Leu Lys Lys Val Arg Ser
    120                 125                 130 gtc aac tcc ttg atg gtg gcc tct ctg act tac aaa gac aaa gtc tac        486
Val Asn Ser Leu Met Val Ala Ser Leu Thr Tyr Lys Asp Lys Val Tyr
135                 140                 145                 150 ttg aat gtg acc act gac aat acc tcc ctg gat gac ttc cat gtg aat        534
Leu Asn Val Thr Thr Asp Asn Thr Ser Leu Asp Asp Phe His Val Asn
                155                 160                 165 ggc gga gaa ctg att ctt atc cat caa aat cct ggt gaa ttc tgt gtc        582
Gly Gly Glu Leu Ile Leu Ile His Gln Asn Pro Gly Glu Phe Cys Val
                170                 175                 180
```

Figure 34B. Registered sequence of the OX40 ligand of human origin (SEQ ID NO: 21).

| | |
|---|---:|
| ctt tgaggggctg atggcaatat ctaaaaccag gcaccagcat gaacaccaag | 635 |
| Leu | |
| ctgggggtgg acagggcatg gattcttcat tgcaagtgaa ggagcctccc agctcagcca | 695 |
| cgtgggatgt gacaagaagc agatcctggc cctcccgccc ccacccctca gggatattta | 755 |
| aaacttattt tatataccag ttaatcttat ttatccttat attttctaaa ttgcctagcc | 815 |
| gtcacacccc aagattgcct tgagcctact aggcaccttt gtgagaaaga aaaaatagat | 875 |
| gcctcttctt caagatgcat tgtttctatt ggtcaggcaa ttgtcataat aaacttatgt | 935 |
| cattgaaaac ggtacctgac taccatttgc tggaaatttg acatgtgtgt ggcattatca | 995 |
| aaatgaagag gagcaaggag tgaaggagtg gggttatgaa tctgccaaag gtggtatgaa | 1055 |
| ccaacccctg gaagccaaag cggcctctcc aaggttaaat tgattgcagt ttgcatattg | 1115 |
| cctaaattta aactttctca tttggtgggg gttcaaaaga gaatcagct tgtgaaaaat | 1175 |
| caggacttga agagagccgt ctaagaaata ccacgtgctt tttttcttta ccattttgct | 1235 |
| ttcccagcct ccaaacatag ttaatagaaa tttccttca aagaactgtc tggggatgtg | 1295 |
| atgctttgaa aaatctaatc agtgacttaa gagagattt cttgtataca gggagagtga | 1355 |
| gataacttat tgtgaagggt tagctttact gtacaggata gcagggaact ggacatctca | 1415 |
| gggtaaaagt cagtacggat tttaatagcc tggggaggaa aacacattct ttgccacaga | 1475 |
| caggcaaagc aacacatgct catcctcctg cctatgctga gatacgcact cagctccatg | 1535 |
| tcttgtacac acagaaacat tgctggtttc aagaaatgag gtgatcctat tatcaaattc | 1595 |
| aatctgatgt caaatagcac taagaagtta ttgtgcctta tgaaaaataa tgatctctgt | 1655 |
| ctagaaatac catagaccat atatagtctc acattgataa ttgaaactag aagggtctat | 1715 |
| atcagcctat gccagggctt caatggaata gtatcccctt atgtttagtt gaaatgtccc | 1775 |
| cttaacttga tataatgtgt tatgcttatg gcgctgtgac aatctgattt tcatgtcaa | 1835 |
| cttccagatg atttgtaact tctctgtgcc aaacctttta taaacataaa tttttgagat | 1895 |
| atgtatttta aaattgtagc acatgtttcc ctgacatttt caatagagga tacaacatca | 1955 |

Figure 34C. Registered sequence of the OX40 ligand of human origin (SEQ ID NO: 21).

| | | | | | | |
|---|---|---|---|---|---|---|
| cagaatcttt | ctggatgatt | ctgtgttatc | aaggaattgt | actgtgctac | aattatctct | 2015 |
| agaatctcca | gaaaggtgga | gggctgttcg | cccttacact | aaatggtctc | agttggattt | 2075 |
| tttttcctg | ttttctattt | cctcttaagt | acaccttcaa | ctatattccc | atccctctat | 2135 |
| tttaatctgt | tatgaaggaa | ggtaaataaa | aatgctaaat | agaagaaatt | gtaggtaagg | 2195 |
| taagaggaat | caagttctga | gtggctgcca | aggcactcac | agaatcataa | tcatggctaa | 2255 |
| atatttatgg | agggcctact | gtggaccagg | cactggctaa | atacttacat | ttacaagaat | 2315 |
| cattctgaga | cagatattca | atgatatctg | gcttcactac | tcagaagatt | gtgtgtgtgt | 2375 |
| ttgtgtgtgt | gtgtgtgtgt | gtatttcact | ttttgttatt | gaccatgttc | tgcaaaattg | 2435 |
| cagttactca | gtgagtgata | tccgaaaaag | taaacgttta | tgactatagg | taatatttaa | 2495 |
| gaaaatgcat | ggttcatttt | taagtttgga | attttatct | atatttctca | cagatgtgca | 2555 |
| gtgcacatgc | aggcctaagt | atatgttgtg | tgtgtttgtc | tttgacgtca | tggtcccctc | 2615 |
| tcttaggtgc | tcactcgctt | tgggtgcacc | tggcctgctc | ttcccatgtt | ggcctctgca | 2675 |
| accacacagg | gatatttctg | ctatgcacca | gcctcactcc | accttccttc | catcaaaaat | 2735 |
| atgtgtgtgt | gtctcagtcc | ctgtaagtca | tgtccttcac | agggagaatt | aacccttcga | 2795 |
| tatacatggc | agagttttgt | gggaaaagaa | ttgaatgaaa | agtcaggaga | tcagaattt | 2855 |
| aaatttgact | tagccactaa | ctagccatgt | aaccttggga | aagtcatttc | ccatttctgg | 2915 |
| gtcttgcttt | tctttctgtt | aaatgagagg | aatgttaaat | atctaacagt | ttagaatctt | 2975 |
| atgcttacag | tgttatctgt | gaatgcacat | attaaatgtc | tatgttcttg | ttgctatgag | 3035 |
| tcaaggagtg | tacacttctc | ctttactatg | ttgaatgtat | tttttctgg | acaagcttac | 3095 |
| atcttcctca | gccatctttg | tgagtccttc | aagagcagtt | atcaattgtt | agttagatat | 3155 |
| tttctattta | gagaatgctt | aagggattcc | aatcccgatc | caaatcataa | tttgttctta | 3215 |
| agtatactgg | gcaggtcccc | tattttaagt | cataattttg | tatttagtgc | tttcctggct | 3275 |
| ctcagagagt | attaatattg | atattaataa | tatagttaat | agtaatattg | ctatttacat | 3335 |
| ggaaacaaat | aaaagatctc | agaattc | | | | 3362 |

Figure 35A. Registered sequence of the 4-1BB ligand of human origin (SEQ ID NO: 23).

| | | | | | | | | | | | | | |
|---|---|---|---|---|---|---|---|---|---|---|---|---|---|
| aaaaagcggc | gcgctgtgtc | ttcccgcagt | ctctcgtc | atg<br>Met<br>1 | gaa<br>Glu | tac<br>Tyr | gcc<br>Ala | tct<br>Ser<br>5 | gac<br>Asp | | | | 56 |
| gct<br>Ala | tca<br>Ser | ctg<br>Leu | gac<br>Asp<br>10 | ccc<br>Pro | gaa<br>Glu | gcc<br>Ala | ccg<br>Pro | tgg<br>Trp<br>15 | cct<br>Pro | ccc<br>Pro | gcg<br>Ala | ccc<br>Pro | cgc<br>Arg<br>20 | gct<br>Ala | cgc<br>Arg | 104 |
| gcc<br>Ala | tgc<br>Cys | cgc<br>Arg<br>25 | gta<br>Val | ctg<br>Leu | cct<br>Pro | tgg<br>Trp | gcc<br>Ala<br>30 | ctg<br>Leu | gtc<br>Val | gcg<br>Ala | ggg<br>Gly | ctg<br>Leu<br>35 | ctg<br>Leu | ctg<br>Leu | 152 |
| ctg<br>Leu | ctg<br>Leu | ctc<br>Leu<br>40 | gct<br>Ala | gcc<br>Ala | gcc<br>Ala | tgc<br>Cys<br>45 | gcc<br>Ala | gtc<br>Val | ttc<br>Phe | ctc<br>Leu | gcc<br>Ala<br>50 | tgc<br>Cys | ccc<br>Pro | tgg<br>Trp | gcc<br>Ala | 200 |
| gtg<br>Val<br>55 | tcc<br>Ser | ggg<br>Gly | gct<br>Ala | cgc<br>Arg | gcc<br>Ala<br>60 | tcg<br>Ser | ccc<br>Pro | ggc<br>Gly | tcc<br>Ser | gcg<br>Ala<br>65 | gcc<br>Ala | agc<br>Ser | ccg<br>Pro | aga<br>Arg | ctc<br>Leu<br>70 | 248 |
| cgc<br>Arg | gag<br>Glu | ggt<br>Gly | ccc<br>Pro | gag<br>Glu<br>75 | ctt<br>Leu | tcg<br>Ser | ccc<br>Pro | gac<br>Asp | gat<br>Asp<br>80 | ccc<br>Pro | gcc<br>Ala | ggc<br>Gly | ctc<br>Leu | ttg<br>Leu<br>85 | gac<br>Asp | 296 |
| ctg<br>Leu | cgg<br>Arg | cag<br>Gln | ggc<br>Gly<br>90 | atg<br>Met | ttt<br>Phe | gcg<br>Ala | cag<br>Gln | ctg<br>Leu<br>95 | gtg<br>Val | gcc<br>Ala | caa<br>Gln | aat<br>Asn | gtt<br>Val<br>100 | ctg<br>Leu | ctg<br>Leu | 344 |
| atc<br>Ile | gat<br>Asp | ggg<br>Gly | ccc<br>Pro<br>105 | ctg<br>Leu | agc<br>Ser | tgg<br>Trp | tac<br>Tyr | agt<br>Ser<br>110 | gac<br>Asp | cca<br>Pro | ggc<br>Gly | ctg<br>Leu | gca<br>Ala<br>115 | ggc<br>Gly | gtg<br>Val | 392 |
| tcc<br>Ser | ctg<br>Leu | acg<br>Thr<br>120 | ggg<br>Gly | ggc<br>Gly | ctg<br>Leu | agc<br>Ser | tac<br>Tyr<br>125 | aaa<br>Lys | gag<br>Glu | gac<br>Asp | acg<br>Thr | aag<br>Lys<br>130 | gag<br>Glu | ctg<br>Leu | gtg<br>Val | 440 |
| gtg<br>Val<br>135 | gcc<br>Ala | aag<br>Lys | gct<br>Ala | gga<br>Gly | gtc<br>Val<br>140 | tac<br>Tyr | tat<br>Tyr | gtc<br>Val | ttc<br>Phe | ttt<br>Phe<br>145 | caa<br>Gln | cta<br>Leu | gag<br>Glu | ctg<br>Leu | cgg<br>Arg<br>150 | 488 |
| cgc<br>Arg | gtg<br>Val | gtg<br>Val | gcc<br>Ala | ggc<br>Gly<br>155 | gag<br>Glu | ggc<br>Gly | tca<br>Ser | ggc<br>Gly | tcc<br>Ser<br>160 | gtt<br>Val | tca<br>Ser | ctt<br>Leu | gcg<br>Ala | ctg<br>Leu<br>165 | cac<br>His | 536 |
| ctg<br>Leu | cag<br>Gln | cca<br>Pro | ctg<br>Leu<br>170 | cgc<br>Arg | tct<br>Ser | gct<br>Ala | gct<br>Ala | ggg<br>Gly<br>175 | gcc<br>Ala | gcc<br>Ala | gcc<br>Ala | ctg<br>Leu | gct<br>Ala<br>180 | ttg<br>Leu | acc<br>Thr | 584 |

Figure 35B. Registered sequence of the 4-1BB ligand of human origin (SEQ ID NO: 23).

| | | | | | | | | | | | | | | | |
|---|---|---|---|---|---|---|---|---|---|---|---|---|---|---|---|
| gtg | gac | ctg | cca | ccc | gcc | tcc | tcc | gag | gct | cgg | aac | tcg | gcc | ttc | ggt | 632 |
| Val | Asp | Leu | Pro | Pro | Ala | Ser | Ser | Glu | Ala | Arg | Asn | Ser | Ala | Phe | Gly |
| | | 185 | | | | | 190 | | | | | 195 | | | |

| ttc | cag | ggc | cgc | ttg | ctg | cac | ctg | agt | gcc | ggc | cag | cgc | ctg | ggc | gtc | 680 |
|---|---|---|---|---|---|---|---|---|---|---|---|---|---|---|---|---|
| Phe | Gln | Gly | Arg | Leu | Leu | His | Leu | Ser | Ala | Gly | Gln | Arg | Leu | Gly | Val |
| | | 200 | | | | | 205 | | | | | 210 | | | |

| cat | ctt | cac | act | gag | gcc | agg | gca | cgc | cat | gcc | tgg | cag | ctt | acc | cag | 728 |
|---|---|---|---|---|---|---|---|---|---|---|---|---|---|---|---|---|
| His | Leu | His | Thr | Glu | Ala | Arg | Ala | Arg | His | Ala | Trp | Gln | Leu | Thr | Gln |
| 215 | | | | | 220 | | | | | 225 | | | | | 230 |

| ggc | gcc | aca | gtc | ttg | gga | ctc | ttc | cgg | gtg | acc | ccc | gaa | atc | cca | gcc | 776 |
|---|---|---|---|---|---|---|---|---|---|---|---|---|---|---|---|---|
| Gly | Ala | Thr | Val | Leu | Gly | Leu | Phe | Arg | Val | Thr | Pro | Glu | Ile | Pro | Ala |
| | | | | 235 | | | | | 240 | | | | | 245 | |

| gga | ctc | cct | tca | ccg | agg | tcg | gaa | taacgtccag | cctgggtgca | gcccacctgg | 830 |
|---|---|---|---|---|---|---|---|---|---|---|---|
| Gly | Leu | Pro | Ser | Pro | Arg | Ser | Glu | | | | |
| | | | | 250 | | | | | | | |

| | | | | |
|---|---|---|---|---|
| acagagtccg | aatcctactc | catccttcat | ggagacccct | ggtgctgggt | ccctgctgct | 890 |
| ttctctacct | caaggggctt | ggcaggggtc | cctgctgctg | acctcccctt | gaggaccctc | 950 |
| ctcacccact | ccttccccaa | gttggacctt | gatatttatt | ctgagcctga | gctcagataa | 1010 |
| tatattatat | atattatata | tatatatata | tttctattta | aagaggatcc | tgagtttgtg | 1070 |
| aatggacttt | tttagaggag | ttgttttggg | gggggggggg | tcttcgacat | tgccgaggct | 1130 |
| ggtcttgaac | tcctggactt | agacgatcct | cctgcctcag | cctcccaagc | aactgggatt | 1190 |
| catcctttct | attaattcat | tgtacttatt | tgcttatttg | tgtgtattga | gcatctgtaa | 1250 |
| tgtgccagca | ttgtgcccag | gctaggggggc | tatagaaaca | tctagaaata | gactgaaaga | 1310 |
| aaatctgagt | tatggtaata | cgtgaggaat | ttaaagactc | atccccagcc | tccacctcct | 1370 |
| gtgtgatact | tgggggctag | cttttttctt | tctttctttt | ttttgagatg | gtcttgttct | 1430 |
| gtcaaccagg | ctagaatgca | gcggtgcaat | catgagtcaa | tgcagcctcc | agcctcgacc | 1490 |
| tcccgaggct | caggtgatcc | tcccatctca | gcctctcgag | tagctgggac | cacagttgtg | 1550 |
| tgccaccaca | cttggctaac | tttttaattt | ttttgcggag | acggtattgc | tatgttgcca | 1610 |
| aggttgttta | catgccagta | caatttataa | taaacactca | ttttcctcc | ctctgaaaaa | 1670 |

Figure 35C. Registered sequence of the 4-1BB ligand of human origin (SEQ ID NO: 23).

aaaaaaaaaa                                                                                          1680

Figure 36A. Nucleotide sequence and amino acid sequence of the OX40L-4-1BBL-IgFc (SEQ ID NO: 25).

| | |
|---|---|
| gctagc atg ggg gta ctg ctc aca cag agg acg ctg ctc agt ctg gtc<br>       Met Gly Val Leu Leu Thr Gln Arg Thr Leu Leu Ser Leu Val<br>       -25                 -20                   -15 | 48 |
| ctt gca ctc ctg ttt cca agc atg gcg agc atg ctc gag cag gta tca<br>Leu Ala Leu Leu Phe Pro Ser Met Ala Ser Met Leu Glu Gln Val Ser<br>    -10             -5            -1 1             5 | 96 |
| cat cgg tat cct cga att caa agt atc aaa gta caa ttt acc gaa tat<br>His Arg Tyr Pro Arg Ile Gln Ser Ile Lys Val Gln Phe Thr Glu Tyr<br>              10               15              20 | 144 |
| aag aag gag aaa ggt ttc atc ctc act tcc caa aag gag gat gaa atc<br>Lys Lys Glu Lys Gly Phe Ile Leu Thr Ser Gln Lys Glu Asp Glu Ile<br>        25               30              35 | 192 |
| atg aag gtg cag aac aac tca gtc atc atc aac tgt gat ggg ttt tat<br>Met Lys Val Gln Asn Asn Ser Val Ile Ile Asn Cys Asp Gly Phe Tyr<br>        40               45              50 | 240 |
| ctc atc tcc ctg aag ggc tac ttc tcc cag gaa gtc aac att agc ctt<br>Leu Ile Ser Leu Lys Gly Tyr Phe Ser Gln Glu Val Asn Ile Ser Leu<br>    55                 60              65 | 288 |
| cat tac cag aag gat gag gag ccc ctc ttc caa ctg aag aag gtc agg<br>His Tyr Gln Lys Asp Glu Glu Pro Leu Phe Gln Leu Lys Lys Val Arg<br>70              75               80              85 | 336 |
| tct gtc aac tcc ttg atg gtg gcc tct ctg act tac aaa gac aaa gtc<br>Ser Val Asn Ser Leu Met Val Ala Ser Leu Thr Tyr Lys Asp Lys Val<br>              90               95             100 | 384 |
| tac ttg aat gtg acc act gac aat acc tcc ctg gat gac ttc cat gtg<br>Tyr Leu Asn Val Thr Thr Asp Asn Thr Ser Leu Asp Asp Phe His Val<br>           105               110            115 | 432 |
| aat ggc gga gaa ctg att ctt atc cat caa aat cct ggt gaa ttc tgt<br>Asn Gly Gly Glu Leu Ile Leu Ile His Gln Asn Pro Gly Glu Phe Cys<br>         120               125            130 | 480 |
| gtc ctt acg cgt gcc tgc ccc tgg gcc gtg tcc ggg gct cgc gcc tcg<br>Val Leu Thr Arg Ala Cys Pro Trp Ala Val Ser Gly Ala Arg Ala Ser<br>     135              140             145 | 528 |
| ccc ggc tcc gcg gcc agc ccg aga ctc cgc gag ggt ccc gag ctt tcg<br>Pro Gly Ser Ala Ala Ser Pro Arg Leu Arg Glu Gly Pro Glu Leu Ser<br>150              155             160             165 | 576 |

Figure 36B. Nucleotide sequence and amino acid sequence of the OX40L-4-1BBL-IgFc (SEQ ID NO: 25).

| | | | | | | | | | | | | | | | |
|---|---|---|---|---|---|---|---|---|---|---|---|---|---|---|---|
| ccc | gac | gat | ccc | gcc | ggc | ctc | ttg | gac | ctg | cgg | cag | ggc | atg | ttt | gcg | 624 |
| Pro | Asp | Asp | Pro | Ala | Gly | Leu | Leu | Asp | Leu | Arg | Gln | Gly | Met | Phe | Ala | |
| | | | 170 | | | | | 175 | | | | | 180 | | | |

| cag | ctg | gtg | gcc | caa | aat | gtt | ctg | ctg | atc | gat | ggg | ccc | ctg | agc | tgg | 672 |
| Gln | Leu | Val | Ala | Gln | Asn | Val | Leu | Leu | Ile | Asp | Gly | Pro | Leu | Ser | Trp |
| | | | 185 | | | | | 190 | | | | | 195 | | |

| tac | agt | gac | cca | ggc | ctg | gca | ggc | gtg | tcc | ctg | acg | ggg | ggc | ctg | agc | 720 |
| Tyr | Ser | Asp | Pro | Gly | Leu | Ala | Gly | Val | Ser | Leu | Thr | Gly | Gly | Leu | Ser |
| | | | 200 | | | | 205 | | | | | 210 | | | |

| tac | aaa | gag | gac | acg | aag | gag | ctg | gtg | gtg | gcc | aag | gct | gga | gtc | tac | 768 |
| Tyr | Lys | Glu | Asp | Thr | Lys | Glu | Leu | Val | Val | Ala | Lys | Ala | Gly | Val | Tyr |
| | 215 | | | | | 220 | | | | | 225 | | | | |

| tat | gtc | ttc | ttt | caa | cta | gag | ctg | cgg | cgc | gtg | gtg | gcc | ggc | gag | ggc | 816 |
| Tyr | Val | Phe | Phe | Gln | Leu | Glu | Leu | Arg | Arg | Val | Val | Ala | Gly | Glu | Gly |
| 230 | | | | | 235 | | | | | 240 | | | | | 245 |

| tca | ggc | tcc | gtt | tca | ctt | gcg | ctg | cac | ctg | cag | cca | ctg | cgc | tct | gct | 864 |
| Ser | Gly | Ser | Val | Ser | Leu | Ala | Leu | His | Leu | Gln | Pro | Leu | Arg | Ser | Ala |
| | | | 250 | | | | | 255 | | | | | 260 | | |

| gct | ggg | gcc | gcc | gcc | ctg | gct | ttg | acc | gtg | gac | ctg | cca | ccc | gcc | tcc | 912 |
| Ala | Gly | Ala | Ala | Ala | Leu | Ala | Leu | Thr | Val | Asp | Leu | Pro | Pro | Ala | Ser |
| | | | 265 | | | | | 270 | | | | | 275 | | |

| tcc | gag | gct | cgg | aac | tcg | gcc | ttc | ggt | ttc | cag | ggc | cgc | ttg | ctg | cac | 960 |
| Ser | Glu | Ala | Arg | Asn | Ser | Ala | Phe | Gly | Phe | Gln | Gly | Arg | Leu | Leu | His |
| | | | 280 | | | | | 285 | | | | | 290 | | |

| ctg | agt | gcc | ggc | cag | cgc | ctg | ggc | gtc | cat | ctt | cac | act | gag | gcc | agg | 1008 |
| Leu | Ser | Ala | Gly | Gln | Arg | Leu | Gly | Val | His | Leu | His | Thr | Glu | Ala | Arg |
| | 295 | | | | | 300 | | | | | 305 | | | | |

| gca | cgc | cat | gcc | tgg | cag | ctt | acc | cag | ggc | gcc | aca | gtc | ttg | gga | ctc | 1056 |
| Ala | Arg | His | Ala | Trp | Gln | Leu | Thr | Gln | Gly | Ala | Thr | Val | Leu | Gly | Leu |
| 310 | | | | | 315 | | | | | 320 | | | | | 325 |

| ttc | cgg | gtg | acc | ccc | gaa | atc | cca | gcc | gga | ctc | cct | tca | ccg | agg | tcg | 1104 |
| Phe | Arg | Val | Thr | Pro | Glu | Ile | Pro | Ala | Gly | Leu | Pro | Ser | Pro | Arg | Ser |
| | | | 330 | | | | | 335 | | | | | 340 | | |

| gaa | ggt | acc | tct | aga | ccc | aaa | tct | tgt | gac | aaa | act | cac | aca | tgc | cca | 1152 |
| Glu | Gly | Thr | Ser | Arg | Pro | Lys | Ser | Cys | Asp | Lys | Thr | His | Thr | Cys | Pro |
| | | | 345 | | | | | 350 | | | | | 355 | | |

Figure 36C. Nucleotide sequence and amino acid sequence of the OX40L-4-1BBL-IgFc (SEQ ID NO: 25).

| | |
|---|---:|
| ccg tgc cca gca cct gaa ctc ctg ggg gga ccg tca gtc ttc ctc ttc<br>Pro Cys Pro Ala Pro Glu Leu Leu Gly Gly Pro Ser Val Phe Leu Phe<br>     360                       365                      370 | 1200 |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>     375                       380                      385 | 1248 |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>390                       395                      400                      405 | 1296 |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>                       410                      415                      420 | 1344 |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>                       425                      430                      435 | 1392 |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>         440                       445                      450 | 1440 |
| tcc aac aaa gcc ctc cca gcc ccc atc gag aaa acc atc tcc aaa gcc<br>Ser Asn Lys Ala Leu Pro Ala Pro Ile Glu Lys Thr Ile Ser Lys Ala<br>     455                       460                      465 | 1488 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>470                       475                      480                      485 | 1536 |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>                   490                      495                      500 | 1584 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>              505                      510                      515 | 1632 |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>             520                      525                      530 | 1680 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>535                       540                      545 | 1728 |

Figure 36D. Nucleotide sequence and amino acid sequence of the OX40L-4-1BBL-IgFc (SEQ ID NO: 25).

| | | | | | | | | | | | | | | | |
|---|---|---|---|---|---|---|---|---|---|---|---|---|---|---|---|
| ggg | aac | gtc | ttc | tca | tgc | tcc | gtg | atg | cat | gag | gct | ctg | cac | aac | cac |
| Gly | Asn | Val | Phe | Ser | Cys | Ser | Val | Met | His | Glu | Ala | Leu | His | Asn | His |
| 550 | | | | 555 | | | | | 560 | | | | | 565 | |

1776

| | | | | | | | | | | |
|---|---|---|---|---|---|---|---|---|---|---|
| tac | acg | cag | aag | agc | ctc | tcc | ctg | tct | ccg | ggt | aaa | tgatctaga |
| Tyr | Thr | Gln | Lys | Ser | Leu | Ser | Leu | Ser | Pro | Gly | Lys | |
| | | | 570 | | | | | 575 | | | |

1821

Figure 37A. Nucleotide sequence and amino acid sequence of the OX40L-IgFc (SEQ ID NO: 27).

| | | | | | | | | | | | | | | | |
|---|---|---|---|---|---|---|---|---|---|---|---|---|---|---|---|
| gctagc | atg | ggg | gta | ctg | ctc | aca | cag | agg | acg | ctg | ctc | agt | ctg | gtc | 48 |
| | Met | Gly | Val | Leu | Leu | Thr | Gln | Arg | Thr | Leu | Leu | Ser | Leu | Val | |
| | -25 | | | | | -20 | | | | | -15 | | | | |
| ctt | gca | ctc | ctg | ttt | cca | agc | atg | gcg | agc | atg | ctc | gag | cag | gta | tca | 96 |
| Leu | Ala | Leu | Leu | Phe | Pro | Ser | Met | Ala | Ser | Met | Leu | Glu | Gln | Val | Ser |
| | -10 | | | | | -5 | | | | -1 | 1 | | | | 5 |
| cat | cgg | tat | cct | cga | att | caa | agt | atc | aaa | gta | caa | ttt | acc | gaa | tat | 144 |
| His | Arg | Tyr | Pro | Arg | Ile | Gln | Ser | Ile | Lys | Val | Gln | Phe | Thr | Glu | Tyr |
| | | | | 10 | | | | 15 | | | | | 20 | | |
| aag | aag | gag | aaa | ggt | ttc | atc | ctc | act | tcc | caa | aag | gag | gat | gaa | atc | 192 |
| Lys | Lys | Glu | Lys | Gly | Phe | Ile | Leu | Thr | Ser | Gln | Lys | Glu | Asp | Glu | Ile |
| | | | 25 | | | | 30 | | | | | 35 | | | |
| atg | aag | gtg | cag | aac | aac | tca | gtc | atc | atc | aac | tgt | gat | ggg | ttt | tat | 240 |
| Met | Lys | Val | Gln | Asn | Asn | Ser | Val | Ile | Ile | Asn | Cys | Asp | Gly | Phe | Tyr |
| | | | 40 | | | | 45 | | | | | 50 | | | |
| ctc | atc | tcc | ctg | aag | ggc | tac | ttc | tcc | cag | gaa | gtc | aac | att | agc | ctt | 288 |
| Leu | Ile | Ser | Leu | Lys | Gly | Tyr | Phe | Ser | Gln | Glu | Val | Asn | Ile | Ser | Leu |
| | 55 | | | | | 60 | | | | | 65 | | | | |
| cat | tac | cag | aag | gat | gag | gag | ccc | ctc | ttc | caa | ctg | aag | aag | gtc | agg | 336 |
| His | Tyr | Gln | Lys | Asp | Glu | Glu | Pro | Leu | Phe | Gln | Leu | Lys | Lys | Val | Arg |
| 70 | | | | | 75 | | | | | 80 | | | | | 85 |
| tct | gtc | aac | tcc | ttg | atg | gtg | gcc | tct | ctg | act | tac | aaa | gac | aaa | gtc | 384 |
| Ser | Val | Asn | Ser | Leu | Met | Val | Ala | Ser | Leu | Thr | Tyr | Lys | Asp | Lys | Val |
| | | | | | 90 | | | | 95 | | | | | 100 | |
| tac | ttg | aat | gtg | acc | act | gac | aat | acc | tcc | ctg | gat | gac | ttc | cat | gtg | 432 |
| Tyr | Leu | Asn | Val | Thr | Thr | Asp | Asn | Thr | Ser | Leu | Asp | Asp | Phe | His | Val |
| | | | 105 | | | | 110 | | | | | 115 | | | |
| aat | ggc | gga | gaa | ctg | att | ctt | atc | cat | caa | aat | cct | ggt | gaa | ttc | tgt | 480 |
| Asn | Gly | Gly | Glu | Leu | Ile | Leu | Ile | His | Gln | Asn | Pro | Gly | Glu | Phe | Cys |
| | | 120 | | | | | 125 | | | | | 130 | | | |
| gtc | ctt | acg | cgt | ggt | acc | tct | aga | ccc | aaa | tct | tgt | gac | aaa | act | cac | 528 |
| Val | Leu | Thr | Arg | Gly | Thr | Ser | Arg | Pro | Lys | Ser | Cys | Asp | Lys | Thr | His |
| | 135 | | | | | 140 | | | | | 145 | | | | |

Figure 37B. Nucleotide sequence and amino acid sequence of the OX40L-IgFc (SEQ ID NO: 27).

```
aca tgc cca ccg tgc cca gca cct gaa ctc ctg ggg gga ccg tca gtc      576
Thr Cys Pro Pro Cys Pro Ala Pro Glu Leu Leu Gly Gly Pro Ser Val
150             155                 160                 165 ttc ctc ttc ccc cca aaa ccc aag gac acc ctc atg atc tcc cgg acc      624
Phe Leu Phe Pro Pro Lys Pro Lys Asp Thr Leu Met Ile Ser Arg Thr
                170                 175                 180 cct gag gtc aca tgc gtg gtg gtg gac gtg agc cac gaa gac cct gag      672
Pro Glu Val Thr Cys Val Val Val Asp Val Ser His Glu Asp Pro Glu
            185                 190                 195 gtc aag ttc aac tgg tac gtg gac ggc gtg gag gtg cat aat gcc aag      720
Val Lys Phe Asn Trp Tyr Val Asp Gly Val Glu Val His Asn Ala Lys
        200                 205                 210 aca aag ccg cgg gag gag cag tac aac agc acg tac cgt gtg gtc agc      768
Thr Lys Pro Arg Glu Glu Gln Tyr Asn Ser Thr Tyr Arg Val Val Ser
    215                 220                 225 gtc ctc acc gtc ctg cac cag gac tgg ctg aat ggc aag gag tac aag      816
Val Leu Thr Val Leu His Gln Asp Trp Leu Asn Gly Lys Glu Tyr Lys
230                 235                 240                 245 tgc aag gtc tcc aac aaa gcc ctc cca gcc ccc atc gag aaa acc atc      864
Cys Lys Val Ser Asn Lys Ala Leu Pro Ala Pro Ile Glu Lys Thr Ile
                250                 255                 260 tcc aaa gcc aaa ggg cag ccc cga gaa cca cag gtg tac acc ctg ccc      912
Ser Lys Ala Lys Gly Gln Pro Arg Glu Pro Gln Val Tyr Thr Leu Pro
            265                 270                 275 cca tcc cgg gat gag ctg acc aag aac cag gtc agc ctg acc tgc ctg      960
Pro Ser Arg Asp Glu Leu Thr Lys Asn Gln Val Ser Leu Thr Cys Leu
        280                 285                 290 gtc aaa ggc ttc tat ccc agc gac atc gcc gtg gag tgg gag agc aat      1008
Val Lys Gly Phe Tyr Pro Ser Asp Ile Ala Val Glu Trp Glu Ser Asn
    295                 300                 305 ggg cag ccg gag aac aac tac aag acc acg cct ccc gtg ctg gac tcc      1056
Gly Gln Pro Glu Asn Asn Tyr Lys Thr Thr Pro Pro Val Leu Asp Ser
310                 315                 320                 325 gac ggc tcc ttc ttc ctc tac agc aag ctc acc gtg gac aag agc agg      1104
Asp Gly Ser Phe Phe Leu Tyr Ser Lys Leu Thr Val Asp Lys Ser Arg
                330                 335                 340
```

Figure 37C. Nucleotide sequence and amino acid sequence of the OX40L-IgFc (SEQ ID NO: 27).

| | | | | | | | | | | | | | | | |
|---|---|---|---|---|---|---|---|---|---|---|---|---|---|---|---|
| tgg | cag | cag | ggg | aac | gtc | ttc | tca | tgc | tcc | gtg | atg | cat | gag | gct | ctg | 1152 |
| Trp | Gln | Gln | Gly | Asn | Val | Phe | Ser | Cys | Ser | Val | Met | His | Glu | Ala | Leu |
| | | | 345 | | | | | 350 | | | | | 355 | | |

| | | | | | | | | | | | | |
|---|---|---|---|---|---|---|---|---|---|---|---|---|
| cac | aac | cac | tac | acg | cag | aag | agc | ctc | tcc | ctg | tct | ccg | ggt | aaa | 1197 |
| His | Asn | His | Tyr | Thr | Gln | Lys | Ser | Leu | Ser | Leu | Ser | Pro | Gly | Lys |
| | | | 360 | | | | 365 | | | | | 370 | | | tgatctaga                                                                 1206

Figure 38A. Nucleotide sequence and amino acid sequence of the 4-1BBL-IgFc (SEQ ID NO: 29).

```
gctagc atg ggg gta ctg ctc aca cag agg acg ctg ctc agt ctg gtc        48
       Met Gly Val Leu Leu Thr Gln Arg Thr Leu Leu Ser Leu Val
       -25             -20                     -15 ctt gca ctc ctg ttt cca agc atg gcg agc atg ctc gag gcc tgc ccc        96
Leu Ala Leu Leu Phe Pro Ser Met Ala Ser Met Leu Glu Ala Cys Pro
        -10             -5              -1  1               5 tgg gcc gtg tcc ggg gct cgc gcc tcg ccc ggc tcg gcg gcc agc ccg       144
Trp Ala Val Ser Gly Ala Arg Ala Ser Pro Gly Ser Ala Ala Ser Pro
                10                  15                  20 aga ctc cgc gag ggt ccc gag ctt tcg ccc gac gat ccc gcc ggc ctc       192
Arg Leu Arg Glu Gly Pro Glu Leu Ser Pro Asp Asp Pro Ala Gly Leu
            25                  30                  35 ttg gac ctg cgg cag ggc atg ttt gcg cag ctg gtg gcc caa aat gtt       240
Leu Asp Leu Arg Gln Gly Met Phe Ala Gln Leu Val Ala Gln Asn Val
        40                  45                  50 ctg ctg atc gat ggg ccc ctg agc tgg tac agt gac cca ggc ctg gca       288
Leu Leu Ile Asp Gly Pro Leu Ser Trp Tyr Ser Asp Pro Gly Leu Ala
        55                  60                  65 ggc gtg tcc ctg acg ggg ggc ctg agc tac aaa gag gac acg aag gag       336
Gly Val Ser Leu Thr Gly Gly Leu Ser Tyr Lys Glu Asp Thr Lys Glu
70                  75                  80                  85 ctg gtg gtg gcc aag gct gga gtc tac tat gtc ttc ttt caa cta gag       384
Leu Val Val Ala Lys Ala Gly Val Tyr Tyr Val Phe Phe Gln Leu Glu
                90                  95                  100 ctg cgg cgc gtg gtg gcc ggc gag ggc tca ggc tcc gtt tca ctt gcg       432
Leu Arg Arg Val Val Ala Gly Glu Gly Ser Gly Ser Val Ser Leu Ala
                105                 110                 115 ctg cac ctg cag cca ctg cgc tct gct gct ggg gcc gcc gcc ctg gct       480
Leu His Leu Gln Pro Leu Arg Ser Ala Ala Gly Ala Ala Ala Leu Ala
        120                 125                 130 ttg acc gtg gac ctg cca ccc gcc tcc tcc gag gct cgg aac tcg gcc       528
Leu Thr Val Asp Leu Pro Pro Ala Ser Ser Glu Ala Arg Asn Ser Ala
        135                 140                 145 ttc ggt ttc cag ggc cgc ttg ctg cac ctg agt gcc ggc cag cgc ctg       576
Phe Gly Phe Gln Gly Arg Leu Leu His Leu Ser Ala Gly Gln Arg Leu
150                 155                 160                 165
```

Figure 38B. Nucleotide sequence and amino acid sequence of the 4-1BBL-IgFc (SEQ ID NO: 29).

| | | | | | | | | | | | | | | |
|---|---|---|---|---|---|---|---|---|---|---|---|---|---|---|
| ggc | gtc | cat | ctt | cac | act | gag | gcc | agg | gca | cgc | cat | gcc | tgg | cag | ctt | 624 |
| Gly | Val | His | Leu | His | Thr | Glu | Ala | Arg | Ala | Arg | His | Ala | Trp | Gln | Leu |
| | | | | 170 | | | | | 175 | | | | | 180 |

| acc | cag | ggc | gcc | aca | gtc | ttg | gga | ctc | ttc | cgg | gtg | acc | ccc | gaa | atc | 672 |
| Thr | Gln | Gly | Ala | Thr | Val | Leu | Gly | Leu | Phe | Arg | Val | Thr | Pro | Glu | Ile |
| | | | 185 | | | | | 190 | | | | | 195 |

| cca | gcc | gga | ctc | cct | tca | ccg | agg | tcg | gaa | acg | cgt | ggt | acc | tct | aga | 720 |
| Pro | Ala | Gly | Leu | Pro | Ser | Pro | Arg | Ser | Glu | Thr | Arg | Gly | Thr | Ser | Arg |
| | | | 200 | | | | | 205 | | | | | 210 |

| ccc | aaa | tct | tgt | gac | aaa | act | cac | aca | tgc | cca | ccg | tgc | cca | gca | cct | 768 |
| Pro | Lys | Ser | Cys | Asp | Lys | Thr | His | Thr | Cys | Pro | Pro | Cys | Pro | Ala | Pro |
| | 215 | | | | 220 | | | | | 225 |

| gaa | ctc | ctg | ggg | gga | ccg | tca | gtc | ttc | ctc | ttc | ccc | cca | aaa | ccc | aag | 816 |
| Glu | Leu | Leu | Gly | Gly | Pro | Ser | Val | Phe | Leu | Phe | Pro | Pro | Lys | Pro | Lys |
| 230 | | | | | 235 | | | | | 240 | | | | | 245 |

| gac | acc | ctc | atg | atc | tcc | cgg | acc | cct | gag | gtc | aca | tgc | gtg | gtg | gtg | 864 |
| Asp | Thr | Leu | Met | Ile | Ser | Arg | Thr | Pro | Glu | Val | Thr | Cys | Val | Val | Val |
| | | | | 250 | | | | | 255 | | | | | 260 |

| gac | gtg | agc | cac | gaa | gac | cct | gag | gtc | aag | ttc | aac | tgg | tac | gtg | gac | 912 |
| Asp | Val | Ser | His | Glu | Asp | Pro | Glu | Val | Lys | Phe | Asn | Trp | Tyr | Val | Asp |
| | | | 265 | | | | | 270 | | | | | 275 |

| ggc | gtg | gag | gtg | cat | aat | gcc | aag | aca | aag | ccg | cgg | gag | gag | cag | tac | 960 |
| Gly | Val | Glu | Val | His | Asn | Ala | Lys | Thr | Lys | Pro | Arg | Glu | Glu | Gln | Tyr |
| | | | 280 | | | | | 285 | | | | | 290 |

| aac | agc | acg | tac | cgt | gtg | gtc | agc | gtc | ctc | acc | gtc | ctg | cac | cag | gac | 1008 |
| Asn | Ser | Thr | Tyr | Arg | Val | Val | Ser | Val | Leu | Thr | Val | Leu | His | Gln | Asp |
| | 295 | | | | 300 | | | | | 305 |

| tgg | ctg | aat | ggc | aag | gag | tac | aag | tgc | aag | gtc | tcc | aac | aaa | gcc | ctc | 1056 |
| Trp | Leu | Asn | Gly | Lys | Glu | Tyr | Lys | Cys | Lys | Val | Ser | Asn | Lys | Ala | Leu |
| 310 | | | | | 315 | | | | | 320 | | | | | 325 |

| cca | gcc | ccc | atc | gag | aaa | acc | atc | tcc | aaa | gcc | aaa | ggg | cag | ccc | cga | 1104 |
| Pro | Ala | Pro | Ile | Glu | Lys | Thr | Ile | Ser | Lys | Ala | Lys | Gly | Gln | Pro | Arg |
| | | | | 330 | | | | | 335 | | | | | 340 |

Figure 38C. Nucleotide sequence and amino acid sequence of the 4-1BBL-IgFc (SEQ ID NO: 29).

| | | | | | | | | | | | | | | | |
|---|---|---|---|---|---|---|---|---|---|---|---|---|---|---|---|
| gaa | cca | cag | gtg | tac | acc | ctg | ccc | cca | tcc | cgg | gat | gag | ctg | acc | aag | 1152 |
| Glu | Pro | Gln | Val | Tyr | Thr | Leu | Pro | Pro | Ser | Arg | Asp | Glu | Leu | Thr | Lys |
| | | | 345 | | | | 350 | | | | | 355 | | | |

| aac | cag | gtc | agc | ctg | acc | tgc | ctg | gtc | aaa | ggc | ttc | tat | ccc | agc | gac | 1200 |
|---|---|---|---|---|---|---|---|---|---|---|---|---|---|---|---|---|
| Asn | Gln | Val | Ser | Leu | Thr | Cys | Leu | Val | Lys | Gly | Phe | Tyr | Pro | Ser | Asp |
| | | 360 | | | | | 365 | | | | | 370 | | | |

| atc | gcc | gtg | gag | tgg | gag | agc | aat | ggg | cag | ccg | gag | aac | aac | tac | aag | 1248 |
|---|---|---|---|---|---|---|---|---|---|---|---|---|---|---|---|---|
| Ile | Ala | Val | Glu | Trp | Glu | Ser | Asn | Gly | Gln | Pro | Glu | Asn | Asn | Tyr | Lys |
| | 375 | | | | | 380 | | | | | 385 | | | | |

| acc | acg | cct | ccc | gtg | ctg | gac | tcc | gac | ggc | tcc | ttc | ttc | ctc | tac | agc | 1296 |
|---|---|---|---|---|---|---|---|---|---|---|---|---|---|---|---|---|
| Thr | Thr | Pro | Pro | Val | Leu | Asp | Ser | Asp | Gly | Ser | Phe | Phe | Leu | Tyr | Ser |
| 390 | | | | | 395 | | | | 400 | | | | | 405 | |

| aag | ctc | acc | gtg | gac | aag | agc | agg | tgg | cag | cag | ggg | aac | gtc | ttc | tca | 1344 |
|---|---|---|---|---|---|---|---|---|---|---|---|---|---|---|---|---|
| Lys | Leu | Thr | Val | Asp | Lys | Ser | Arg | Trp | Gln | Gln | Gly | Asn | Val | Phe | Ser |
| | | | | 410 | | | | | 415 | | | | | 420 | |

| tgc | tcc | gtg | atg | cat | gag | gct | ctg | cac | aac | cac | tac | acg | cag | aag | agc | 1392 |
|---|---|---|---|---|---|---|---|---|---|---|---|---|---|---|---|---|
| Cys | Ser | Val | Met | His | Glu | Ala | Leu | His | Asn | His | Tyr | Thr | Gln | Lys | Ser |
| | | | 425 | | | | | 430 | | | | | 435 | | |

| ctc | tcc | ctg | tct | ccg | ggt | aaa | tgatctaga | | | | | | | | | 1422 |
|---|---|---|---|---|---|---|---|---|---|---|---|---|---|---|---|---|
| Leu | Ser | Leu | Ser | Pro | Gly | Lys | | | | | | | | | |
| | | 440 | | | | | | | | | | | | | |

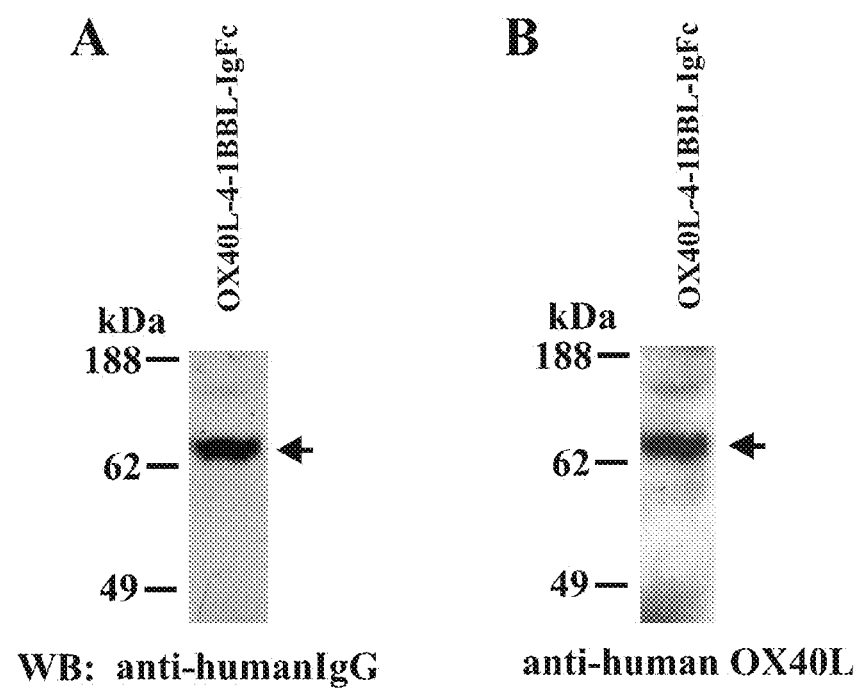
Figure 39. Western blotting analysis of OX40L-4-1BBL-IgFc.

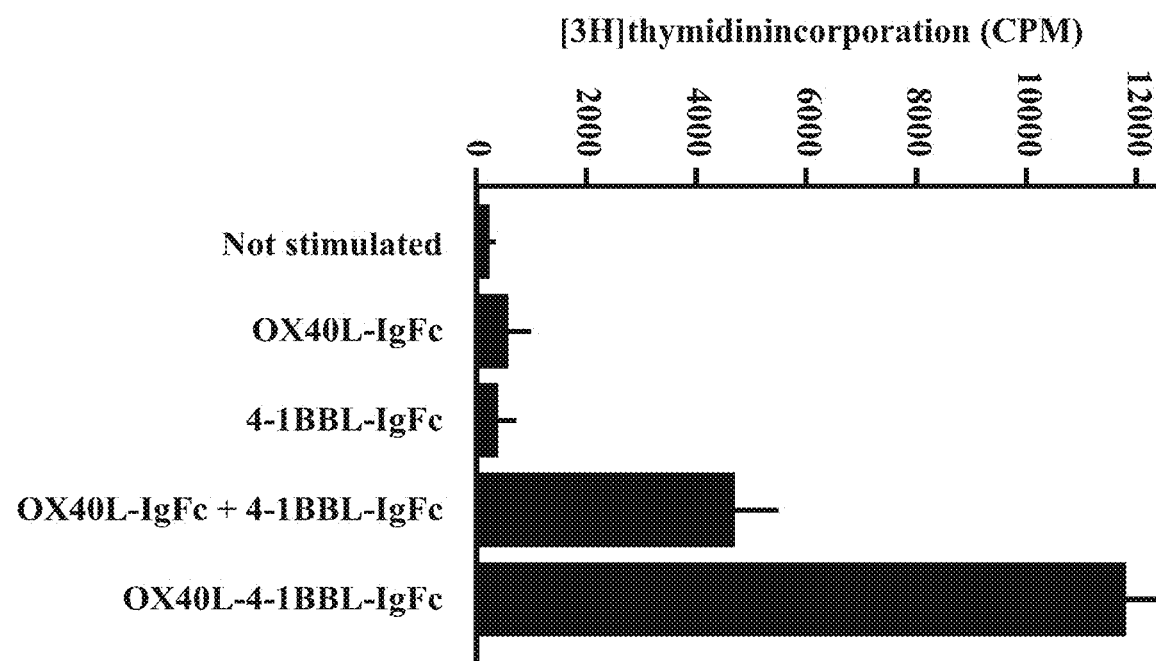
Figure 40. Activation of PBMCs by OX40L-4-1BBL-IgFc.

Figure 41. Adjuvant activity of OX40L-4-1BBL-IgFc/PCIneo in mice against Influenza hemaglutinin.
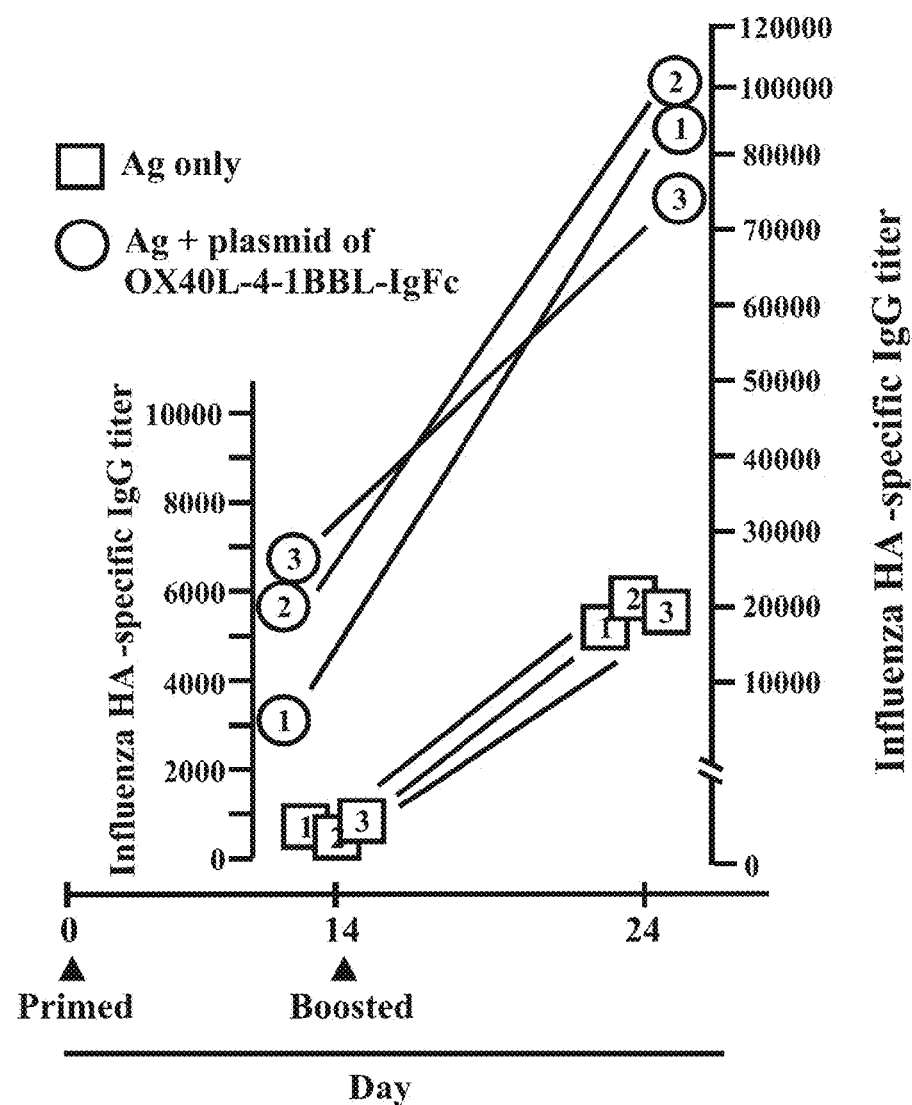

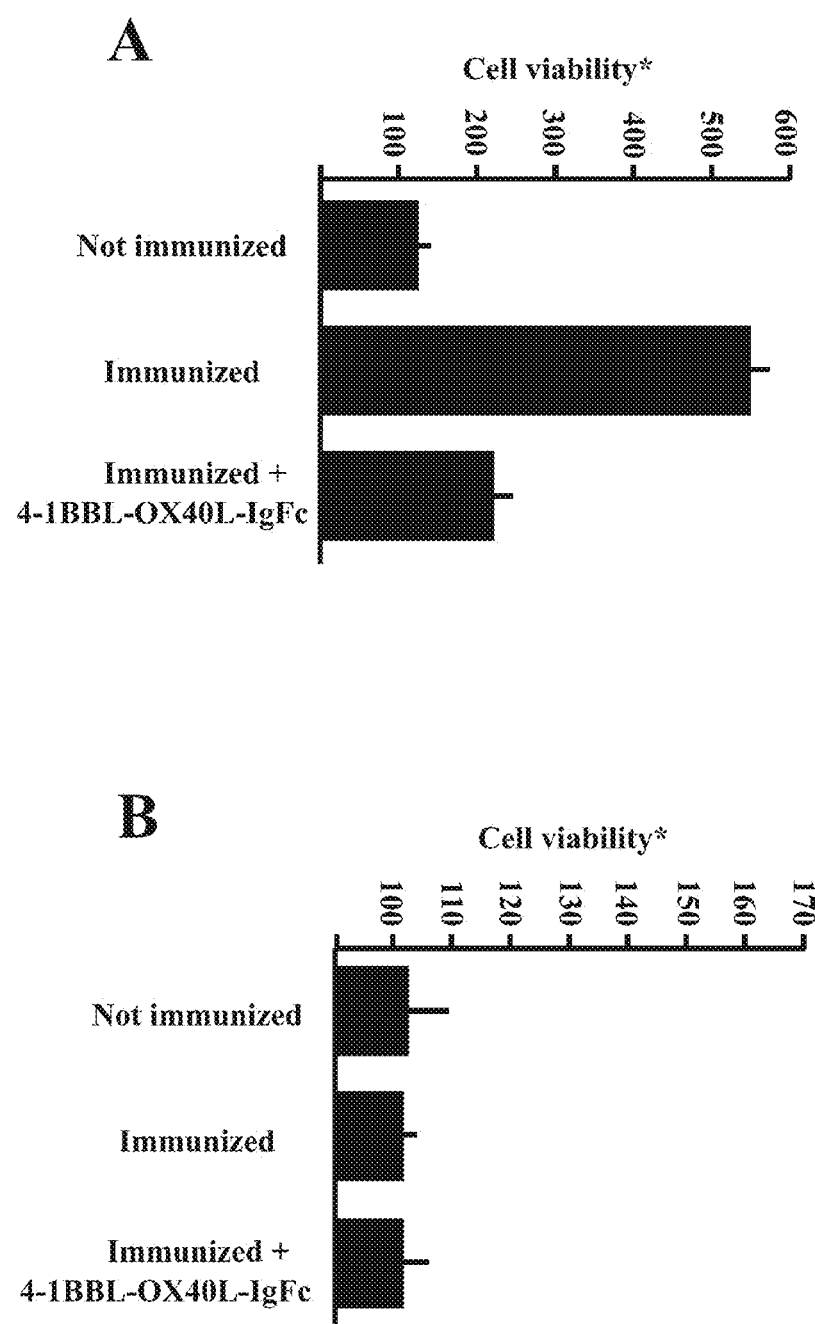
Figure 42. Adjuvant activity of OX40L-4-1BBL-IgFc in mice against Influenza hemaglutinin-specific T cell response.

Figure 43A. Registered sequence of ICOS of human origin (SEQ ID NO: 31).

```
ctgaacgcga ggactgttaa ctgtttctgg caaac atg aag tca ggc ctc tgg              53
                                       Met Lys Ser Gly Leu Trp
                                       -20                 -15 tat ttc ttt ctc ttc tgc ttg cgc att aaa gtt tta aca gga gaa atc            101
Tyr Phe Phe Leu Phe Cys Leu Arg Ile Lys Val Leu Thr Gly Glu Ile
            -10                 -5                  -1  1 aat ggt tct gcc aat tat gag atg ttt ata ttt cac aac gga ggt gta            149
Asn Gly Ser Ala Asn Tyr Glu Met Phe Ile Phe His Asn Gly Gly Val
        5                   10                  15 caa att tta tgc aaa tat cct gac att gtc cag caa ttt aaa atg cag            197
Gln Ile Leu Cys Lys Tyr Pro Asp Ile Val Gln Gln Phe Lys Met Gln
    20                  25                  30 ttg ctg aaa ggg ggg caa ata ctc tgc gat ctc act aag aca aaa gga            245
Leu Leu Lys Gly Gly Gln Ile Leu Cys Asp Leu Thr Lys Thr Lys Gly
35                  40                  45                  50 agt gga aac aca gtg tcc att aag agt ctg aaa ttc tgc cat tct cag            293
Ser Gly Asn Thr Val Ser Ile Lys Ser Leu Lys Phe Cys His Ser Gln
            55                  60                  65 tta tcc aac aac agt gtc tct ttt tta tac aac ttg gac cat tct              341
Leu Ser Asn Asn Ser Val Ser Phe Phe Leu Tyr Asn Leu Asp His Ser
        70                  75                  80 cat gcc aac tat tac ttc tgc aac cta tca att ttt gat cct cct cct            389
His Ala Asn Tyr Tyr Phe Cys Asn Leu Ser Ile Phe Asp Pro Pro Pro
        85                  90                  95 ttt aaa gta act ctt aca gga gga tat ttg cat att tat gaa tca caa            437
Phe Lys Val Thr Leu Thr Gly Gly Tyr Leu His Ile Tyr Glu Ser Gln
        100             105                 110 ctt tgt tgc cag ctg aag ttc tgg tta ccc ata gga tgt gca gcc ttt            485
Leu Cys Cys Gln Leu Lys Phe Trp Leu Pro Ile Gly Cys Ala Ala Phe
115                 120                 125                 130 gtt gta gtc tgc att ttg gga tgc ata ctt att tgt tgg ctt aca aaa            533
Val Val Val Cys Ile Leu Gly Cys Ile Leu Ile Cys Trp Leu Thr Lys
            135                 140                 145 aag aag tat tca tcc agt gtg cac gac cct aac ggt gaa tac atg ttc            581
Lys Lys Tyr Ser Ser Ser Val His Asp Pro Asn Gly Glu Tyr Met Phe
        150                 155                 160
```

Figure 43B. Registered sequence of ICOS of human origin (SEQ ID NO: 31).

| | |
|---|---:|
| atg aga gca gtg aac aca gcc aaa aaa tct aga ctc aca gat gtg acc<br>Met Arg Ala Val Asn Thr Ala Lys Lys Ser Arg Leu Thr Asp Val Thr<br>            165                   170                  175 | 629 |
| cta taatatggaa ctctggcacc caggcatgaa gcacgttggc cagttttcct<br>Leu | 682 |
| caacttgaag tgcaagattc tcttatttcc gggaccacgg agagtctgac ttaactacat | 742 |
| acatcttctg ctggtgtttt gttcaatctg gaagaatgac tgtatcagtc aatggggatt | 802 |
| ttaacagact gccttggtac tgccgagtcc tctcaaaaca acaccctct tgcaaccagc | 862 |
| tttggagaaa gcccagctcc tgtgtgctca ctgggagtgg aatccctgtc tccacatctg | 922 |
| ctcctagcag tgcatcagcc agtaaaacaa acacatttac aagaaaaatg ttttaaagat | 982 |
| gccaggggta ctgaatctgc aaagcaaatg agcagccaag gaccagcatc tgtccgcatt | 1042 |
| tcactatcat actacctctt ctttctgtag ggatgagaat cctcttttta atcagtcaag | 1102 |
| ggagatgctt caaagctgga gctattttat ttctgagatg ttgatgtgaa ctgtacatta | 1162 |
| gtacatactc agtactctcc ttcaattgct gaacccagt tgaccatttt accaagactt | 1222 |
| tagatgcttt cttgtgccct caattttctt tttaaaaata cttctacatg actgcttgac | 1282 |
| agcccaacag ccactctcaa tagagagcta tgtcttacat tctttcctct gctgctcaat | 1342 |
| agttttatat atctatgcat acatatatac acacatatgt atataaaatt cataatgaat | 1402 |
| atatttgcct atattctccc tacaagaata tttttgctcc agaaagacat gttcttttct | 1462 |
| caaattcagt taaaatggtt tactttgttc aagttagtgg taggaaacat tgcccggaat | 1522 |
| tgaaagcaaa tttattttat tatcctattt tctaccatta tctatgtttt catggtgcta | 1582 |
| ttaattacaa gtttagttct ttttgtagat catattaaaa ttgcaaacaa aatcatcttt | 1642 |
| aatgggccag cattctcatg gggtagagca gaatattcat ttagcctgaa agctgcagtt | 1702 |
| actataggtt gctgtcagac tatacccatg gtgcctctgg gcttgacagg tcaaaatggt | 1762 |
| ccccatcagc ctggagcagc cctccagacc tgggtggaat tccagggttg agagactccc | 1822 |
| ctgagccaga ggccactagg tattcttgct cccagaggct gaagtcaccc tgggaatcac | 1882 |

Figure 43C. Registered sequence of ICOS of human origin (SEQ ID NO: 31).

```
agtggtctac ctgcattcat aattccagga tctgtgaaga gcacatatgt gtcagggcac    1942
aattccctct cataaaaacc acacagcctg gaaattggcc ctggcccttc aagatagcct    2002
tctttagaat atgatttggc tagaaagatt cttaaatatg tggaatatga ttattcttag    2062
ctggaatatt ttctctactt cctgtctgca tgcccaaggc ttctgaagca gccaatgtcg    2122
atgcaacaac atttgtaact ttaggtaaac tgggattatg ttgtagttta acattttgta    2182
actgtgtgct tatagtttac aagtgagacc cgatatgtca ttatgcatac ttatattatc    2242
ttaagcatgt gtaatgctgg atgtgtacag tacagtactg aacttgtaat ttgaatctag    2302
tatggtgttc tgttttcagc tgacttggac aacctgactg gctttgcaca ggtgttccct    2362
gagttgtttg caggtttctg tgtgtggggt ggggtatggg gaggagaacc ttcatggtgg    2422
cccacctggc ctggttgtcc aagctgtgcc tcgacacatc ctcatcccca gcatgggaca    2482
cctcaagatg aataataatt cacaaaattt ctgtgaaatc aaatccagtt ttaagaggag    2542
ccacttatca aagagatttt aacagtagta agaaggcaaa gaataaacat ttgatattca    2602
gcaactgaaa aaaaaaaa                                                  2620
```

Figure 44A. Nucleotide sequence and amino acid sequence of CD40L-ICOS-IgFc (SEQ ID NO: 33).

```
gctagc atg ggg gta ctg ctc aca cag agg acg ctg ctc agt ctg gtc              48
       Met Gly Val Leu Leu Thr Gln Arg Thr Leu Leu Ser Leu Val
       -25              -20                      -15 ctt gca ctc ctg ttt cca agc atg gcg agc atg ctt cat aga agg ttg             96
Leu Ala Leu Leu Phe Pro Ser Met Ala Ser Met Leu His Arg Arg Leu
    -10             -5              -1  1                   5 gac aag ata gaa gat gaa agg aat ctt cat gaa gat ttt gta ttc atg            144
Asp Lys Ile Glu Asp Glu Arg Asn Leu His Glu Asp Phe Val Phe Met
            10                  15                  20 aaa acg ata cag aga tgc aac aca gga gaa aga tcc tta tcc tta ctg            192
Lys Thr Ile Gln Arg Cys Asn Thr Gly Glu Arg Ser Leu Ser Leu Leu
                25              30                  35 aac tgt gag gag att aaa agc cag ttt gaa ggc ttt gtg aag gat ata            240
Asn Cys Glu Glu Ile Lys Ser Gln Phe Glu Gly Phe Val Lys Asp Ile
            40                  45                  50 atg tta aac aaa gag gag acg aag aaa gaa aac agc ttt gaa atg caa            288
Met Leu Asn Lys Glu Glu Thr Lys Lys Glu Asn Ser Phe Glu Met Gln
    55                  60                  65 aaa ggt gat cag aat cct caa att gcg gca cat gtc ata agt gag gcc            336
Lys Gly Asp Gln Asn Pro Gln Ile Ala Ala His Val Ile Ser Glu Ala
70              75                  80                  85 agc agt aaa aca aca tct gtg tta cag tgg gct gaa aaa gga tac tac            384
Ser Ser Lys Thr Thr Ser Val Leu Gln Trp Ala Glu Lys Gly Tyr Tyr
            90                  95                  100 acc atg agc aac aac ttg gta acc ctg gaa aat ggg aaa cag ctg acc            432
Thr Met Ser Asn Asn Leu Val Thr Leu Glu Asn Gly Lys Gln Leu Thr
            105                 110                 115 gtt aaa aga caa gga ctc tat tat atc tat gcc caa gtc acc ttc tgt            480
Val Lys Arg Gln Gly Leu Tyr Tyr Ile Tyr Ala Gln Val Thr Phe Cys
        120                 125                 130 tcc aat cgg gaa gct tcg agt caa gct cca ttt ata gcc agc ctc tgc            528
Ser Asn Arg Glu Ala Ser Ser Gln Ala Pro Phe Ile Ala Ser Leu Cys
        135                 140                 145 cta aag tcc ccc ggt aga ttc gag aga atc tta ctc aga gct gca aat            576
Leu Lys Ser Pro Gly Arg Phe Glu Arg Ile Leu Leu Arg Ala Ala Asn
150             155                 160                 165
```

Figure 44B. Nucleotide sequence and amino acid sequence of CD40L-ICOS-IgFc (SEQ ID NO: 33).

| | |
|---|---|
| acc cac agt tcc gcc aaa cct tgc ggg caa caa tcc att cac ttg gga<br>Thr His Ser Ser Ala Lys Pro Cys Gly Gln Gln Ser Ile His Leu Gly<br>170                        175                          180 | 624 |
| gga gta ttt gaa ttg caa cca ggt gct tcg gtg ttt gtc aat gtg act<br>Gly Val Phe Glu Leu Gln Pro Gly Ala Ser Val Phe Val Asn Val Thr<br>            185                        190                      195 | 672 |
| gat cca agc caa gtg agc cat ggc act ggc ttc acg tcc ttt ggc tta<br>Asp Pro Ser Gln Val Ser His Gly Thr Gly Phe Thr Ser Phe Gly Leu<br>        200                        205                      210 | 720 |
| ctc aaa ctc gag gga gaa atc aat ggt tct gcc aat tat gag atg ttt<br>Leu Lys Leu Glu Gly Glu Ile Asn Gly Ser Ala Asn Tyr Glu Met Phe<br>215                        220                        225 | 768 |
| ata ttt cac aac gga ggt gta caa att tta tgc aaa tat cct gac att<br>Ile Phe His Asn Gly Gly Val Gln Ile Leu Cys Lys Tyr Pro Asp Ile<br>230                        235                        240                      245 | 816 |
| gtc cag caa ttt aaa atg cag ttg ctg aaa ggg ggg caa ata ctc tgc<br>Val Gln Gln Phe Lys Met Gln Leu Leu Lys Gly Gly Gln Ile Leu Cys<br>                250                        255                      260 | 864 |
| gat ctc act aag aca aaa gga agt gga aac aca gtg tcc att aag agt<br>Asp Leu Thr Lys Thr Lys Gly Ser Gly Asn Thr Val Ser Ile Lys Ser<br>            265                        270                      275 | 912 |
| ctg aaa ttc tgc cat tct cag tta tcc aac aac agt gtc tcc ttt ttt<br>Leu Lys Phe Cys His Ser Gln Leu Ser Asn Asn Ser Val Ser Phe Phe<br>        280                        285                      290 | 960 |
| cta tac aac ttg gac cat tct cat gcc aac tat tac ttc tgt aac cta<br>Leu Tyr Asn Leu Asp His Ser His Ala Asn Tyr Tyr Phe Cys Asn Leu<br>295                        300                        305 | 1008 |
| tca att ttt gat cct cct cct ttt aaa gta act ctt aca gga gga tat<br>Ser Ile Phe Asp Pro Pro Pro Phe Lys Val Thr Leu Thr Gly Gly Tyr<br>310                        315                        320                      325 | 1056 |
| ttg cat att tat gaa tca caa ctt tgt tgc cag ctg aag ttc ctc gag<br>Leu His Ile Tyr Glu Ser Gln Leu Cys Cys Gln Leu Lys Phe Leu Glu<br>                330                        335                      340 | 1104 |
| ccc aaa tct tgt gac aaa act cac aca tgc cca ccg tgc cca gca cct<br>Pro Lys Ser Cys Asp Lys Thr His Thr Cys Pro Pro Cys Pro Ala Pro<br>            345                        350                      355 | 1152 |

Figure 44C. Nucleotide sequence and amino acid sequence of CD40L-ICOS-IgFc (SEQ ID NO: 33).

| | | | | | | | | | | | | | | | | |
|---|---|---|---|---|---|---|---|---|---|---|---|---|---|---|---|---|
| gaa | ctc | ctg | ggg | gga | ccg | tca | gtc | ttc | ctc | ttc | ccc | cca | aaa | ccc | aag | 1200 |
| Glu | Leu | Leu | Gly | Gly | Pro | Ser | Val | Phe | Leu | Phe | Pro | Pro | Lys | Pro | Lys | |
| | | 360 | | | | 365 | | | | | 370 | | | | | |
| gac | acc | ctc | atg | atc | tcc | cgg | acc | cct | gag | gtc | aca | tgc | gtg | gtg | gtg | 1248 |
| Asp | Thr | Leu | Met | Ile | Ser | Arg | Thr | Pro | Glu | Val | Thr | Cys | Val | Val | Val | |
| | 375 | | | | | 380 | | | | | 385 | | | | | |
| gac | gtg | agc | cac | gaa | gac | cct | gag | gtc | aag | ttc | aac | tgg | tac | gtg | gac | 1296 |
| Asp | Val | Ser | His | Glu | Asp | Pro | Glu | Val | Lys | Phe | Asn | Trp | Tyr | Val | Asp | |
| 390 | | | | | 395 | | | | | 400 | | | | | 405 | |
| ggc | gtg | gag | gtg | cat | aat | gcc | aag | aca | aag | ccg | cgg | gag | gag | cag | tac | 1344 |
| Gly | Val | Glu | Val | His | Asn | Ala | Lys | Thr | Lys | Pro | Arg | Glu | Glu | Gln | Tyr | |
| | | | | 410 | | | | | 415 | | | | | 420 | | |
| aac | agc | acg | tac | cgt | gtg | gtc | agc | gtc | ctc | acc | gtc | ctg | cac | cag | gac | 1392 |
| Asn | Ser | Thr | Tyr | Arg | Val | Val | Ser | Val | Leu | Thr | Val | Leu | His | Gln | Asp | |
| | | | 425 | | | | | 430 | | | | | 435 | | | |
| tgg | ctg | aat | ggc | aag | gag | tac | aag | tgc | aag | gtc | tcc | aac | aaa | gcc | ctc | 1440 |
| Trp | Leu | Asn | Gly | Lys | Glu | Tyr | Lys | Cys | Lys | Val | Ser | Asn | Lys | Ala | Leu | |
| | | | 440 | | | | | 445 | | | | | 450 | | | |
| cca | gcc | ccc | atc | gag | aaa | acc | atc | tcc | aaa | gcc | aaa | ggg | cag | ccc | cga | 1488 |
| Pro | Ala | Pro | Ile | Glu | Lys | Thr | Ile | Ser | Lys | Ala | Lys | Gly | Gln | Pro | Arg | |
| | | 455 | | | | | 460 | | | | | 465 | | | | |
| gaa | cca | cag | gtg | tac | acc | ctg | ccc | cca | tcc | cgg | gat | gag | ctg | acc | aag | 1536 |
| Glu | Pro | Gln | Val | Tyr | Thr | Leu | Pro | Pro | Ser | Arg | Asp | Glu | Leu | Thr | Lys | |
| 470 | | | | | 475 | | | | | 480 | | | | | 485 | |
| aac | cag | gtc | agc | ctg | acc | tgc | ctg | gtc | aaa | ggc | ttc | tat | ccc | agc | gac | 1584 |
| Asn | Gln | Val | Ser | Leu | Thr | Cys | Leu | Val | Lys | Gly | Phe | Tyr | Pro | Ser | Asp | |
| | | | | 490 | | | | | 495 | | | | | 500 | | |
| atc | gcc | gtg | gag | tgg | gag | agc | aat | ggg | cag | ccg | gag | aac | aac | tac | aag | 1632 |
| Ile | Ala | Val | Glu | Trp | Glu | Ser | Asn | Gly | Gln | Pro | Glu | Asn | Asn | Tyr | Lys | |
| | | | | 505 | | | | | 510 | | | | | 515 | | |
| acc | acg | cct | ccc | gtg | ctg | gac | tcc | gac | ggc | tcc | ttc | ttc | ctc | tac | agc | 1680 |
| Thr | Thr | Pro | Pro | Val | Leu | Asp | Ser | Asp | Gly | Ser | Phe | Phe | Leu | Tyr | Ser | |
| | | | 520 | | | | | 525 | | | | | 530 | | | |
| aag | ctc | acc | gtg | gac | aag | agc | agg | tgg | cag | cag | ggg | aac | gtc | ttc | tca | 1728 |
| Lys | Leu | Thr | Val | Asp | Lys | Ser | Arg | Trp | Gln | Gln | Gly | Asn | Val | Phe | Ser | |
| | | | 535 | | | | | 540 | | | | | 545 | | | |

Figure 44D. Nucleotide sequence and amino acid sequence of CD40L-ICOS-IgFc (SEQ ID NO: 33).

```
tgc tcc gtg atg cat gag gct ctg cac aac cac tac acg cag aag agc         1776
Cys Ser Val Met His Glu Ala Leu His Asn His Tyr Thr Gln Lys Ser
550             555                 560                 565 ctc tcc ctg tct ccg ggt aaa tgatctaga                                    1806
Leu Ser Leu Ser Pro Gly Lys
                570
```

Figure 45. Western blotting analysis of CD40L-ICOS-IgFc.
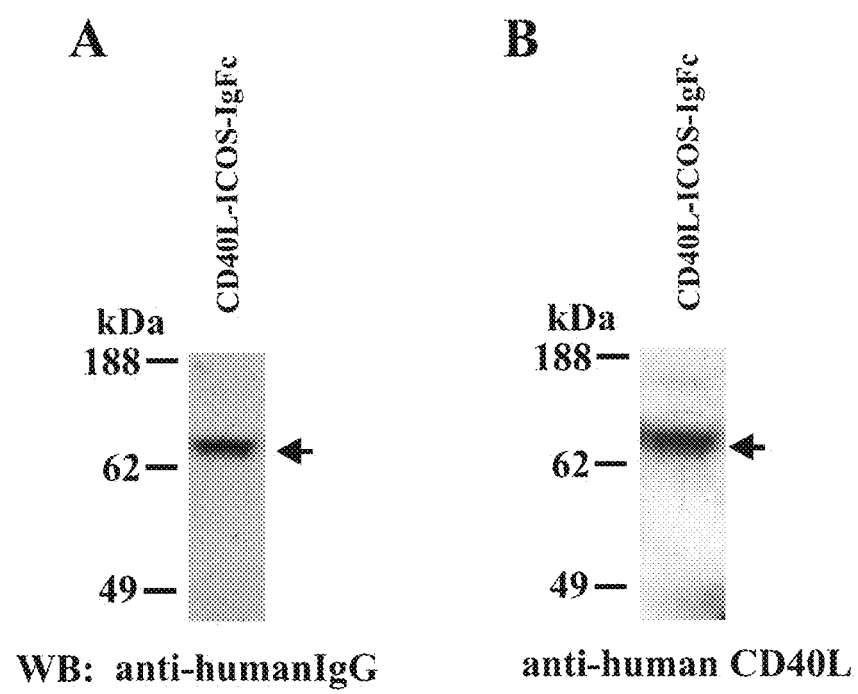

Figure 46. Adjuvant activity of Plasmid DNA of CD40L-ICOS-IgFc in mice against Influenza hemaglutinin.

Figure 47. Adjuvant activity of CD40L-ICOS-IgFc/PCIneo in mice against Influenza hemaglutinin-specific T cell response.
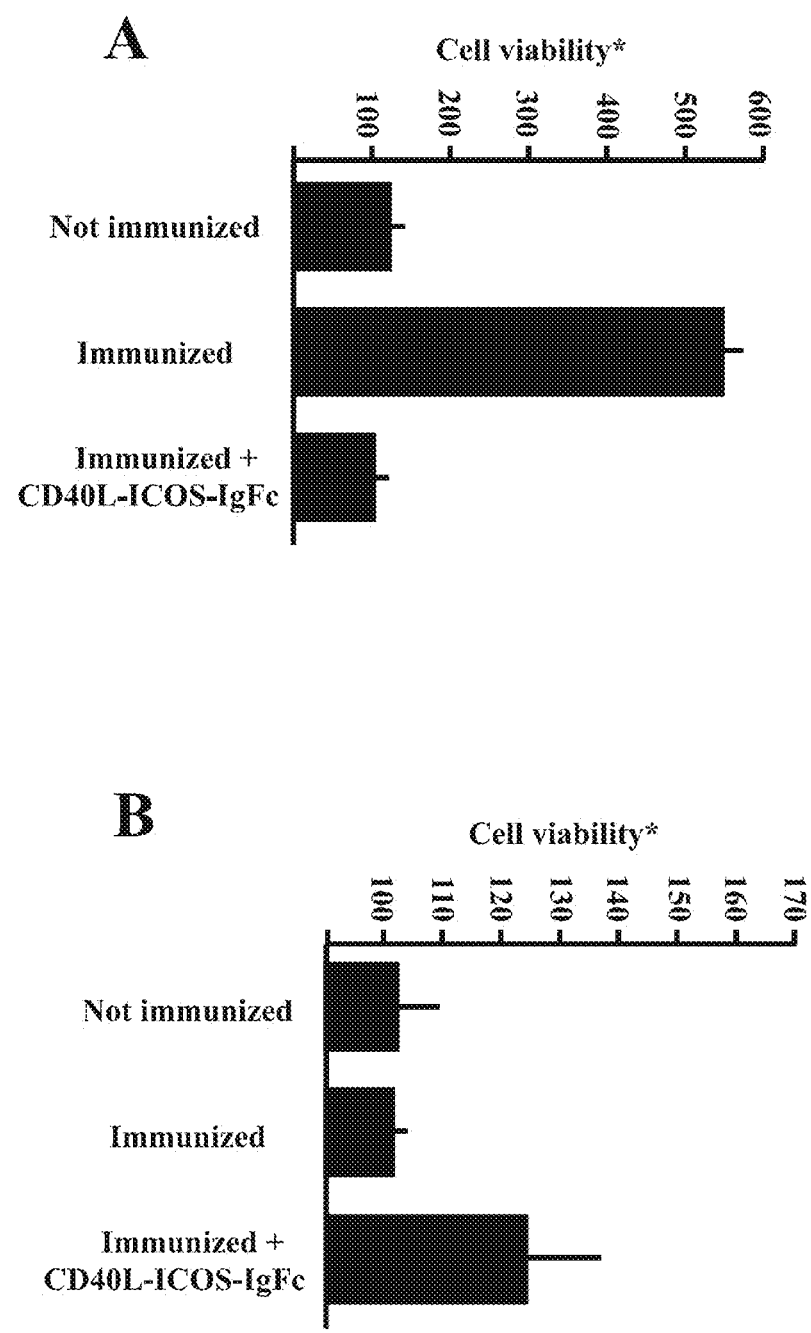

Figure 48A. Registered sequences of NGFβ of human origin (SEQ ID NO: 35).

```
agagagcgct gggagccgga ggggagcgca gcgagttttg gccagtggtc gtgcagtcca      60
aggggctgga tggcatgctg gacccaagct cagctcagcg tccggaccca ataacagttt     120
taccaaggga gcagcttttct atcctggcca cactgaggtg catagcgta atg tcc atg    178
                                                       Met Ser Met
                                                               -15 ttg ttc tac act ctg atc aca gct ttt ctg atc ggc ata cag gcg gaa       226
Leu Phe Tyr Thr Leu Ile Thr Ala Phe Leu Ile Gly Ile Gln Ala Glu
            -10                 -5                  -1  1 cca cac tca gag agc aat gtc cct gca gga cac acc atc ccc caa gcc       274
Pro His Ser Glu Ser Asn Val Pro Ala Gly His Thr Ile Pro Gln Ala
         5               10                  15 cac tgg act aaa ctt cag cat tcc ctt gac act gcc ctt cgc aga gcc       322
His Trp Thr Lys Leu Gln His Ser Leu Asp Thr Ala Leu Arg Arg Ala
         20              25                  30 cgc agc gcc ccg gca gcg gcg ata gct gca cgc gtg gcg ggg cag acc       370
Arg Ser Ala Pro Ala Ala Ala Ile Ala Ala Arg Val Ala Gly Gln Thr
35              40                  45                  50 cgc aac att act gtg gac ccc agg ctg ttt aaa aag cgg cga ctc cgt       418
Arg Asn Ile Thr Val Asp Pro Arg Leu Phe Lys Lys Arg Arg Leu Arg
                    55                  60                  65 tca ccc cgt gtg ctg ttt agc acc cag cct ccc cgt gaa gct gca gac       466
Ser Pro Arg Val Leu Phe Ser Thr Gln Pro Pro Arg Glu Ala Ala Asp
            70                  75                  80 act cag gat ctg gac ttc gag gtc ggt ggt gct gcc ccc ttc aac agg       514
Thr Gln Asp Leu Asp Phe Glu Val Gly Gly Ala Ala Pro Phe Asn Arg
        85                  90                  95 act cac agg agc aag cgg tca tca tcc cat ccc atc ttc cac agg ggc       562
Thr His Arg Ser Lys Arg Ser Ser Ser His Pro Ile Phe His Arg Gly
        100                 105                 110 gaa ttc tcg gtg tgt gac agt gtc agc gtg tgg gtt ggg gat aag acc       610
Glu Phe Ser Val Cys Asp Ser Val Ser Val Trp Val Gly Asp Lys Thr
115                 120                 125                 130 acc gcc aca gac atc aag ggc aag gag gtg atg gtg ttg gga gag gtg       658
Thr Ala Thr Asp Ile Lys Gly Lys Glu Val Met Val Leu Gly Glu Val
                    135                 140                 145
```

Figure 48B. Registered sequences of NGFβ of human origin (SEQ ID NO: 35).

```
aac att aac aac agt gta ttc aaa cag tac ttt ttt gag acc aag tgc      706
Asn Ile Asn Asn Ser Val Phe Lys Gln Tyr Phe Phe Glu Thr Lys Cys
            150                 155                 160 cgg gac cca aat ccc gtt gac agc ggg tgc cgg ggc att gac tca aag      754
Arg Asp Pro Asn Pro Val Asp Ser Gly Cys Arg Gly Ile Asp Ser Lys
            165                 170                 175 cac tgg aac tca tat tgt acc acg act cac acc ttt gtc aag gcg ctg      802
His Trp Asn Ser Tyr Cys Thr Thr Thr His Thr Phe Val Lys Ala Leu
            180                 185                 190 acc atg gat ggc aag cag gct gcc tgg cgg ttt atc cgg ata gat acg      850
Thr Met Asp Gly Lys Gln Ala Ala Trp Arg Phe Ile Arg Ile Asp Thr
195                 200                 205                 210 gcc tgt gtg tgt gtg ctc agc agg aag gct gtg aga aga gcc                892
Ala Cys Val Cys Val Leu Ser Arg Lys Ala Val Arg Arg Ala
            215                 220 tgacctgccg acacgctccc tccccctgcc ccttctacac tctcctgggc ccctccctac     952
ctcaacctgt aaattatttt aaattataag gactgcatgg taatttatag tttatacagt    1012
tttaaagaat cattatttat taaatttttg gaagcataaa                          1052
```

Figure 49A. Nucleotide sequence and amino acid sequence of the NGFβ -FasL-IgFc fusion protein (SEQ ID NO: 37).

| | |
|---|---|
| gctagc atg ggg gta ctg ctc aca cag agg acg ctg ctc agt ctg gtc<br>       Met Gly Val Leu Leu Thr Gln Arg Thr Leu Leu Ser Leu Val<br>       -25               -20                     -15 | 48 |
| ctt gca ctc ctg ttt cca agc atg gcg agc atg ctc gag tca tca tcc<br>Leu Ala Leu Leu Phe Pro Ser Met Ala Ser Met Leu Glu Ser Ser Ser<br>      -10               -5              -1 1          5 | 96 |
| cat ccc atc ttc cac agg ggc gaa ttc tcg gtg tgt gac agt gtc agc<br>His Pro Ile Phe His Arg Gly Glu Phe Ser Val Cys Asp Ser Val Ser<br>              10                   15                  20 | 144 |
| gtg tgg gtt ggg gat aag acc acc gcc aca gac atc aag ggc aag gag<br>Val Trp Val Gly Asp Lys Thr Thr Ala Thr Asp Ile Lys Gly Lys Glu<br>            25                30                  35 | 192 |
| gtg atg gtg ttg gga gag gtg agc att aac aac agt gta ttc aaa cag<br>Val Met Val Leu Gly Glu Val Ser Ile Asn Asn Ser Val Phe Lys Gln<br>            40                45                50 | 240 |
| tac ttt ttt gag acc aag tgc cgg gac cca aat ccc gtt gac agc ggg<br>Tyr Phe Phe Glu Thr Lys Cys Arg Asp Pro Asn Pro Val Asp Ser Gly<br>  55                  60                65 | 288 |
| tgc cgg ggc att gac tca aag cac tgg aac tca tat tgt acc acg act<br>Cys Arg Gly Ile Asp Ser Lys His Trp Asn Ser Tyr Cys Thr Thr Thr<br>70                75                80              85 | 336 |
| cac acc ttt gtc aag gcg ctg acc atg gat ggc aag cag gct gcc tgg<br>His Thr Phe Val Lys Ala Leu Thr Met Asp Gly Lys Gln Ala Ala Trp<br>            90                95              100 | 384 |
| cgg ttt atc cgg ata gat acg gcc tgt atg tgt gtg ctc agc agg aag<br>Arg Phe Ile Arg Ile Asp Thr Ala Cys Met Cys Val Leu Ser Arg Lys<br>          105               110             115 | 432 |
| gct gtg aga aga gcc ctc gag cag ctc ttc cac cta cag aag gag ctg<br>Ala Val Arg Arg Ala Leu Glu Gln Leu Phe His Leu Gln Lys Glu Leu<br>          120             125             130 | 480 |
| gca gaa ctc cga gag tct acc agc cag atg cac aca gca tca tct ttg<br>Ala Glu Leu Arg Glu Ser Thr Ser Gln Met His Thr Ala Ser Ser Leu<br>          135             140             145 | 528 |
| gag aag caa ata ggc cac ccc agt cca ccc cct gaa aaa aag gag ctg<br>Glu Lys Gln Ile Gly His Pro Ser Pro Pro Pro Glu Lys Lys Glu Leu<br>150                 155             160             165 | 576 |

Figure 49B. Nucleotide sequence and amino acid sequence of the NGFβ -FasL-IgFc fusion protein (SEQ ID NO: 37).

| | |
|---|---|
| agg aaa gtg gcc cat tta aca ggc aag tcc aac tca agg tcc atg cct<br>Arg Lys Val Ala His Leu Thr Gly Lys Ser Asn Ser Arg Ser Met Pro<br>170                      175                    180 | 624 |
| ctg gaa tgg gaa gac acc tat gga att gtc ctg ctt tct gga gtg aag<br>Leu Glu Trp Glu Asp Thr Tyr Gly Ile Val Leu Leu Ser Gly Val Lys<br>185                      190                    195 | 672 |
| tat aag aag ggt ggc ctt gtg atc aat gaa act ggg ctg tac ttt gta<br>Tyr Lys Lys Gly Gly Leu Val Ile Asn Glu Thr Gly Leu Tyr Phe Val<br>200                      205                    210 | 720 |
| tat tcc aaa gta tac ttc cgg ggt caa tct tgc aac aac ctg ccc ctg<br>Tyr Ser Lys Val Tyr Phe Arg Gly Gln Ser Cys Asn Asn Leu Pro Leu<br>215                      220                    225 | 768 |
| agc cac aag gtc tac atg agg aac tct aag tat ccc cag gat ctg gtg<br>Ser His Lys Val Tyr Met Arg Asn Ser Lys Tyr Pro Gln Asp Leu Val<br>230                      235                    240                    245 | 816 |
| atg atg gag ggg aag atg atg agc tac tgc act act ggg cag atg tgg<br>Met Met Glu Gly Lys Met Met Ser Tyr Cys Thr Thr Gly Gln Met Trp<br>250                      255                    260 | 864 |
| gcc cgc agc agc tac ctg ggg gca gtg ttc aat ctt acc agt gct gat<br>Ala Arg Ser Ser Tyr Leu Gly Ala Val Phe Asn Leu Thr Ser Ala Asp<br>265                      270                    275 | 912 |
| cat tta tat gtc aac gta tct gag ctc tct ctg gtc aat ttt gag gaa<br>His Leu Tyr Val Asn Val Ser Glu Leu Ser Leu Val Asn Phe Glu Glu<br>280                      285                    290 | 960 |
| tct cag acg ttt ttc ggc tta tat aag tct gag ccc aaa tct tgt gac<br>Ser Gln Thr Phe Phe Gly Leu Tyr Lys Ser Glu Pro Lys Ser Cys Asp<br>295                      300                    305 | 1008 |
| aaa act cac aca tgc cca ccg tgc cca gca cct gaa ctc ctg ggg gga<br>Lys Thr His Thr Cys Pro Pro Cys Pro Ala Pro Glu Leu Leu Gly Gly<br>310                      315                    320                    325 | 1056 |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>330                      335                    340 | 1104 |
| tcc cgg acc cct gag gtc aca tgc gtg gtg gtg gac gtg agc cac gaa<br>Ser Arg Thr Pro Glu Val Thr Cys Val Val Val Asp Val Ser His Glu<br>345                      350                    355 | 1152 |

Figure 49C. Nucleotide sequence and amino acid sequence of the NGFβ -FasL-IgFc fusion protein (SEQ ID NO: 37).

| | | | | | | | | | | | | | | | |
|---|---|---|---|---|---|---|---|---|---|---|---|---|---|---|---|
| gac | cct | gag | gtc | aag | ttc | aac | tgg | tac | gtg | gac | ggc | gtg | gag | gtg | cat | 1200 |
| Asp | Pro | Glu | Val | Lys | Phe | Asn | Trp | Tyr | Val | Asp | Gly | Val | Glu | Val | His | |
| | | 360 | | | | 365 | | | | 370 | | | | | | |

| | | | | | | | | | | | | | | | |
|---|---|---|---|---|---|---|---|---|---|---|---|---|---|---|---|
| aat | gcc | aag | aca | aag | ccg | cgg | gag | gag | cag | tac | aac | agc | acg | tac | cgt | 1248 |
| Asn | Ala | Lys | Thr | Lys | Pro | Arg | Glu | Glu | Gln | Tyr | Asn | Ser | Thr | Tyr | Arg | |
| | 375 | | | | 380 | | | | 385 | | | | | | | |

| | | | | | | | | | | | | | | | |
|---|---|---|---|---|---|---|---|---|---|---|---|---|---|---|---|
| gtg | gtc | agc | gtc | ctc | acc | gtc | ctg | cac | cag | gac | tgg | ctg | aat | ggc | aag | 1296 |
| Val | Val | Ser | Val | Leu | Thr | Val | Leu | His | Gln | Asp | Trp | Leu | Asn | Gly | Lys | |
| 390 | | | | | 395 | | | | 400 | | | | | 405 | | |

| | | | | | | | | | | | | | | | |
|---|---|---|---|---|---|---|---|---|---|---|---|---|---|---|---|
| gag | tac | aag | tgc | aag | gtc | tcc | aac | aaa | gcc | ctc | cca | gcc | ccc | atc | gag | 1344 |
| Glu | Tyr | Lys | Cys | Lys | Val | Ser | Asn | Lys | Ala | Leu | Pro | Ala | Pro | Ile | Glu | |
| | | | 410 | | | | | 415 | | | | | 420 | | | |

| | | | | | | | | | | | | | | | |
|---|---|---|---|---|---|---|---|---|---|---|---|---|---|---|---|
| aaa | acc | atc | tcc | aaa | gcc | aaa | ggg | cag | ccc | cga | gaa | cca | cag | gtg | tac | 1392 |
| Lys | Thr | Ile | Ser | Lys | Ala | Lys | Gly | Gln | Pro | Arg | Glu | Pro | Gln | Val | Tyr | |
| | | | 425 | | | | 430 | | | | | 435 | | | | |

| | | | | | | | | | | | | | | | |
|---|---|---|---|---|---|---|---|---|---|---|---|---|---|---|---|
| acc | ctg | ccc | cca | tcc | cgg | gat | gag | ctg | acc | aag | aac | cag | gtc | agc | ctg | 1440 |
| Thr | Leu | Pro | Pro | Ser | Arg | Asp | Glu | Leu | Thr | Lys | Asn | Gln | Val | Ser | Leu | |
| | | 440 | | | | 445 | | | | 450 | | | | | | |

| | | | | | | | | | | | | | | | |
|---|---|---|---|---|---|---|---|---|---|---|---|---|---|---|---|
| acc | tgc | ctg | gtc | aaa | ggc | ttc | tat | ccc | agc | gac | atc | gcc | gtg | gag | tgg | 1488 |
| Thr | Cys | Leu | Val | Lys | Gly | Phe | Tyr | Pro | Ser | Asp | Ile | Ala | Val | Glu | Trp | |
| | 455 | | | | 460 | | | | 465 | | | | | | | |

| | | | | | | | | | | | | | | | |
|---|---|---|---|---|---|---|---|---|---|---|---|---|---|---|---|
| gag | agc | aat | ggg | cag | ccg | gag | aac | aac | tac | aag | acc | acg | cct | ccc | gtg | 1536 |
| Glu | Ser | Asn | Gly | Gln | Pro | Glu | Asn | Asn | Tyr | Lys | Thr | Thr | Pro | Pro | Val | |
| 470 | | | | 475 | | | | | 480 | | | | | 485 | | |

| | | | | | | | | | | | | | | | |
|---|---|---|---|---|---|---|---|---|---|---|---|---|---|---|---|
| ctg | gac | tcc | gac | ggc | tcc | ttc | ttc | ctc | tac | agc | aag | ctc | acc | gtg | gac | 1584 |
| Leu | Asp | Ser | Asp | Gly | Ser | Phe | Phe | Leu | Tyr | Ser | Lys | Leu | Thr | Val | Asp | |
| | | | | 490 | | | | 495 | | | | | 500 | | | |

| | | | | | | | | | | | | | | | |
|---|---|---|---|---|---|---|---|---|---|---|---|---|---|---|---|
| aag | agc | agg | tgg | cag | cag | ggg | aac | gtc | ttc | tca | tgc | tcc | gtg | atg | cat | 1632 |
| Lys | Ser | Arg | Trp | Gln | Gln | Gly | Asn | Val | Phe | Ser | Cys | Ser | Val | Met | His | |
| | | | 505 | | | | | 510 | | | | | 515 | | | |

| | | | | | | | | | | | | | | | |
|---|---|---|---|---|---|---|---|---|---|---|---|---|---|---|---|
| gag | gct | ctg | cac | aac | cac | tac | acg | cag | aag | agc | ctc | tcc | ctg | tct | ccg | 1680 |
| Glu | Ala | Leu | His | Asn | His | Tyr | Thr | Gln | Lys | Ser | Leu | Ser | Leu | Ser | Pro | |
| | | | 520 | | | | 525 | | | | | 530 | | | | |

| | | | | | |
|---|---|---|---|---|---|
| ggt | aaa | tgagcggccg | c | | 1697 |
| Gly | Lys | | | | |
| | 535 | | | | |

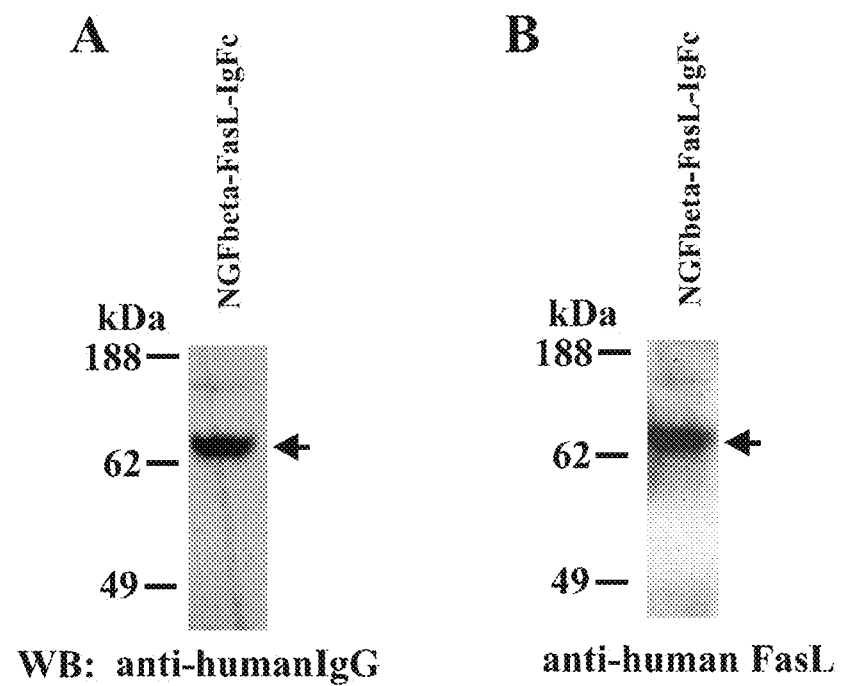
Figure 50. Western blotting analysis of NGFβ-FasL-IgFc.

Figure 51. Adjuvant activity of Plasmid DNA of NGFβ-FasL-IgFc in mice against Influenza hemaglutinin.

Figure 52. Adjuvant activity of NGFβ-FasL-IgFc /PCIneo in mice against Influenza hemaglutinin-specific T cell response.

A

Cell viability*

- Not immunized
- Immunized
- Immunized + NGF-FasL-IgFc

B

Cell viability*

- Not immunized
- Immunized
- Immunized + NGF-FasL-IgFc

Figure 53A. Registered sequence of IL-2 of human origin (SEQ ID NO: 39).

```
agttccctat cactctcttt aatcactact cacagtaacc tcaactcctg ccaca atg        58
                                                            Met
                                                            1 tac agg atg caa ctc ctg tct tgc att gca cta agt ctt gca ctt gtc        106
Tyr Arg Met Gln Leu Leu Ser Cys Ile Ala Leu Ser Leu Ala Leu Val
            5               10              15 aca aac agt gca cct act tca agt tct aca aag aaa aca cag cta caa        154
Thr Asn Ser Ala Pro Thr Ser Ser Ser Thr Lys Lys Thr Gln Leu Gln
            20              25              30 ctg gag cat tta ctg ctg gat tta cag atg att ttg aat gga att aat        202
Leu Glu His Leu Leu Leu Asp Leu Gln Met Ile Leu Asn Gly Ile Asn
        35              40              45 aat tac aag aat ccc aaa ctc acc agg atg ctc aca ttt aag ttt tac        250
Asn Tyr Lys Asn Pro Lys Leu Thr Arg Met Leu Thr Phe Lys Phe Tyr
50              55              60              65 atg ccc aag aag gcc aca gaa ctg aaa cat ctt cag tgt cta gaa gaa        298
Met Pro Lys Lys Ala Thr Glu Leu Lys His Leu Gln Cys Leu Glu Glu
            70              75              80 gaa ctc aaa cct ctg gag gaa gtg cta aat tta gct caa agc aaa aac        346
Glu Leu Lys Pro Leu Glu Glu Val Leu Asn Leu Ala Gln Ser Lys Asn
            85              90              95 ttt cac tta aga ccc agg gac tta atc agc aat atc aac gta ata gtt        394
Phe His Leu Arg Pro Arg Asp Leu Ile Ser Asn Ile Asn Val Ile Val
            100             105             110 ctg gaa cta aag gga tct gaa aca aca ttc atg tgt gaa tat gct gat        442
Leu Glu Leu Lys Gly Ser Glu Thr Thr Phe Met Cys Glu Tyr Ala Asp
            115             120             125 gag aca gca acc att gta gaa ttt ctg aac aga tgg att acc ttt tgt        490
Glu Thr Ala Thr Ile Val Glu Phe Leu Asn Arg Trp Ile Thr Phe Cys
130             135             140             145 caa agc atc atc tca aca ctg act tgataattaa gtgcttccca cttaaaacat       544
Gln Ser Ile Ile Ser Thr Leu Thr
            150 atcaggcctt ctatttattt aaatatttaa attttatatt tattgttgaa tgtatggttt      604 gctacctatt gtaactatta ttcttaatct taaaactata aatatggatc ttttatgatt      664
```

Figure 53B. Registered sequence of IL-2 of human origin (SEQ ID NO: 39).

cttttttgtaa gccctagggg ctctaaaatg gtttcactta tttatcccaa aatatttatt      724
attatgttga atgttaaata tagtatctat gtagattggt tagtaaaact atttaataaa      784
tttgataaat ataaaaaaaa aaaaaaaaa aaaaaaaa      822

Figure 54A. Nucleotide sequence and amino acid sequence of IL-2-FasL-IgFc (SEQ ID NO: 41).

```
gctagc atg ggg gta ctg ctc aca cag agg acg ctg ctc agt ctg gtc              48
       Met Gly Val Leu Leu Thr Gln Arg Thr Leu Leu Ser Leu Val
       -25              -20                      -15 ctt gca ctc ctg ttt cca agc atg gcg agc atg gaa ttc gca cct act             96
Leu Ala Leu Leu Phe Pro Ser Met Ala Ser Met Glu Phe Ala Pro Thr
-10                  -5               -1  1               5 tca agt tct aca aag aaa aca cag cta caa ctg gag cat tta ctg ctg            144
Ser Ser Ser Thr Lys Lys Thr Gln Leu Gln Leu Glu His Leu Leu Leu
                10              15                  20 gat tta cag atg att ttg aat gga att aat aat tac aag aat ccc aaa            192
Asp Leu Gln Met Ile Leu Asn Gly Ile Asn Asn Tyr Lys Asn Pro Lys
            25                  30                  35 ctc acc agg atg ctc aca ttt aag ttt tac atg ccc aag aag gcc aca            240
Leu Thr Arg Met Leu Thr Phe Lys Phe Tyr Met Pro Lys Lys Ala Thr
            40                  45                  50 gaa ctg aaa cat ctt cag tgt cta gaa gaa gaa ctc aaa cct ctg                288
Glu Leu Lys His Leu Gln Cys Leu Glu Glu Glu Leu Lys Pro Leu
55                  60                  65 gag gaa gtg cta aat tta gct caa agc aaa aac ttt cac tta aga ccc            336
Glu Glu Val Leu Asn Leu Ala Gln Ser Lys Asn Phe His Leu Arg Pro
70              75                  80                  85 agg gac tta atc agc aat atc aac gta ata gtt ctg gaa cta aag gga            384
Arg Asp Leu Ile Ser Asn Ile Asn Val Ile Val Leu Glu Leu Lys Gly
                90                  95                  100 tct gaa aca aca ttc atg tgt gaa tat gct gat gag aca gca acc att            432
Ser Glu Thr Thr Phe Met Cys Glu Tyr Ala Asp Glu Thr Ala Thr Ile
            105                 110                 115 gta gaa ttt ctg aac aga tgg att acc ttt tgt caa agc atc atc tca            480
Val Glu Phe Leu Asn Arg Trp Ile Thr Phe Cys Gln Ser Ile Ile Ser
            120                 125                 130 aca ctg act acg cgt ggt acc cag ctc ttc cac cta cag aag gag ctg            528
Thr Leu Thr Thr Arg Gly Thr Gln Leu Phe His Leu Gln Lys Glu Leu
135                 140                 145 gca gaa ctc cga gag tct acc agc cag atg cac aca gca tca tct ttg            576
Ala Glu Leu Arg Glu Ser Thr Ser Gln Met His Thr Ala Ser Ser Leu
150                 155                 160                 165
```

Figure 54B. Nucleotide sequence and amino acid sequence of IL-2-FasL-IgFc (SEQ ID NO: 41).

| | |
|---|---|
| gag aag caa ata ggc cac ccc agt cca ccc cct gaa aaa aag gag ctg<br>Glu Lys Gln Ile Gly His Pro Ser Pro Pro Pro Glu Lys Lys Glu Leu<br>170                            175                         180 | 624 |
| agg aaa gtg gcc cat tta aca ggc aag tcc aac tca agg tcc atg cct<br>Arg Lys Val Ala His Leu Thr Gly Lys Ser Asn Ser Arg Ser Met Pro<br>              185                          190                      195 | 672 |
| ctg gaa tgg gaa gac acc tat gga att gtc ctg ctt tct gga gtg aag<br>Leu Glu Trp Glu Asp Thr Tyr Gly Ile Val Leu Leu Ser Gly Val Lys<br>        200                        205                         210 | 720 |
| tat aag aag ggt ggc ctt gtg atc aat gaa act ggg ctg tac ttt gta<br>Tyr Lys Lys Gly Gly Leu Val Ile Asn Glu Thr Gly Leu Tyr Phe Val<br>    215                        220                        225 | 768 |
| tat tcc aaa gta tac ttc cgg ggt caa tct tgc aac aac ctg ccc ctg<br>Tyr Ser Lys Val Tyr Phe Arg Gly Gln Ser Cys Asn Asn Leu Pro Leu<br>230                          235                        240                      245 | 816 |
| agc cac aag gtc tac atg agg aac tct aag tat ccc cag gat ctg gtg<br>Ser His Lys Val Tyr Met Arg Asn Ser Lys Tyr Pro Gln Asp Leu Val<br>            250                        255                        260 | 864 |
| atg atg gag ggg aag atg atg agc tac tgc act act ggg cag atg tgg<br>Met Met Glu Gly Lys Met Met Ser Tyr Cys Thr Thr Gly Gln Met Trp<br>              265                        270                        275 | 912 |
| gcc cgc agc agc tac ctg ggg gca gtg ttc aat ctt acc agt gct gat<br>Ala Arg Ser Ser Tyr Leu Gly Ala Val Phe Asn Leu Thr Ser Ala Asp<br>        280                        285                        290 | 960 |
| cat tta tat gtc aac gta tct gag ctc tct ctg gtc aat ttt gag gaa<br>His Leu Tyr Val Asn Val Ser Glu Leu Ser Leu Val Asn Phe Glu Glu<br>    295                        300                        305 | 1008 |
| tct cag acg ttt ttc ggc tta tat aag ctc gag ccc aaa tct tgt gac<br>Ser Gln Thr Phe Phe Gly Leu Tyr Lys Leu Glu Pro Lys Ser Cys Asp<br>310                          315                        320                      325 | 1056 |
| aaa act cac aca tgc cca ccg tgc cca gca cct gaa ctc ctg ggg gga<br>Lys Thr His Thr Cys Pro Pro Cys Pro Ala Pro Glu Leu Leu Gly Gly<br>                  330                        335                        340 | 1104 |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>              345                        350                        355 | 1152 |

Figure 54C. Nucleotide sequence and amino acid sequence of IL-2-FasL-IgFc (SEQ ID NO: 41).

| | | | | | | | | | | | | | |
|---|---|---|---|---|---|---|---|---|---|---|---|---|---|
| tcc | cgg | acc | cct | gag | gtc | aca | tgc | gtg | gtg | gtg | gac | gtg | agc | cac | gaa | 1200 |
| Ser | Arg | Thr | Pro | Glu | Val | Thr | Cys | Val | Val | Val | Asp | Val | Ser | His | Glu |
| | | 360 | | | | 365 | | | | 370 | | | |

| gac | cct | gag | gtc | aag | ttc | aac | tgg | tac | gtg | gac | ggc | gtg | gag | gtg | cat | 1248 |
| Asp | Pro | Glu | Val | Lys | Phe | Asn | Trp | Tyr | Val | Asp | Gly | Val | Glu | Val | His |
| | 375 | | | | 380 | | | | 385 | | | | |

| aat | gcc | aag | aca | aag | ccg | cgg | gag | gag | cag | tac | aac | agc | acg | tac | cgt | 1296 |
| Asn | Ala | Lys | Thr | Lys | Pro | Arg | Glu | Glu | Gln | Tyr | Asn | Ser | Thr | Tyr | Arg |
| 390 | | | | | 395 | | | | 400 | | | | | 405 |

| gtg | gtc | agc | gtc | ctc | acc | gtc | ctg | cac | cag | gac | tgg | ctg | aat | ggc | aag | 1344 |
| Val | Val | Ser | Val | Leu | Thr | Val | Leu | His | Gln | Asp | Trp | Leu | Asn | Gly | Lys |
| | | | | 410 | | | | 415 | | | | | 420 |

| gag | tac | aag | tgc | aag | gtc | tcc | aac | aaa | gcc | ctc | cca | gcc | ccc | atc | gag | 1392 |
| Glu | Tyr | Lys | Cys | Lys | Val | Ser | Asn | Lys | Ala | Leu | Pro | Ala | Pro | Ile | Glu |
| | | | 425 | | | | 430 | | | | 435 | | |

| aaa | acc | atc | tcc | aaa | gcc | aaa | ggg | cag | ccc | cga | gaa | cca | cag | gtg | tac | 1440 |
| Lys | Thr | Ile | Ser | Lys | Ala | Lys | Gly | Gln | Pro | Arg | Glu | Pro | Gln | Val | Tyr |
| | | 440 | | | | 445 | | | | 450 | | | |

| acc | ctg | ccc | cca | tcc | cgg | gat | gag | ctg | acc | aag | aac | cag | gtc | agc | ctg | 1488 |
| Thr | Leu | Pro | Pro | Ser | Arg | Asp | Glu | Leu | Thr | Lys | Asn | Gln | Val | Ser | Leu |
| | 455 | | | | 460 | | | | 465 | | | | |

| acc | tgc | ctg | gtc | aaa | ggc | ttc | tat | ccc | agc | gac | atc | gcc | gtg | gag | tgg | 1536 |
| Thr | Cys | Leu | Val | Lys | Gly | Phe | Tyr | Pro | Ser | Asp | Ile | Ala | Val | Glu | Trp |
| 470 | | | | 475 | | | | 480 | | | | 485 |

| gag | agc | aat | ggg | cag | ccg | gag | aac | aac | tac | aag | acc | acg | cct | ccc | gtg | 1584 |
| Glu | Ser | Asn | Gly | Gln | Pro | Glu | Asn | Asn | Tyr | Lys | Thr | Thr | Pro | Pro | Val |
| | | | 490 | | | | 495 | | | | 500 | | |

| ctg | gac | tcc | gac | ggc | tcc | ttc | ttc | ctc | tac | agc | aag | ctc | acc | gtg | gac | 1632 |
| Leu | Asp | Ser | Asp | Gly | Ser | Phe | Phe | Leu | Tyr | Ser | Lys | Leu | Thr | Val | Asp |
| | | 505 | | | | 510 | | | | 515 | | | |

| aag | agc | agg | tgg | cag | cag | ggg | aac | gtc | ttc | tca | tgc | tcc | gtg | atg | cat | 1680 |
| Lys | Ser | Arg | Trp | Gln | Gln | Gly | Asn | Val | Phe | Ser | Cys | Ser | Val | Met | His |
| | | 520 | | | | 525 | | | | 530 | | | |

| gag | gct | ctg | cac | aac | cac | tac | acg | cag | aag | agc | ctc | tcc | ctg | tct | ccg | 1728 |
| Glu | Ala | Leu | His | Asn | His | Tyr | Thr | Gln | Lys | Ser | Leu | Ser | Leu | Ser | Pro |
| | 535 | | | | 540 | | | | 545 | | | | |

Figure 54D. Nucleotide sequence and amino acid sequence of IL-2-FasL-IgFc (SEQ ID NO: 41).

```
ggt aaa tgatctaga                                                    1743
Gly Lys
550
```

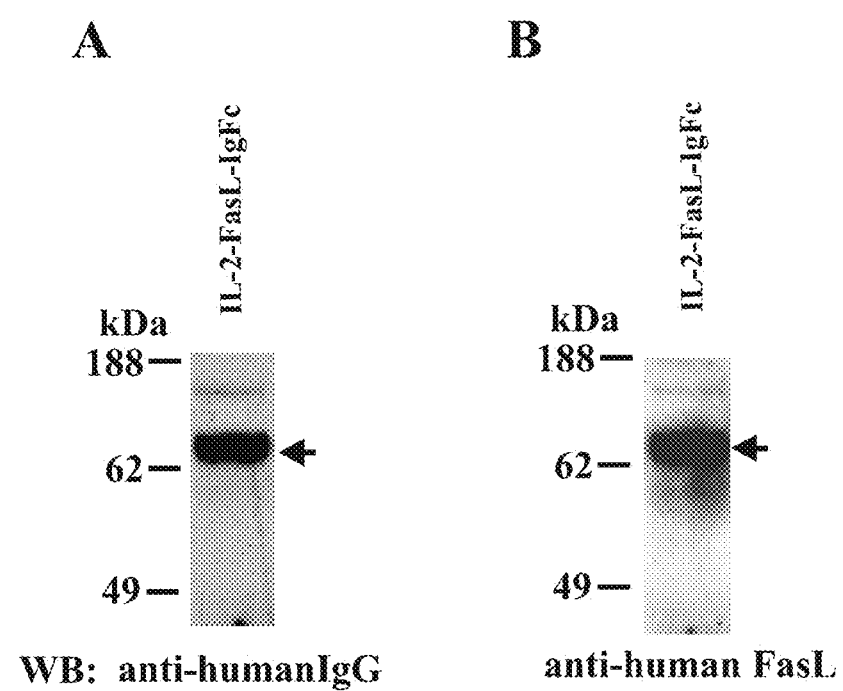
Figure 55. Western blotting analysis of IL-2-FasL-IgFc.

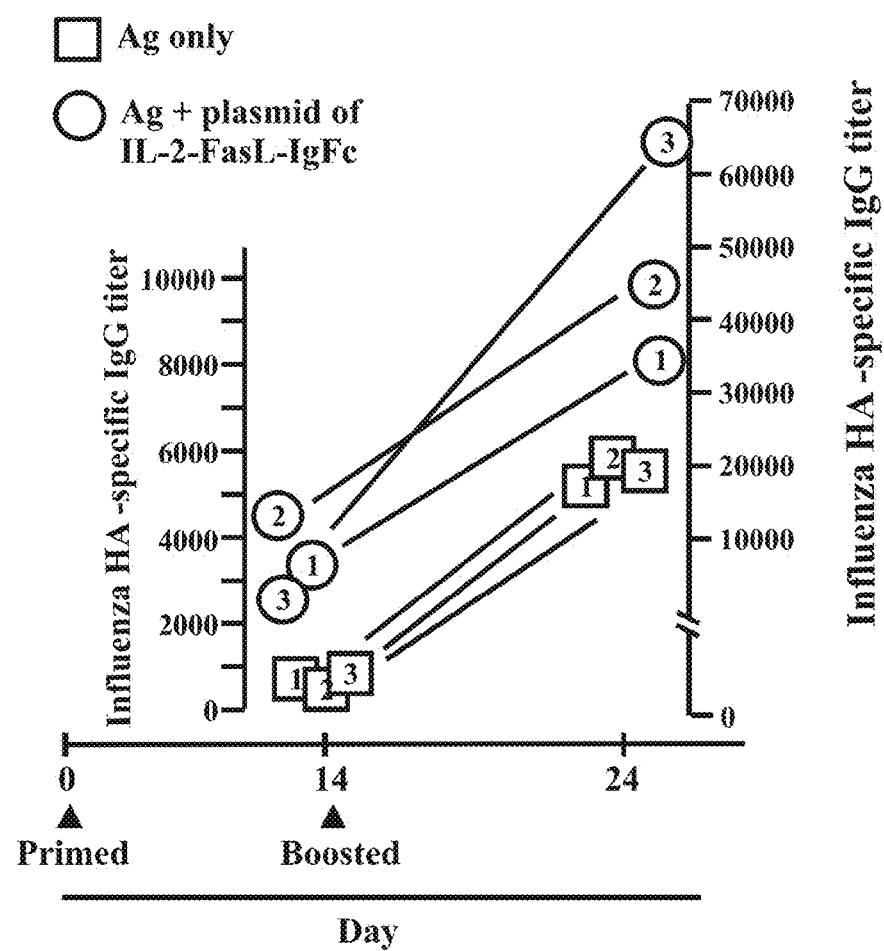
Figure 56. Adjuvant activity of Plasmid DNA of IL-2-FasL-IgFc in mice against Influenza hemaglutinin.

Figure 57. Suppressant activity of IL-2-FasL-IgFc/PCIneo in mice against Influenza hemaglutinin-specific T cell response.

A

Cell viability*

| | 100 | 200 | 300 | 400 | 500 | 600 |

Not immunized

Immunized

Immunized + IL-2-FasL-IgFc

B

Cell viability*

| | 100 | 110 | 120 | 130 | 140 | 150 | 160 | 170 |

Not immunized

Immunized

Immunized + IL-2-FasL-IgFc

```
                              SEQUENCE LISTING

<160> NUMBER OF SEQ ID NOS: 62

<210> SEQ ID NO 1
<211> LENGTH: 1834
<212> TYPE: DNA
<213> ORGANISM: Homo sapiens
<220> FEATURE:
<221> NAME/KEY: CDS
<222> LOCATION: (73)..(855)

<400> SEQUENCE: 1
actttgacag tcttctcatg ctgcctctgc caccttctct gccagaagat accatttcaa        60
ctttaacaca gc atg atc gaa aca tac aac caa act tct ccc cga tct gcg      111
              Met Ile Glu Thr Tyr Asn Gln Thr Ser Pro Arg Ser Ala
                1               5                  10 gcc act gga ctg ccc atc agc atg aaa att ttt atg tat tta ctt act         159
Ala Thr Gly Leu Pro Ile Ser Met Lys Ile Phe Met Tyr Leu Leu Thr
     15                  20                  25 gtt ttt ctt atc acc cag atg att ggg tca gca ctt ttt gct gtg tat         207
Val Phe Leu Ile Thr Gln Met Ile Gly Ser Ala Leu Phe Ala Val Tyr
 30                  35                  40                  45 ctt cat aga agg ttg gac aag ata gaa gat gaa agg aat ctt cat gaa         255
Leu His Arg Arg Leu Asp Lys Ile Glu Asp Glu Arg Asn Leu His Glu
                 50                  55                  60 gat ttt gta ttc atg aaa acg ata cag aga tgc aac aca gga gaa aga         303
Asp Phe Val Phe Met Lys Thr Ile Gln Arg Cys Asn Thr Gly Glu Arg
             65                  70                  75 tcc tta tcc tta ctg aac tgt gag gag att aaa agc cag ttt gaa ggc         351
Ser Leu Ser Leu Leu Asn Cys Glu Glu Ile Lys Ser Gln Phe Glu Gly
         80                  85                  90 ttt gtg aag gat ata atg tta aac aaa gag gag acg aag aaa gaa aac         399
Phe Val Lys Asp Ile Met Leu Asn Lys Glu Glu Thr Lys Lys Glu Asn
     95                  100                 105 agc ttt gaa atg caa aaa ggt gat cag aat cct caa att gcg gca cat         447
Ser Phe Glu Met Gln Lys Gly Asp Gln Asn Pro Gln Ile Ala Ala His
110                 115                 120                 125 gtc ata agt gag gcc agc agt aaa aca aca tct gtg tta cag tgg gct         495
Val Ile Ser Glu Ala Ser Ser Lys Thr Thr Ser Val Leu Gln Trp Ala
                 130                 135                 140 gaa aaa gga tac tac acc atg agc aac aac ttg gta acc ctg gaa aat         543
Glu Lys Gly Tyr Tyr Thr Met Ser Asn Asn Leu Val Thr Leu Glu Asn
             145                 150                 155 ggg aaa cag ctg acc gtt aaa aga caa gga ctc tat tat atc tat gcc         591
```

-continued

```
Gly Lys Gln Leu Thr Val Lys Arg Gln Gly Leu Tyr Tyr Ile Tyr Ala
            160                 165                 170 caa gtc acc ttc tgt tcc aat cgg gaa gct tcg agt caa gct cca ttt    639
Gln Val Thr Phe Cys Ser Asn Arg Glu Ala Ser Ser Gln Ala Pro Phe
        175                 180                 185 ata gcc agc ctc tgc cta aag tcc ccc ggt aga ttc gag aga atc tta    687
Ile Ala Ser Leu Cys Leu Lys Ser Pro Gly Arg Phe Glu Arg Ile Leu
190                 195                 200                 205 ctc aga gct gca aat acc cac agt tcc gcc aaa cct tgc ggg caa caa    735
Leu Arg Ala Ala Asn Thr His Ser Ser Ala Lys Pro Cys Gly Gln Gln
                210                 215                 220 tcc att cac ttg gga gga gta ttt gaa ttg caa cca ggt gct tcg gtg    783
Ser Ile His Leu Gly Gly Val Phe Glu Leu Gln Pro Gly Ala Ser Val
            225                 230                 235 ttt gtc aat gtg act gat cca agc caa gtg agc cat ggc act ggc ttc    831
Phe Val Asn Val Thr Asp Pro Ser Gln Val Ser His Gly Thr Gly Phe
        240                 245                 250 acg tcc ttt ggc tta ctc aaa ctc tgaacagtgt caccttgcag gctgtggtgg   885
Thr Ser Phe Gly Leu Leu Lys Leu
        255                 260 agctgacgct gggagtcttc ataatacagc acagcggtta agcccacccc ctgttaactg    945
cctatttata accctaggat cctccttatg agaactatt tattatacac tccaaggcat     1005
gtagaactgt aataagtgaa ttacaggtca catgaaacca aaacgggccc tgctccataa    1065
gagcttatat atctgaagca gcaaccccac tgatgcagac atccagagag tcctatgaaa    1125
agacaaggcc attatgcaca ggttgaattc tgagtaaaca gcagataact tgccaagttc    1185
agttttgttt ctttgcgtgc agtgtctttc catggataat gcatttgatt tatcagtgaa    1245
gatgcagaag ggaaatgggg agcctcagct cacattcagt tatggttgac tctgggttcc    1305
tatggccttg ttggagggg ccaggctcta gaacgtctaa cacagtggag aaccgaaacc     1365 ccccccccc cccgccacc ctctcggaca gttattcatt ctctttcaat ctctctctct      1425
ccatctctct ctttcagtct ctctctctca acctctttct tccaatctct ctttctcaat    1485
ctctctgttt ccctttgtca gtctcttccc tcccccagtc tctcttctca atccccttt     1545 ctaacacaca cacacacaca cacacacaca cacacacaca cacacacaca cacacagagt    1605
caggccgttg ctagtcagtt ctcttctttc caccctgtcc ctatctctac cactatagat    1665
gagggtgagg agtagggagt gcagccctga gcctgcccac tcctcattac gaaatgactg    1725
tatttaaagg aaatctattg tatctacctg cagtctccat tgtttccaga gtgaacttgt    1785
aattatcttg ttatttattt tttgaataat aaagacctct taacattaa               1834
```

<210> SEQ ID NO 2
<211> LENGTH: 261
<212> TYPE: PRT
<213> ORGANISM: Homo sapiens

<400> SEQUENCE: 2

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60
```

```
                                    -continued

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 1880
<212> TYPE: DNA
<213> ORGANISM: Homo sapiens
<220> FEATURE:
<221> NAME/KEY: CDS
<222> LOCATION: (53)..(808)
<220> FEATURE:
<221> NAME/KEY: sig_peptide
<222> LOCATION: (53)..(127)
<220> FEATURE:
<221> NAME/KEY: mat_peptide
<222> LOCATION: (128)..(808)

<400> SEQUENCE: 3
agccgagagg tgtcaccccc agcgggcgcg ggccggagca cgggcaccca gc atg ggg      58
                                                         Met Gly
                                                         -25 gta ctg ctc aca cag agg acg ctg ctc agt ctg gtc ctt gca ctc ctg      106
Val Leu Leu Thr Gln Arg Thr Leu Leu Ser Leu Val Leu Ala Leu Leu
        -20                 -15                 -10 ttt cca agc atg gcg agc atg gcg gct ata ggc agc tgc tcg aaa gag      154
Phe Pro Ser Met Ala Ser Met Ala Ala Ile Gly Ser Cys Ser Lys Glu
    -5              -1   1               5 tac cgc gtg ctc ctt ggc cag ctc cag aag cag aca gat ctc atg cag      202
Tyr Arg Val Leu Leu Gly Gln Leu Gln Lys Gln Thr Asp Leu Met Gln
 10              15                  20                  25 gac acc agc aga ctc ctg gac ccc tat ata cgt atc caa ggc ctg gat      250
Asp Thr Ser Arg Leu Leu Asp Pro Tyr Ile Arg Ile Gln Gly Leu Asp
            30                  35                  40 gtt cct aaa ctg aga gag cac tgc agg gag cgc ccc ggg gcc ttc ccc      298
Val Pro Lys Leu Arg Glu His Cys Arg Glu Arg Pro Gly Ala Phe Pro
        45                  50                  55
```

```
agt gag gag acc ctg agg ggg ctg ggc agg cgg ggc ttc ctg cag acc      346
Ser Glu Glu Thr Leu Arg Gly Leu Gly Arg Arg Gly Phe Leu Gln Thr
         60                  65                  70 ctc aat gcc aca ctg ggc tgc gtc ctg cac aga ctg gcc gac tta gag      394
Leu Asn Ala Thr Leu Gly Cys Val Leu His Arg Leu Ala Asp Leu Glu
 75                  80                  85 cag cgc ctc ccc aag gcc cag gat ttg gag agg tct ggg ctg aac atc      442
Gln Arg Leu Pro Lys Ala Gln Asp Leu Glu Arg Ser Gly Leu Asn Ile
90                   95                 100                 105 gag gac ttg gag aag ctg cag atg gcg agg ccg aac atc ctc ggg ctc      490
Glu Asp Leu Glu Lys Leu Gln Met Ala Arg Pro Asn Ile Leu Gly Leu
                110                 115                 120 agg aac aac atc tac tgc atg gcc cag ctg ctg gac aac tca gac acg      538
Arg Asn Asn Ile Tyr Cys Met Ala Gln Leu Leu Asp Asn Ser Asp Thr
            125                 130                 135 gct gag ccc acg aag gct ggc cgg ggg gcc tct cag ccg ccc acc ccc      586
Ala Glu Pro Thr Lys Ala Gly Arg Gly Ala Ser Gln Pro Pro Thr Pro
        140                 145                 150 acc cct gcc tcg gat gct ttt cag cgc aag ctg gag ggc tgc agg ttc      634
Thr Pro Ala Ser Asp Ala Phe Gln Arg Lys Leu Glu Gly Cys Arg Phe
    155                 160                 165 ctg cat ggc tac cat cgc ttc atg cac tca gtg ggg cgg gtc ttc agc      682
Leu His Gly Tyr His Arg Phe Met His Ser Val Gly Arg Val Phe Ser
170                 175                 180                 185 aag tgg ggg gag agc ccg aac cgg agc cgg aga cac agc ccc cac cag      730
Lys Trp Gly Glu Ser Pro Asn Arg Ser Arg Arg His Ser Pro His Gln
                190                 195                 200 gcc ctg agg aag ggg gtg cgc agg acc aga ccc tcc agg aaa ggc aag      778
Ala Leu Arg Lys Gly Val Arg Arg Thr Arg Pro Ser Arg Lys Gly Lys
            205                 210                 215 aga ctc atg acc agg gga cag ctg ccc cgg tagcctcgag agcccccctt        828
Arg Leu Met Thr Arg Gly Gln Leu Pro Arg
        220                 225 gccggtgaag gatgcggcag gtgctctgtg gatgagagga accatcgcag gatgacagct    888
cccgggtccc caaacctgtt cccctctgct actagccact gagaagtgca ctttaagagg    948
tgggagctgg gcagacccct ctacctcctc caggctggga gacagagtca ggctgttgcg   1008
ctcccacctc agccccaagt tccccaggcc cagtggggtg gccgggcggg ccacgcggga   1068
ccgactttcc attgattcag gggtctgatg acacaggctg actcatggcc gggctgactg   1128
cccccctgcc ttgctccccg aggcctgccg gtccttccct ctcatgactt gcagggccgt   1188
tgcccccaga cttcctcctt tccgtgtttc tgaaggggag gtcacagcct gagctggcct   1248
cctatgcctc atcatgtccc aaaccagaca cctggatgtc tgggtgacct cactttaggc   1308
agctgtaaca gcggcagggt gtcccaggag ccctgatccg ggggtccagg gaatggagct   1368
caggtcccag gccagccccg aagtcgccac gtggcctggg gcaggtcact ttacctctgt   1428
ggacctgttt tctctttgtg aagctaggga gttagaggct gtacaaggcc cccactgccc   1488
gtcggttgct tggattccct gacgtaaggt ggatattaaa aatctgtaaa tcaggacagg   1548
tggtgcaaat ggcgctggga ggtgtacacg gaggtctctg taaaagcaga cccacctccc   1608
agcgccggga agcccgtctt gggtcctcgc tgctggctgc tccccctggt ggtggatcct   1668
ggaattttct cacgcaggag ccattgctct cctagagggg gtctcagaaa ctgcgaggcc   1728
agttccttgg agggacatga ctaatttatc gattttttatc aatttttatc agttttatat   1788
ttataagcct tatttatgat gtatatttaa tgttaatatt gtgcaaactt atatttaaaa   1848
```
cttgcctggt ttctaaaaaa aaaaaaaaaa aa                              1880

<210> SEQ ID NO 4
<211> LENGTH: 252
<212> TYPE: PRT
<213> ORGANISM: Homo sapiens

<400> SEQUENCE: 4

Met Gly Val Leu Leu Thr Gln Arg Thr Leu Leu Ser Leu Val Leu Ala
-25                 -20                 -15                 -10

Leu Leu Phe Pro Ser Met Ala Ser Met Ala Ala Ile Gly Ser Cys Ser
            -5                  -1   1               5

Lys Glu Tyr Arg Val Leu Leu Gly Gln Leu Gln Lys Gln Thr Asp Leu
            10                  15                  20

Met Gln Asp Thr Ser Arg Leu Leu Asp Pro Tyr Ile Arg Ile Gln Gly
        25                  30                  35

Leu Asp Val Pro Lys Leu Arg Glu His Cys Arg Glu Arg Pro Gly Ala
40                  45                  50                  55

Phe Pro Ser Glu Glu Thr Leu Arg Gly Leu Gly Arg Arg Gly Phe Leu
                60                  65                  70

Gln Thr Leu Asn Ala Thr Leu Gly Cys Val Leu His Arg Leu Ala Asp
            75                  80                  85

Leu Glu Gln Arg Leu Pro Lys Ala Gln Asp Leu Glu Arg Ser Gly Leu
        90                  95                  100

Asn Ile Glu Asp Leu Glu Lys Leu Gln Met Ala Arg Pro Asn Ile Leu
    105                 110                 115

Gly Leu Arg Asn Asn Ile Tyr Cys Met Ala Gln Leu Leu Asp Asn Ser
120                 125                 130                 135

Asp Thr Ala Glu Pro Thr Lys Ala Gly Arg Gly Ala Ser Gln Pro Pro
                140                 145                 150

Thr Pro Thr Pro Ala Ser Asp Ala Phe Gln Arg Lys Leu Glu Gly Cys
            155                 160                 165

Arg Phe Leu His Gly Tyr His Arg Phe Met His Ser Val Gly Arg Val
        170                 175                 180

Phe Ser Lys Trp Gly Glu Ser Pro Asn Arg Ser Arg Arg His Ser Pro
    185                 190                 195

His Gln Ala Leu Arg Lys Gly Val Arg Arg Thr Arg Pro Ser Arg Lys
200                 205                 210                 215

Gly Lys Arg Leu Met Thr Arg Gly Gln Leu Pro Arg
                220                 225

<210> SEQ ID NO 5
<211> LENGTH: 768
<212> TYPE: DNA
<213> ORGANISM: Homo sapiens
<220> FEATURE:
<221> NAME/KEY: CDS
<222> LOCATION: (1)..(765)

<400> SEQUENCE: 5 atg aaa aag aca gct atc gcg att gca gtg gca ctg gct ggt ttc gct      48
Met Lys Lys Thr Ala Ile Ala Ile Ala Val Ala Leu Ala Gly Phe Ala
1               5                   10                  15 acc gta gcg cag gcc gac gtc gag tcc aaa tct tgt gac aaa act cac      96
Thr Val Ala Gln Ala Asp Val Glu Ser Lys Ser Cys Asp Lys Thr His
            20                  25                  30 aca tgc cca ccg tgc cca gca cct gaa ctc ctg ggg gga ccg tca gtc     144
Thr Cys Pro Pro Cys Pro Ala Pro Glu Leu Leu Gly Gly Pro Ser Val -continued

```
                        35                  40                  45
ttc ctc ttc ccc cca aaa ccc aag gac acc ctc atg atc tcc cgg acc        192
Phe Leu Phe Pro Pro Lys Pro Lys Asp Thr Leu Met Ile Ser Arg Thr
 50                  55                  60 cct gag gtc aca tgc gtg gtg gtg gac gtg agc cac gaa gac cct gag        240
Pro Glu Val Thr Cys Val Val Val Asp Val Ser His Glu Asp Pro Glu
 65                  70                  75                  80 gtc aag ttc aac tgg tac gtg gac ggc gtg gag gtg cat aat gcc aag        288
Val Lys Phe Asn Trp Tyr Val Asp Gly Val Glu Val His Asn Ala Lys
                 85                  90                  95 aca aag ccg cgg gag gag cag tac aac agc acg tac cgt gtg gtc agc        336
Thr Lys Pro Arg Glu Glu Gln Tyr Asn Ser Thr Tyr Arg Val Val Ser
            100                 105                 110 gtc ctc acc gtc ctg cac cag gac tgg ctg aat ggc aag gag tac aag        384
Val Leu Thr Val Leu His Gln Asp Trp Leu Asn Gly Lys Glu Tyr Lys
        115                 120                 125 tgc aag gtc tcc aac aaa gcc ctc cca gcc ccc atc gag aaa acc atc        432
Cys Lys Val Ser Asn Lys Ala Leu Pro Ala Pro Ile Glu Lys Thr Ile
    130                 135                 140 tcc aaa gcc aaa ggg cag ccc cga gag cca cag gtg tac acc ctg ccc        480
Ser Lys Ala Lys Gly Gln Pro Arg Glu Pro Gln Val Tyr Thr Leu Pro
145                 150                 155                 160 cca tcc cgg gat gag ctg acc aag aac cag gtc agc ctg acc tgc ctg        528
Pro Ser Arg Asp Glu Leu Thr Lys Asn Gln Val Ser Leu Thr Cys Leu
                165                 170                 175 gtc aaa ggc ttc tat ccc agc gac atc gcc gtg gag tgg gag agc aat        576
Val Lys Gly Phe Tyr Pro Ser Asp Ile Ala Val Glu Trp Glu Ser Asn
            180                 185                 190 ggg cag ccg gag aac aac tac aag acc acg cct ccc gtg ctg gac tcc        624
Gly Gln Pro Glu Asn Asn Tyr Lys Thr Thr Pro Pro Val Leu Asp Ser
        195                 200                 205 gac ggc tcc ttc ttc ctc tac agc aag ctc acc gtg gac aag agc agg        672
Asp Gly Ser Phe Phe Leu Tyr Ser Lys Leu Thr Val Asp Lys Ser Arg
    210                 215                 220 tgg cag cag ggg aac gtc ttc tca tgc tcc gtg atg cat gag gct ctg        720
Trp Gln Gln Gly Asn Val Phe Ser Cys Ser Val Met His Glu Ala Leu
225                 230                 235                 240 cac aac cac tac acg cag aag agc ctc tcc ctg tct ccg ggt aaa tga        768
His Asn His Tyr Thr Gln Lys Ser Leu Ser Leu Ser Pro Gly Lys
                245                 250                 255
```

<210> SEQ ID NO 6
<211> LENGTH: 255
<212> TYPE: PRT
<213> ORGANISM: Homo sapiens

<400> SEQUENCE: 6

```
Met Lys Lys Thr Ala Ile Ala Ile Ala Val Ala Leu Ala Gly Phe Ala
 1               5                  10                  15

Thr Val Ala Gln Ala Asp Val Glu Ser Lys Ser Cys Asp Lys Thr His
                20                  25                  30

Thr Cys Pro Pro Cys Pro Ala Pro Glu Leu Leu Gly Gly Pro Ser Val
            35                  40                  45

Phe Leu Phe Pro Pro Lys Pro Lys Asp Thr Leu Met Ile Ser Arg Thr
 50                  55                  60

Pro Glu Val Thr Cys Val Val Val Asp Val Ser His Glu Asp Pro Glu
 65                  70                  75                  80

Val Lys Phe Asn Trp Tyr Val Asp Gly Val Glu Val His Asn Ala Lys
                 85                  90                  95
```

```
Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Pro Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys
                245                 250                 255

<210> SEQ ID NO 7
<211> LENGTH: 1434
<212> TYPE: DNA
<213> ORGANISM: Homo sapiens
<220> FEATURE:
<221> NAME/KEY: CDS
<222> LOCATION: (7)..(1425)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1425)

<400> SEQUENCE: 7 gctagc atg ggg gta ctg ctc aca cag agg acg ctg ctc agt ctg gtc     48
       Met Gly Val Leu Leu Thr Gln Arg Thr Leu Leu Ser Leu Val
       -25                 -20                 -15 ctt gca ctc ctg ttt cca agc atg gcg agc atg ctt cat aga agg ttg    96
Leu Ala Leu Leu Phe Pro Ser Met Ala Ser Met Leu His Arg Arg Leu
    -10                 -5              -1  1               5 gac aag ata gaa gat gaa agg aat ctt cat gaa gat ttt gta ttc atg   144
Asp Lys Ile Glu Asp Glu Arg Asn Leu His Glu Asp Phe Val Phe Met
                10                  15                  20 aaa acg ata cag aga tgc aac aca gga gaa aga tcc tta tcc tta ctg   192
Lys Thr Ile Gln Arg Cys Asn Thr Gly Glu Arg Ser Leu Ser Leu Leu
            25                  30                  35 aac tgt gag gag att aaa agc cag ttt gaa ggc ttt gtg aag gat ata   240
Asn Cys Glu Glu Ile Lys Ser Gln Phe Glu Gly Phe Val Lys Asp Ile
        40                  45                  50 atg tta aac aaa gag gag acg aag aaa gaa aac agc ttt gaa atg caa   288
Met Leu Asn Lys Glu Glu Thr Lys Lys Glu Asn Ser Phe Glu Met Gln
55                  60                  65 aaa ggt gat cag aat cct caa att gcg gca cat gtc ata agt gag gcc   336
Lys Gly Asp Gln Asn Pro Gln Ile Ala Ala His Val Ile Ser Glu Ala
70                  75                  80                  85 agc agt aaa aca aca tct gtg tta cag tgg gct gaa aaa gga tac tac   384
Ser Ser Lys Thr Thr Ser Val Leu Gln Trp Ala Glu Lys Gly Tyr Tyr
                90                  95                  100
```

```
acc atg agc aac aac ttg gta acc ctg gaa aat ggg aaa cag ctg acc      432
Thr Met Ser Asn Asn Leu Val Thr Leu Glu Asn Gly Lys Gln Leu Thr
        105                 110                 115 gtt aaa aga caa gga ctc tat tat atc tat gcc caa gtc acc ttc tgt      480
Val Lys Arg Gln Gly Leu Tyr Tyr Ile Tyr Ala Gln Val Thr Phe Cys
    120                 125                 130 tcc aat cgg gaa gct tcg agt caa gct cca ttt ata gcc agc ctc tgc      528
Ser Asn Arg Glu Ala Ser Ser Gln Ala Pro Phe Ile Ala Ser Leu Cys
135                 140                 145 cta aag tcc ccc ggt aga ttc gag aga atc tta ctc aga gct gca aat      576
Leu Lys Ser Pro Gly Arg Phe Glu Arg Ile Leu Leu Arg Ala Ala Asn
150                 155                 160                 165 acc cac agt tcc gcc aaa cct tgc ggg caa caa tcc att cac ttg gga      624
Thr His Ser Ser Ala Lys Pro Cys Gly Gln Gln Ser Ile His Leu Gly
                170                 175                 180 gga gta ttt gaa ttg caa cca ggt gct tcg gtg ttt gtc aat gtg act      672
Gly Val Phe Glu Leu Gln Pro Gly Ala Ser Val Phe Val Asn Val Thr
            185                 190                 195 gat cca agc caa gtg agc cat ggc act ggc ttc acg tcc ttt ggc tta      720
Asp Pro Ser Gln Val Ser His Gly Thr Gly Phe Thr Ser Phe Gly Leu
        200                 205                 210 ctc aaa ctc gag ccc aaa tct tgt gac aaa act cac aca tgc cca ccg      768
Leu Lys Leu Glu Pro Lys Ser Cys Asp Lys Thr His Thr Cys Pro Pro
    215                 220                 225 tgc cca gca cct gaa ctc ctg ggg gga ccg tca gtc ttc ctc ttc ccc      816
Cys Pro Ala Pro Glu Leu Leu Gly Gly Pro Ser Val Phe Leu Phe Pro
230                 235                 240                 245 cca aaa ccc aag gac acc ctc atg atc tcc cgg acc cct gag gtc aca      864
Pro Lys Pro Lys Asp Thr Leu Met Ile Ser Arg Thr Pro Glu Val Thr
                250                 255                 260 tgc gtg gtg gtg gac gtg agc cac gaa gac cct gag gtc aag ttc aac      912
Cys Val Val Val Asp Val Ser His Glu Asp Pro Glu Val Lys Phe Asn
            265                 270                 275 tgg tac gtg gac ggc gtg gag gtg cat aat gcc aag aca aag ccg cgg      960
Trp Tyr Val Asp Gly Val Glu Val His Asn Ala Lys Thr Lys Pro Arg
        280                 285                 290 gag gag cag tac aac agc acg tac cgt gtg gtc agc gtc ctc acc gtc     1008
Glu Glu Gln Tyr Asn Ser Thr Tyr Arg Val Val Ser Val Leu Thr Val
    295                 300                 305 ctg cac cag gac tgg ctg aat ggc aag gag tac aag tgc aag gtc tcc     1056
Leu His Gln Asp Trp Leu Asn Gly Lys Glu Tyr Lys Cys Lys Val Ser
310                 315                 320                 325 aac aaa gcc ctc cca gcc ccc atc gag aaa acc atc tcc aaa gcc aaa     1104
Asn Lys Ala Leu Pro Ala Pro Ile Glu Lys Thr Ile Ser Lys Ala Lys
                330                 335                 340 ggg cag ccc cga gaa cca cag gtg tac acc ctg ccc cca tcc cgg gat     1152
Gly Gln Pro Arg Glu Pro Gln Val Tyr Thr Leu Pro Pro Ser Arg Asp
            345                 350                 355 gag ctg acc aag aac cag gtc agc ctg acc tgc ctg gtc aaa ggc ttc     1200
Glu Leu Thr Lys Asn Gln Val Ser Leu Thr Cys Leu Val Lys Gly Phe
        360                 365                 370 tat ccc agc gac atc gcc gtg gag tgg gag agc aat ggg cag ccg gag     1248
Tyr Pro Ser Asp Ile Ala Val Glu Trp Glu Ser Asn Gly Gln Pro Glu
    375                 380                 385 aac aac tac aag acc acg cct ccc gtg ctg gac tcc gac ggc tcc ttc     1296
Asn Asn Tyr Lys Thr Thr Pro Pro Val Leu Asp Ser Asp Gly Ser Phe
390                 395                 400                 405 ttc ctc tac agc aag ctc acc gtg gac aag agc agg tgg cag cag ggg     1344
Phe Leu Tyr Ser Lys Leu Thr Val Asp Lys Ser Arg Trp Gln Gln Gly
```

```
           410                 415                 420
aac gtc ttc tca tgc tcc gtg atg cat gag gct ctg cac aac cac tac     1392
Asn Val Phe Ser Cys Ser Val Met His Glu Ala Leu His Asn His Tyr
            425                 430                 435 acg cag aag agc ctc tcc ctg tct ccg ggt aaa tgatctaga               1434
Thr Gln Lys Ser Leu Ser Leu Ser Pro Gly Lys
            440                 445

<210> SEQ ID NO 8
<211> LENGTH: 473
<212> TYPE: PRT
<213> ORGANISM: Homo sapiens

<400> SEQUENCE: 8

Met Gly Val Leu Leu Thr Gln Arg Thr Leu Leu Ser Leu Val Leu Ala
-25                 -20                 -15                 -10

Leu Leu Phe Pro Ser Met Ala Ser Met Leu His Arg Arg Leu Asp Lys
                -5                  -1  1               5

Ile Glu Asp Glu Arg Asn Leu His Glu Asp Phe Val Phe Met Lys Thr
            10                  15                  20

Ile Gln Arg Cys Asn Thr Gly Glu Arg Ser Leu Ser Leu Leu Asn Cys
        25                  30                  35

Glu Glu Ile Lys Ser Gln Phe Glu Gly Phe Val Lys Asp Ile Met Leu
40                  45                  50                  55

Asn Lys Glu Glu Thr Lys Lys Glu Asn Ser Phe Glu Met Gln Lys Gly
                60                  65                  70

Asp Gln Asn Pro Gln Ile Ala Ala His Val Ile Ser Glu Ala Ser Ser
            75                  80                  85

Lys Thr Thr Ser Val Leu Gln Trp Ala Glu Lys Gly Tyr Tyr Thr Met
        90                  95                  100

Ser Asn Asn Leu Val Thr Leu Glu Asn Gly Lys Gln Leu Thr Val Lys
    105                 110                 115

Arg Gln Gly Leu Tyr Tyr Ile Tyr Ala Gln Val Thr Phe Cys Ser Asn
120                 125                 130                 135

Arg Glu Ala Ser Ser Gln Ala Pro Phe Ile Ala Ser Leu Cys Leu Lys
                140                 145                 150

Ser Pro Gly Arg Phe Glu Arg Ile Leu Leu Arg Ala Ala Asn Thr His
            155                 160                 165

Ser Ser Ala Lys Pro Cys Gly Gln Gln Ser Ile His Leu Gly Gly Val
        170                 175                 180

Phe Glu Leu Gln Pro Gly Ala Ser Val Phe Val Asn Val Thr Asp Pro
185                 190                 195

Ser Gln Val Ser His Gly Thr Gly Phe Thr Ser Phe Gly Leu Leu Lys
200                 205                 210                 215

Leu Glu Pro Lys Ser Cys Asp Lys Thr His Thr Cys Pro Pro Cys Pro
                220                 225                 230

Ala Pro Glu Leu Leu Gly Gly Pro Ser Val Phe Leu Phe Pro Pro Lys
            235                 240                 245

Pro Lys Asp Thr Leu Met Ile Ser Arg Thr Pro Glu Val Thr Cys Val
        250                 255                 260

Val Val Asp Val Ser His Glu Asp Pro Glu Val Lys Phe Asn Trp Tyr
    265                 270                 275

Val Asp Gly Val Glu Val His Asn Ala Lys Thr Lys Pro Arg Glu Glu
280                 285                 290                 295

Gln Tyr Asn Ser Thr Tyr Arg Val Val Ser Val Leu Thr Val Leu His
```

```
                           300                 305                 310
       Gln Asp Trp Leu Asn Gly Lys Glu Tyr Lys Cys Lys Val Ser Asn Lys
                       315                 320                 325

Ala Leu Pro Ala Pro Ile Glu Lys Thr Ile Ser Lys Ala Lys Gly Gln
                   330                 335                 340

Pro Arg Glu Pro Gln Val Tyr Thr Leu Pro Pro Ser Arg Asp Glu Leu
               345                 350                 355

Thr Lys Asn Gln Val Ser Leu Thr Cys Leu Val Lys Gly Phe Tyr Pro
       360                 365                 370                 375

Ser Asp Ile Ala Val Glu Trp Glu Ser Asn Gly Gln Pro Glu Asn Asn
                       380                 385                 390

Tyr Lys Thr Thr Pro Pro Val Leu Asp Ser Asp Gly Ser Phe Phe Leu
                   395                 400                 405

Tyr Ser Lys Leu Thr Val Asp Lys Ser Arg Trp Gln Gln Gly Asn Val
               410                 415                 420

Phe Ser Cys Ser Val Met His Glu Ala Leu His Asn His Tyr Thr Gln
       425                 430                 435

Lys Ser Leu Ser Leu Ser Pro Gly Lys
       440                 445

<210> SEQ ID NO 9
<211> LENGTH: 1909
<212> TYPE: DNA
<213> ORGANISM: Homo sapiens
<220> FEATURE:
<221> NAME/KEY: CDS
<222> LOCATION: (158)..(1000)

<400> SEQUENCE: 9
gaggtgtttc ccttagctat ggaaactcta taagagagat ccagcttgcc tcctcttgag    60
cagtcagcaa cagggtcccg tccttgacac ctcagcctct acaggactga aagaagtaa    120 aaccgtttgc tggggctggc ctgactcacc agctgcc atg cag cag ccc ttc aat    175
                                        Met Gln Gln Pro Phe Asn
                                          1               5 tac cca tat ccc cag atc tac tgg gtg gac agc agt gcc agc tct ccc    223
Tyr Pro Tyr Pro Gln Ile Tyr Trp Val Asp Ser Ser Ala Ser Ser Pro
            10                  15                  20 tgg gcc cct cca ggc aca gtt ctt ccc tgt cca acc tct gtg ccc aga    271
Trp Ala Pro Pro Gly Thr Val Leu Pro Cys Pro Thr Ser Val Pro Arg
    25                  30                  35 agg cct ggt caa agg agg cca cca cca ccg cca ccg cca cca cta        319
Arg Pro Gly Gln Arg Arg Pro Pro Pro Pro Pro Pro Pro Pro Leu
40                  45                  50 cca cct ccg ccg ccg ccg cca cca ctg cct cca cta ccg ctg cca ccc    367
Pro Pro Pro Pro Pro Pro Pro Leu Pro Pro Leu Pro Leu Pro Pro
55                  60                  65                  70 ctg aag aag aga ggg aac cac agc aca ggc ctg tgt ctc ctt gtg atg    415
Leu Lys Lys Arg Gly Asn His Ser Thr Gly Leu Cys Leu Leu Val Met
                75                  80                  85 ttt ttc atg gtt ctg gtt gcc ttg gta gga ttg ggc ctg ggg atg ttt    463
Phe Phe Met Val Leu Val Ala Leu Val Gly Leu Gly Leu Gly Met Phe
            90                  95                 100 cag ctc ttc cac cta cag aag gag ctg gca gaa ctc cga gag tct acc    511
Gln Leu Phe His Leu Gln Lys Glu Leu Ala Glu Leu Arg Glu Ser Thr
        105                 110                 115 agc cag atg cac aca gca tca tct ttg gag aag caa ata ggc cac ccc    559
Ser Gln Met His Thr Ala Ser Ser Leu Glu Lys Gln Ile Gly His Pro
    120                 125                 130
```

```
agt cca ccc cct gaa aaa aag gag ctg agg aaa gtg gcc cat tta aca      607
Ser Pro Pro Pro Glu Lys Lys Glu Leu Arg Lys Val Ala His Leu Thr
135                 140                 145                 150 ggc aag tcc aac tca agg tcc atg cct ctg gaa tgg gaa gac acc tat      655
Gly Lys Ser Asn Ser Arg Ser Met Pro Leu Glu Trp Glu Asp Thr Tyr
                155                 160                 165 gga att gtc ctg ctt tct gga gtg aag tat aag aag ggt ggc ctt gtg      703
Gly Ile Val Leu Leu Ser Gly Val Lys Tyr Lys Lys Gly Gly Leu Val
            170                 175                 180 atc aat gaa act ggg ctg tac ttt gta tat tcc aaa gta tac ttc cgg      751
Ile Asn Glu Thr Gly Leu Tyr Phe Val Tyr Ser Lys Val Tyr Phe Arg
        185                 190                 195 ggt caa tct tgc aac aac ctg ccc ctg agc cac aag gtc tac atg agg      799
Gly Gln Ser Cys Asn Asn Leu Pro Leu Ser His Lys Val Tyr Met Arg
    200                 205                 210 aac tct aag tat ccc cag gat ctg gtg atg atg gag ggg aag atg atg      847
Asn Ser Lys Tyr Pro Gln Asp Leu Val Met Met Glu Gly Lys Met Met
215                 220                 225                 230 agc tac tgc act act ggg cag atg tgg gcc cgc agc agc tac ctg ggg      895
Ser Tyr Cys Thr Thr Gly Gln Met Trp Ala Arg Ser Ser Tyr Leu Gly
                235                 240                 245 gca gtg ttc aat ctt acc agt gct gat cat tta tat gtc aac gta tct      943
Ala Val Phe Asn Leu Thr Ser Ala Asp His Leu Tyr Val Asn Val Ser
            250                 255                 260 gag ctc tct ctg gtc aat ttt gag gaa tct cag acg ttt ttc ggc tta      991
Glu Leu Ser Leu Val Asn Phe Glu Glu Ser Gln Thr Phe Phe Gly Leu
        265                 270                 275 tat aag ctc taagagaagc actttgggat tctttccatt atgattcttt             1040
Tyr Lys Leu
    280 gttacaggca ccgagaatgt tgtattcagt gagggtcttc ttacatgcat ttgaggtcaa   1100 gtaagaagac atgaaccaag tggaccttga gaccacaggg ttcaaaatgt ctgtagctcc   1160 tcaactcacc taatgtttat gagccagaca atggaggaa tatgacggaa gaacatagaa    1220 ctctgggctg ccatgtgaag agggagaagc atgaaaaagc agctaccagg tgttctacac   1280 tcatcttagt gcctgagagt attaggcag attgaaaagg acaccttta actcacctct     1340 caaggtgggc cttgctacct caaggggac tgtctttcag atacatggtt gtgacctgag    1400 gatttaaggg atggaaaagg aagactagag gcttgcataa taagctaaag aggctgaaag   1460 aggccaatgc cccactggca gcatcttcac ttctaaatgc atatcctgag ccatcggtga   1520 aactaacaga taagcaagag agatgttttg gggactcatt tcattcctaa cacagcatgt   1580 gtatttccag tgcaattgta ggggtgtgtg tgtgtgtgtg tgtgtgtgtg tgtatgac     1640 taaagagaga atgtagatat tgtgaagtac atattaggaa aatatgggtt gcatttggtc   1700 aagattttga atgcttcctg acaatcaact ctaatagtgc ttaaaaatca ttgattgtca   1760 gctactaatg atgttttcct ataatataat aaatatttat gtagatgtgc attttttgtga  1820 aatgaaaaca tgtaataaaa agtatatgtt aggatacaaa aaaaaaaaaa aaaaaaaaa    1880 aaaaaaaaa aaaaaaaaa aaaaaaaa                                        1909
```

<210> SEQ ID NO 10
<211> LENGTH: 281
<212> TYPE: PRT
<213> ORGANISM: Homo sapiens

<400> SEQUENCE: 10

```
Met Gln Gln Pro Phe Asn Tyr Pro Tyr Pro Gln Ile Tyr Trp Val Asp
1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

<210> SEQ ID NO 11
<211> LENGTH: 1329
<212> TYPE: DNA
<213> ORGANISM: Homo sapiens
<220> FEATURE:
<221> NAME/KEY: CDS
<222> LOCATION: (7)..(1320)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1320)

<400> SEQUENCE: 11

```
gctagc atg ggg gta ctg ctc aca cag agg acg ctg ctc agt ctg gtc         48
       Met Gly Val Leu Leu Thr Gln Arg Thr Leu Leu Ser Leu Val
       -25                 -20                 -15 ctt gca ctc ctg ttt cca agc atg gcg agc atg ctc gag cag ctc ttc       96
Leu Ala Leu Leu Phe Pro Ser Met Ala Ser Met Leu Glu Gln Leu Phe
    -10                 -5              -1  1               5
```

```
cac cta cag aag gag ctg gca gaa ctc cga gag tct acc agc cag atg     144
His Leu Gln Lys Glu Leu Ala Glu Leu Arg Glu Ser Thr Ser Gln Met
         10                  15                  20 cac aca gca tca tct ttg gag aag caa ata ggc cac ccc agt cca ccc     192
His Thr Ala Ser Ser Leu Glu Lys Gln Ile Gly His Pro Ser Pro Pro
     25                  30                  35 cct gaa aaa aag gag ctg agg aaa gtg gcc cat tta aca ggc aag tcc     240
Pro Glu Lys Lys Glu Leu Arg Lys Val Ala His Leu Thr Gly Lys Ser
         40                  45                  50 aac tca agg tcc atg cct ctg gaa tgg gaa gac acc tat gga att gtc     288
Asn Ser Arg Ser Met Pro Leu Glu Trp Glu Asp Thr Tyr Gly Ile Val
     55                  60                  65 ctg ctt tct gga gtg aag tat aag aag ggt ggc ctt gtg atc aat gaa     336
Leu Leu Ser Gly Val Lys Tyr Lys Lys Gly Gly Leu Val Ile Asn Glu
70                  75                  80                  85 act ggg ctg tac ttt gta tat tcc aaa gta tac ttc cgg ggt caa tct     384
Thr Gly Leu Tyr Phe Val Tyr Ser Lys Val Tyr Phe Arg Gly Gln Ser
         90                  95                 100 tgc aac aac ctg ccc ctg agc cac aag gtc tac atg agg aac tct aag     432
Cys Asn Asn Leu Pro Leu Ser His Lys Val Tyr Met Arg Asn Ser Lys
        105                 110                 115 tat ccc cag gat ctg gtg atg atg gag ggg aag atg atg agc tac tgc     480
Tyr Pro Gln Asp Leu Val Met Met Glu Gly Lys Met Met Ser Tyr Cys
        120                 125                 130 act act ggg cag atg tgg gcc cgc agc agc tac ctg ggg gca gtg ttc     528
Thr Thr Gly Gln Met Trp Ala Arg Ser Ser Tyr Leu Gly Ala Val Phe
        135                 140                 145 aat ctt acc agt gct gat cat tta tat gtc aac gta tct gag ctc tct     576
Asn Leu Thr Ser Ala Asp His Leu Tyr Val Asn Val Ser Glu Leu Ser
150                 155                 160                 165 ctg gtc aat ttt gag gaa tct cag acg ttt ttc ggc tta tat aag ctc     624
Leu Val Asn Phe Glu Glu Ser Gln Thr Phe Phe Gly Leu Tyr Lys Leu
                170                 175                 180 gag ccc aaa tct tgt gac aaa act cac aca tgc cca ccg tgc cca gca     672
Glu Pro Lys Ser Cys Asp Lys Thr His Thr Cys Pro Pro Cys Pro Ala
        185                 190                 195 cct gaa ctc ctg ggg gga ccg tca gtc ttc ctc ttc ccc cca aaa ccc     720
Pro Glu Leu Leu Gly Gly Pro Ser Val Phe Leu Phe Pro Pro Lys Pro
        200                 205                 210 aag gac acc ctc atg atc tcc cgg acc cct gag gtc aca tgc gtg gtg     768
Lys Asp Thr Leu Met Ile Ser Arg Thr Pro Glu Val Thr Cys Val Val
        215                 220                 225 gtg gac gtg agc cac gaa gac cct gag gtc aag ttc aac tgg tac gtg     816
Val Asp Val Ser His Glu Asp Pro Glu Val Lys Phe Asn Trp Tyr Val
230                 235                 240                 245 gac ggc gtg gag gtg cat aat gcc aag aca aag ccg cgg gag gag cag     864
Asp Gly Val Glu Val His Asn Ala Lys Thr Lys Pro Arg Glu Glu Gln
                250                 255                 260 tac aac agc acg tac cgt gtg gtc agc gtc ctc acc gtc ctg cac cag     912
Tyr Asn Ser Thr Tyr Arg Val Val Ser Val Leu Thr Val Leu His Gln
        265                 270                 275 gac tgg ctg aat ggc aag gag tac aag tgc aag gtc tcc aac aaa gcc     960
Asp Trp Leu Asn Gly Lys Glu Tyr Lys Cys Lys Val Ser Asn Lys Ala
        280                 285                 290 ctc cca gcc ccc atc gag aaa acc atc tcc aaa gcc aaa ggg cag ccc    1008
Leu Pro Ala Pro Ile Glu Lys Thr Ile Ser Lys Ala Lys Gly Gln Pro
        295                 300                 305 cga gaa cca cag gtg tac acc ctg ccc cca tcc cgg gat gag ctg acc    1056
Arg Glu Pro Gln Val Tyr Thr Leu Pro Pro Ser Arg Asp Glu Leu Thr
310                 315                 320                 325
```

```
aag aac cag gtc agc ctg acc tgc ctg gtc aaa ggc ttc tat ccc agc   1104
Lys Asn Gln Val Ser Leu Thr Cys Leu Val Lys Gly Phe Tyr Pro Ser
            330                 335                 340 gac atc gcc gtg gag tgg gag agc aat ggg cag ccg gag aac aac tac   1152
Asp Ile Ala Val Glu Trp Glu Ser Asn Gly Gln Pro Glu Asn Asn Tyr
            345                 350                 355 aag acc acg cct ccc gtg ctg gac tcc gac ggc tcc ttc ttc ctc tac   1200
Lys Thr Thr Pro Pro Val Leu Asp Ser Asp Gly Ser Phe Phe Leu Tyr
            360                 365                 370 agc aag ctc acc gtg gac aag agc agg tgg cag cag ggg aac gtc ttc   1248
Ser Lys Leu Thr Val Asp Lys Ser Arg Trp Gln Gln Gly Asn Val Phe
            375                 380             385 tca tgc tcc gtg atg cat gag gct ctg cac aac cac tac acg cag aag   1296
Ser Cys Ser Val Met His Glu Ala Leu His Asn His Tyr Thr Gln Lys
390             395                 400                 405 agc ctc tcc ctg tct ccg ggt aaa tgatctaga                         1329
Ser Leu Ser Leu Ser Pro Gly Lys
            410
```

<210> SEQ ID NO 12
<211> LENGTH: 438
<212> TYPE: PRT
<213> ORGANISM: Homo sapiens

<400> SEQUENCE: 12

```
Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Gln Leu Phe His Leu
            -5                  -1  1                   5

Gln Lys Glu Leu Ala Glu Leu Arg Glu Ser Thr Ser Gln Met His Thr
            10                  15                  20

Ala Ser Ser Leu Glu Lys Gln Ile Gly His Pro Ser Pro Pro Pro Glu
        25                  30                  35

Lys Lys Glu Leu Arg Lys Val Ala His Leu Thr Gly Lys Ser Asn Ser
40                  45                  50                  55

Arg Ser Met Pro Leu Glu Trp Glu Asp Thr Tyr Gly Ile Val Leu Leu
            60                  65                  70

Ser Gly Val Lys Tyr Lys Lys Gly Gly Leu Val Ile Asn Glu Thr Gly
            75                  80                  85

Leu Tyr Phe Val Tyr Ser Lys Val Tyr Phe Arg Gly Gln Ser Cys Asn
            90                  95                  100

Asn Leu Pro Leu Ser His Lys Val Tyr Met Arg Asn Ser Lys Tyr Pro
        105                 110                 115

Gln Asp Leu Val Met Met Glu Gly Lys Met Met Ser Tyr Cys Thr Thr
120                 125                 130                 135

Gly Gln Met Trp Ala Arg Ser Ser Tyr Leu Gly Ala Val Phe Asn Leu
            140                 145                 150

Thr Ser Ala Asp His Leu Tyr Val Asn Val Ser Glu Leu Ser Leu Val
            155                 160                 165

Asn Phe Glu Glu Ser Gln Thr Phe Phe Gly Leu Tyr Lys Leu Glu Pro
        170                 175                 180

Lys Ser Cys Asp Lys Thr His Thr Cys Pro Pro Cys Pro Ala Pro Glu
        185                 190                 195

Leu Leu Gly Gly Pro Ser Val Phe Leu Phe Pro Pro Lys Pro Lys Asp
200                 205                 210                 215

Thr Leu Met Ile Ser Arg Thr Pro Glu Val Thr Cys Val Val Val Asp
```

```
                    220                 225                 230
Val Ser His Glu Asp Pro Glu Val Lys Phe Asn Trp Tyr Val Asp Gly
            235                 240                 245

Val Glu Val His Asn Ala Lys Thr Lys Pro Arg Glu Glu Gln Tyr Asn
            250                 255                 260

Ser Thr Tyr Arg Val Val Ser Val Leu Thr Val Leu His Gln Asp Trp
            265                 270                 275

Leu Asn Gly Lys Glu Tyr Lys Cys Lys Val Ser Asn Lys Ala Leu Pro
280                 285                 290                 295

Ala Pro Ile Glu Lys Thr Ile Ser Lys Ala Lys Gly Gln Pro Arg Glu
                300                 305                 310

Pro Gln Val Tyr Thr Leu Pro Pro Ser Arg Asp Glu Leu Thr Lys Asn
                315                 320                 325

Gln Val Ser Leu Thr Cys Leu Val Lys Gly Phe Tyr Pro Ser Asp Ile
                330                 335                 340

Ala Val Glu Trp Glu Ser Asn Gly Gln Pro Glu Asn Asn Tyr Lys Thr
                345                 350                 355

Thr Pro Pro Val Leu Asp Ser Asp Gly Ser Phe Phe Leu Tyr Ser Lys
360                 365                 370                 375

Leu Thr Val Asp Lys Ser Arg Trp Gln Gln Gly Asn Val Phe Ser Cys
                380                 385                 390

Ser Val Met His Glu Ala Leu His Asn His Tyr Thr Gln Lys Ser Leu
                395                 400                 405

Ser Leu Ser Pro Gly Lys
            410

<210> SEQ ID NO 13
<211> LENGTH: 1974
<212> TYPE: DNA
<213> ORGANISM: Homo sapiens
<220> FEATURE:
<221> NAME/KEY: CDS
<222> LOCATION: (7)..(1965)
<220> FEATURE:
<221> NAME/KEY: sig_peptide
<222> LOCATION: (7)..(81)
<220> FEATURE:
<221> NAME/KEY: sig_peptide
<222> LOCATION: (82)..(1965)

<400> SEQUENCE: 13 gctagc atg ggg gta ctg ctc aca cag agg acg ctg ctc agt ctg gtc        48
       Met Gly Val Leu Leu Thr Gln Arg Thr Leu Leu Ser Leu Val
       1               5                   10 ctt gca ctc ctg ttt cca agc atg gcg agc atg ctt cat aga agg ttg       96
Leu Ala Leu Leu Phe Pro Ser Met Ala Ser Met Leu His Arg Arg Leu
15              20                  25                  30 gac aag ata gaa gat gaa agg aat ctt cat gaa gat ttt gta ttc atg      144
Asp Lys Ile Glu Asp Glu Arg Asn Leu His Glu Asp Phe Val Phe Met
                35                  40                  45 aaa acg ata cag aga tgc aac aca gga gaa aga tcc tta tcc tta ctg      192
Lys Thr Ile Gln Arg Cys Asn Thr Gly Glu Arg Ser Leu Ser Leu Leu
            50                  55                  60 aac tgt gag gag att aaa agc cag ttt gaa ggc ttt gtg aag gat ata      240
Asn Cys Glu Glu Ile Lys Ser Gln Phe Glu Gly Phe Val Lys Asp Ile
65              70                  75 atg tta aac aaa gag gag acg aag aaa gaa aac agc ttt gaa atg caa      288
Met Leu Asn Lys Glu Glu Thr Lys Lys Glu Asn Ser Phe Glu Met Gln
        80                  85                  90
```

| | | |
|---|---|---|
| aaa ggt gat cag aat cct caa att gcg gca cat gtc ata agt gag gcc<br>Lys Gly Asp Gln Asn Pro Gln Ile Ala Ala His Val Ile Ser Glu Ala<br>95                        100                   105                   110 | | 336 |
| agc agt aaa aca aca tct gtg tta cag tgg gct gaa aaa gga tac tac<br>Ser Ser Lys Thr Thr Ser Val Leu Gln Trp Ala Glu Lys Gly Tyr Tyr<br>               115                   120                   125 | | 384 |
| acc atg agc aac aac ttg gta acc ctg gaa aat ggg aaa cag ctg acc<br>Thr Met Ser Asn Asn Leu Val Thr Leu Glu Asn Gly Lys Gln Leu Thr<br>                      130                   135                   140 | | 432 |
| gtt aaa aga caa gga ctc tat tat atc tat gcc caa gtc acc ttc tgt<br>Val Lys Arg Gln Gly Leu Tyr Tyr Ile Tyr Ala Gln Val Thr Phe Cys<br>145                       150                   155 | | 480 |
| tcc aat cgg gaa gct tcg agt caa gct cca ttt ata gcc agc ctc tgc<br>Ser Asn Arg Glu Ala Ser Ser Gln Ala Pro Phe Ile Ala Ser Leu Cys<br>         160                   165                   170 | | 528 |
| cta aag tcc ccc ggt aga ttc gag aga atc tta ctc aga gct gca aat<br>Leu Lys Ser Pro Gly Arg Phe Glu Arg Ile Leu Leu Arg Ala Ala Asn<br>175                       180                   185                   190 | | 576 |
| acc cac agt tcc gcc aaa cct tgc ggg caa caa tcc att cac ttg gga<br>Thr His Ser Ser Ala Lys Pro Cys Gly Gln Gln Ser Ile His Leu Gly<br>                         195                   200                   205 | | 624 |
| gga gta ttt gaa ttg caa cca ggt gct tcg gtg ttt gtc aat gtg act<br>Gly Val Phe Glu Leu Gln Pro Gly Ala Ser Val Phe Val Asn Val Thr<br>               210                   215                   220 | | 672 |
| gat cca agc caa gtg agc cat ggc act ggc ttc acg tcc ttt ggc tta<br>Asp Pro Ser Gln Val Ser His Gly Thr Gly Phe Thr Ser Phe Gly Leu<br>         225                   230                   235 | | 720 |
| ctc aaa ctc gag cag ctc ttc cac cta cag aag gag ctg gca gaa ctc<br>Leu Lys Leu Glu Gln Leu Phe His Leu Gln Lys Glu Leu Ala Glu Leu<br>240                       245                   250 | | 768 |
| cga gag tct acc agc cag atg cac aca gca tca tct ttg gag aag caa<br>Arg Glu Ser Thr Ser Gln Met His Thr Ala Ser Ser Leu Glu Lys Gln<br>255                       260                   265                   270 | | 816 |
| ata ggc cac ccc agt cca ccc cct gaa aaa aag gag ctg agg aaa gtg<br>Ile Gly His Pro Ser Pro Pro Pro Glu Lys Lys Glu Leu Arg Lys Val<br>               275                   280                   285 | | 864 |
| gcc cat tta aca ggc aag tcc aac tca agg tcc atg cct ctg gaa tgg<br>Ala His Leu Thr Gly Lys Ser Asn Ser Arg Ser Met Pro Leu Glu Trp<br>         290                   295                   300 | | 912 |
| gaa gac acc tat gga att gtc ctg ctt tct gga gtg aag tat aag aag<br>Glu Asp Thr Tyr Gly Ile Val Leu Leu Ser Gly Val Lys Tyr Lys Lys<br>305                       310                   315 | | 960 |
| ggt ggc ctt gtg atc aat gaa act ggg ctg tac ttt gta tat tcc aaa<br>Gly Gly Leu Val Ile Asn Glu Thr Gly Leu Tyr Phe Val Tyr Ser Lys<br>320                       325                   330 | | 1008 |
| gta tac ttc cgg ggt caa tct tgc aac aac ctg ccc ctg agc cac aag<br>Val Tyr Phe Arg Gly Gln Ser Cys Asn Asn Leu Pro Leu Ser His Lys<br>335                       340                   345                   350 | | 1056 |
| gtc tac atg agg aac tct aag tat ccc cag gat ctg gtg atg atg gag<br>Val Tyr Met Arg Asn Ser Lys Tyr Pro Gln Asp Leu Val Met Met Glu<br>                      355                   360                   365 | | 1104 |
| ggg aag atg atg agc tac tgc act act ggg cag atg tgg gcc cgc agc<br>Gly Lys Met Met Ser Tyr Cys Thr Thr Gly Gln Met Trp Ala Arg Ser<br>         370                   375                   380 | | 1152 |
| agc tac ctg ggg gca gtg ttc aat ctt acc agt gct gat cat tta tat<br>Ser Tyr Leu Gly Ala Val Phe Asn Leu Thr Ser Ala Asp His Leu Tyr<br>385                       390                   395 | | 1200 |
| gtc aac gta tct gag ctc tct ctg gtc aat ttt gag gaa tct cag acg<br>Val Asn Val Ser Glu Leu Ser Leu Val Asn Phe Glu Glu Ser Gln Thr<br>400                       405                   410 | | 1248 |

```
ttt ttc ggc tta tat aag ctc gag ccc aaa tct tgt gac aaa act cac    1296
Phe Phe Gly Leu Tyr Lys Leu Glu Pro Lys Ser Cys Asp Lys Thr His
415                 420                 425                 430 aca tgc cca ccg tgc cca gca cct gaa ctc ctg ggg gga ccg tca gtc    1344
Thr Cys Pro Pro Cys Pro Ala Pro Glu Leu Leu Gly Gly Pro Ser Val
                435                 440                 445 ttc ctc ttc ccc cca aaa ccc aag gac acc ctc atg atc tcc cgg acc    1392
Phe Leu Phe Pro Pro Lys Pro Lys Asp Thr Leu Met Ile Ser Arg Thr
            450                 455                 460 cct gag gtc aca tgc gtg gtg gtg gac gtg agc cac gaa gac cct gag    1440
Pro Glu Val Thr Cys Val Val Val Asp Val Ser His Glu Asp Pro Glu
        465                 470                 475 gtc aag ttc aac tgg tac gtg gac ggc gtg gag gtg cat aat gcc aag    1488
Val Lys Phe Asn Trp Tyr Val Asp Gly Val Glu Val His Asn Ala Lys
    480                 485                 490 aca aag ccg cgg gag gag cag tac aac agc acg tac cgt gtg gtc agc    1536
Thr Lys Pro Arg Glu Glu Gln Tyr Asn Ser Thr Tyr Arg Val Val Ser
495                 500                 505                 510 gtc ctc acc gtc ctg cac cag gac tgg ctg aat ggc aag gag tac aag    1584
Val Leu Thr Val Leu His Gln Asp Trp Leu Asn Gly Lys Glu Tyr Lys
                515                 520                 525 tgc aag gtc tcc aac aaa gcc ctc cca gcc ccc atc gag aaa acc atc    1632
Cys Lys Val Ser Asn Lys Ala Leu Pro Ala Pro Ile Glu Lys Thr Ile
            530                 535                 540 tcc aaa gcc aaa ggg cag ccc cga gaa cca cag gtg tac acc ctg ccc    1680
Ser Lys Ala Lys Gly Gln Pro Arg Glu Pro Gln Val Tyr Thr Leu Pro
        545                 550                 555 cca tcc cgg gat gag ctg acc aag aac cag gtc agc ctg acc tgc ctg    1728
Pro Ser Arg Asp Glu Leu Thr Lys Asn Gln Val Ser Leu Thr Cys Leu
    560                 565                 570 gtc aaa ggc ttc tat ccc agc gac atc gcc gtg gag tgg gag agc aat    1776
Val Lys Gly Phe Tyr Pro Ser Asp Ile Ala Val Glu Trp Glu Ser Asn
575                 580                 585                 590 ggg cag ccg gag aac aac tac aag acc acg cct ccc gtg ctg gac tcc    1824
Gly Gln Pro Glu Asn Asn Tyr Lys Thr Thr Pro Pro Val Leu Asp Ser
                595                 600                 605 gac ggc tcc ttc ttc ctc tac agc aag ctc acc gtg gac aag agc agg    1872
Asp Gly Ser Phe Phe Leu Tyr Ser Lys Leu Thr Val Asp Lys Ser Arg
            610                 615                 620 tgg cag cag ggg aac gtc ttc tca tgc tcc gtg atg cat gag gct ctg    1920
Trp Gln Gln Gly Asn Val Phe Ser Cys Ser Val Met His Glu Ala Leu
        625                 630                 635 cac aac cac tac acg cag aag agc ctc tcc ctg tct ccg ggt aaa        1965
His Asn His Tyr Thr Gln Lys Ser Leu Ser Leu Ser Pro Gly Lys
    640                 645                 650 tgatctaga                                                          1974

<210> SEQ ID NO 14
<211> LENGTH: 653
<212> TYPE: PRT
<213> ORGANISM: Homo sapiens

<400> SEQUENCE: 14

Met Gly Val Leu Leu Thr Gln Arg Thr Leu Leu Ser Leu Val Leu Ala
1               5                   10                  15

Leu Leu Phe Pro Ser Met Ala Ser Met Leu His Arg Arg Leu Asp Lys
            20                  25                  30

Ile Glu Asp Glu Arg Asn Leu His Glu Asp Phe Val Phe Met Lys Thr
        35                  40                  45
```

```
Ile Gln Arg Cys Asn Thr Gly Glu Arg Ser Leu Ser Leu Leu Asn Cys
 50                  55                  60

Glu Glu Ile Lys Ser Gln Phe Glu Gly Phe Val Lys Asp Ile Met Leu
 65                  70                  75                  80

Asn Lys Glu Glu Thr Lys Lys Glu Asn Ser Phe Glu Met Gln Lys Gly
                 85                  90                  95

Asp Gln Asn Pro Gln Ile Ala Ala His Val Ile Ser Glu Ala Ser Ser
            100                 105                 110

Lys Thr Thr Ser Val Leu Gln Trp Ala Glu Lys Gly Tyr Tyr Thr Met
        115                 120                 125

Ser Asn Asn Leu Val Thr Leu Glu Asn Gly Lys Gln Leu Thr Val Lys
130                 135                 140

Arg Gln Gly Leu Tyr Tyr Ile Tyr Ala Gln Val Thr Phe Cys Ser Asn
145                 150                 155                 160

Arg Glu Ala Ser Ser Gln Ala Pro Phe Ile Ala Ser Leu Cys Leu Lys
                165                 170                 175

Ser Pro Gly Arg Phe Glu Arg Ile Leu Leu Arg Ala Ala Asn Thr His
            180                 185                 190

Ser Ser Ala Lys Pro Cys Gly Gln Gln Ser Ile His Leu Gly Gly Val
        195                 200                 205

Phe Glu Leu Gln Pro Gly Ala Ser Val Phe Val Asn Val Thr Asp Pro
210                 215                 220

Ser Gln Val Ser His Gly Thr Gly Phe Thr Ser Phe Gly Leu Leu Lys
225                 230                 235                 240

Leu Glu Gln Leu Phe His Leu Gln Lys Glu Leu Ala Glu Leu Arg Glu
                245                 250                 255

Ser Thr Ser Gln Met His Thr Ala Ser Ser Leu Glu Lys Gln Ile Gly
            260                 265                 270

His Pro Ser Pro Pro Glu Lys Lys Glu Leu Arg Lys Val Ala His
        275                 280                 285

Leu Thr Gly Lys Ser Asn Ser Arg Ser Met Pro Leu Glu Trp Glu Asp
290                 295                 300

Thr Tyr Gly Ile Val Leu Leu Ser Gly Val Lys Tyr Lys Lys Gly Gly
305                 310                 315                 320

Leu Val Ile Asn Glu Thr Gly Leu Tyr Phe Val Tyr Ser Lys Val Tyr
                325                 330                 335

Phe Arg Gly Gln Ser Cys Asn Asn Leu Pro Leu Ser His Lys Val Tyr
            340                 345                 350

Met Arg Asn Ser Lys Tyr Pro Gln Asp Leu Val Met Met Glu Gly Lys
        355                 360                 365

Met Met Ser Tyr Cys Thr Thr Gly Gln Met Trp Ala Arg Ser Ser Tyr
370                 375                 380

Leu Gly Ala Val Phe Asn Leu Thr Ser Ala Asp His Leu Tyr Val Asn
385                 390                 395                 400

Val Ser Glu Leu Ser Leu Val Asn Phe Glu Glu Ser Gln Thr Phe Phe
                405                 410                 415

Gly Leu Tyr Lys Leu Glu Pro Lys Ser Cys Asp Lys Thr His Thr Cys
            420                 425                 430

Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
450                 455                 460
```

-continued

```
Val Thr Cys Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560

Arg Asp Glu Leu Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
        595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
                645                 650

<210> SEQ ID NO 15
<211> LENGTH: 2807
<212> TYPE: DNA
<213> ORGANISM: Homo sapiens
<220> FEATURE:
<221> NAME/KEY: CDS
<222> LOCATION: (148)..(1116)
<220> FEATURE:
<221> NAME/KEY: sig_peptide
<222> LOCATION: (148)..(195)
<220> FEATURE:
<221> NAME/KEY: mat_peptide
<222> LOCATION: (196)..(1116)

<400> SEQUENCE: 15
aggagcctta ggaggtacgg ggagctcgca aatactcctt tggtttatt cttaccacct      60 tgcttctgtg ttccttggga atgctgctgt gcttatgcat ctggtctctt tttggagcta    120
cagtggacag gcatttgtga cagcact atg gga ctg agt aac att ctc ttt gtg   174
                              Met Gly Leu Ser Asn Ile Leu Phe Val
                                  -15                 -10 atg gcc ttc ctg ctc tct ggt gct gct cct ctg aag att caa gct tat    222
Met Ala Phe Leu Leu Ser Gly Ala Ala Pro Leu Lys Ile Gln Ala Tyr
    -5              -1   1               5 ttc aat gag act gca gac ctg cca tgc caa ttt gca aac tct caa aac    270
Phe Asn Glu Thr Ala Asp Leu Pro Cys Gln Phe Ala Asn Ser Gln Asn
10                  15                  20                  25 caa agc ctg agt gag cta gta gta ttt tgg cag gac cag gaa aac ttg    318
Gln Ser Leu Ser Glu Leu Val Val Phe Trp Gln Asp Gln Glu Asn Leu
                30                  35                  40 gtt ctg aat gag gta tac tta ggc aaa gag aaa ttt gac agt gtt cat    366
Val Leu Asn Glu Val Tyr Leu Gly Lys Glu Lys Phe Asp Ser Val His
            45                  50                  55 tcc aag tat atg ggc cgc aca agt ttt gat tcg gac agt tgg acc ctg    414
Ser Lys Tyr Met Gly Arg Thr Ser Phe Asp Ser Asp Ser Trp Thr Leu
```

-continued

```
              60                  65                  70
aga ctt cac aat ctt cag atc aag gac aag ggc ttg tat caa tgt atc       462
Arg Leu His Asn Leu Gln Ile Lys Asp Lys Gly Leu Tyr Gln Cys Ile
    75                  80                  85 atc cat cac aaa aag ccc aca gga atg att cgc atc cac cag atg aat       510
Ile His His Lys Lys Pro Thr Gly Met Ile Arg Ile His Gln Met Asn
 90                  95                 100                 105 tct gaa ctg tca gtg ctt gct aac ttc agt caa cct gaa ata gta cca       558
Ser Glu Leu Ser Val Leu Ala Asn Phe Ser Gln Pro Glu Ile Val Pro
                110                 115                 120 att tct aat ata aca gaa aat gtg tac ata aat ttg acc tgc tca tct       606
Ile Ser Asn Ile Thr Glu Asn Val Tyr Ile Asn Leu Thr Cys Ser Ser
                125                 130                 135 ata cac ggt tac cca gaa cct aag aag atg agt gtt ttg cta aga acc       654
Ile His Gly Tyr Pro Glu Pro Lys Lys Met Ser Val Leu Leu Arg Thr
                140                 145                 150 aag aat tca act atc gag tat gat ggt gtt atg cag aaa tct caa gat       702
Lys Asn Ser Thr Ile Glu Tyr Asp Gly Val Met Gln Lys Ser Gln Asp
    155                 160                 165 aat gtc aca gaa ctg tac gac gtt tcc atc agc ttg tct gtt tca gac       750
Asn Val Thr Glu Leu Tyr Asp Val Ser Ile Ser Leu Ser Val Ser Asp
170                 175                 180                 185 aag acg cgg ctt tta tct tca cct ttc tct ata gag ctt gag ttc cct       798
Lys Thr Arg Leu Leu Ser Ser Pro Phe Ser Ile Glu Leu Glu Phe Pro
                190                 195                 200 gat gtt acg agc aat atg acc atc ttc tgt att ctg gaa act gac cct       846
Asp Val Thr Ser Asn Met Thr Ile Phe Cys Ile Leu Glu Thr Asp Pro
                205                 210                 215 cag cct ccc cca gac cac att cct tgg att aca gct gta ctt cca aca       894
Gln Pro Pro Pro Asp His Ile Pro Trp Ile Thr Ala Val Leu Pro Thr
    220                 225                 230 gtt att ata tgt gtg atg gtt ttc tgt cta att cta tgg aaa tgg aag       942
Val Ile Ile Cys Val Met Val Phe Cys Leu Ile Leu Trp Lys Trp Lys
    235                 240                 245 aag aag aag cgg cct cgc aac tct tat aaa tgt gga acc aac aca atg       990
Lys Lys Lys Arg Pro Arg Asn Ser Tyr Lys Cys Gly Thr Asn Thr Met
250                 255                 260                 265 gag agg gaa gag agt gaa cag acc aag aaa aga gaa aaa atc cat ata      1038
Glu Arg Glu Glu Ser Glu Gln Thr Lys Lys Arg Glu Lys Ile His Ile
                270                 275                 280 cct gaa aga tct gat gaa gcc cag cgt gtt ttt aaa agt tcg aag aca      1086
Pro Glu Arg Ser Asp Glu Ala Gln Arg Val Phe Lys Ser Ser Lys Thr
                285                 290                 295 tct tca tgc gac aaa agt gat aca tgt ttt taaataaaga gtaaagccca       1136
Ser Ser Cys Asp Lys Ser Asp Thr Cys Phe
                300                 305 tacaagtatt cattttttct acccttcct ttgtaagttc ctgggcaacc tttttgattt    1196
cttccagaag gcaaaaagac attaccatga gtaataaggg ggctccagga ctccctctaa   1256
gtggaatagc ctccctgtaa ctccagctct gctccgtatg ccaagaggag actttaattc   1316
tcttactgct tcttttcact tcagagcaca cttatgggcc aagcccagct taatggctca   1376
tgacctggaa ataaaattta ggaccaatac ctcctccaga tcagattctt ctcttaattt   1436
catagattgt gttttttttt taaatagacc tctcaatttc tggaaaactg ccttttatct   1496
gcccagaatt ctaagctggt gccccactga attttgtgtg tacctgtgac taaacaacta   1556
cctcctcagt ctgggtggga cttatgtatt tatgacctta tagtgttaat atcttgaaac   1616
atagagatct atgtactgta atagtgtgat tactatgctc tagagaaaag tctacccctg   1676
```

```
ctaaggagtt ctcatccctc tgtcagggtc agtaaggaaa acggtggcct agggtacagg    1736
caacaatgag cagaccaacc taaatttggg gaaattagga gaggcagaga tagaacctgg    1796
agccacttct atctgggctg ttgctaatat tgaggaggct tgccccaccc aacaagccat    1856
agtggagaga actgaataaa caggaaaatg ccagagcttg tgaaccctgt ttctcttgaa    1916
gaactgacta gtgagatggc ctggggaagc tgtgaaagaa ccaaaagaga tcacaatact    1976
caaaagagag agagagagaa aaagagagag tcttgatcca cagaaataca tgaaatgtct    2036
ggtctgtcca ccccatcaac aagtcttgaa acaagcaaca gatggatagt ctgtccaaat    2096
ggacataaga cagacagcag tttccctggt ggtcagggag gggttttggt gatacccaag    2156
ttattgggat gtcatcttcc tggaagcaga gctggggagg gagagccatc accttgataa    2216
tgggatgaat ggaaggaggc ttaggacttt ccactcctgg ctgagagagg aagagctgca    2276
acggaattag gaagaccaag acacagatca cccgggggctt acttagccta cagatgtcct    2336
acgggaacgt gggctggccc agcatagggc tagcaaattt gagttggatg attgttttttg    2396 ctcaaggcaa ccagaggaaa cttgcataca gagacagata tactgggaga aatgactttg    2456
aaaacctggc tctaaggtgg gatcactaag ggatggggca gtctctgccc aaacataaag    2516
agaactctgg ggagcctgag ccacaaaaat gttcctttat tttatgtaaa ccctcaaggg    2576
ttatagactg ccatgctaga caagcttgtc catgtaatat tcccatgttt ttaccctgcc    2636
cctgccttga ttagactcct agcacctggc tagtttctaa catgttttgt gcagcacagt    2696
ttttaataaa tgcttgttac attcaaaaaa aaaaaaaaaa aaaaaaaaaa aaaaaaaaaa    2756
aaaaaaaaaa aaaaaaaaaa aaaaaaaaaa aaaaaaaaaa aaaaaaaaaa a            2807

<210> SEQ ID NO 16
<211> LENGTH: 323
<212> TYPE: PRT
<213> ORGANISM: Homo sapiens

<400> SEQUENCE: 16

Met Gly Leu Ser Asn Ile Leu Phe Val Met Ala Phe Leu Leu Ser Gly
    -15                 -10                 -5                  -1

Ala Ala Pro Leu Lys Ile Gln Ala Tyr Phe Asn Glu Thr Ala Asp Leu
1               5                   10                  15

Pro Cys Gln Phe Ala Asn Ser Gln Asn Gln Ser Leu Ser Glu Leu Val
            20                  25                  30

Val Phe Trp Gln Asp Gln Glu Asn Leu Val Leu Asn Glu Val Tyr Leu
        35                  40                  45

Gly Lys Glu Lys Phe Asp Ser Val His Ser Lys Tyr Met Gly Arg Thr
    50                  55                  60

Ser Phe Asp Ser Asp Ser Trp Thr Leu Arg Leu His Asn Leu Gln Ile
65                  70                  75                  80

Lys Asp Lys Gly Leu Tyr Gln Cys Ile Ile His His Lys Lys Pro Thr
                85                  90                  95

Gly Met Ile Arg Ile His Gln Met Asn Ser Glu Leu Ser Val Leu Ala
            100                 105                 110

Asn Phe Ser Gln Pro Glu Ile Val Pro Ile Ser Asn Ile Thr Glu Asn
        115                 120                 125

Val Tyr Ile Asn Leu Thr Cys Ser Ser Ile His Gly Tyr Pro Glu Pro
    130                 135                 140

Lys Lys Met Ser Val Leu Leu Arg Thr Lys Asn Ser Thr Ile Glu Tyr
145                 150                 155                 160
```

```
Asp Gly Val Met Gln Lys Ser Gln Asp Asn Val Thr Glu Leu Tyr Asp
            165                 170                 175

Val Ser Ile Ser Leu Ser Val Ser Asp Lys Thr Arg Leu Leu Ser Ser
        180                 185                 190

Pro Phe Ser Ile Glu Leu Glu Phe Pro Asp Val Thr Ser Asn Met Thr
            195                 200                 205

Ile Phe Cys Ile Leu Glu Thr Asp Pro Gln Pro Pro Asp His Ile
        210                 215                 220

Pro Trp Ile Thr Ala Val Leu Pro Thr Val Ile Cys Val Met Val
225                 230                 235                 240

Phe Cys Leu Ile Leu Trp Lys Trp Lys Lys Lys Arg Pro Arg Asn
                245                 250                 255

Ser Tyr Lys Cys Gly Thr Asn Thr Met Glu Arg Glu Ser Glu Gln
            260                 265                 270

Thr Lys Lys Arg Glu Lys Ile His Ile Pro Glu Arg Ser Asp Glu Ala
        275                 280                 285

Gln Arg Val Phe Lys Ser Ser Lys Thr Ser Ser Cys Asp Lys Ser Asp
        290                 295                 300

Thr Cys Phe
305

<210> SEQ ID NO 17
<211> LENGTH: 2019
<212> TYPE: DNA
<213> ORGANISM: Homo sapiens
<220> FEATURE:
<221> NAME/KEY: CDS
<222> LOCATION: (7)..(2010)
<220> FEATURE:
<221> NAME/KEY: sig_peptide
<222> LOCATION: (7)..(81)
<220> FEATURE:
<221> NAME/KEY: mat_peptide
<222> LOCATION: (82)..(2010)

<400> SEQUENCE: 17 gctagc atg ggg gta ctg ctc aca cag agg acg ctg ctc agt ctg gtc        48
       Met Gly Val Leu Leu Thr Gln Arg Thr Leu Leu Ser Leu Val
       -25                 -20                 -15 ctt gca ctc ctg ttt cca agc atg gcg agc atg gaa ttc acg cgt gct       96
Leu Ala Leu Leu Phe Pro Ser Met Ala Ser Met Glu Phe Thr Arg Ala
    -10                 -5                  -1  1               5 cct ctg aag att caa gct tat ttc aat gag act gca gac ctg cca tgc      144
Pro Leu Lys Ile Gln Ala Tyr Phe Asn Glu Thr Ala Asp Leu Pro Cys
                10                  15                  20 caa ttt gca aac tct caa aac caa agc ctg agt gag cta gta gta ttt      192
Gln Phe Ala Asn Ser Gln Asn Gln Ser Leu Ser Glu Leu Val Val Phe
            25                  30                  35 tgg cag gac cag gaa aac ttg gtt ctg aat gag gta tac tta ggc aaa      240
Trp Gln Asp Gln Glu Asn Leu Val Leu Asn Glu Val Tyr Leu Gly Lys
        40                  45                  50 gag aaa ttt gac agt gtt cat tcc aag tat atg ggc cgc aca agt ttt      288
Glu Lys Phe Asp Ser Val His Ser Lys Tyr Met Gly Arg Thr Ser Phe
55                  60                  65 gat tcg gac agt tgg acc ctg aga ctt cac aat ctt cag atc aag gac      336
Asp Ser Asp Ser Trp Thr Leu Arg Leu His Asn Leu Gln Ile Lys Asp
70                  75                  80                  85 aag ggc ttg tat caa tgt atc atc cat cac aaa aag ccc aca gga atg      384
Lys Gly Leu Tyr Gln Cys Ile Ile His His Lys Lys Pro Thr Gly Met
            90                  95                  100
```

```
att cgc atc cac cag atg aat tct gaa ctg tca gtt ctt gct aac ttc      432
Ile Arg Ile His Gln Met Asn Ser Glu Leu Ser Val Leu Ala Asn Phe
        105                 110                 115 agt caa cct gaa ata gta cca att tct aat ata aca gaa aat gtg tac      480
Ser Gln Pro Glu Ile Val Pro Ile Ser Asn Ile Thr Glu Asn Val Tyr
    120                 125                 130 ata aat ttg acc tgc tca tct ata cac ggt tac cca gaa cct aag aag      528
Ile Asn Leu Thr Cys Ser Ser Ile His Gly Tyr Pro Glu Pro Lys Lys
135                 140                 145 atg agt gtt ttg cta aga acc aag aat tca act atc gag tat gat ggt      576
Met Ser Val Leu Leu Arg Thr Lys Asn Ser Thr Ile Glu Tyr Asp Gly
150                 155                 160                 165 gtt atg cag aaa tct caa gat aat gtc aca gaa ctg tac gac gtt tcc      624
Val Met Gln Lys Ser Gln Asp Asn Val Thr Glu Leu Tyr Asp Val Ser
            170                 175                 180 atc agc ttg tct gtt tca ttc cct gat gtt acg agc aat atg acc atc      672
Ile Ser Leu Ser Val Ser Phe Pro Asp Val Thr Ser Asn Met Thr Ile
                185                 190                 195 ttc tgt att ctg gaa act gac aag acg cgg ctt tta tct tca cct ttc      720
Phe Cys Ile Leu Glu Thr Asp Lys Thr Arg Leu Leu Ser Ser Pro Phe
            200                 205                 210 tct ata gag ctt gag gac cct cag cct ccc cca gac cac att cct acg      768
Ser Ile Glu Leu Glu Asp Pro Gln Pro Pro Pro Asp His Ile Pro Thr
    215                 220                 225 cgt ggt acc cag ctc ttc cac cta cag aag gag ctg gca gaa ctc cga      816
Arg Gly Thr Gln Leu Phe His Leu Gln Lys Glu Leu Ala Glu Leu Arg
230                 235                 240                 245 gag tct acc agc cag atg cac aca gca tca tct ttg gag aag caa ata      864
Glu Ser Thr Ser Gln Met His Thr Ala Ser Ser Leu Glu Lys Gln Ile
                250                 255                 260 ggc cac ccc agt cca ccc cct gaa aaa aag gag ctg agg aaa gtg gcc      912
Gly His Pro Ser Pro Pro Pro Glu Lys Lys Glu Leu Arg Lys Val Ala
            265                 270                 275 cat tta aca ggc aag tcc aac tca agg tcc atg cct ctg gaa tgg gaa      960
His Leu Thr Gly Lys Ser Asn Ser Arg Ser Met Pro Leu Glu Trp Glu
        280                 285                 290 gac acc tat gga att gtc ctg ctt tct gga gtg aag tat aag aag ggt     1008
Asp Thr Tyr Gly Ile Val Leu Leu Ser Gly Val Lys Tyr Lys Lys Gly
    295                 300                 305 ggc ctt gtg atc aat gaa act ggg ctg tac ttt gta tat tcc aaa gta     1056
Gly Leu Val Ile Asn Glu Thr Gly Leu Tyr Phe Val Tyr Ser Lys Val
310                 315                 320                 325 tac ttc cgg ggt caa tct tgc aac aac ctg ccc ctg agc cac aag gtc     1104
Tyr Phe Arg Gly Gln Ser Cys Asn Asn Leu Pro Leu Ser His Lys Val
                330                 335                 340 tac atg agg aac tct aag tat ccc cag gat ctg gtg atg atg gag ggg     1152
Tyr Met Arg Asn Ser Lys Tyr Pro Gln Asp Leu Val Met Met Glu Gly
            345                 350                 355 aag atg atg agc tac tgc act act ggg cag atg tgg gcc cgc agc agc     1200
Lys Met Met Ser Tyr Cys Thr Thr Gly Gln Met Trp Ala Arg Ser Ser
        360                 365                 370 tac ctg ggg gca gtg ttc aat ctt acc agt gct gat cat tta tat gtc     1248
Tyr Leu Gly Ala Val Phe Asn Leu Thr Ser Ala Asp His Leu Tyr Val
    375                 380                 385 aac gta tct gag ctc tct ctg gtc aat ttt gag gaa tct cag acg ttt     1296
Asn Val Ser Glu Leu Ser Leu Val Asn Phe Glu Glu Ser Gln Thr Phe
390                 395                 400                 405 ttc ggc tta tat aag ctc gag ccc aaa tct tgt gac aaa act cac aca     1344
Phe Gly Leu Tyr Lys Leu Glu Pro Lys Ser Cys Asp Lys Thr His Thr
```

| | | |
|---|---|---|
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>425 430 435 | 1392 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>440 445 450 | 1440 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>455 460 465 | 1488 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>470 475 480 485 | 1536 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>490 495 500 | 1584 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>505 510 515 | 1632 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>520 525 530 | 1680 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>535 540 545 | 1728 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>550 555 560 565 | 1776 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>570 575 580 | 1824 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>585 590 595 | 1872 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>600 605 610 | 1920 |
| cag cag ggg aac gtc ttc tca tgc tcc gtg atg cat gag gct ctg cac<br>Gln Gln Gly Asn Val Phe Ser Cys Ser Val Met His Glu Ala Leu His<br>615 620 625 | 1968 |
| aac cac tac acg cag aag agc ctc tcc ctg tct ccg ggt aaa tgatctaga<br>Asn His Tyr Thr Gln Lys Ser Leu Ser Leu Ser Pro Gly Lys<br>630 635 640 | 2019 |

<210> SEQ ID NO 18
<211> LENGTH: 668
<212> TYPE: PRT
<213> ORGANISM: Homo sapiens

<400> SEQUENCE: 18

Met Gly Val Leu Leu Thr Gln Arg Thr Leu Leu Ser Leu Val Leu Ala
-25                 -20                 -15                 -10

Leu Leu Phe Pro Ser Met Ala Ser Met Glu Phe Thr Arg Ala Pro Leu
            -5                  -1  1               5

Lys Ile Gln Ala Tyr Phe Asn Glu Thr Ala Asp Leu Pro Cys Gln Phe
                10                  15                  20

Ala Asn Ser Gln Asn Gln Ser Leu Ser Glu Leu Val Val Phe Trp Gln
            25                  30                  35

Asp Gln Glu Asn Leu Val Leu Asn Glu Val Tyr Leu Gly Lys Glu Lys

-continued

```
            40                  45                  50                  55
        Phe Asp Ser Val His Ser Lys Tyr Met Gly Arg Thr Ser Phe Asp Ser
                            60                  65                  70

Asp Ser Trp Thr Leu Arg Leu His Asn Leu Gln Ile Lys Asp Lys Gly
                    75                  80                  85

Leu Tyr Gln Cys Ile Ile His Lys Lys Pro Thr Gly Met Ile Arg
                90                  95                 100

Ile His Gln Met Asn Ser Glu Leu Ser Val Leu Ala Asn Phe Ser Gln
            105                 110                 115

Pro Glu Ile Val Pro Ile Ser Asn Ile Thr Glu Asn Val Tyr Ile Asn
        120                 125                 130                 135

Leu Thr Cys Ser Ser Ile His Gly Tyr Pro Glu Pro Lys Lys Met Ser
                        140                 145                 150

Val Leu Leu Arg Thr Lys Asn Ser Thr Ile Glu Tyr Asp Gly Val Met
                    155                 160                 165

Gln Lys Ser Gln Asp Asn Val Thr Glu Leu Tyr Asp Val Ser Ile Ser
                170                 175                 180

Leu Ser Val Ser Phe Pro Asp Val Thr Ser Asn Met Thr Ile Phe Cys
            185                 190                 195

Ile Leu Glu Thr Asp Lys Thr Arg Leu Leu Ser Ser Pro Phe Ser Ile
        200                 205                 210                 215

Glu Leu Glu Asp Pro Gln Pro Pro Pro Asp His Ile Pro Thr Arg Gly
                        220                 225                 230

Thr Gln Leu Phe His Leu Gln Lys Glu Leu Ala Glu Leu Arg Glu Ser
                    235                 240                 245

Thr Ser Gln Met His Thr Ala Ser Ser Leu Glu Lys Gln Ile Gly His
                250                 255                 260

Pro Ser Pro Pro Pro Glu Lys Lys Glu Leu Arg Lys Val Ala His Leu
            265                 270                 275

Thr Gly Lys Ser Asn Ser Arg Ser Met Pro Leu Glu Trp Glu Asp Thr
        280                 285                 290                 295

Tyr Gly Ile Val Leu Leu Ser Gly Val Lys Tyr Lys Lys Gly Gly Leu
                        300                 305                 310

Val Ile Asn Glu Thr Gly Leu Tyr Phe Val Tyr Ser Lys Val Tyr Phe
                    315                 320                 325

Arg Gly Gln Ser Cys Asn Asn Leu Pro Leu Ser His Lys Val Tyr Met
                330                 335                 340

Arg Asn Ser Lys Tyr Pro Gln Asp Leu Val Met Met Glu Gly Lys Met
        345                 350                 355

Met Ser Tyr Cys Thr Thr Gly Gln Met Trp Ala Arg Ser Ser Tyr Leu
        360                 365                 370                 375

Gly Ala Val Phe Asn Leu Thr Ser Ala Asp His Leu Tyr Val Asn Val
                        380                 385                 390

Ser Glu Leu Ser Leu Val Asn Phe Glu Glu Ser Gln Thr Phe Phe Gly
                    395                 400                 405

Leu Tyr Lys Leu Glu Pro Lys Ser Cys Asp Lys Thr His Thr Cys Pro
                410                 415                 420

Pro Cys Pro Ala Pro Glu Leu Leu Gly Gly Pro Ser Val Phe Leu Phe
        425                 430                 435

Pro Pro Lys Pro Lys Asp Thr Leu Met Ile Ser Arg Thr Pro Glu Val
        440                 445                 450                 455

Thr Cys Val Val Val Asp Val Ser His Glu Asp Pro Glu Val Lys Phe
                        460                 465                 470
```

```
Asn Trp Tyr Val Asp Gly Val Glu Val His Asn Ala Lys Thr Lys Pro
            475                 480                 485

Arg Glu Glu Gln Tyr Asn Ser Thr Tyr Arg Val Val Ser Val Leu Thr
        490                 495                 500

Val Leu His Gln Asp Trp Leu Asn Gly Lys Glu Tyr Lys Cys Lys Val
    505                 510                 515

Ser Asn Lys Ala Leu Pro Ala Pro Ile Glu Lys Thr Ile Ser Lys Ala
520                 525                 530                 535

Lys Gly Gln Pro Arg Glu Pro Gln Val Tyr Thr Leu Pro Pro Ser Arg
                540                 545                 550

Asp Glu Leu Thr Lys Asn Gln Val Ser Leu Thr Cys Leu Val Lys Gly
            555                 560                 565

Phe Tyr Pro Ser Asp Ile Ala Val Glu Trp Glu Ser Asn Gly Gln Pro
        570                 575                 580

Glu Asn Asn Tyr Lys Thr Thr Pro Pro Val Leu Asp Ser Asp Gly Ser
585                 590                 595

Phe Phe Leu Tyr Ser Lys Leu Thr Val Asp Lys Ser Arg Trp Gln Gln
600                 605                 610                 615

Gly Asn Val Phe Ser Cys Ser Val Met His Glu Ala Leu His Asn His
                620                 625                 630

Tyr Thr Gln Lys Ser Leu Ser Leu Ser Pro Gly Lys
            635                 640

<210> SEQ ID NO 19
<211> LENGTH: 1469
<212> TYPE: DNA
<213> ORGANISM: Homo sapiens
<220> FEATURE:
<221> NAME/KEY: CDS
<222> LOCATION: (7)..(1458)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1458)

<400> SEQUENCE: 19 gctagc atg ggg gta ctg ctc aca cag agg acg ctg ctc agt ctg gtc        48
       Met Gly Val Leu Leu Thr Gln Arg Thr Leu Leu Ser Leu Val
       -25                 -20                 -15 ctt gca ctc ctg ttt cca agc atg gcg agc atg ctc gag gct cct ctg       96
Leu Ala Leu Leu Phe Pro Ser Met Ala Ser Met Leu Glu Ala Pro Leu
    -10                 -5                 -1 1                 5 aag att caa gct tat ttc aat gag act gca gac ctg cca tgc caa ttt      144
Lys Ile Gln Ala Tyr Phe Asn Glu Thr Ala Asp Leu Pro Cys Gln Phe
                10                  15                  20 gca aac tct caa aac caa agc ctg agt gag cta gta gta ttt tgg cag      192
Ala Asn Ser Gln Asn Gln Ser Leu Ser Glu Leu Val Val Phe Trp Gln
            25                  30                  35 gac cag gaa aac ttg gtt ctg aat gag gta tac tta ggc aaa gag aaa      240
Asp Gln Glu Asn Leu Val Leu Asn Glu Val Tyr Leu Gly Lys Glu Lys
        40                  45                  50 ttt gac agt gtt cat tcc aag tat atg ggc cgc aca agt ttt gat tcg      288
Phe Asp Ser Val His Ser Lys Tyr Met Gly Arg Thr Ser Phe Asp Ser
    55                  60                  65 gac agt tgg acc ctg aga ctt cgc aat ctt cag atc aag gac aag ggc      336
Asp Ser Trp Thr Leu Arg Leu Arg Asn Leu Gln Ile Lys Asp Lys Gly
70                  75                  80                  85
```

```
ttg tat caa tgt atc atc cat cac aaa aag ccc aca gga atg att cgc    384
Leu Tyr Gln Cys Ile Ile His His Lys Lys Pro Thr Gly Met Ile Arg
            90              95              100 atc cac cag atg aat tct gaa ctg tca gtg ctt gct aac ttc agt caa    432
Ile His Gln Met Asn Ser Glu Leu Ser Val Leu Ala Asn Phe Ser Gln
        105             110             115 cct gaa ata gta cca att tct aat ata aca gaa aat gtg tac ata aat    480
Pro Glu Ile Val Pro Ile Ser Asn Ile Thr Glu Asn Val Tyr Ile Asn
        120             125             130 ttg acc tgc tca tct ata cac ggt tac cca gaa cct aag aag atg agt    528
Leu Thr Cys Ser Ser Ile His Gly Tyr Pro Glu Pro Lys Lys Met Ser
    135             140             145 gtt ttg cta aga acc aag aat tca act atc gag tat gat ggt gtt atg    576
Val Leu Leu Arg Thr Lys Asn Ser Thr Ile Glu Tyr Asp Gly Val Met
150             155             160             165 cag aaa tct caa gat aat gtc aca gaa ctg tac gac gtt tcc atc agc    624
Gln Lys Ser Gln Asp Asn Val Thr Glu Leu Tyr Asp Val Ser Ile Ser
            170             175             180 ttg tct gtt tca ttc cct gat gtt acg agc aat atg acc atc ttc tgt    672
Leu Ser Val Ser Phe Pro Asp Val Thr Ser Asn Met Thr Ile Phe Cys
        185             190             195 att ctg gaa act gac aag acg cgg ctt tta tct tca cct ttc tct ata    720
Ile Leu Glu Thr Asp Lys Thr Arg Leu Leu Ser Ser Pro Phe Ser Ile
        200             205             210 gag ctt gag gac cct cag cct ccc cca gac cac att cct tct aga ccc    768
Glu Leu Glu Asp Pro Gln Pro Pro Pro Asp His Ile Pro Ser Arg Pro
    215             220             225 aaa tct tgt gac aaa act cac aca tgc cca ccg tgc cca gca cct gaa    816
Lys Ser Cys Asp Lys Thr His Thr Cys Pro Pro Cys Pro Ala Pro Glu
230             235             240             245 ctc ctg ggg gga ccg tca gtc ttc ctc ttc ccc cca aaa ccc aag gac    864
Leu Leu Gly Gly Pro Ser Val Phe Leu Phe Pro Pro Lys Pro Lys Asp
            250             255             260 acc ctc atg atc tcc cgg acc cct gag gtc aca tgc gtg gtg gtg gac    912
Thr Leu Met Ile Ser Arg Thr Pro Glu Val Thr Cys Val Val Val Asp
        265             270             275 gtg agc cac gaa gac cct gag gtc aag ttc aac tgg tac gtg gac ggc    960
Val Ser His Glu Asp Pro Glu Val Lys Phe Asn Trp Tyr Val Asp Gly
        280             285             290 gtg gag gtg cat aat gcc aag aca aag ccg cgg gag gag cag tac aac    1008
Val Glu Val His Asn Ala Lys Thr Lys Pro Arg Glu Glu Gln Tyr Asn
    295             300             305 agc acg tac cgt gtg gtc agc gtc ctc acc gtc ctg cac cag gac tgg    1056
Ser Thr Tyr Arg Val Val Ser Val Leu Thr Val Leu His Gln Asp Trp
310             315             320             325 ctg aat ggc aag gag tac aag tgc aag gtc tcc aac aaa gcc ctc cca    1104
Leu Asn Gly Lys Glu Tyr Lys Cys Lys Val Ser Asn Lys Ala Leu Pro
            330             335             340 gcc ccc atc gag aaa acc atc tcc aaa gcc aaa ggg cag ccc cga gaa    1152
Ala Pro Ile Glu Lys Thr Ile Ser Lys Ala Lys Gly Gln Pro Arg Glu
        345             350             355 cca cag gtg tac acc ctg ccc cca tcc cgg gat gag ctg acc aag aac    1200
Pro Gln Val Tyr Thr Leu Pro Pro Ser Arg Asp Glu Leu Thr Lys Asn
        360             365             370 cag gtc agc ctg acc tgc ctg gtc aaa ggc ttc tat ccc agc gac atc    1248
Gln Val Ser Leu Thr Cys Leu Val Lys Gly Phe Tyr Pro Ser Asp Ile
    375             380             385 gcc gtg gag tgg gag agc aat ggg cag ccg gag aac aac tac aag acc    1296
Ala Val Glu Trp Glu Ser Asn Gly Gln Pro Glu Asn Asn Tyr Lys Thr
390             395             400             405
```

```
acg cct ccc gtg ctg gac tcc gac ggc tcc ttc ttc ctc tac agc aag    1344
Thr Pro Pro Val Leu Asp Ser Asp Gly Ser Phe Phe Leu Tyr Ser Lys
            410                 415                 420 ctc acc gtg gac aag agc agg tgg cag cag ggg aac gtc ttc tca tgc    1392
Leu Thr Val Asp Lys Ser Arg Trp Gln Gln Gly Asn Val Phe Ser Cys
        425                 430                 435 tcc gtg atg cat gag gct ctg cac aac cac tac acg cag aag agc ctc    1440
Ser Val Met His Glu Ala Leu His Asn His Tyr Thr Gln Lys Ser Leu
440                 445                 450 tcc ctg tct ccg ggt aaa tgagcggccg c                               1469
Ser Leu Ser Pro Gly Lys
    455

<210> SEQ ID NO 20
<211> LENGTH: 484
<212> TYPE: PRT
<213> ORGANISM: Homo sapiens

<400> SEQUENCE: 20

Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Ala Pro Leu Lys Ile
                -5              -1  1                   5

Gln Ala Tyr Phe Asn Glu Thr Ala Asp Leu Pro Cys Gln Phe Ala Asn
            10                  15                  20

Ser Gln Asn Gln Ser Leu Ser Glu Leu Val Val Phe Trp Gln Asp Gln
        25                  30                  35

Glu Asn Leu Val Leu Asn Glu Val Tyr Leu Gly Lys Glu Lys Phe Asp
40                  45                  50                  55

Ser Val His Ser Lys Tyr Met Gly Arg Thr Ser Phe Asp Ser Asp Ser
                60                  65                  70

Trp Thr Leu Arg Leu Arg Asn Leu Gln Ile Lys Asp Lys Gly Leu Tyr
            75                  80                  85

Gln Cys Ile Ile His His Lys Lys Pro Thr Gly Met Ile Arg Ile His
        90                  95                  100

Gln Met Asn Ser Glu Leu Ser Val Leu Ala Asn Phe Ser Gln Pro Glu
    105                 110                 115

Ile Val Pro Ile Ser Asn Ile Thr Glu Asn Val Tyr Ile Asn Leu Thr
120                 125                 130                 135

Cys Ser Ser Ile His Gly Tyr Pro Glu Pro Lys Lys Met Ser Val Leu
                140                 145                 150

Leu Arg Thr Lys Asn Ser Thr Ile Glu Tyr Asp Gly Val Met Gln Lys
            155                 160                 165

Ser Gln Asp Asn Val Thr Glu Leu Tyr Asp Val Ser Ile Ser Leu Ser
        170                 175                 180

Val Ser Phe Pro Asp Val Thr Ser Asn Met Thr Ile Phe Cys Ile Leu
    185                 190                 195

Glu Thr Asp Lys Thr Arg Leu Leu Ser Ser Pro Phe Ser Ile Glu Leu
200                 205                 210                 215

Glu Asp Pro Gln Pro Pro Pro Asp His Ile Pro Ser Arg Pro Lys Ser
                220                 225                 230

Cys Asp Lys Thr His Thr Cys Pro Pro Cys Pro Ala Pro Glu Leu Leu
            235                 240                 245

Gly Gly Pro Ser Val Phe Leu Phe Pro Pro Lys Pro Lys Asp Thr Leu
        250                 255                 260
```

```
Met Ile Ser Arg Thr Pro Glu Val Thr Cys Val Val Val Asp Val Ser
    265                 270                 275
His Glu Asp Pro Glu Val Lys Phe Asn Trp Tyr Val Asp Gly Val Glu
280                 285                 290                 295
Val His Asn Ala Lys Thr Lys Pro Arg Glu Glu Gln Tyr Asn Ser Thr
                300                 305                 310
Tyr Arg Val Val Ser Val Leu Thr Val Leu His Gln Asp Trp Leu Asn
            315                 320                 325
Gly Lys Glu Tyr Lys Cys Lys Val Ser Asn Lys Ala Leu Pro Ala Pro
        330                 335                 340
Ile Glu Lys Thr Ile Ser Lys Ala Lys Gly Gln Pro Arg Glu Pro Gln
    345                 350                 355
Val Tyr Thr Leu Pro Pro Ser Arg Asp Glu Leu Thr Lys Asn Gln Val
360                 365                 370                 375
Ser Leu Thr Cys Leu Val Lys Gly Phe Tyr Pro Ser Asp Ile Ala Val
                380                 385                 390
Glu Trp Glu Ser Asn Gly Gln Pro Glu Asn Asn Tyr Lys Thr Thr Pro
            395                 400                 405
Pro Val Leu Asp Ser Asp Gly Ser Phe Phe Leu Tyr Ser Lys Leu Thr
        410                 415                 420
Val Asp Lys Ser Arg Trp Gln Gln Gly Asn Val Phe Ser Cys Ser Val
    425                 430                 435
Met His Glu Ala Leu His Asn His Tyr Thr Gln Lys Ser Leu Ser Leu
440                 445                 450                 455
Ser Pro Gly Lys

<210> SEQ ID NO 21
<211> LENGTH: 3362
<212> TYPE: DNA
<213> ORGANISM: Homo sapiens
<220> FEATURE:
<221> NAME/KEY: CDS
<222> LOCATION: (37)..(585)

<400> SEQUENCE: 21
ccatatcttc atcttccctc tacccagatt gtgaag atg gaa agg gtc caa ccc      54
                                       Met Glu Arg Val Gln Pro
                                       1               5 ctg gaa gag aat gtg gga aat gca gcc agg cca aga ttc gag agg aac     102
Leu Glu Glu Asn Val Gly Asn Ala Ala Arg Pro Arg Phe Glu Arg Asn
            10                  15                  20 aag cta ttg ctg gtg gcc tct gta att cag gga ctg ggg ctg ctc ctg     150
Lys Leu Leu Leu Val Ala Ser Val Ile Gln Gly Leu Gly Leu Leu Leu
        25                  30                  35 tgc ttc acc tac atc tgc ctg cac ttc tct gct ctt cag gta tca cat     198
Cys Phe Thr Tyr Ile Cys Leu His Phe Ser Ala Leu Gln Val Ser His
    40                  45                  50 cgg tat cct cga att caa agt atc aaa gta caa ttt acc gaa tat aag     246
Arg Tyr Pro Arg Ile Gln Ser Ile Lys Val Gln Phe Thr Glu Tyr Lys
55                  60                  65                  70 aag gag aaa ggt ttc atc ctc act tcc caa aag gag gat gaa atc atg     294
Lys Glu Lys Gly Phe Ile Leu Thr Ser Gln Lys Glu Asp Glu Ile Met
                75                  80                  85 aag gtg cag aac aac tca gtc atc atc aac tgt gat ggg ttt tat ctc     342
Lys Val Gln Asn Asn Ser Val Ile Ile Asn Cys Asp Gly Phe Tyr Leu
            90                  95                  100 atc tcc ctg aag ggc tac ttc tcc cag gaa gtc aac att agc ctt cat     390
Ile Ser Leu Lys Gly Tyr Phe Ser Gln Glu Val Asn Ile Ser Leu His
```

```
                  105                 110                 115
tac cag aag gat gag gag ccc ctc ttc caa ctg aag aag gtc agg tct      438
Tyr Gln Lys Asp Glu Glu Pro Leu Phe Gln Leu Lys Lys Val Arg Ser
        120                 125                 130 gtc aac tcc ttg atg gtg gcc tct ctg act tac aaa gac aaa gtc tac      486
Val Asn Ser Leu Met Val Ala Ser Leu Thr Tyr Lys Asp Lys Val Tyr
135                 140                 145                 150 ttg aat gtg acc act gac aat acc tcc ctg gat gac ttc cat gtg aat      534
Leu Asn Val Thr Thr Asp Asn Thr Ser Leu Asp Asp Phe His Val Asn
                155                 160                 165 ggc gga gaa ctg att ctt atc cat caa aat cct ggt gaa ttc tgt gtc      582
Gly Gly Glu Leu Ile Leu Ile His Gln Asn Pro Gly Glu Phe Cys Val
        170                 175                 180 ctt tgaggggctg atggcaatat ctaaaaccag gcaccagcat gaacaccaag            635
Leu ctggggtgg acagggcatg gattcttcat tgcaagtgaa ggagcctccc agctcagcca     695
cgtgggatgt gacaagaagc agatcctggc cctcccgccc ccaccctca gggatattta     755 aaacttattt tatataccag ttaatcttat ttatccttat attttctaaa ttgcctagcc    815
gtcacacccc aagattgcct tgagcctact aggcaccttt gtgagaaaga aaaaatagat    875
gcctcttctt caagatgcat tgtttctatt ggtcaggcaa ttgtcataat aaacttatgt    935
cattgaaaac ggtacctgac taccatttgc tggaaatttg acatgtgtgt ggcattatca    995
aaatgaagag gagcaaggag tgaaggagtg gggttatgaa tctgccaaag gtggtatgaa   1055 ccaaccctg gaagccaaag cggcctctcc aaggttaaat tgattgcagt ttgcatattg    1115
cctaaattta aactttctca tttggtgggg gttcaaaaga gaatcagct tgtgaaaaat    1175 caggacttga agagagccgt ctaagaaata ccacgtgctt ttttctttta ccattttgct   1235
ttcccagcct ccaaacatag ttaatagaaa tttcccttca aagaactgtc tggggatgtg   1295
atgctttgaa aaatctaatc agtgacttaa gagagatttt cttgtataca gggagagtga   1355
gataacttat tgtgaagggt tagctttact gtacaggata gcagggaact ggacatctca   1415
gggtaaaagt cagtacggat tttaatagcc tggggaggaa acacattct ttgccacaga    1475 caggcaaagc aacacatgct catcctcctg cctatgctga gatacgcact cagctccatg   1535
tcttgtacac acagaaacat tgctggtttc aagaaatgag gtgatcctat tatcaaattc   1595
aatctgatgt caaatagcac taagaagtta ttgtgcctta tgaaaaataa tgatctctgt   1655
ctagaaatac catagaccat atatagtctc acattgataa ttgaaactag aagggtctat   1715
atcagcctat gccagggctt caatggaata gtatccccctt atgtttagtt gaaatgtccc  1775
cttaacttga tataatgtgt tatgcttatg gcgctgtgac aatctgattt ttcatgtcaa   1835
cttccagatg atttgtaact tctctgtgcc aaacctttta taaacataaa tttttgagat   1895
atgtatttta aaattgtagc acatgtttcc ctgacatttt caatagagga tacaacatca   1955
cagaatcttt ctggatgatt ctgtgttatc aaggaattgt actgtgctac aattatctct   2015
agaatctcca gaaaggtgga gggctgttcg cccttacact aaatggtctc agttggattt   2075
ttttttcctg ttttctattt cctcttaagt acaccttcaa ctatattccc atccctctat   2135
tttaatctgt tatgaaggaa ggtaaataaa aatgctaaat agaagaaatt gtaggtaagg   2195
taagaggaat caagttctga gtggctgcca aggcactcac agaatcataa tcatggctaa   2255
atatttatgg agggcctact gtggaccagg cactggctaa atacttacat ttacaagaat   2315
cattctgaga cagatattca atgatatctg gcttcactac tcagaagatt gtgtgtgtgt   2375
```

```
ttgtgtgtgt gtgtgtgtgt gtatttcact ttttgttatt gaccatgttc tgcaaaattg    2435
cagttactca gtgagtgata tccgaaaaag taaacgttta tgactatagg taatatttaa    2495
gaaaatgcat ggttcatttt taagtttgga attttatct atatttctca cagatgtgca    2555
gtgcacatgc aggcctaagt atatgttgtg tgtgtttgtc tttgacgtca tggtcccctc    2615
tcttaggtgc tcactcgctt tgggtgcacc tggcctgctc ttcccatgtt ggcctctgca    2675
accacacagg gatatttctg ctatgcacca gcctcactcc accttccttc catcaaaaat    2735
atgtgtgtgt gtctcagtcc ctgtaagtca tgtccttcac agggagaatt aacccttcga    2795
tatacatggc agagttttgt gggaaaagaa ttgaatgaaa agtcaggaga tcagaatttt    2855
aaatttgact tagccactaa ctagccatgt aaccttggga aagtcatttc ccatttctgg    2915
gtcttgcttt tctttctgtt aaatgagagg aatgttaaat atctaacagt ttagaatctt    2975
atgcttacag tgttatctgt gaatgcacat attaaatgtc tatgttcttg ttgctatgag    3035
tcaaggagtg tacacttctc ctttactatg ttgaatgtat ttttttctgg acaagcttac    3095
atcttcctca gccatctttg tgagtccttc aagagcagtt atcaattgtt agttagatat    3155
tttctattta gagaatgctt aagggattcc aatcccgatc caaatcataa tttgttctta    3215
agtatactgg gcaggtcccc tattttaagt cataattttg tatttagtgc tttcctggct    3275
ctcagagagt attaatattg atattaataa tatagttaat agtaatattg ctatttacat    3335
ggaaacaaat aaaagatctc agaattc                                        3362
```

<210> SEQ ID NO 22
<211> LENGTH: 183
<212> TYPE: PRT
<213> ORGANISM: Homo sapiens

<400> SEQUENCE: 22

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

```
<210> SEQ ID NO 23
<211> LENGTH: 1680
<212> TYPE: DNA
<213> ORGANISM: Homo sapiens
<220> FEATURE:
<221> NAME/KEY: CDS
<222> LOCATION: (39)..(800)

<400> SEQUENCE: 23
aaaaagcggc gcgctgtgtc ttcccgcagt ctctcgtc atg gaa tac gcc tct gac        56
                                          Met Glu Tyr Ala Ser Asp
                                          1               5 gct tca ctg gac ccc gaa gcc ccg tgg cct ccc gcg ccc cgc gct cgc         104
Ala Ser Leu Asp Pro Glu Ala Pro Trp Pro Pro Ala Pro Arg Ala Arg
            10                  15                  20 gcc tgc cgc gta ctg cct tgg gcc ctg gtc gcg ggg ctg ctg ctg ctg         152
Ala Cys Arg Val Leu Pro Trp Ala Leu Val Ala Gly Leu Leu Leu Leu
        25                  30                  35 ctg ctg ctc gct gcc gcc tgc gcc gtc ttc ctc gcc tgc ccc tgg gcc         200
Leu Leu Leu Ala Ala Ala Cys Ala Val Phe Leu Ala Cys Pro Trp Ala
40                  45                  50 gtg tcc ggg gct cgc gcc tcg ccc ggc tcc gcg gcc agc ccg aga ctc         248
Val Ser Gly Ala Arg Ala Ser Pro Gly Ser Ala Ala Ser Pro Arg Leu
55                  60                  65                  70 cgc gag ggt ccc gag ctt tcg ccc gat gat ccc gcc ggc ctc ttg gac         296
Arg Glu Gly Pro Glu Leu Ser Pro Asp Asp Pro Ala Gly Leu Leu Asp
                75                  80                  85 ctg cgg cag ggc atg ttt gcg cag ctg gtg gcc caa aat gtt ctg ctg         344
Leu Arg Gln Gly Met Phe Ala Gln Leu Val Ala Gln Asn Val Leu Leu
            90                  95                 100 atc gat ggg ccc ctg agc tgg tac agt gac cca ggc ctg gca ggc gtg         392
Ile Asp Gly Pro Leu Ser Trp Tyr Ser Asp Pro Gly Leu Ala Gly Val
        105                 110                 115 tcc ctg acg ggg ggc ctg agc tac aaa gag gac acg aag gag ctg gtg         440
Ser Leu Thr Gly Gly Leu Ser Tyr Lys Glu Asp Thr Lys Glu Leu Val
    120                 125                 130 gtg gcc aag gct gga gtc tac tat gtc ttc ttt caa cta gag ctg cgg         488
Val Ala Lys Ala Gly Val Tyr Tyr Val Phe Phe Gln Leu Glu Leu Arg
135                 140                 145                 150 cgc gtg gtg gcc ggc gag ggc tca ggc tcc gtt tca ctt gcg ctg cac         536
Arg Val Val Ala Gly Glu Gly Ser Gly Ser Val Ser Leu Ala Leu His
                155                 160                 165 ctg cag cca ctg cgc tct gct gct ggg gcc gcc gcc ctg gct ttg acc         584
Leu Gln Pro Leu Arg Ser Ala Ala Gly Ala Ala Ala Leu Ala Leu Thr
            170                 175                 180 gtg gac ctg cca ccc gcc tcc tcc gag gct cgg aac tcg gcc ttc ggt         632
Val Asp Leu Pro Pro Ala Ser Ser Glu Ala Arg Asn Ser Ala Phe Gly
        185                 190                 195 ttc cag ggc cgc ttg ctg cac ctg agt gcc ggc cag cgc ctg ggc gtc         680
Phe Gln Gly Arg Leu Leu His Leu Ser Ala Gly Gln Arg Leu Gly Val
    200                 205                 210 cat ctt cac act gag gcc agg gca cgc cat gcc tgg cag ctt acc cag         728
His Leu His Thr Glu Ala Arg Ala Arg His Ala Trp Gln Leu Thr Gln
215                 220                 225                 230 ggc gcc aca gtc ttg gga ctc ttc cgg gtg acc ccc gaa atc cca gcc         776
Gly Ala Thr Val Leu Gly Leu Phe Arg Val Thr Pro Glu Ile Pro Ala
                235                 240                 245 gga ctc cct tca ccg agg tcg gaa taacgtccag cctgggtgca gcccacctgg        830
Gly Leu Pro Ser Pro Arg Ser Glu
                250 acagagtccg aatcctactc catccttcat ggagacccct ggtgctgggt ccctgctgct       890
```

-continued

```
ttctctacct caaggggctt ggcaggggtc cctgctgctg acctcccctt gaggaccctc    950
ctcacccact ccttcccaa gttggacctt gatatttatt ctgagcctga gctcagataa   1010
tatattatat atattatata tatatatata tttctattta aagaggatcc tgagtttgtg   1070
aatggacttt tttagaggag ttgttttggg ggggggggg tcttcgacat tgccgaggct   1130
ggtcttgaac tcctggactt agacgatcct cctgcctcag cctcccaagc aactgggatt   1190
catcctttct attaattcat tgtacttatt tgcttatttg tgtgtattga gcatctgtaa   1250
tgtgccagca ttgtgcccag ctagggggc tatagaaaca tctagaaata gactgaaaga   1310
aaatctgagt tatggtaata cgtgaggaat ttaaagactc atccccagcc tccacctcct   1370
gtgtgatact tgggggctag cttttttctt tctttctttt ttttgagatg gtcttgttct   1430
gtcaaccagg ctagaatgca gcggtgcaat catgagtcaa tgcagcctcc agcctcgacc   1490
tcccgaggct caggtgatcc tcccatctca gcctctcgag tagctgggac cacagttgtg   1550
tgccaccaca cttggctaac ttttaattt ttttgcggag acggtattgc tatgttgcca   1610
aggttgttta catgccagta caatttataa taaacactca ttttcctcc ctctgaaaaa   1670
aaaaaaaaa                                                          1680
```

<210> SEQ ID NO 24
<211> LENGTH: 254
<212> TYPE: PRT
<213> ORGANISM: Homo sapiens

<400> SEQUENCE: 24

```
Met Glu Tyr Ala Ser Asp Ala Ser Leu Asp Pro Glu Ala Pro Trp Pro
 1               5                  10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220
```

```
Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 25
<211> LENGTH: 1821
<212> TYPE: DNA
<213> ORGANISM: Homo sapiens
<220> FEATURE:
<221> NAME/KEY: CDS
<222> LOCATION: (7)..(1812)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1812)

<400> SEQUENCE: 25 gctagc atg ggg gta ctg ctc aca cag agg acg ctg ctc agt ctg gtc         48
       Met Gly Val Leu Leu Thr Gln Arg Thr Leu Leu Ser Leu Val
           -25                 -20                 -15 ctt gca ctc ctg ttt cca agc atg gcg agc atg ctc gag cag gta tca        96
Leu Ala Leu Leu Phe Pro Ser Met Ala Ser Met Leu Glu Gln Val Ser
    -10                 -5                  -1  1               5 cat cgg tat cct cga att caa agt atc aaa gta caa ttt acc gaa tat       144
His Arg Tyr Pro Arg Ile Gln Ser Ile Lys Val Gln Phe Thr Glu Tyr
                10                  15                  20 aag aag gag aaa ggt ttc atc ctc act tcc caa aag gag gat gaa atc       192
Lys Lys Glu Lys Gly Phe Ile Leu Thr Ser Gln Lys Glu Asp Glu Ile
            25                  30                  35 atg aag gtg cag aac aac tca gtc atc atc aac tgt gat ggg ttt tat       240
Met Lys Val Gln Asn Asn Ser Val Ile Ile Asn Cys Asp Gly Phe Tyr
        40                  45                  50 ctc atc tcc ctg aag ggc tac ttc tcc cag gaa gtc aac att agc ctt       288
Leu Ile Ser Leu Lys Gly Tyr Phe Ser Gln Glu Val Asn Ile Ser Leu
    55                  60                  65 cat tac cag aag gat gag gag ccc ctc ttc caa ctg aag aag gtc agg       336
His Tyr Gln Lys Asp Glu Glu Pro Leu Phe Gln Leu Lys Lys Val Arg
70                  75                  80                  85 tct gtc aac tcc ttg atg gtg gcc tct ctg act tac aaa gac aaa gtc       384
Ser Val Asn Ser Leu Met Val Ala Ser Leu Thr Tyr Lys Asp Lys Val
                90                  95                  100 tac ttg aat gtg acc act gac aat acc tcc ctg gat gac ttc cat gtg       432
Tyr Leu Asn Val Thr Thr Asp Asn Thr Ser Leu Asp Asp Phe His Val
            105                 110                 115 aat ggc gga gaa ctg att ctt atc cat caa aat cct ggt gaa ttc tgt       480
Asn Gly Gly Glu Leu Ile Leu Ile His Gln Asn Pro Gly Glu Phe Cys
        120                 125                 130 gtc ctt acg cgt gcc tgc ccc tgg gcc gtg tcc ggg gct cgc gcc tcg       528
Val Leu Thr Arg Ala Cys Pro Trp Ala Val Ser Gly Ala Arg Ala Ser
    135                 140                 145 ccc ggc tcc gcg gcc agc ccg aga ctc cgc gag ggt ccc gag ctt tcg       576
Pro Gly Ser Ala Ala Ser Pro Arg Leu Arg Glu Gly Pro Glu Leu Ser
150                 155                 160                 165 ccc gac gat ccc gcc ggc ctc ttg gac ctg cgg cag ggc atg ttt gcg       624
Pro Asp Asp Pro Ala Gly Leu Leu Asp Leu Arg Gln Gly Met Phe Ala
                170                 175                 180 cag ctg gtg gcc caa aat gtt ctg ctg atc gat ggg ccc ctg agc tgg       672
Gln Leu Val Ala Gln Asn Val Leu Leu Ile Asp Gly Pro Leu Ser Trp
            185                 190                 195
```

| | | |
|---|---|---|
| tac agt gac cca ggc ctg gca ggc gtg tcc ctg acg ggg ggc ctg agc<br>Tyr Ser Asp Pro Gly Leu Ala Gly Val Ser Leu Thr Gly Gly Leu Ser<br>200 205 210 | 720 | |
| tac aaa gag gac acg aag gag ctg gtg gtg gcc aag gct gga gtc tac<br>Tyr Lys Glu Asp Thr Lys Glu Leu Val Val Ala Lys Ala Gly Val Tyr<br>215 220 225 | 768 | |
| tat gtc ttc ttt caa cta gag ctg cgg cgt gtg gtg gcc ggc gag ggc<br>Tyr Val Phe Phe Gln Leu Glu Leu Arg Arg Val Val Ala Gly Glu Gly<br>230 235 240 245 | 816 | |
| tca ggc tcc gtt tca ctt gcg ctg cac ctg cag cca ctg cgc tct gct<br>Ser Gly Ser Val Ser Leu Ala Leu His Leu Gln Pro Leu Arg Ser Ala<br>250 255 260 | 864 | |
| gct ggg gcc gcc gcc ctg gct ttg acc gtg gac ctg cca ccc gcc tcc<br>Ala Gly Ala Ala Ala Leu Ala Leu Thr Val Asp Leu Pro Pro Ala Ser<br>265 270 275 | 912 | |
| tcc gag gct cgg aac tcg gcc ttc ggt ttc cag ggc cgc ttg ctg cac<br>Ser Glu Ala Arg Asn Ser Ala Phe Gly Phe Gln Gly Arg Leu Leu His<br>280 285 290 | 960 | |
| ctg agt gcc ggc cag cgc ctg ggc gtc cat ctt cac act gag gcc agg<br>Leu Ser Ala Gly Gln Arg Leu Gly Val His Leu His Thr Glu Ala Arg<br>295 300 305 | 1008 | |
| gca cgc cat gcc tgg cag ctt acc cag ggc gcc aca gtc ttg gga ctc<br>Ala Arg His Ala Trp Gln Leu Thr Gln Gly Ala Thr Val Leu Gly Leu<br>310 315 320 325 | 1056 | |
| ttc cgg gtg acc ccc gaa atc cca gcc gga ctc cct tca ccg agg tcg<br>Phe Arg Val Thr Pro Glu Ile Pro Ala Gly Leu Pro Ser Pro Arg Ser<br>330 335 340 | 1104 | |
| gaa ggt acc tct aga ccc aaa tct tgt gac aaa act cac aca tgc cca<br>Glu Gly Thr Ser Arg Pro Lys Ser Cys Asp Lys Thr His Thr Cys Pro<br>345 350 355 | 1152 | |
| ccg tgc cca gca cct gaa ctc ctg ggg gga ccg tca gtc ttc ctc ttc<br>Pro Cys Pro Ala Pro Glu Leu Leu Gly Gly Pro Ser Val Phe Leu Phe<br>360 365 370 | 1200 | |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>375 380 385 | 1248 | |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>390 395 400 405 | 1296 | |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>410 415 420 | 1344 | |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>425 430 435 | 1392 | |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>440 445 450 | 1440 | |
| tcc aac aaa gcc ctc cca gcc ccc atc gag aaa acc atc tcc aaa gcc<br>Ser Asn Lys Ala Leu Pro Ala Pro Ile Glu Lys Thr Ile Ser Lys Ala<br>455 460 465 | 1488 | |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>470 475 480 485 | 1536 | |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>490 495 500 | 1584 | |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>505 510 515 | 1632 | |

```
gag aac aac tac aag acc acg cct ccc gtg ctg gac tcc gac ggc tcc    1680
Glu Asn Asn Tyr Lys Thr Thr Pro Pro Val Leu Asp Ser Asp Gly Ser
            520                 525                 530 ttc ttc ctc tac agc aag ctc acc gtg gac aag agc agg tgg cag cag    1728
Phe Phe Leu Tyr Ser Lys Leu Thr Val Asp Lys Ser Arg Trp Gln Gln
    535                 540                 545 ggg aac gtc ttc tca tgc tcc gtg atg cat gag gct ctg cac aac cac    1776
Gly Asn Val Phe Ser Cys Ser Val Met His Glu Ala Leu His Asn His
550                 555                 560                 565 tac acg cag aag agc ctc tcc ctg tct ccg ggt aaa tgatctaga          1821
Tyr Thr Gln Lys Ser Leu Ser Leu Ser Pro Gly Lys
                570                 575

<210> SEQ ID NO 26
<211> LENGTH: 602
<212> TYPE: PRT
<213> ORGANISM: Homo sapiens

<400> SEQUENCE: 26

Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Gln Val Ser His Arg
                -5              -1  1               5

Tyr Pro Arg Ile Gln Ser Ile Lys Val Gln Phe Thr Glu Tyr Lys Lys
                10                  15                  20

Glu Lys Gly Phe Ile Leu Thr Ser Gln Lys Glu Asp Glu Ile Met Lys
            25                  30                  35

Val Gln Asn Asn Ser Val Ile Ile Asn Cys Asp Gly Phe Tyr Leu Ile
40                  45                  50                  55

Ser Leu Lys Gly Tyr Phe Ser Gln Glu Val Asn Ile Ser Leu His Tyr
                60                  65                  70

Gln Lys Asp Glu Glu Pro Leu Phe Gln Leu Lys Lys Val Arg Ser Val
            75                  80                  85

Asn Ser Leu Met Val Ala Ser Leu Thr Tyr Lys Asp Lys Val Tyr Leu
        90                  95                  100

Asn Val Thr Thr Asp Asn Thr Ser Leu Asp Asp Phe His Val Asn Gly
    105                 110                 115

Gly Glu Leu Ile Leu Ile His Gln Asn Pro Gly Glu Phe Cys Val Leu
120                 125                 130                 135

Thr Arg Ala Cys Pro Trp Ala Val Ser Gly Ala Arg Ala Ser Pro Gly
                140                 145                 150

Ser Ala Ala Ser Pro Arg Leu Arg Glu Gly Pro Glu Leu Ser Pro Asp
            155                 160                 165

Asp Pro Ala Gly Leu Leu Asp Leu Arg Gln Gly Met Phe Ala Gln Leu
        170                 175                 180

Val Ala Gln Asn Val Leu Leu Ile Asp Gly Pro Leu Ser Trp Tyr Ser
    185                 190                 195

Asp Pro Gly Leu Ala Gly Val Ser Leu Thr Gly Gly Leu Ser Tyr Lys
200                 205                 210                 215

Glu Asp Thr Lys Glu Leu Val Val Ala Lys Ala Gly Val Tyr Tyr Val
                220                 225                 230

Phe Phe Gln Leu Glu Leu Arg Arg Val Val Ala Gly Glu Gly Ser Gly
            235                 240                 245

Ser Val Ser Leu Ala Leu His Leu Gln Pro Leu Arg Ser Ala Ala Gly
        250                 255                 260
```

Ala Ala Ala Leu Ala Leu Thr Val Asp Leu Pro Pro Ala Ser Ser Glu
265                 270                 275

Ala Arg Asn Ser Ala Phe Gly Phe Gln Gly Arg Leu Leu His Leu Ser
280                 285                 290                 295

Ala Gly Gln Arg Leu Gly Val His Leu His Thr Glu Ala Arg Ala Arg
            300                 305                 310

His Ala Trp Gln Leu Thr Gln Gly Ala Thr Val Leu Gly Leu Phe Arg
            315                 320                 325

Val Thr Pro Glu Ile Pro Ala Gly Leu Pro Ser Pro Arg Ser Glu Gly
            330                 335                 340

Thr Ser Arg Pro Lys Ser Cys Asp Lys Thr His Thr Cys Pro Pro Cys
345                 350                 355

Pro Ala Pro Glu Leu Leu Gly Gly Pro Ser Val Phe Leu Phe Pro Pro
360                 365                 370                 375

Lys Pro Lys Asp Thr Leu Met Ile Ser Arg Thr Pro Glu Val Thr Cys
            380                 385                 390

Val Val Val Asp Val Ser His Glu Asp Pro Glu Val Lys Phe Asn Trp
            395                 400                 405

Tyr Val Asp Gly Val Glu Val His Asn Ala Lys Thr Lys Pro Arg Glu
            410                 415                 420

Glu Gln Tyr Asn Ser Thr Tyr Arg Val Val Ser Val Leu Thr Val Leu
425                 430                 435

His Gln Asp Trp Leu Asn Gly Lys Glu Tyr Lys Cys Lys Val Ser Asn
440                 445                 450                 455

Lys Ala Leu Pro Ala Pro Ile Glu Lys Thr Ile Ser Lys Ala Lys Gly
            460                 465                 470

Gln Pro Arg Glu Pro Gln Val Tyr Thr Leu Pro Pro Ser Arg Asp Glu
            475                 480                 485

Leu Thr Lys Asn Gln Val Ser Leu Thr Cys Leu Val Lys Gly Phe Tyr
            490                 495                 500

Pro Ser Asp Ile Ala Val Glu Trp Glu Ser Asn Gly Gln Pro Glu Asn
505                 510                 515

Asn Tyr Lys Thr Thr Pro Pro Val Leu Asp Ser Asp Gly Ser Phe Phe
520                 525                 530                 535

Leu Tyr Ser Lys Leu Thr Val Asp Lys Ser Arg Trp Gln Gln Gly Asn
            540                 545                 550

Val Phe Ser Cys Ser Val Met His Glu Ala Leu His Asn His Tyr Thr
            555                 560                 565

Gln Lys Ser Leu Ser Leu Ser Pro Gly Lys
            570                 575

<210> SEQ ID NO 27
<211> LENGTH: 1206
<212> TYPE: DNA
<213> ORGANISM: Homo sapiens
<220> FEATURE:
<221> NAME/KEY: CDS
<222> LOCATION: (7)..(1197)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1197)

<400> SEQUENCE: 27 gctagc atg ggg gta ctg ctc aca cag agg acg ctg ctc agt ctg gtc    48
       Met Gly Val Leu Leu Thr Gln Arg Thr Leu Leu Ser Leu Val -continued

|  | -25 |  |  |  |  | -20 |  |  |  |  | -15 |  |  |  |  |  |
|---|---|---|---|---|---|---|---|---|---|---|---|---|---|---|---|---|
| ctt | gca | ctc | ctg | ttt | cca | agc | atg | gcg | agc | atg | ctc | gag | cag | gta | tca | 96 |
| Leu | Ala | Leu | Leu | Phe | Pro | Ser | Met | Ala | Ser | Met | Leu | Glu | Gln | Val | Ser |  |
|  | -10 |  |  |  | -5 |  |  |  |  | -1 | 1 |  |  |  | 5 |  |
| cat | cgg | tat | cct | cga | att | caa | agt | atc | aaa | gta | caa | ttt | acc | gaa | tat | 144 |
| His | Arg | Tyr | Pro | Arg | Ile | Gln | Ser | Ile | Lys | Val | Gln | Phe | Thr | Glu | Tyr |  |
|  |  |  |  | 10 |  |  |  |  | 15 |  |  |  |  | 20 |  |  |
| aag | aag | gag | aaa | ggt | ttc | atc | ctc | act | tcc | caa | aag | gag | gat | gaa | atc | 192 |
| Lys | Lys | Glu | Lys | Gly | Phe | Ile | Leu | Thr | Ser | Gln | Lys | Glu | Asp | Glu | Ile |  |
|  |  |  | 25 |  |  |  |  | 30 |  |  |  |  | 35 |  |  |  |
| atg | aag | gtg | cag | aac | aac | tca | gtc | atc | atc | aac | tgt | gat | ggg | ttt | tat | 240 |
| Met | Lys | Val | Gln | Asn | Asn | Ser | Val | Ile | Ile | Asn | Cys | Asp | Gly | Phe | Tyr |  |
|  |  | 40 |  |  |  |  | 45 |  |  |  |  | 50 |  |  |  |  |
| ctc | atc | tcc | ctg | aag | ggc | tac | ttc | tcc | cag | gaa | gtc | aac | att | agc | ctt | 288 |
| Leu | Ile | Ser | Leu | Lys | Gly | Tyr | Phe | Ser | Gln | Glu | Val | Asn | Ile | Ser | Leu |  |
|  | 55 |  |  |  |  | 60 |  |  |  |  | 65 |  |  |  |  |  |
| cat | tac | cag | aag | gat | gag | gag | ccc | ctc | ttc | caa | ctg | aag | aag | gtc | agg | 336 |
| His | Tyr | Gln | Lys | Asp | Glu | Glu | Pro | Leu | Phe | Gln | Leu | Lys | Lys | Val | Arg |  |
| 70 |  |  |  |  | 75 |  |  |  |  | 80 |  |  |  |  | 85 |  |
| tct | gtc | aac | tcc | ttg | atg | gtg | gcc | tct | ctg | act | tac | aaa | gac | aaa | gtc | 384 |
| Ser | Val | Asn | Ser | Leu | Met | Val | Ala | Ser | Leu | Thr | Tyr | Lys | Asp | Lys | Val |  |
|  |  |  |  |  | 90 |  |  |  |  | 95 |  |  |  |  | 100 |  |
| tac | ttg | aat | gtg | acc | act | gac | aat | acc | tcc | ctg | gat | gac | ttc | cat | gtg | 432 |
| Tyr | Leu | Asn | Val | Thr | Thr | Asp | Asn | Thr | Ser | Leu | Asp | Asp | Phe | His | Val |  |
|  |  |  |  | 105 |  |  |  |  | 110 |  |  |  |  | 115 |  |  |
| aat | ggc | gga | gaa | ctg | att | ctt | atc | cat | caa | aat | cct | ggt | gaa | ttc | tgt | 480 |
| Asn | Gly | Gly | Glu | Leu | Ile | Leu | Ile | His | Gln | Asn | Pro | Gly | Glu | Phe | Cys |  |
|  |  | 120 |  |  |  |  | 125 |  |  |  |  | 130 |  |  |  |  |
| gtc | ctt | acg | cgt | ggt | acc | tct | aga | ccc | aaa | tct | tgt | gac | aaa | act | cac | 528 |
| Val | Leu | Thr | Arg | Gly | Thr | Ser | Arg | Pro | Lys | Ser | Cys | Asp | Lys | Thr | His |  |
|  | 135 |  |  |  |  | 140 |  |  |  |  | 145 |  |  |  |  |  |
| aca | tgc | cca | ccg | tgc | cca | gca | cct | gaa | ctc | ctg | ggg | gga | ccg | tca | gtc | 576 |
| Thr | Cys | Pro | Pro | Cys | Pro | Ala | Pro | Glu | Leu | Leu | Gly | Gly | Pro | Ser | Val |  |
| 150 |  |  |  |  | 155 |  |  |  |  | 160 |  |  |  |  | 165 |  |
| ttc | ctc | ttc | ccc | cca | aaa | ccc | aag | gac | acc | ctc | atg | atc | tcc | cgg | acc | 624 |
| Phe | Leu | Phe | Pro | Pro | Lys | Pro | Lys | Asp | Thr | Leu | Met | Ile | Ser | Arg | Thr |  |
|  |  |  |  |  | 170 |  |  |  |  | 175 |  |  |  |  | 180 |  |
| cct | gag | gtc | aca | tgc | gtg | gtg | gtg | gac | gtg | agc | cac | gaa | gac | cct | gag | 672 |
| Pro | Glu | Val | Thr | Cys | Val | Val | Val | Asp | Val | Ser | His | Glu | Asp | Pro | Glu |  |
|  |  |  | 185 |  |  |  |  | 190 |  |  |  |  | 195 |  |  |  |
| gtc | aag | ttc | aac | tgg | tac | gtg | gac | ggc | gtg | gag | gtg | cat | aat | gcc | aag | 720 |
| Val | Lys | Phe | Asn | Trp | Tyr | Val | Asp | Gly | Val | Glu | Val | His | Asn | Ala | Lys |  |
|  |  | 200 |  |  |  |  | 205 |  |  |  |  | 210 |  |  |  |  |
| aca | aag | ccg | cgg | gag | gag | cag | tac | aac | agc | acg | tac | cgt | gtg | gtc | agc | 768 |
| Thr | Lys | Pro | Arg | Glu | Glu | Gln | Tyr | Asn | Ser | Thr | Tyr | Arg | Val | Val | Ser |  |
| 215 |  |  |  |  | 220 |  |  |  |  | 225 |  |  |  |  |  |  |
| gtc | ctc | acc | gtc | ctg | cac | cag | gac | tgg | ctg | aat | ggc | aag | gag | tac | aag | 816 |
| Val | Leu | Thr | Val | Leu | His | Gln | Asp | Trp | Leu | Asn | Gly | Lys | Glu | Tyr | Lys |  |
| 230 |  |  |  |  | 235 |  |  |  |  | 240 |  |  |  |  | 245 |  |
| tgc | aag | gtc | tcc | aac | aaa | gcc | ctc | cca | gcc | ccc | atc | gag | aaa | acc | atc | 864 |
| Cys | Lys | Val | Ser | Asn | Lys | Ala | Leu | Pro | Ala | Pro | Ile | Glu | Lys | Thr | Ile |  |
|  |  |  |  | 250 |  |  |  |  | 255 |  |  |  |  | 260 |  |  |
| tcc | aaa | gcc | aaa | ggg | cag | ccc | cga | gaa | cca | cag | gtg | tac | acc | ctg | ccc | 912 |
| Ser | Lys | Ala | Lys | Gly | Gln | Pro | Arg | Glu | Pro | Gln | Val | Tyr | Thr | Leu | Pro |  |
|  |  |  | 265 |  |  |  |  | 270 |  |  |  |  | 275 |  |  |  |
| cca | tcc | cgg | gat | gag | ctg | acc | aag | aac | cag | gtc | agc | ctg | acc | tgc | ctg | 960 |
| Pro | Ser | Arg | Asp | Glu | Leu | Thr | Lys | Asn | Gln | Val | Ser | Leu | Thr | Cys | Leu |  |
|  |  | 280 |  |  |  |  | 285 |  |  |  |  | 290 |  |  |  |  |
| gtc | aaa | ggc | ttc | tat | ccc | agc | gac | atc | gcc | gtg | gag | tgg | gag | agc | aat | 1008 |

```
Val Lys Gly Phe Tyr Pro Ser Asp Ile Ala Val Glu Trp Glu Ser Asn
    295                 300                 305 ggg cag ccg gag aac aac tac aag acc acg cct ccc gtg ctg gac tcc    1056
Gly Gln Pro Glu Asn Asn Tyr Lys Thr Thr Pro Pro Val Leu Asp Ser
310                 315                 320                 325 gac ggc tcc ttc ttc ctc tac agc aag ctc acc gtg gac aag agc agg    1104
Asp Gly Ser Phe Phe Leu Tyr Ser Lys Leu Thr Val Asp Lys Ser Arg
                330                 335                 340 tgg cag cag ggg aac gtc ttc tca tgc tcc gtg atg cat gag gct ctg    1152
Trp Gln Gln Gly Asn Val Phe Ser Cys Ser Val Met His Glu Ala Leu
            345                 350                 355 cac aac cac tac acg cag aag agc ctc tcc ctg tct ccg ggt aaa        1197
His Asn His Tyr Thr Gln Lys Ser Leu Ser Leu Ser Pro Gly Lys
        360                 365                 370 tgatctaga                                                           1206

<210> SEQ ID NO 28
<211> LENGTH: 397
<212> TYPE: PRT
<213> ORGANISM: Homo sapiens

<400> SEQUENCE: 28

Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Gln Val Ser His Arg
                -5              -1  1               5

Tyr Pro Arg Ile Gln Ser Ile Lys Val Gln Phe Thr Glu Tyr Lys Lys
                10                  15                  20

Glu Lys Gly Phe Ile Leu Thr Ser Gln Lys Glu Asp Glu Ile Met Lys
        25                  30                  35

Val Gln Asn Asn Ser Val Ile Ile Asn Cys Asp Gly Phe Tyr Leu Ile
40                  45                  50                  55

Ser Leu Lys Gly Tyr Phe Ser Gln Glu Val Asn Ile Ser Leu His Tyr
                60                  65                  70

Gln Lys Asp Glu Glu Pro Leu Phe Gln Leu Lys Lys Val Arg Ser Val
            75                  80                  85

Asn Ser Leu Met Val Ala Ser Leu Thr Tyr Lys Asp Lys Val Tyr Leu
        90                  95                  100

Asn Val Thr Thr Asp Asn Thr Ser Leu Asp Asp Phe His Val Asn Gly
    105                 110                 115

Gly Glu Leu Ile Leu Ile His Gln Asn Pro Gly Glu Phe Cys Val Leu
120                 125                 130                 135

Thr Arg Gly Thr Ser Arg Pro Lys Ser Cys Asp Lys Thr His Thr Cys
                140                 145                 150

Pro Pro Cys Pro Ala Pro Glu Leu Leu Gly Gly Pro Ser Val Phe Leu
            155                 160                 165

Phe Pro Pro Lys Pro Lys Asp Thr Leu Met Ile Ser Arg Thr Pro Glu
        170                 175                 180

Val Thr Cys Val Val Val Asp Val Ser His Glu Asp Pro Glu Val Lys
    185                 190                 195

Phe Asn Trp Tyr Val Asp Gly Val Glu Val His Asn Ala Lys Thr Lys
200                 205                 210                 215

Pro Arg Glu Glu Gln Tyr Asn Ser Thr Tyr Arg Val Val Ser Val Leu
                220                 225                 230

Thr Val Leu His Gln Asp Trp Leu Asn Gly Lys Glu Tyr Lys Cys Lys
            235                 240                 245
```

```
Val Ser Asn Lys Ala Leu Pro Ala Pro Ile Glu Lys Thr Ile Ser Lys
        250                 255                 260

Ala Lys Gly Gln Pro Arg Glu Pro Gln Val Tyr Thr Leu Pro Pro Ser
265                 270                 275

Arg Asp Glu Leu Thr Lys Asn Gln Val Ser Leu Thr Cys Leu Val Lys
280                 285                 290                 295

Gly Phe Tyr Pro Ser Asp Ile Ala Val Glu Trp Ser Asn Gly Gln
                300                 305                 310

Pro Glu Asn Asn Tyr Lys Thr Thr Pro Pro Val Leu Asp Ser Asp Gly
                315                 320                 325

Ser Phe Phe Leu Tyr Ser Lys Leu Thr Val Asp Lys Ser Arg Trp Gln
            330                 335                 340

Gln Gly Asn Val Phe Ser Cys Ser Val Met His Glu Ala Leu His Asn
        345                 350                 355

His Tyr Thr Gln Lys Ser Leu Ser Leu Ser Pro Gly Lys
360                 365                 370
```

```
<210> SEQ ID NO 29
<211> LENGTH: 1422
<212> TYPE: DNA
<213> ORGANISM: Homo sapiens
<220> FEATURE:
<221> NAME/KEY: CDS
<222> LOCATION: (7)..(1413)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1413)

<400> SEQUENCE: 29
```

```
gctagc atg ggg gta ctg ctc aca cag agg acg ctg ctc agt ctg gtc        48
       Met Gly Val Leu Leu Thr Gln Arg Thr Leu Leu Ser Leu Val
           -25                 -20                 -15 ctt gca ctc ctg ttt cca agc atg gcg agc atg ctc gag gcc tgc ccc       96
Leu Ala Leu Leu Phe Pro Ser Met Ala Ser Met Leu Glu Ala Cys Pro
    -10                 -5                  -1  1                5 tgg gcc gtg tcc ggg gct cgc gcc tcg ccc ggc tcc gcg gcc agc ccg      144
Trp Ala Val Ser Gly Ala Arg Ala Ser Pro Gly Ser Ala Ala Ser Pro
                10                  15                  20 aga ctc cgc gag ggt ccc gag ctt tcg ccc gac gat ccc gcc ggc ctc      192
Arg Leu Arg Glu Gly Pro Glu Leu Ser Pro Asp Asp Pro Ala Gly Leu
                    25                  30                  35 ttg gac ctg cgg cag ggc atg ttt gcg cag ctg gtg gcc caa aat gtt      240
Leu Asp Leu Arg Gln Gly Met Phe Ala Gln Leu Val Ala Gln Asn Val
            40                  45                  50 ctg ctg atc gat ggg ccc ctg agc tgg tac agt gac cca ggc ctg gca      288
Leu Leu Ile Asp Gly Pro Leu Ser Trp Tyr Ser Asp Pro Gly Leu Ala
        55                  60                  65 ggc gtg tcc ctg acg ggg ggc ctg agc tac aaa gag gac acg aag gag      336
Gly Val Ser Leu Thr Gly Gly Leu Ser Tyr Lys Glu Asp Thr Lys Glu
70                  75                  80                  85 ctg gtg gtg gcc aag gct gga gtc tac tat gtc ttc ttt caa cta gag      384
Leu Val Val Ala Lys Ala Gly Val Tyr Tyr Val Phe Phe Gln Leu Glu
                    90                  95                 100 ctg cgg cgc gtg gtg gcc ggc gag ggc tca ggc tcc gtt tca ctt gcg      432
Leu Arg Arg Val Val Ala Gly Glu Gly Ser Gly Ser Val Ser Leu Ala
                105                 110                 115 ctg cac ctg cag cca ctg cgc tct gct gct ggg gcc gcc gcc ctg gct      480
```

```
                Leu His Leu Gln Pro Leu Arg Ser Ala Ala Gly Ala Ala Leu Ala
                        120                 125                 130 ttg acc gtg gac ctg cca ccc gcc tcc tcc gag gct cgg aac tcg gcc        528
Leu Thr Val Asp Leu Pro Pro Ala Ser Ser Glu Ala Arg Asn Ser Ala
        135                 140                 145 ttc ggt ttc cag ggc cgc ttg ctg cac ctg agt gcc ggc cag cgc ctg        576
Phe Gly Phe Gln Gly Arg Leu Leu His Leu Ser Ala Gly Gln Arg Leu
150                 155                 160                 165 ggc gtc cat ctt cac act gag gcc agg gca cgc cat gcc tgg cag ctt        624
Gly Val His Leu His Thr Glu Ala Arg Ala Arg His Ala Trp Gln Leu
                170                 175                 180 acc cag ggc gcc aca gtc ttg gga ctc ttc cgg gtg acc ccc gaa atc        672
Thr Gln Gly Ala Thr Val Leu Gly Leu Phe Arg Val Thr Pro Glu Ile
        185                 190                 195 cca gcc gga ctc cct tca ccg agg tcg gaa acg cgt ggt acc tct aga        720
Pro Ala Gly Leu Pro Ser Pro Arg Ser Glu Thr Arg Gly Thr Ser Arg
        200                 205                 210 ccc aaa tct tgt gac aaa act cac aca tgc cca ccg tgc cca gca cct        768
Pro Lys Ser Cys Asp Lys Thr His Thr Cys Pro Pro Cys Pro Ala Pro
215                 220                 225 gaa ctc ctg ggg gga ccg tca gtc ttc ctc ttc ccc cca aaa ccc aag        816
Glu Leu Leu Gly Gly Pro Ser Val Phe Leu Phe Pro Pro Lys Pro Lys
230                 235                 240                 245 gac acc ctc atg atc tcc cgg acc cct gag gtc aca tgc gtg gtg gtg        864
Asp Thr Leu Met Ile Ser Arg Thr Pro Glu Val Thr Cys Val Val Val
                250                 255                 260 gac gtg agc cac gaa gac cct gag gtc aag ttc aac tgg tac gtg gac        912
Asp Val Ser His Glu Asp Pro Glu Val Lys Phe Asn Trp Tyr Val Asp
        265                 270                 275 ggc gtg gag gtg cat aat gcc aag aca aag ccg cgg gag gag cag tac        960
Gly Val Glu Val His Asn Ala Lys Thr Lys Pro Arg Glu Glu Gln Tyr
        280                 285                 290 aac agc acg tac cgt gtg gtc agc gtc ctc acc gtc ctg cac cag gac       1008
Asn Ser Thr Tyr Arg Val Val Ser Val Leu Thr Val Leu His Gln Asp
295                 300                 305 tgg ctg aat ggc aag gag tac aag tgc aag gtc tcc aac aaa gcc ctc       1056
Trp Leu Asn Gly Lys Glu Tyr Lys Cys Lys Val Ser Asn Lys Ala Leu
310                 315                 320                 325 cca gcc ccc atc gag aaa acc atc tcc aaa gcc aaa ggg cag ccc cga       1104
Pro Ala Pro Ile Glu Lys Thr Ile Ser Lys Ala Lys Gly Gln Pro Arg
                330                 335                 340 gaa cca cag gtg tac acc ctg ccc cca tcc cgg gat gag ctg acc aag       1152
Glu Pro Gln Val Tyr Thr Leu Pro Pro Ser Arg Asp Glu Leu Thr Lys
        345                 350                 355 aac cag gtc agc ctg acc tgc ctg gtc aaa ggc ttc tat ccc agc gac       1200
Asn Gln Val Ser Leu Thr Cys Leu Val Lys Gly Phe Tyr Pro Ser Asp
        360                 365                 370 atc gcc gtg gag tgg gag agc aat ggg cag ccg gag aac aac tac aag       1248
Ile Ala Val Glu Trp Glu Ser Asn Gly Gln Pro Glu Asn Asn Tyr Lys
375                 380                 385 acc acg cct ccc gtg ctg gac tcc gac ggc tcc ttc ttc ctc tac agc       1296
Thr Thr Pro Pro Val Leu Asp Ser Asp Gly Ser Phe Phe Leu Tyr Ser
390                 395                 400                 405 aag ctc acc gtg gac aag agc agg tgg cag cag ggg aac gtc ttc tca       1344
Lys Leu Thr Val Asp Lys Ser Arg Trp Gln Gln Gly Asn Val Phe Ser
                410                 415                 420 tgc tcc gtg atg cat gag gct ctg cac aac cac tac acg cag aag agc       1392
Cys Ser Val Met His Glu Ala Leu His Asn His Tyr Thr Gln Lys Ser
        425                 430                 435
```

-continued

```
ctc tcc ctg tct ccg ggt aaa tgatctaga                                    1422
Leu Ser Leu Ser Pro Gly Lys
        440
```

<210> SEQ ID NO 30
<211> LENGTH: 469
<212> TYPE: PRT
<213> ORGANISM: Homo sapiens

<400> SEQUENCE: 30

```
Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Ala Cys Pro Trp Ala
            -5                  -1  1                    5

Val Ser Gly Ala Arg Ala Ser Pro Gly Ser Ala Ala Ser Pro Arg Leu
                10                  15                  20

Arg Glu Gly Pro Glu Leu Ser Pro Asp Asp Pro Ala Gly Leu Leu Asp
            25                  30                  35

Leu Arg Gln Gly Met Phe Ala Gln Leu Val Ala Gln Asn Val Leu Leu
40                  45                  50                  55

Ile Asp Gly Pro Leu Ser Trp Tyr Ser Asp Pro Gly Leu Ala Gly Val
                60                  65                  70

Ser Leu Thr Gly Gly Leu Ser Tyr Lys Glu Asp Thr Lys Glu Leu Val
            75                  80                  85

Val Ala Lys Ala Gly Val Tyr Tyr Val Phe Phe Gln Leu Glu Leu Arg
            90                  95                  100

Arg Val Val Ala Gly Glu Gly Ser Gly Ser Val Ser Leu Ala Leu His
105                 110                 115

Leu Gln Pro Leu Arg Ser Ala Ala Gly Ala Ala Ala Leu Ala Leu Thr
120                 125                 130                 135

Val Asp Leu Pro Pro Ala Ser Ser Glu Ala Arg Asn Ser Ala Phe Gly
                140                 145                 150

Phe Gln Gly Arg Leu Leu His Leu Ser Ala Gly Gln Arg Leu Gly Val
            155                 160                 165

His Leu His Thr Glu Ala Arg Ala Arg His Ala Trp Gln Leu Thr Gln
        170                 175                 180

Gly Ala Thr Val Leu Gly Leu Phe Arg Val Thr Pro Glu Ile Pro Ala
        185                 190                 195

Gly Leu Pro Ser Pro Arg Ser Glu Thr Arg Gly Thr Ser Arg Pro Lys
200                 205                 210                 215

Ser Cys Asp Lys Thr His Thr Cys Pro Pro Cys Pro Ala Pro Glu Leu
                220                 225                 230

Leu Gly Pro Ser Val Phe Leu Phe Pro Pro Lys Pro Lys Asp Thr
            235                 240                 245

Leu Met Ile Ser Arg Thr Pro Glu Val Thr Cys Val Val Val Asp Val
        250                 255                 260

Ser His Glu Asp Pro Glu Val Lys Phe Asn Trp Tyr Val Asp Gly Val
    265                 270                 275

Glu Val His Asn Ala Lys Thr Lys Pro Arg Glu Glu Gln Tyr Asn Ser
280                 285                 290                 295

Thr Tyr Arg Val Val Ser Val Leu Thr Val Leu His Gln Asp Trp Leu
            300                 305                 310

Asn Gly Lys Glu Tyr Lys Cys Lys Val Ser Asn Lys Ala Leu Pro Ala
        315                 320                 325

Pro Ile Glu Lys Thr Ile Ser Lys Ala Lys Gly Gln Pro Arg Glu Pro
```

```
                330                 335                 340
Gln Val Tyr Thr Leu Pro Pro Ser Arg Asp Glu Leu Thr Lys Asn Gln
            345                 350                 355

Val Ser Leu Thr Cys Leu Val Lys Gly Phe Tyr Pro Ser Asp Ile Ala
360                 365                 370                 375

Val Glu Trp Glu Ser Asn Gly Gln Pro Glu Asn Asn Tyr Lys Thr Thr
                380                 385                 390

Pro Pro Val Leu Asp Ser Asp Gly Ser Phe Phe Leu Tyr Ser Lys Leu
            395                 400                 405

Thr Val Asp Lys Ser Arg Trp Gln Gln Gly Asn Val Phe Ser Cys Ser
        410                 415                 420

Val Met His Glu Ala Leu His Asn His Tyr Thr Gln Lys Ser Leu Ser
425                 430                 435

Leu Ser Pro Gly Lys
440

<210> SEQ ID NO 31
<211> LENGTH: 2620
<212> TYPE: DNA
<213> ORGANISM: Homo sapiens
<220> FEATURE:
<221> NAME/KEY: CDS
<222> LOCATION: (36)..(632)
<220> FEATURE:
<221> NAME/KEY: sig_peptide
<222> LOCATION: (36)..(95)
<220> FEATURE:
<221> NAME/KEY: mat_peptide
<222> LOCATION: (96)..(632)

<400> SEQUENCE: 31
ctgaacgcga ggactgttaa ctgtttctgg caaac atg aag tca ggc ctc tgg       53
                                      Met Lys Ser Gly Leu Trp
                                          -20             -15 tat ttc ttt ctc ttc tgc ttg cgc att aaa gtt tta aca gga gaa atc    101
Tyr Phe Phe Leu Phe Cys Leu Arg Ile Lys Val Leu Thr Gly Glu Ile
                -10                 -5              -1  1 aat ggt tct gcc aat tat gag atg ttt ata ttt cac aac gga ggt gta    149
Asn Gly Ser Ala Asn Tyr Glu Met Phe Ile Phe His Asn Gly Gly Val
            5                   10                  15 caa att tta tgc aaa tat cct gac att gtc cag caa ttt aaa atg cag    197
Gln Ile Leu Cys Lys Tyr Pro Asp Ile Val Gln Gln Phe Lys Met Gln
        20                  25                  30 ttg ctg aaa ggg ggg caa ata ctc tgc gat ctc act aag aca aaa gga    245
Leu Leu Lys Gly Gly Gln Ile Leu Cys Asp Leu Thr Lys Thr Lys Gly
35                  40                  45                  50 agt gga aac aca gtg tcc att aag agt ctg aaa ttc tgc cat tct cag    293
Ser Gly Asn Thr Val Ser Ile Lys Ser Leu Lys Phe Cys His Ser Gln
                55                  60                  65 tta tcc aac aac agt gtc tct ttt tta tac aac ttg gac cat tct        341
Leu Ser Asn Asn Ser Val Ser Phe Phe Leu Tyr Asn Leu Asp His Ser
            70                  75                  80 cat gcc aac tat tac ttc tgc aac cta tca att ttt gat cct cct cct    389
His Ala Asn Tyr Tyr Phe Cys Asn Leu Ser Ile Phe Asp Pro Pro Pro
        85                  90                  95 ttt aaa gta act ctt aca gga gga tat ttg cat att tat gaa tca caa    437
Phe Lys Val Thr Leu Thr Gly Gly Tyr Leu His Ile Tyr Glu Ser Gln
100                 105                 110 ctt tgt tgc cag ctg aag ttc tgg tta ccc ata gga tgt gca gcc ttt    485
Leu Cys Cys Gln Leu Lys Phe Trp Leu Pro Ile Gly Cys Ala Ala Phe
115                 120                 125                 130
```

```
gtt gta gtc tgc att ttg gga tgc ata ctt att tgt tgg ctt aca aaa      533
Val Val Val Cys Ile Leu Gly Cys Ile Leu Ile Cys Trp Leu Thr Lys
            135                 140                 145 aag aag tat tca tcc agt gtg cac gac cct aac ggt gaa tac atg ttc      581
Lys Lys Tyr Ser Ser Ser Val His Asp Pro Asn Gly Glu Tyr Met Phe
            150                 155                 160 atg aga gca gtg aac aca gcc aaa aaa tct aga ctc aca gat gtg acc      629
Met Arg Ala Val Asn Thr Ala Lys Lys Ser Arg Leu Thr Asp Val Thr
            165                 170                 175 cta taatatggaa ctctggcacc caggcatgaa gcacgttggc cagttttcct            682
Leu caacttgaag tgcaagattc tcttatttcc gggaccacgg agagtctgac ttaactacat    742
acatcttctg ctggtgtttt gttcaatctg gaagaatgac tgtatcagtc aatggggatt   802
ttaacagact gccttggtac tgccgagtcc tctcaaaaca acaccctct tgcaaccagc    862 tttggagaaa gcccagctcc tgtgtgctca ctgggagtgg aatccctgtc tccacatctg   922
ctcctagcag tgcatcagcc agtaaaacaa acacatttac aagaaaaatg ttttaaagat   982
gccaggggta ctgaatctgc aaagcaaatg agcagccaag gaccagcatc tgtccgcatt  1042
tcactatcat actacctctt ctttctgtag ggatgagaat tcctctttta atcagtcaag  1102
ggagatgctt caaagctgga gctattttat ttctgagatg ttgatgtgaa ctgtacatta  1162
gtacatactc agtactctcc ttcaattgct gaacccagt tgaccatttt accaagactt   1222
tagatgcttt cttgtgccct caatttttctt tttaaaaata cttctacatg actgcttgac 1282 agcccaacag ccactctcaa tagagagcta tgtcttacat tctttcctct gctgctcaat  1342
agttttatat atctatgcat acatatatac acacatatgt atataaaatt cataatgaat  1402
atatttgcct atattctccc tacaagaata tttttgctcc agaaagacat gttcttttct  1462
caaattcagt taaaatggtt tactttgttc aagttagtgg taggaaacat tgcccggaat  1522
tgaaagcaaa tttatttat tatcctattt tctaccatta tctatgtttt catggtgcta   1582
ttaattacaa gtttagttct ttttgtagat catattaaaa ttgcaaacaa aatcatcttt  1642
aatgggccag cattctcatg gggtagagca gaatattcat ttagcctgaa agctgcagtt  1702
actataggtt gctgtcagac tatacccatg gtgcctctgg gcttgacagg tcaaaatggt  1762
ccccatcagc ctggagcagc cctccagacc tgggtggaat tccagggttg agagactccc  1822
ctgagccaga ggccactagg tattcttgct cccagaggct gaagtcaccc tgggaatcac  1882
agtggtctac ctgcattcat aattccagga tctgtgaaga gcacatatgt gtcagggcac  1942
aattccctct cataaaaacc acacagcctg gaaattggcc ctggcccttc aagatagcct  2002
tctttagaat atgatttggc tagaaagatt cttaaatatg tggaatatga ttattcttag  2062
ctggaatatt ttctctactt cctgtctgca tgcccaaggc ttctgaagca gccaatgtcg  2122
atgcaacaac atttgtaact ttaggtaaac tgggattatg ttgtagttta acattttgta  2182
actgtgtgct tatagtttac aagtgagacc cgatatgtca ttatgcatac ttatattatc  2242
ttaagcatgt gtaatgctgg atgtgtacag tacagtactg aacttgtaat ttgaatctag  2302
tatggtgttc tgttttcagc tgacttggac aacctgactg gctttgcaca ggtgttccct  2362
gagttgtttg caggtttctg tgtgtggggt ggggtatggg gaggagaacc ttcatggtgg  2422
cccacctggc ctggttgtcc aagctgtgcc tcgacacatc ctcatcccca gcatgggaca  2482
cctcaagatg aataataatt cacaaaattt ctgtgaaatc aaatccagtt ttaagaggag  2542
ccacttatca aagagatttt aacagtagta agaaggcaaa gaataaacat tgatattca   2602
```
gcaactgaaa aaaaaaaa                                              2620

<210> SEQ ID NO 32
<211> LENGTH: 199
<212> TYPE: PRT
<213> ORGANISM: Homo sapiens

<400> SEQUENCE: 32

Met Lys Ser Gly Leu Trp Tyr Phe Phe Leu Phe Cys Leu Arg Ile Lys
-20                 -15                 -10                  -5

Val Leu Thr Gly Glu Ile Asn Gly Ser Ala Asn Tyr Glu Met Phe Ile
            -1  1               5                   10

Phe His Asn Gly Gly Val Gln Ile Leu Cys Lys Tyr Pro Asp Ile Val
         15                  20                  25

Gln Gln Phe Lys Met Gln Leu Leu Lys Gly Gly Gln Ile Leu Cys Asp
     30                  35                  40

Leu Thr Lys Thr Lys Gly Ser Gly Asn Thr Val Ser Ile Lys Ser Leu
45                  50                  55                  60

Lys Phe Cys His Ser Gln Leu Ser Asn Asn Ser Val Ser Phe Phe Leu
                 65                  70                  75

Tyr Asn Leu Asp His Ser His Ala Asn Tyr Tyr Phe Cys Asn Leu Ser
             80                  85                  90

Ile Phe Asp Pro Pro Pro Phe Lys Val Thr Leu Thr Gly Gly Tyr Leu
         95                 100                 105

His Ile Tyr Glu Ser Gln Leu Cys Cys Gln Leu Lys Phe Trp Leu Pro
    110                 115                 120

Ile Gly Cys Ala Ala Phe Val Val Cys Ile Leu Gly Cys Ile Leu
125                 130                 135                 140

Ile Cys Trp Leu Thr Lys Lys Lys Tyr Ser Ser Ser Val His Asp Pro
                145                 150                 155

Asn Gly Glu Tyr Met Phe Met Arg Ala Val Asn Thr Ala Lys Lys Ser
                160                 165                 170

Arg Leu Thr Asp Val Thr Leu
        175

<210> SEQ ID NO 33
<211> LENGTH: 1806
<212> TYPE: DNA
<213> ORGANISM: Homo sapiens
<220> FEATURE:
<221> NAME/KEY: CDS
<222> LOCATION: (7)..(1797)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1797)

<400> SEQUENCE: 33 gctagc atg ggg gta ctg ctc aca cag agg acg ctg ctc agt ctg gtc       48
       Met Gly Val Leu Leu Thr Gln Arg Thr Leu Leu Ser Leu Val
           -25                 -20                 -15 ctt gca ctc ctg ttt cca agc atg gcg agc atg ctt cat aga agg ttg      96
Leu Ala Leu Leu Phe Pro Ser Met Ala Ser Met Leu His Arg Arg Leu
    -10                  -5              -1  1               5 gac aag ata gaa gat gaa agg aat ctt cat gaa gat ttt gta ttc atg     144
Asp Lys Ile Glu Asp Glu Arg Asn Leu His Glu Asp Phe Val Phe Met
            10                  15                  20

| | | |
|---|---|---|
| aaa acg ata cag aga tgc aac aca gga gaa aga tcc tta tcc tta ctg<br>Lys Thr Ile Gln Arg Cys Asn Thr Gly Glu Arg Ser Leu Ser Leu Leu<br>           25                    30                    35 | | 192 |
| aac tgt gag gag att aaa agc cag ttt gaa ggc ttt gtg aag gat ata<br>Asn Cys Glu Glu Ile Lys Ser Gln Phe Glu Gly Phe Val Lys Asp Ile<br>        40                    45                    50 | | 240 |
| atg tta aac aaa gag gag acg aag aaa gaa aac agc ttt gaa atg caa<br>Met Leu Asn Lys Glu Glu Thr Lys Lys Glu Asn Ser Phe Glu Met Gln<br>55                    60                    65 | | 288 |
| aaa ggt gat cag aat cct caa att gcg gca cat gtc ata agt gag gcc<br>Lys Gly Asp Gln Asn Pro Gln Ile Ala Ala His Val Ile Ser Glu Ala<br>70                    75                    80                    85 | | 336 |
| agc agt aaa aca aca tct gtg tta cag tgg gct gaa aaa gga tac tac<br>Ser Ser Lys Thr Thr Ser Val Leu Gln Trp Ala Glu Lys Gly Tyr Tyr<br>                    90                    95                    100 | | 384 |
| acc atg agc aac aac ttg gta acc ctg gaa aat ggg aaa cag ctg acc<br>Thr Met Ser Asn Asn Leu Val Thr Leu Glu Asn Gly Lys Gln Leu Thr<br>                105                   110                  115 | | 432 |
| gtt aaa aga caa gga ctc tat tat atc tat gcc caa gtc acc ttc tgt<br>Val Lys Arg Gln Gly Leu Tyr Tyr Ile Tyr Ala Gln Val Thr Phe Cys<br>120                    125                   130 | | 480 |
| tcc aat cgg gaa gct tcg agt caa gct cca ttt ata gcc agc ctc tgc<br>Ser Asn Arg Glu Ala Ser Ser Gln Ala Pro Phe Ile Ala Ser Leu Cys<br>135                    140                   145 | | 528 |
| cta aag tcc ccc ggt aga ttc gag aga atc tta ctc aga gct gca aat<br>Leu Lys Ser Pro Gly Arg Phe Glu Arg Ile Leu Leu Arg Ala Ala Asn<br>150                    155                   160                   165 | | 576 |
| acc cac agt tcc gcc aaa cct tgc ggg caa caa tcc att cac ttg gga<br>Thr His Ser Ser Ala Lys Pro Cys Gly Gln Gln Ser Ile His Leu Gly<br>                170                   175                  180 | | 624 |
| gga gta ttt gaa ttg caa cca ggt gct tcg gtg ttt gtc aat gtg act<br>Gly Val Phe Glu Leu Gln Pro Gly Ala Ser Val Phe Val Asn Val Thr<br>                    185                   190                  195 | | 672 |
| gat cca agc caa gtg agc cat ggc act ggc ttc acg tcc ttt ggc tta<br>Asp Pro Ser Gln Val Ser His Gly Thr Gly Phe Thr Ser Phe Gly Leu<br>                200                   205                  210 | | 720 |
| ctc aaa ctc gag gga gaa atc aat ggt tct gcc aat tat gag atg ttt<br>Leu Lys Leu Glu Gly Glu Ile Asn Gly Ser Ala Asn Tyr Glu Met Phe<br>215                    220                   225 | | 768 |
| ata ttt cac aac gga ggt gta caa att tta tgc aaa tat cct gac att<br>Ile Phe His Asn Gly Gly Val Gln Ile Leu Cys Lys Tyr Pro Asp Ile<br>230                    235                   240                   245 | | 816 |
| gtc cag caa ttt aaa atg cag ttg ctg aaa ggg ggg caa ata ctc tgc<br>Val Gln Gln Phe Lys Met Gln Leu Leu Lys Gly Gly Gln Ile Leu Cys<br>                250                   255                  260 | | 864 |
| gat ctc act aag aca aaa gga agt gga aac aca gtg tcc att aag agt<br>Asp Leu Thr Lys Thr Lys Gly Ser Gly Asn Thr Val Ser Ile Lys Ser<br>                265                   270                  275 | | 912 |
| ctg aaa ttc tgc cat tct cag tta tcc aac aac agt gtc tcc ttt ttt<br>Leu Lys Phe Cys His Ser Gln Leu Ser Asn Asn Ser Val Ser Phe Phe<br>                280                   285                  290 | | 960 |
| cta tac aac ttg gac cat tct cat gcc aac tat tac ttc tgt aac cta<br>Leu Tyr Asn Leu Asp His Ser His Ala Asn Tyr Tyr Phe Cys Asn Leu<br>295                    300                   305 | | 1008 |
| tca att ttt gat cct cct cct ttt aaa gta act ctt aca gga gga tat<br>Ser Ile Phe Asp Pro Pro Pro Phe Lys Val Thr Leu Thr Gly Gly Tyr<br>310                    315                   320                   325 | | 1056 |
| ttg cat att tat gaa tca caa ctt tgt tgc cag ctg aag ttc ctc gag<br>Leu His Ile Tyr Glu Ser Gln Leu Cys Cys Gln Leu Lys Phe Leu Glu<br>                    330                   335                  340 | | 1104 |

-continued

```
ccc aaa tct tgt gac aaa act cac aca tgc cca ccg tgc cca gca cct    1152
Pro Lys Ser Cys Asp Lys Thr His Thr Cys Pro Pro Cys Pro Ala Pro
        345                 350                 355 gaa ctc ctg ggg gga ccg tca gtc ttc ctc ttc ccc cca aaa ccc aag    1200
Glu Leu Leu Gly Gly Pro Ser Val Phe Leu Phe Pro Pro Lys Pro Lys
            360                 365                 370 gac acc ctc atg atc tcc cgg acc cct gag gtc aca tgc gtg gtg gtg    1248
Asp Thr Leu Met Ile Ser Arg Thr Pro Glu Val Thr Cys Val Val Val
    375                 380                 385 gac gtg agc cac gaa gac cct gag gtc aag ttc aac tgg tac gtg gac    1296
Asp Val Ser His Glu Asp Pro Glu Val Lys Phe Asn Trp Tyr Val Asp
390                 395                 400                 405 ggc gtg gag gtg cat aat gcc aag aca aag ccg cgg gag gag cag tac    1344
Gly Val Glu Val His Asn Ala Lys Thr Lys Pro Arg Glu Glu Gln Tyr
                410                 415                 420 aac agc acg tac cgt gtg gtc agc gtc ctc acc gtc ctg cac cag gac    1392
Asn Ser Thr Tyr Arg Val Val Ser Val Leu Thr Val Leu His Gln Asp
            425                 430                 435 tgg ctg aat ggc aag gag tac aag tgc aag gtc tcc aac aaa gcc ctc    1440
Trp Leu Asn Gly Lys Glu Tyr Lys Cys Lys Val Ser Asn Lys Ala Leu
    440                 445                 450 cca gcc ccc atc gag aaa acc atc tcc aaa gcc aaa ggg cag ccc cga    1488
Pro Ala Pro Ile Glu Lys Thr Ile Ser Lys Ala Lys Gly Gln Pro Arg
455                 460                 465 gaa cca cag gtg tac acc ctg ccc cca tcc cgg gat gag ctg acc aag    1536
Glu Pro Gln Val Tyr Thr Leu Pro Pro Ser Arg Asp Glu Leu Thr Lys
470                 475                 480                 485 aac cag gtc agc ctg acc tgc ctg gtc aaa ggc ttc tat ccc agc gac    1584
Asn Gln Val Ser Leu Thr Cys Leu Val Lys Gly Phe Tyr Pro Ser Asp
                490                 495                 500 atc gcc gtg gag tgg gag agc aat ggg cag ccg gag aac aac tac aag    1632
Ile Ala Val Glu Trp Glu Ser Asn Gly Gln Pro Glu Asn Asn Tyr Lys
            505                 510                 515 acc acg cct ccc gtg ctg gac tcc gac ggc tcc ttc ttc ctc tac agc    1680
Thr Thr Pro Pro Val Leu Asp Ser Asp Gly Ser Phe Phe Leu Tyr Ser
    520                 525                 530 aag ctc acc gtg gac aag agc agg tgg cag cag ggg aac gtc ttc tca    1728
Lys Leu Thr Val Asp Lys Ser Arg Trp Gln Gln Gly Asn Val Phe Ser
535                 540                 545 tgc tcc gtg atg cat gag gct ctg cac aac cac tac acg cag aag agc    1776
Cys Ser Val Met His Glu Ala Leu His Asn His Tyr Thr Gln Lys Ser
550                 555                 560                 565 ctc tcc ctg tct ccg ggt aaa tgatctaga                              1806
Leu Ser Leu Ser Pro Gly Lys
                570
```

<210> SEQ ID NO 34
<211> LENGTH: 597
<212> TYPE: PRT
<213> ORGANISM: Homo sapiens

<400> SEQUENCE: 34

```
Met Gly Val Leu Leu Thr Gln Arg Thr Leu Leu Ser Leu Val Leu Ala
-25                 -20                 -15                 -10

Leu Leu Phe Pro Ser Met Ala Ser Met Leu His Arg Arg Leu Asp Lys
                -5                  -1  1               5

Ile Glu Asp Glu Arg Asn Leu His Glu Asp Phe Val Phe Met Lys Thr
                10                  15                  20

Ile Gln Arg Cys Asn Thr Gly Glu Arg Ser Leu Ser Leu Leu Asn Cys
```

```
            25                  30                  35
Glu Glu Ile Lys Ser Gln Phe Glu Gly Phe Val Lys Asp Ile Met Leu
40                  45                  50                  55
Asn Lys Glu Glu Thr Lys Lys Glu Asn Ser Phe Glu Met Gln Lys Gly
                60                  65                  70
Asp Gln Asn Pro Gln Ile Ala Ala His Val Ile Ser Glu Ala Ser Ser
            75                  80                  85
Lys Thr Thr Ser Val Leu Gln Trp Ala Glu Lys Gly Tyr Tyr Thr Met
                90                  95                  100
Ser Asn Asn Leu Val Thr Leu Glu Asn Gly Lys Gln Leu Thr Val Lys
            105                 110                 115
Arg Gln Gly Leu Tyr Tyr Ile Tyr Ala Gln Val Thr Phe Cys Ser Asn
120                 125                 130                 135
Arg Glu Ala Ser Ser Gln Ala Pro Phe Ile Ala Ser Leu Cys Leu Lys
                140                 145                 150
Ser Pro Gly Arg Phe Glu Arg Ile Leu Leu Arg Ala Ala Asn Thr His
            155                 160                 165
Ser Ser Ala Lys Pro Cys Gly Gln Gln Ser Ile His Leu Gly Gly Val
            170                 175                 180
Phe Glu Leu Gln Pro Gly Ala Ser Val Phe Val Asn Val Thr Asp Pro
185                 190                 195
Ser Gln Val Ser His Gly Thr Gly Phe Thr Ser Phe Gly Leu Leu Lys
200                 205                 210                 215
Leu Glu Gly Glu Ile Asn Gly Ser Ala Asn Tyr Glu Met Phe Ile Phe
                220                 225                 230
His Asn Gly Gly Val Gln Ile Leu Cys Lys Tyr Pro Asp Ile Val Gln
            235                 240                 245
Gln Phe Lys Met Gln Leu Leu Lys Gly Gln Ile Leu Cys Asp Leu
            250                 255                 260
Thr Lys Thr Lys Gly Ser Gly Asn Thr Val Ser Ile Lys Ser Leu Lys
265                 270                 275
Phe Cys His Ser Gln Leu Ser Asn Asn Ser Val Ser Phe Phe Leu Tyr
280                 285                 290                 295
Asn Leu Asp His Ser His Ala Asn Tyr Tyr Phe Cys Asn Leu Ser Ile
                300                 305                 310
Phe Asp Pro Pro Phe Lys Val Thr Leu Thr Gly Gly Tyr Leu His
            315                 320                 325
Ile Tyr Glu Ser Gln Leu Cys Cys Gln Leu Lys Phe Leu Glu Pro Lys
            330                 335                 340
Ser Cys Asp Lys Thr His Thr Cys Pro Pro Cys Pro Ala Pro Glu Leu
            345                 350                 355
Leu Gly Gly Pro Ser Val Phe Leu Phe Pro Pro Lys Pro Lys Asp Thr
360                 365                 370                 375
Leu Met Ile Ser Arg Thr Pro Glu Val Thr Cys Val Val Val Asp Val
                380                 385                 390
Ser His Glu Asp Pro Glu Val Lys Phe Asn Trp Tyr Val Asp Gly Val
            395                 400                 405
Glu Val His Asn Ala Lys Thr Lys Pro Arg Glu Glu Gln Tyr Asn Ser
            410                 415                 420
Thr Tyr Arg Val Val Ser Val Leu Thr Val Leu His Gln Asp Trp Leu
            425                 430                 435
Asn Gly Lys Glu Tyr Lys Cys Lys Val Ser Asn Lys Ala Leu Pro Ala
440                 445                 450                 455
```

```
Pro Ile Glu Lys Thr Ile Ser Lys Ala Lys Gly Gln Pro Arg Glu Pro
            460                 465                 470

Gln Val Tyr Thr Leu Pro Pro Ser Arg Asp Glu Leu Thr Lys Asn Gln
        475                 480                 485

Val Ser Leu Thr Cys Leu Val Lys Gly Phe Tyr Pro Ser Asp Ile Ala
    490                 495                 500

Val Glu Trp Glu Ser Asn Gly Gln Pro Glu Asn Asn Tyr Lys Thr Thr
505                 510                 515

Pro Pro Val Leu Asp Ser Asp Gly Ser Phe Phe Leu Tyr Ser Lys Leu
520                 525                 530                 535

Thr Val Asp Lys Ser Arg Trp Gln Gln Gly Asn Val Phe Ser Cys Ser
            540                 545                 550

Val Met His Glu Ala Leu His Asn His Tyr Thr Gln Lys Ser Leu Ser
            555                 560                 565

Leu Ser Pro Gly Lys
        570

<210> SEQ ID NO 35
<211> LENGTH: 1052
<212> TYPE: DNA
<213> ORGANISM: Homo sapiens
<220> FEATURE:
<221> NAME/KEY: CDS
<222> LOCATION: (170)..(892)
<220> FEATURE:
<221> NAME/KEY: sig_peptide
<222> LOCATION: (170)..(220)
<220> FEATURE:
<221> NAME/KEY: mat_peptide
<222> LOCATION: (221)..(892)

<400> SEQUENCE: 35
agagagcgct gggagccgga ggggagcgca gcgagttttg gccagtggtc gtgcagtcca      60
aggggctgga tggcatgctg gacccaagct cagctcagcg tccggaccca ataacagttt     120
taccaaggga gcagctttct atcctggcca cactgaggtg catagcgta atg tcc atg     178
                                                        Met Ser Met
                                                             -15 ttg ttc tac act ctg atc aca gct ttt ctg atc ggc ata cag gcg gaa       226
Leu Phe Tyr Thr Leu Ile Thr Ala Phe Leu Ile Gly Ile Gln Ala Glu
            -10                 -5                  -1   1 cca cac tca gag agc aat gtc cct gca gga cac acc atc ccc caa gcc       274
Pro His Ser Glu Ser Asn Val Pro Ala Gly His Thr Ile Pro Gln Ala
        5                   10                  15 cac tgg act aaa ctt cag cat tcc ctt gac act gcc ctt cgc aga gcc       322
His Trp Thr Lys Leu Gln His Ser Leu Asp Thr Ala Leu Arg Arg Ala
    20                  25                  30 cgc agc gcc ccg gca gcg gcg ata gct gca cgc gtg gcg ggg cag acc       370
Arg Ser Ala Pro Ala Ala Ala Ile Ala Ala Arg Val Ala Gly Gln Thr
35                  40                  45                  50 cgc aac att act gtg gac ccc agg ctg ttt aaa aag cgg cga ctc cgt       418
Arg Asn Ile Thr Val Asp Pro Arg Leu Phe Lys Lys Arg Arg Leu Arg
                55                  60                  65 tca ccc cgt gtg ctg ttt agc acc cag cct ccc cgt gaa gct gca gac       466
Ser Pro Arg Val Leu Phe Ser Thr Gln Pro Pro Arg Glu Ala Ala Asp
            70                  75                  80 act cag gat ctg gac ttc gag gtc ggt ggt gct gcc ccc ttc aac agg       514
Thr Gln Asp Leu Asp Phe Glu Val Gly Gly Ala Ala Pro Phe Asn Arg
        85                  90                  95 act cac agg agc aag cgg tca tca tcc cat ccc atc ttc cac agg ggc       562
```

```
             Thr His Arg Ser Lys Arg Ser Ser His Pro Ile Phe His Arg Gly
                 100                 105                 110 gaa ttc tcg gtg tgt gac agt gtc agc gtg tgg gtt ggg gat aag acc      610
Glu Phe Ser Val Cys Asp Ser Val Ser Val Trp Val Gly Asp Lys Thr
115                 120                 125                 130 acc gcc aca gac atc aag ggc aag gag gtg atg gtg ttg gga gag gtg      658
Thr Ala Thr Asp Ile Lys Gly Lys Glu Val Met Val Leu Gly Glu Val
                    135                 140                 145 aac att aac aac agt gta ttc aaa cag tac ttt ttt gag acc aag tgc      706
Asn Ile Asn Asn Ser Val Phe Lys Gln Tyr Phe Phe Glu Thr Lys Cys
                150                 155                 160 cgg gac cca aat ccc gtt gac agc ggg tgc cgg ggc att gac tca aag      754
Arg Asp Pro Asn Pro Val Asp Ser Gly Cys Arg Gly Ile Asp Ser Lys
            165                 170                 175 cac tgg aac tca tat tgt acc acg act cac acc ttt gtc aag gcg ctg      802
His Trp Asn Ser Tyr Cys Thr Thr Thr His Thr Phe Val Lys Ala Leu
        180                 185                 190 acc atg gat ggc aag cag gct gcc tgg cgg ttt atc cgg ata gat acg      850
Thr Met Asp Gly Lys Gln Ala Ala Trp Arg Phe Ile Arg Ile Asp Thr
195                 200                 205                 210 gcc tgt gtg tgt gtg ctc agc agg aag gct gtg aga aga gcc                  892
Ala Cys Val Cys Val Leu Ser Arg Lys Ala Val Arg Arg Ala
                215                 220 tgacctgccg acacgctccc tccccctgcc ccttctacac tctcctgggc ccctccctac        952
ctcaacctgt aaattatttt aaattataag gactgcatgg taatttatag tttatacagt       1012
tttaaagaat cattatttat taaattttg gaagcataaa                               1052

<210> SEQ ID NO 36
<211> LENGTH: 241
<212> TYPE: PRT
<213> ORGANISM: Homo sapiens

<400> SEQUENCE: 36

Met Ser Met Leu Phe Tyr Thr Leu Ile Thr Ala Phe Leu Ile Gly Ile
        -15                 -10                  -5

Gln Ala Glu Pro His Ser Glu Ser Asn Val Pro Ala Gly His Thr Ile
 -1  1               5                  10                  15

Pro Gln Ala His Trp Thr Lys Leu Gln His Ser Leu Asp Thr Ala Leu
                20                  25                  30

Arg Arg Ala Arg Ser Ala Pro Ala Ala Ala Ile Ala Ala Arg Val Ala
                35                  40                  45

Gly Gln Thr Arg Asn Ile Thr Val Asp Pro Arg Leu Phe Lys Lys Arg
            50                  55                  60

Arg Leu Arg Ser Pro Arg Val Leu Phe Ser Thr Gln Pro Pro Arg Glu
65                  70                  75

Ala Ala Asp Thr Gln Asp Leu Asp Phe Glu Val Gly Gly Ala Ala Pro
80                  85                  90                  95

Phe Asn Arg Thr His Arg Ser Lys Arg Ser Ser His Pro Ile Phe
                100                 105                 110

His Arg Gly Glu Phe Ser Val Cys Asp Ser Val Ser Val Trp Val Gly
                115                 120                 125

Asp Lys Thr Thr Ala Thr Asp Ile Lys Gly Lys Glu Val Met Val Leu
            130                 135                 140

Gly Glu Val Asn Ile Asn Asn Ser Val Phe Lys Gln Tyr Phe Phe Glu
        145                 150                 155

Thr Lys Cys Arg Asp Pro Asn Pro Val Asp Ser Gly Cys Arg Gly Ile
```

```
            160                 165                 170                 175
Asp Ser Lys His Trp Asn Ser Tyr Cys Thr Thr Thr His Thr Phe Val
                180                 185                 190

Lys Ala Leu Thr Met Asp Gly Lys Gln Ala Ala Trp Arg Phe Ile Arg
            195                 200                 205

Ile Asp Thr Ala Cys Val Cys Val Leu Ser Arg Lys Ala Val Arg Arg
        210                 215                 220

Ala

<210> SEQ ID NO 37
<211> LENGTH: 1697
<212> TYPE: DNA
<213> ORGANISM: Homo sapiens
<220> FEATURE:
<221> NAME/KEY: CDS
<222> LOCATION: (7)..(1686)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1686)

<400> SEQUENCE: 37 gctagc atg ggg gta ctg ctc aca cag agg acg ctg ctc agt ctg gtc       48
       Met Gly Val Leu Leu Thr Gln Arg Thr Leu Leu Ser Leu Val
       -25                 -20                 -15 ctt gca ctc ctg ttt cca agc atg gcg agc atg ctc gag tca tca tcc      96
Leu Ala Leu Leu Phe Pro Ser Met Ala Ser Met Leu Glu Ser Ser Ser
       -10                 -5              -1  1               5 cat ccc atc ttc cac agg ggc gaa ttc tcg gtg tgt gac agt gtc agc     144
His Pro Ile Phe His Arg Gly Glu Phe Ser Val Cys Asp Ser Val Ser
                    10                  15                  20 gtg tgg gtt ggg gat aag acc acc gcc aca gac atc aag ggc aag gag     192
Val Trp Val Gly Asp Lys Thr Thr Ala Thr Asp Ile Lys Gly Lys Glu
                25                  30                  35 gtg atg gtg ttg gga gag gtg agc att aac aac agt gta ttc aaa cag     240
Val Met Val Leu Gly Glu Val Ser Ile Asn Asn Ser Val Phe Lys Gln
        40                  45                  50 tac ttt ttt gag acc aag tgc cgg gac cca aat ccc gtt gac agc ggg     288
Tyr Phe Phe Glu Thr Lys Cys Arg Asp Pro Asn Pro Val Asp Ser Gly
    55                  60                  65 tgc cgg ggc att gac tca aag cac tgg aac tca tat tgt acc acg act     336
Cys Arg Gly Ile Asp Ser Lys His Trp Asn Ser Tyr Cys Thr Thr Thr
70                  75                  80                  85 cac acc ttt gtc aag gcg ctg acc atg gat ggc aag cag gct gcc tgg     384
His Thr Phe Val Lys Ala Leu Thr Met Asp Gly Lys Gln Ala Ala Trp
                90                  95                  100 cgg ttt atc cgg ata gat acg gcc tgt atg tgt gtg ctc agc agg aag     432
Arg Phe Ile Arg Ile Asp Thr Ala Cys Met Cys Val Leu Ser Arg Lys
            105                 110                 115 gct gtg aga aga gcc ctc gag cag ctc ttc cac cta cag aag gag ctg     480
Ala Val Arg Arg Ala Leu Glu Gln Leu Phe His Leu Gln Lys Glu Leu
        120                 125                 130 gca gaa ctc cga gag tct acc agc cag atg cac aca gca tca tct ttg     528
Ala Glu Leu Arg Glu Ser Thr Ser Gln Met His Thr Ala Ser Ser Leu
    135                 140                 145 gag aag caa ata ggc cac ccc agt cca ccc cct gaa aaa aag gag ctg     576
Glu Lys Gln Ile Gly His Pro Ser Pro Pro Pro Glu Lys Lys Glu Leu
150                 155                 160                 165 agg aaa gtg gcc cat tta aca ggc aag tcc aac tca agg tcc atg cct     624
```

```
Arg Lys Val Ala His Leu Thr Gly Lys Ser Asn Ser Arg Ser Met Pro
            170                 175                 180 ctg gaa tgg gaa gac acc tat gga att gtc ctg ctt tct gga gtg aag    672
Leu Glu Trp Glu Asp Thr Tyr Gly Ile Val Leu Leu Ser Gly Val Lys
            185                 190                 195 tat aag aag ggt ggc ctt gtg atc aat gaa act ggg ctg tac ttt gta    720
Tyr Lys Lys Gly Gly Leu Val Ile Asn Glu Thr Gly Leu Tyr Phe Val
            200                 205                 210 tat tcc aaa gta tac ttc cgg ggt caa tct tgc aac aac ctg ccc ctg    768
Tyr Ser Lys Val Tyr Phe Arg Gly Gln Ser Cys Asn Asn Leu Pro Leu
            215                 220                 225 agc cac aag gtc tac atg agg aac tct aag tat ccc cag gat ctg gtg    816
Ser His Lys Val Tyr Met Arg Asn Ser Lys Tyr Pro Gln Asp Leu Val
230                 235                 240                 245 atg atg gag ggg aag atg atg agc tac tgc act act ggg cag atg tgg    864
Met Met Glu Gly Lys Met Met Ser Tyr Cys Thr Thr Gly Gln Met Trp
            250                 255                 260 gcc cgc agc agc tac ctg ggg gca gtg ttc aat ctt acc agt gct gat    912
Ala Arg Ser Ser Tyr Leu Gly Ala Val Phe Asn Leu Thr Ser Ala Asp
            265                 270                 275 cat tta tat gtc aac gta tct gag ctc tct ctg gtc aat ttt gag gaa    960
His Leu Tyr Val Asn Val Ser Glu Leu Ser Leu Val Asn Phe Glu Glu
            280                 285                 290 tct cag acg ttt ttc ggc tta tat aag tct gag ccc aaa tct tgt gac   1008
Ser Gln Thr Phe Phe Gly Leu Tyr Lys Ser Glu Pro Lys Ser Cys Asp
295                 300                 305 aaa act cac aca tgc cca ccg tgc cca gca cct gaa ctc ctg ggg gga   1056
Lys Thr His Thr Cys Pro Pro Cys Pro Ala Pro Glu Leu Leu Gly Gly
310                 315                 320                 325 ccg tca gtc ttc ctc ttc ccc cca aaa ccc aag gac acc ctc atg atc   1104
Pro Ser Val Phe Leu Phe Pro Pro Lys Pro Lys Asp Thr Leu Met Ile
            330                 335                 340 tcc cgg acc cct gag gtc aca tgc gtg gtg gtg gac gtg agc cac gaa   1152
Ser Arg Thr Pro Glu Val Thr Cys Val Val Val Asp Val Ser His Glu
            345                 350                 355 gac cct gag gtc aag ttc aac tgg tac gtg gac ggc gtg gag gtg cat   1200
Asp Pro Glu Val Lys Phe Asn Trp Tyr Val Asp Gly Val Glu Val His
            360                 365                 370 aat gcc aag aca aag ccg cgg gag gag cag tac aac agc acg tac cgt   1248
Asn Ala Lys Thr Lys Pro Arg Glu Glu Gln Tyr Asn Ser Thr Tyr Arg
375                 380                 385 gtg gtc agc gtc ctc acc gtc ctg cac cag gac tgg ctg aat ggc aag   1296
Val Val Ser Val Leu Thr Val Leu His Gln Asp Trp Leu Asn Gly Lys
390                 395                 400                 405 gag tac aag tgc aag gtc tcc aac aaa gcc ctc cca gcc ccc atc gag   1344
Glu Tyr Lys Cys Lys Val Ser Asn Lys Ala Leu Pro Ala Pro Ile Glu
            410                 415                 420 aaa acc atc tcc aaa gcc aaa ggg cag ccc cga gaa cca cag gtg tac   1392
Lys Thr Ile Ser Lys Ala Lys Gly Gln Pro Arg Glu Pro Gln Val Tyr
            425                 430                 435 acc ctg ccc cca tcc cgg gat gag ctg acc aag aac cag gtc agc ctg   1440
Thr Leu Pro Pro Ser Arg Asp Glu Leu Thr Lys Asn Gln Val Ser Leu
            440                 445                 450 acc tgc ctg gtc aaa ggc ttc tat ccc agc gac atc gcc gtg gag tgg   1488
Thr Cys Leu Val Lys Gly Phe Tyr Pro Ser Asp Ile Ala Val Glu Trp
            455                 460                 465 gag agc aat ggg cag ccg gag aac aac tac aag acc acg cct ccc gtg   1536
Glu Ser Asn Gly Gln Pro Glu Asn Asn Tyr Lys Thr Thr Pro Pro Val
470                 475                 480                 485
```

|  |  |  |  |  |  |  |  |  |  |  |  |  |  |
|---|---|---|---|---|---|---|---|---|---|---|---|---|---|
| ctg | gac | tcc | gac | ggc | tcc | ttc | ttc | ctc | tac | agc | aag | ctc | acc | gtg | gac | 1584 |
| Leu | Asp | Ser | Asp | Gly | Ser | Phe | Phe | Leu | Tyr | Ser | Lys | Leu | Thr | Val | Asp |  |
|  |  |  | 490 |  |  |  |  | 495 |  |  |  |  | 500 |  |  |  |

| aag | agc | agg | tgg | cag | cag | ggg | aac | gtc | ttc | tca | tgc | tcc | gtg | atg | cat | 1632 |
| Lys | Ser | Arg | Trp | Gln | Gln | Gly | Asn | Val | Phe | Ser | Cys | Ser | Val | Met | His |  |
|  |  |  | 505 |  |  |  |  | 510 |  |  |  |  | 515 |  |  |  |

| gag | gct | ctg | cac | aac | cac | tac | acg | cag | aag | agc | ctc | tcc | ctg | tct | ccg | 1680 |
| Glu | Ala | Leu | His | Asn | His | Tyr | Thr | Gln | Lys | Ser | Leu | Ser | Leu | Ser | Pro |  |
|  |  | 520 |  |  |  |  | 525 |  |  |  |  | 530 |  |  |  |  |

| ggt | aaa | tgagcggccg | c |  |  |  |  |  |  |  |  |  |  |  |  | 1697 |
| Gly | Lys |  |  |  |  |  |  |  |  |  |  |  |  |  |  |  |
|  | 535 |  |  |  |  |  |  |  |  |  |  |  |  |  |  |  |

<210> SEQ ID NO 38
<211> LENGTH: 560
<212> TYPE: PRT
<213> ORGANISM: Homo sapiens

<400> SEQUENCE: 38

Met Gly Val Leu Leu Thr Gln Arg Thr Leu Leu Ser Leu Val Leu Ala
-25                 -20                 -15                 -10

Leu Leu Phe Pro Ser Met Ala Ser Met Leu Glu Ser Ser His Pro
                -5              -1  1               5

Ile Phe His Arg Gly Glu Phe Ser Val Cys Asp Ser Val Ser Val Trp
            10                  15                  20

Val Gly Asp Lys Thr Thr Ala Thr Asp Ile Lys Gly Lys Glu Val Met
        25                  30                  35

Val Leu Gly Glu Val Ser Ile Asn Asn Ser Val Phe Lys Gln Tyr Phe
40                  45                  50                  55

Phe Glu Thr Lys Cys Arg Asp Pro Asn Pro Val Asp Ser Gly Cys Arg
                60                  65                  70

Gly Ile Asp Ser Lys His Trp Asn Ser Tyr Cys Thr Thr Thr His Thr
            75                  80                  85

Phe Val Lys Ala Leu Thr Met Asp Gly Lys Gln Ala Ala Trp Arg Phe
        90                  95                  100

Ile Arg Ile Asp Thr Ala Cys Met Cys Val Leu Ser Arg Lys Ala Val
105                 110                 115

Arg Arg Ala Leu Glu Gln Leu Phe His Leu Gln Lys Glu Leu Ala Glu
120                 125                 130                 135

Leu Arg Glu Ser Thr Ser Gln Met His Thr Ala Ser Ser Leu Glu Lys
                140                 145                 150

Gln Ile Gly His Pro Ser Pro Pro Glu Lys Lys Leu Arg Lys
            155                 160                 165

Val Ala His Leu Thr Gly Lys Ser Asn Ser Arg Ser Met Pro Leu Glu
            170                 175                 180

Trp Glu Asp Thr Tyr Gly Ile Val Leu Leu Ser Gly Val Lys Tyr Lys
        185                 190                 195

Lys Gly Gly Leu Val Ile Asn Glu Thr Gly Leu Tyr Phe Val Tyr Ser
200                 205                 210                 215

Lys Val Tyr Phe Arg Gly Gln Ser Cys Asn Asn Leu Pro Leu Ser His
                220                 225                 230

Lys Val Tyr Met Arg Asn Ser Lys Tyr Pro Gln Asp Leu Val Met Met
            235                 240                 245

Glu Gly Lys Met Met Ser Tyr Cys Thr Thr Gly Gln Met Trp Ala Arg
        250                 255                 260

Ser Ser Tyr Leu Gly Ala Val Phe Asn Leu Thr Ser Ala Asp His Leu

```
                265                 270                 275
Tyr Val Asn Val Ser Glu Leu Ser Leu Val Asn Phe Glu Glu Ser Gln
280                 285                 290                 295

Thr Phe Phe Gly Leu Tyr Lys Ser Glu Pro Lys Ser Cys Asp Lys Thr
                300                 305                 310

His Thr Cys Pro Pro Cys Pro Ala Pro Glu Leu Leu Gly Gly Pro Ser
                315                 320                 325

Val Phe Leu Phe Pro Pro Lys Pro Lys Asp Thr Leu Met Ile Ser Arg
                330                 335             340

Thr Pro Glu Val Thr Cys Val Val Val Asp Val Ser His Glu Asp Pro
                345                 350                 355

Glu Val Lys Phe Asn Trp Tyr Val Asp Gly Val Glu Val His Asn Ala
360                 365                 370                 375

Lys Thr Lys Pro Arg Glu Glu Gln Tyr Asn Ser Thr Tyr Arg Val Val
                380                 385                 390

Ser Val Leu Thr Val Leu His Gln Asp Trp Leu Asn Gly Lys Glu Tyr
                395                 400                 405

Lys Cys Lys Val Ser Asn Lys Ala Leu Pro Ala Pro Ile Glu Lys Thr
                410                 415                 420

Ile Ser Lys Ala Lys Gly Gln Pro Arg Glu Pro Gln Val Tyr Thr Leu
                425                 430                 435

Pro Pro Ser Arg Asp Glu Leu Thr Lys Asn Gln Val Ser Leu Thr Cys
440                 445                 450                 455

Leu Val Lys Gly Phe Tyr Pro Ser Asp Ile Ala Val Glu Trp Glu Ser
                460                 465                 470

Asn Gly Gln Pro Glu Asn Asn Tyr Lys Thr Thr Pro Pro Val Leu Asp
                475                 480                 485

Ser Asp Gly Ser Phe Phe Leu Tyr Ser Lys Leu Thr Val Asp Lys Ser
                490                 495                 500

Arg Trp Gln Gln Gly Asn Val Phe Ser Cys Ser Val Met His Glu Ala
                505                 510                 515

Leu His Asn His Tyr Thr Gln Lys Ser Leu Ser Leu Ser Pro Gly Lys
520                 525                 530                 535

<210> SEQ ID NO 39
<211> LENGTH: 822
<212> TYPE: DNA
<213> ORGANISM: Homo sapiens
<220> FEATURE:
<221> NAME/KEY: CDS
<222> LOCATION: (56)..(514)

<400> SEQUENCE: 39
agttccctat cactctcttt aatcactact cacagtaacc tcaactcctg ccaca atg      58
                                                             Met
                                                             1 tac agg atg caa ctc ctg tct tgc att gca cta agt ctt gca ctt gtc     106
Tyr Arg Met Gln Leu Leu Ser Cys Ile Ala Leu Ser Leu Ala Leu Val
         5                  10                  15 aca aac agt gca cct act tca agt tct aca aag aaa aca cag cta caa     154
Thr Asn Ser Ala Pro Thr Ser Ser Ser Thr Lys Lys Thr Gln Leu Gln
     20                  25                  30 ctg gag cat tta ctg ctg gat tta cag atg att ttg aat gga att aat     202
Leu Glu His Leu Leu Leu Asp Leu Gln Met Ile Leu Asn Gly Ile Asn
 35                  40                  45 aat tac aag aat ccc aaa ctc acc agg atg ctc aca ttt aag ttt tac     250
Asn Tyr Lys Asn Pro Lys Leu Thr Arg Met Leu Thr Phe Lys Phe Tyr
```

```
                 50                  55                  60                  65
atg ccc aag aag gcc aca gaa ctg aaa cat ctt cag tgt cta gaa gaa            298
Met Pro Lys Lys Ala Thr Glu Leu Lys His Leu Gln Cys Leu Glu Glu
                 70                  75                  80 gaa ctc aaa cct ctg gag gaa gtg cta aat tta gct caa agc aaa aac            346
Glu Leu Lys Pro Leu Glu Glu Val Leu Asn Leu Ala Gln Ser Lys Asn
             85                  90                  95 ttt cac tta aga ccc agg gac tta atc agc aat atc aac gta ata gtt            394
Phe His Leu Arg Pro Arg Asp Leu Ile Ser Asn Ile Asn Val Ile Val
         100                 105                 110 ctg gaa cta aag gga tct gaa aca aca ttc atg tgt gaa tat gct gat            442
Leu Glu Leu Lys Gly Ser Glu Thr Thr Phe Met Cys Glu Tyr Ala Asp
     115                 120                 125 gag aca gca acc att gta gaa ttt ctg aac aga tgg att acc ttt tgt            490
Glu Thr Ala Thr Ile Val Glu Phe Leu Asn Arg Trp Ile Thr Phe Cys
130                 135                 140                 145 caa agc atc atc tca aca ctg act tgataattaa gtgcttccca cttaaaacat           544
Gln Ser Ile Ile Ser Thr Leu Thr
                150 atcaggcctt ctatttattt aaatatttaa attttatatt tattgttgaa tgtatggttt          604 gctacctatt gtaactatta ttcttaatct taaaactata aatatggatc ttttatgatt          664 cttttttgtaa gccctagggg ctctaaaatg gtttcactta tttatcccaa aatatttatt        724 attatgttga atgttaaata tagtatctat gtagattggt tagtaaaact atttaataaa         784 tttgataaat ataaaaaaaa aaaaaaaaaa aaaaaaaa                                 822

<210> SEQ ID NO 40
<211> LENGTH: 153
<212> TYPE: PRT
<213> ORGANISM: Homo sapiens

<400> SEQUENCE: 40

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 41
<211> LENGTH: 1743
<212> TYPE: DNA
<213> ORGANISM: Homo sapiens
```

```
<220> FEATURE:
<221> NAME/KEY: CDS
<222> LOCATION: (7)..(1734)
<220> FEATURE:
<221> NAME/KEY: sig_peptide
<222> LOCATION: (7)..(81)
<220> FEATURE:
<221> NAME/KEY: mat_peptide
<222> LOCATION: (82)..(1734)

<400> SEQUENCE: 41
```

| | | | | | | | | | | | | | | |
|---|---|---|---|---|---|---|---|---|---|---|---|---|---|---|
| gctagc | atg | ggg | gta | ctg | ctc | aca | cag | agg | acg | ctg | ctc | agt | ctg | gtc | 48 |
| | Met | Gly | Val | Leu | Leu | Thr | Gln | Arg | Thr | Leu | Leu | Ser | Leu | Val | |
| | | -25 | | | | -20 | | | | -15 | | | | | |
| ctt | gca | ctc | ctg | ttt | cca | agc | atg | gcg | agc | atg | gaa | ttc | gca | cct | act | 96 |
| Leu | Ala | Leu | Leu | Phe | Pro | Ser | Met | Ala | Ser | Met | Glu | Phe | Ala | Pro | Thr | |
| | -10 | | | | -5 | | | | -1 | 1 | | | | 5 | | |
| tca | agt | tct | aca | aag | aaa | aca | cag | cta | caa | ctg | gag | cat | tta | ctg | ctg | 144 |
| Ser | Ser | Ser | Thr | Lys | Lys | Thr | Gln | Leu | Gln | Leu | Glu | His | Leu | Leu | Leu | |
| | | | 10 | | | | 15 | | | | 20 | | | | | |
| gat | tta | cag | atg | att | ttg | aat | gga | att | aat | aat | tac | aag | aat | ccc | aaa | 192 |
| Asp | Leu | Gln | Met | Ile | Leu | Asn | Gly | Ile | Asn | Asn | Tyr | Lys | Asn | Pro | Lys | |
| | | | 25 | | | | 30 | | | | | 35 | | | | |
| ctc | acc | agg | atg | ctc | aca | ttt | aag | ttt | tac | atg | ccc | aag | aag | gcc | aca | 240 |
| Leu | Thr | Arg | Met | Leu | Thr | Phe | Lys | Phe | Tyr | Met | Pro | Lys | Lys | Ala | Thr | |
| | | 40 | | | | | 45 | | | | 50 | | | | | |
| gaa | ctg | aaa | cat | ctt | cag | tgt | cta | gaa | gaa | gaa | ctc | aaa | cct | ctg | | 288 |
| Glu | Leu | Lys | His | Leu | Gln | Cys | Leu | Glu | Glu | Glu | Leu | Lys | Pro | Leu | | |
| | | 55 | | | | | 60 | | | | 65 | | | | | |
| gag | gaa | gtg | cta | aat | tta | gct | caa | agc | aaa | aac | ttt | cac | tta | aga | ccc | 336 |
| Glu | Glu | Val | Leu | Asn | Leu | Ala | Gln | Ser | Lys | Asn | Phe | His | Leu | Arg | Pro | |
| 70 | | | | 75 | | | | | 80 | | | | 85 | | | |
| agg | gac | tta | atc | agc | aat | atc | aac | gta | ata | gtt | ctg | gaa | cta | aag | gga | 384 |
| Arg | Asp | Leu | Ile | Ser | Asn | Ile | Asn | Val | Ile | Val | Leu | Glu | Leu | Lys | Gly | |
| | | | 90 | | | | 95 | | | | 100 | | | | | |
| tct | gaa | aca | aca | ttc | atg | tgt | gaa | tat | gct | gat | gag | aca | gca | acc | att | 432 |
| Ser | Glu | Thr | Thr | Phe | Met | Cys | Glu | Tyr | Ala | Asp | Glu | Thr | Ala | Thr | Ile | |
| | | | 105 | | | | 110 | | | | 115 | | | | | |
| gta | gaa | ttt | ctg | aac | aga | tgg | att | acc | ttt | tgt | caa | agc | atc | atc | tca | 480 |
| Val | Glu | Phe | Leu | Asn | Arg | Trp | Ile | Thr | Phe | Cys | Gln | Ser | Ile | Ile | Ser | |
| | | 120 | | | | | 125 | | | | 130 | | | | | |
| aca | ctg | act | acg | cgt | ggt | acc | cag | ctc | ttc | cac | cta | cag | aag | gag | ctg | 528 |
| Thr | Leu | Thr | Thr | Arg | Gly | Thr | Gln | Leu | Phe | His | Leu | Gln | Lys | Glu | Leu | |
| | 135 | | | | | 140 | | | | | 145 | | | | | |
| gca | gaa | ctc | cga | gag | tct | acc | agc | cag | atg | cac | aca | gca | tca | tct | ttg | 576 |
| Ala | Glu | Leu | Arg | Glu | Ser | Thr | Ser | Gln | Met | His | Thr | Ala | Ser | Ser | Leu | |
| 150 | | | | | 155 | | | | | 160 | | | | | 165 | |
| gag | aag | caa | ata | ggc | cac | ccc | agt | cca | ccc | cct | gaa | aaa | aag | gag | ctg | 624 |
| Glu | Lys | Gln | Ile | Gly | His | Pro | Ser | Pro | Pro | Pro | Glu | Lys | Lys | Glu | Leu | |
| | | | 170 | | | | 175 | | | | 180 | | | | | |
| agg | aaa | gtg | gcc | cat | tta | aca | ggc | aag | tcc | aac | tca | agg | tcc | atg | cct | 672 |
| Arg | Lys | Val | Ala | His | Leu | Thr | Gly | Lys | Ser | Asn | Ser | Arg | Ser | Met | Pro | |
| | | | 185 | | | | 190 | | | | | 195 | | | | |
| ctg | gaa | tgg | gaa | gac | acc | tat | gga | att | gtc | ctg | ctt | tct | gga | gtg | aag | 720 |
| Leu | Glu | Trp | Glu | Asp | Thr | Tyr | Gly | Ile | Val | Leu | Leu | Ser | Gly | Val | Lys | |
| | | 200 | | | | | 205 | | | | 210 | | | | | |
| tat | aag | aag | ggt | ggc | ctt | gtg | atc | aat | gaa | act | ggg | ctg | tac | ttt | gta | 768 |
| Tyr | Lys | Lys | Gly | Gly | Leu | Val | Ile | Asn | Glu | Thr | Gly | Leu | Tyr | Phe | Val | |
| | 215 | | | | | 220 | | | | | 225 | | | | | |
| tat | tcc | aaa | gta | tac | ttc | cgg | ggt | caa | tct | tgc | aac | aac | ctg | ccc | ctg | 816 |
| Tyr | Ser | Lys | Val | Tyr | Phe | Arg | Gly | Gln | Ser | Cys | Asn | Asn | Leu | Pro | Leu | |
| 230 | | | | | 235 | | | | | 240 | | | | | 245 | |

```
agc cac aag gtc tac atg agg aac tct aag tat ccc cag gat ctg gtg      864
Ser His Lys Val Tyr Met Arg Asn Ser Lys Tyr Pro Gln Asp Leu Val
            250                 255                 260 atg atg gag ggg aag atg atg agc tac tgc act act ggg cag atg tgg      912
Met Met Glu Gly Lys Met Met Ser Tyr Cys Thr Thr Gly Gln Met Trp
                265                 270                 275 gcc cgc agc agc tac ctg ggg gca gtg ttc aat ctt acc agt gct gat      960
Ala Arg Ser Ser Tyr Leu Gly Ala Val Phe Asn Leu Thr Ser Ala Asp
                280                 285                 290 cat tta tat gtc aac gta tct gag ctc tct ctg gtc aat ttt gag gaa     1008
His Leu Tyr Val Asn Val Ser Glu Leu Ser Leu Val Asn Phe Glu Glu
            295                 300                 305 tct cag acg ttt ttc ggc tta tat aag ctc gag ccc aaa tct tgt gac     1056
Ser Gln Thr Phe Phe Gly Leu Tyr Lys Leu Glu Pro Lys Ser Cys Asp
310                 315                 320                 325 aaa act cac aca tgc cca ccg tgc cca gca cct gaa ctc ctg ggg gga     1104
Lys Thr His Thr Cys Pro Pro Cys Pro Ala Pro Glu Leu Leu Gly Gly
                330                 335                 340 ccg tca gtc ttc ctc ttc ccc cca aaa ccc aag gac acc ctc atg atc     1152
Pro Ser Val Phe Leu Phe Pro Pro Lys Pro Lys Asp Thr Leu Met Ile
                345                 350                 355 tcc cgg acc cct gag gtc aca tgc gtg gtg gtg gac gtg agc cac gaa     1200
Ser Arg Thr Pro Glu Val Thr Cys Val Val Val Asp Val Ser His Glu
            360                 365                 370 gac cct gag gtc aag ttc aac tgg tac gtg gac ggc gtg gag gtg cat     1248
Asp Pro Glu Val Lys Phe Asn Trp Tyr Val Asp Gly Val Glu Val His
            375                 380                 385 aat gcc aag aca aag ccg cgg gag gag cag tac aac agc acg tac cgt     1296
Asn Ala Lys Thr Lys Pro Arg Glu Glu Gln Tyr Asn Ser Thr Tyr Arg
390                 395                 400                 405 gtg gtc agc gtc ctc acc gtc ctg cac cag gac tgg ctg aat ggc aag     1344
Val Val Ser Val Leu Thr Val Leu His Gln Asp Trp Leu Asn Gly Lys
                410                 415                 420 gag tac aag tgc aag gtc tcc aac aaa gcc ctc cca gcc ccc atc gag     1392
Glu Tyr Lys Cys Lys Val Ser Asn Lys Ala Leu Pro Ala Pro Ile Glu
            425                 430                 435 aaa acc atc tcc aaa gcc aaa ggg cag ccc cga gaa cca cag gtg tac     1440
Lys Thr Ile Ser Lys Ala Lys Gly Gln Pro Arg Glu Pro Gln Val Tyr
            440                 445                 450 acc ctg ccc cca tcc cgg gat gag ctg acc aag aac cag gtc agc ctg     1488
Thr Leu Pro Pro Ser Arg Asp Glu Leu Thr Lys Asn Gln Val Ser Leu
            455                 460                 465 acc tgc ctg gtc aaa ggc ttc tat ccc agc gac atc gcc gtg gag tgg     1536
Thr Cys Leu Val Lys Gly Phe Tyr Pro Ser Asp Ile Ala Val Glu Trp
470                 475                 480                 485 gag agc aat ggg cag ccg gag aac aac tac aag acc acg cct ccc gtg     1584
Glu Ser Asn Gly Gln Pro Glu Asn Asn Tyr Lys Thr Thr Pro Pro Val
                490                 495                 500 ctg gac tcc gac ggc tcc ttc ttc ctc tac agc aag ctc acc gtg gac     1632
Leu Asp Ser Asp Gly Ser Phe Phe Leu Tyr Ser Lys Leu Thr Val Asp
                505                 510                 515 aag agc agg tgg cag cag ggg aac gtc ttc tca tgc tcc gtg atg cat     1680
Lys Ser Arg Trp Gln Gln Gly Asn Val Phe Ser Cys Ser Val Met His
            520                 525                 530 gag gct ctg cac aac cac tac acg cag aag agc ctc tcc ctg tct ccg     1728
Glu Ala Leu His Asn His Tyr Thr Gln Lys Ser Leu Ser Leu Ser Pro
            535                 540                 545 ggt aaa tgatctaga                                                    1743
Gly Lys
```

<210> SEQ ID NO 42
<211> LENGTH: 576
<212> TYPE: PRT
<213> ORGANISM: Homo sapiens

<400> SEQUENCE: 42

```
Met Gly Val Leu Leu Thr Gln Arg Thr Leu Leu Ser Leu Val Leu Ala
-25                 -20                 -15                 -10

Leu Leu Phe Pro Ser Met Ala Ser Met Glu Phe Ala Pro Thr Ser Ser
             -5                  -1  1                   5

Ser Thr Lys Lys Thr Gln Leu Gln Leu Glu His Leu Leu Leu Asp Leu
             10                  15                  20

Gln Met Ile Leu Asn Gly Ile Asn Asn Tyr Lys Asn Pro Lys Leu Thr
         25                  30                  35

Arg Met Leu Thr Phe Lys Phe Tyr Met Pro Lys Lys Ala Thr Glu Leu
40                  45                  50                  55

Lys His Leu Gln Cys Leu Glu Glu Glu Leu Lys Pro Leu Glu Glu
                 60                  65                  70

Val Leu Asn Leu Ala Gln Ser Lys Asn Phe His Leu Arg Pro Arg Asp
                 75                  80                  85

Leu Ile Ser Asn Ile Asn Val Ile Val Leu Glu Leu Lys Gly Ser Glu
                 90                  95                 100

Thr Thr Phe Met Cys Glu Tyr Ala Asp Glu Thr Ala Thr Ile Val Glu
             105                 110                 115

Phe Leu Asn Arg Trp Ile Thr Phe Cys Gln Ser Ile Ile Ser Thr Leu
120                 125                 130                 135

Thr Thr Arg Gly Thr Gln Leu Phe His Leu Gln Lys Glu Leu Ala Glu
             140                 145                 150

Leu Arg Glu Ser Thr Ser Gln Met His Thr Ala Ser Ser Leu Glu Lys
             155                 160                 165

Gln Ile Gly His Pro Ser Pro Pro Glu Lys Lys Glu Leu Arg Lys
         170                 175                 180

Val Ala His Leu Thr Gly Lys Ser Asn Ser Arg Ser Met Pro Leu Glu
         185                 190                 195

Trp Glu Asp Thr Tyr Gly Ile Val Leu Leu Ser Gly Val Lys Tyr Lys
200                 205                 210                 215

Lys Gly Gly Leu Val Ile Asn Glu Thr Gly Leu Tyr Phe Val Tyr Ser
                 220                 225                 230

Lys Val Tyr Phe Arg Gly Gln Ser Cys Asn Asn Leu Pro Leu Ser His
             235                 240                 245

Lys Val Tyr Met Arg Asn Ser Lys Tyr Pro Gln Asp Leu Val Met Met
             250                 255                 260

Glu Gly Lys Met Met Ser Tyr Cys Thr Thr Gly Gln Met Trp Ala Arg
265                 270                 275

Ser Ser Tyr Leu Gly Ala Val Phe Asn Leu Thr Ser Ala Asp His Leu
280                 285                 290                 295

Tyr Val Asn Val Ser Glu Leu Ser Leu Val Asn Phe Glu Glu Ser Gln
                 300                 305                 310

Thr Phe Phe Gly Leu Tyr Lys Leu Glu Pro Lys Ser Cys Asp Lys Thr
             315                 320                 325

His Thr Cys Pro Pro Cys Pro Ala Pro Glu Leu Leu Gly Gly Pro Ser
             330                 335                 340
```

Val Phe Leu Phe Pro Pro Lys Pro Lys Asp Thr Leu Met Ile Ser Arg
345                 350                 355

Thr Pro Glu Val Thr Cys Val Val Val Asp Val Ser His Glu Asp Pro
360                 365                 370                 375

Glu Val Lys Phe Asn Trp Tyr Val Asp Gly Val Glu Val His Asn Ala
            380                 385                 390

Lys Thr Lys Pro Arg Glu Glu Gln Tyr Asn Ser Thr Tyr Arg Val Val
            395                 400                 405

Ser Val Leu Thr Val Leu His Gln Asp Trp Leu Asn Gly Lys Glu Tyr
        410                 415                 420

Lys Cys Lys Val Ser Asn Lys Ala Leu Pro Ala Pro Ile Glu Lys Thr
    425                 430                 435

Ile Ser Lys Ala Lys Gly Gln Pro Arg Glu Pro Gln Val Tyr Thr Leu
440                 445                 450                 455

Pro Pro Ser Arg Asp Glu Leu Thr Lys Asn Gln Val Ser Leu Thr Cys
            460                 465                 470

Leu Val Lys Gly Phe Tyr Pro Ser Asp Ile Ala Val Glu Trp Glu Ser
        475                 480                 485

Asn Gly Gln Pro Glu Asn Asn Tyr Lys Thr Thr Pro Pro Val Leu Asp
    490                 495                 500

Ser Asp Gly Ser Phe Phe Leu Tyr Ser Lys Leu Thr Val Asp Lys Ser
505                 510                 515

Arg Trp Gln Gln Gly Asn Val Phe Ser Cys Ser Val Met His Glu Ala
520                 525                 530                 535

Leu His Asn His Tyr Thr Gln Lys Ser Leu Ser Leu Ser Pro Gly Lys
            540                 545                 550

<210> SEQ ID NO 43
<211> LENGTH: 24
<212> TYPE: DNA
<213> ORGANISM: Homo sapiens

<400> SEQUENCE: 43
cttcatagaa ggttggacaa gata                                          24

<210> SEQ ID NO 44
<211> LENGTH: 24
<212> TYPE: DNA
<213> ORGANISM: Homo sapiens

<400> SEQUENCE: 44
gagtttgagt aagccaaagg acgt                                          24

<210> SEQ ID NO 45
<211> LENGTH: 24
<212> TYPE: DNA
<213> ORGANISM: Homo sapiens

<400> SEQUENCE: 45
atgggggtac tgctcacaca gagg                                          24

<210> SEQ ID NO 46
<211> LENGTH: 24
<212> TYPE: DNA
<213> ORGANISM: Homo sapiens

<400> SEQUENCE: 46
catgctcgcc atgcttggaa acag                                          24

<210> SEQ ID NO 47
<211> LENGTH: 44
<212> TYPE: DNA
<213> ORGANISM: Homo sapiens

<400> SEQUENCE: 47
aaactcgaga atcttgtga caaaactcac acatgcccac cgtg                    44

<210> SEQ ID NO 48
<211> LENGTH: 32
<212> TYPE: DNA
<213> ORGANISM: Homo sapiens

<400> SEQUENCE: 48
cgtctagatc atttacccgg agacagggag ag                                32

<210> SEQ ID NO 49
<211> LENGTH: 27
<212> TYPE: DNA
<213> ORGANISM: Homo sapiens

<400> SEQUENCE: 49
ccgctcgagc agctcttcca cctacag                                      27

<210> SEQ ID NO 50
<211> LENGTH: 31
<212> TYPE: DNA
<213> ORGANISM: Homo sapiens

<400> SEQUENCE: 50
ggcctcgagc ttatataagc cgaaaaacgt c                                 31

<210> SEQ ID NO 51
<211> LENGTH: 29
<212> TYPE: DNA
<213> ORGANISM: Homo sapiens

<400> SEQUENCE: 51
ggactcgagg ctcctctgaa gattcaagc                                    29

<210> SEQ ID NO 52
<211> LENGTH: 29
<212> TYPE: DNA
<213> ORGANISM: Homo sapiens

<400> SEQUENCE: 52
aatctcgaga ggaatgtggt ctgggggag                                    29

<210> SEQ ID NO 53
<211> LENGTH: 29
<212> TYPE: DNA
<213> ORGANISM: Homo sapiens

<400> SEQUENCE: 53
ggactcgagc aggtatcaca tcggtatcc                                    29

<210> SEQ ID NO 54
<211> LENGTH: 29
<212> TYPE: DNA
<213> ORGANISM: Homo sapiens

<400> SEQUENCE: 54
ggaacgcgta aggacacaga attcaccag                                    29

<210> SEQ ID NO 55
<211> LENGTH: 29
<212> TYPE: DNA
<213> ORGANISM: Homo sapiens

<400> SEQUENCE: 55
ggaacgcgtg cctgccctgg ccgtgtccg                              29

<210> SEQ ID NO 56
<211> LENGTH: 29
<212> TYPE: DNA
<213> ORGANISM: Homo sapiens

<400> SEQUENCE: 56
aatctcgagt tccgacctcg gtgaaggga                              29

<210> SEQ ID NO 57
<211> LENGTH: 29
<212> TYPE: DNA
<213> ORGANISM: Homo sapiens

<400> SEQUENCE: 57
ggactcgagg gagaaatcaa tggttctgc                              29

<210> SEQ ID NO 58
<211> LENGTH: 29
<212> TYPE: DNA
<213> ORGANISM: Homo sapiens

<400> SEQUENCE: 58
aatctcgagg aacttcagct ggcaacaaa                              29

<210> SEQ ID NO 59
<211> LENGTH: 29
<212> TYPE: DNA
<213> ORGANISM: Homo sapiens

<400> SEQUENCE: 59
ggactcgagt catcatccca tcccatctt                              29

<210> SEQ ID NO 60
<211> LENGTH: 29
<212> TYPE: DNA
<213> ORGANISM: Homo sapiens

<400> SEQUENCE: 60
aatctcgagg gctcttctca cagccttcc                              29

<210> SEQ ID NO 61
<211> LENGTH: 29
<212> TYPE: DNA
<213> ORGANISM: Homo sapiens

<400> SEQUENCE: 61
ggagaattcg cacctacttc aagttctac                              29

<210> SEQ ID NO 62
<211> LENGTH: 30

-continued

```
<212> TYPE: DNA
<213> ORGANISM: Homo sapiens

<400> SEQUENCE: 62
aatacgcgta gtcagtgttg agatgctgct                                        30
```

RECOMBINANT MULTIPLE DOMAIN FUSION PROTEIN MITOGENS AND USE THEREOF FOR INDUCING ENHANCEMENT OR REPRESSION OF ANTIGEN-SPECIFIC IMMUNITY

CROSS-REFERENCE TO RELATED APPLICATION

This application is a continuation of application Ser. No. 12/483,876, filed Jun. 12, 2009, which claims priority to U.S. Provisional Patent Application No. 61/073,010, filed Jun. 16, 2008.

REFERENCE CITED [REFERENCE BY]

U.S. Patent Documents

| | | |
|---|---|---|
| 6,410,711 | Jun. 25, 2002 | Armitage, et al. |
| 6,838,262 | Oct. 13, 2000 | Anderson, et al. |
| 6,046,310 | Apr. 4, 2000 | Queen, et al |
| 5,962,406 | Oct. 5, 1999 | Armitage, et al. |
| 5,942,607 | Aug. 24, 1999 | Freeman, et al. |
| 5,457,035 | Jul. 23, 1993 | Baum, et al. |

Foreign Patent Documents

| | |
|---|---|
| WO/2007/103048 | Feb. 28, 2007 |
| WO/2007/022273 | Aug. 15, 2006 |
| WO/2006/050949 | Nov. 10, 2005 |
| WO/2003/063899 | Jan. 28, 2003 |
| WO/1997/033617 | Nov. 3, 1997 |
| WO/1995/013293 | May 18, 1995 |

OTHER REFERENCES

Alderson, M. R. et al. Fas transduces activation signals in normal human T lymphocytes. J. Exp. Med. 178, 2231-2235 (1993).

Alderson, M. R. et al. Regulation of apoptosis and T cell activation by Fas-specific mAb. Int. Immunol. 6, 1799-1806 (1994).

Alegre, M. L., J. Y. Tso, H. A. Sattar, J. Smith, F. Desalle, M. Cole, J. A. Bluestone. 1995. An anti-murine CD3 monoclonal antibody with a low affinity for Fc receptors suppresses transplantation responses while minimizing acute toxicity and immunogenicity. J. Immunol. 155: 1544.

Allen R C, Armitage R J, Conley M E, et al. CD40 ligand gene defects responsible for X-linked hyper-IgM syndrome. Science 1993; 259:990-3.

Arias M, Campistol J M, Vincenti F. Evolving Evolving trends in induction therapy. Transplant Rev (Orlando). 2009 April; 23(2):94-102.

Armitage R J, Fanslow W C, Strockbine L, et al. Molecular and biological characterization of a murine ligand for CD40. Nature 1992; 357:80-2.

Aruffo, A. & Seed, B. Molecular cloning of a CD28 cDNA by a high-efficiency COS cell expression system. Proc. Natl Acad. Sci. USA 84, 8573-8577 (1987).

Assohou-Luty C, Gerspach J, Siegmund D, Müller N, Huard B, Tiegs G, Pfizenmaier K, Wajant H. A CD40-CD95L fusion protein interferes with CD40L-induced prosurvival signaling and allows membrane CD40L-restricted activation of CD95. J Mol Med. 2006 September; 84(9):785-97.

Azuma, M. et al. B70 antigen is a second ligand for CTLA-4 and CD28. Nature 366, 76-79 (1993).

Beaucage and Caruthers, Tetrahedron Letts. 22:1859-1862 (1981).

Beauchesne P R, Chung N S, Wasan K M. Cyclosporine A: a review of current oral and intravenous delivery systems. Drug Dev Ind Pharm. 2007 March; 33(3):211-20.

Becher, B., D'Souza, S. D., Troutt, A. B. & Antel, J. P. Fas expression on human fetal astrocytes without susceptibility to Fas-mediated cytotoxicity. Neurosciences 84, 627-634 (1998).

Bennett S R, Carbone F R, Karamalis F, Flavell R A, Miller J F, Heath W R. Help for cytotoxic-T-cell responses is mediated by CD40 signalling. Nature 1998; 393:478-80.

Beyersdorf N, Hanke T, Kerkau T, Hünig T. Superagonistic anti-CD28 antibodies: potent activators of regulatory T cells for the therapy of autoimmune diseases. Ann Rheum Dis. 2005 November; 64 Suppl 4:iv91-5.

Biancone, L. et al. Development of inflammatory angiogenesis by local stimulation of Fas in vivo. J. Exp. Med. 186, 147-152 (1997).

Boise, L., Minn, A., Noel, P. & Thompson, C. CD28 costimulation can promote T cell survival by enhancing the expression of Bcl-xl. Immunity 3, 87-98 (1995).

Bremer E, ten Cate B, Samplonius D F, Mueller N, Wajant H, Stel A J, Chamuleau M, van de Loosdrecht A A, Stieglmaier J, Fey G H, Helfrich W. Superior activity of fusion protein scFvRit: sFasL over cotreatment with rituximab and Fas agonists Cancer Res. 2008 Jan. 15; 68(2): 597-604.

Brodie C, Gelfand E W. Functional nerve growth factor receptors on human B lymphocytes. Interaction with IL-2. J Immunol. 1992 Jun. 1; 148(11):3492-7.

Bulfone-Paus S, Rückert R, Krause H, von Bernuth H, Notter M, Pohl T, Tran T H, Paus R, Kunzendorf U. An interleukin-2-IgG-Fas ligand fusion protein surppresses delayed-type hypaersensitivity in mice by triggering apoptosis in activated T cells as a novel strategy for immunosuppression. Transplantation. 2000 Apr. 15; 69(7):1386-91.

Castigli E, Alt F W, Davidson L, et al. CD40-deficient mice generated by recombination-activating gene-2-deficient blastocyst complementation. Proc Natl Acad Sci USA 1994; 91:12135-9.

Chambers, C. A., Kuhns, M. S., Egen, J. G. & Allison, J. P. CTLA-4-mediated inhibition in regulation of T cell responses: mechanisms and manipulation in tumor immunotherapy Annu. Rev. Immunol. 19, 565-594 (2001).

Cheema, Z. F. et al. Fas/Apo (apoptosis)-1 and associated proteins in the differentiating cerebral cortex: induction of caspase-dependent cell death and activation of NF-kB. J. Neurosci. 19, 1754-1770 (1999).

Current Protocols in Molecular Biology (Ausubel et al, eds., 1994-2009).

Daubenberger C A. TLR9 agonists as adjuvants for prophylactic and therapeutic vaccines. Curr Opin Mol Ther. 2007; 9:45-52.

Deng Z B, Lu C M, Huang W D, Shen L Q, Zhu W, Ma H B, Fan P S, Zhang X G. Expression of recombinant human ICOS and in vitro characterization of its bioactivity on B lymphocytes. Sheng Wu Hua Xue Yu Sheng Wu Wu Li Xue Bao (Shanghai). 2003 July; 35(7):601-5.

Desbarats, J. & Newell, M. K. Fas engagement accelerates liver regeneration after partial hepatectomy. Nature Med. 6, 920-923 (2000).

Etzioni A, Ochs H D. The hyper IgM syndrome—an evolving story. Pediatr Res 2004; 56:519-25.

Ferrari S, Giliani S, Insalaco A, et al. Mutations of CD40 gene cause an autosomal recessive form of immunodeficiency with hyper IgM. Proc Natl Acad Sci USA 2001; 98:12614-9.

Freedman, A. S. et al. B7, a B cell restricted antigen which identifies pre-activated B cells. J. Immunol. 137, 3260-3267 (1987).

Freeman, G. J. et al. Cloning of B7-2: a CTLA4 counter-receptor that costimulates human T cell proliferation. Science 262, 909-911 (1993).

Freeman, G. J. et al. Murine B7-2, an alternative CTLA4 counter-receptor that costimulates T cell proliferation and interleukin-2 production. J. Exp. Med. 178, 2185-2192 (1993).

Freeman, G. J. et al. Structure, expression, and T cell costimulatory activity of the murine homologue of the human B lymphocyte activation antigen B7. J. Exp. Med. 174, 625-631 (1991).

Fukunaga, K. & Miyamoto, E. Role of MAP kinase in neurons. Mol. Neurobiol. 16, 79-95 (1998).

Galanaud P M, Crevon C, Delfraissy J F, et al. Antigen-induced and polyclonal B-cell responses in human peripheral blood lymphocyte cultures. Cell. Immunol. 1987; 106:234-241.

Gomez, C. et al. Low concentrations of 1-methyl-4-phenylpyridinium ion induce caspase-mediated apoptosis in human SH-SY5Y neuroblastoma cells. J. Neurosci. Res. 63,421-428 (2001).

Goumenos D S. What have we learned from the use of ciclosporin A in the treatment of nephrotic patients with idiopathic membranous nephropathy? Expert Opin Pharmacother. 2008 July; 9(10):1695-704.

Grewal I S, Flavell R A. CD40 and CD154 in cell-mediated immunity. Annu Rev Immunol 1998; 16:111-35.

Gross, J. A., St John, T. & Allison, J. P. The murine homologue of the T lymphocyte antigen CD28. Molecular cloning and cell surface expression. J. Immunol. 144, 3201-3210 (1990).

Holmstrom, T. et al. MAPK/ERK signaling in activated T cells inhibits CD95/Fas-mediated apoptosis downstream of DISC assembly. EMBO J. 19, 5418-5428 (2000).

Irmler, M. et al. Inhibition of death receptor signals by cellular FLIP. Nature 388, 190-195 (1997).

Karandikar, N. J., Vanderlugt, C. L., Bluestone, J. A. & Miller, S. D. Targeting the B7/CD28:CTLA-4 costimulatory system in CNS autoimmune disease. J. Neuroimmunol. 89, 10-18 (1998).

Kataoka, T. et al. The caspase-8 inhibitor FLIP promotes activation of NF-kB and ERK signaling pathways. Curr. Biol. 10, 640-648 (2000).

Kawabe T, Naka T, Yoshida K, et al. The immune responses in CD40-deficient mice: impaired immunoglobulin class switching and germinal center formation. Immunity 1994; 1:167-78.

Kotzin B L, Leung D Y, Kappler J, Marrack P. Superantigens and their potential role in human disease. Adv Immunol. 1993; 54:99-166.

Kriegler, Gene Transfer and Expression: A Laboratory Manual (1990).

Lim L C, England D M, Glowacki N J, DuChateau B K, Schell R F. Involvement of CD4+T lymphocytes in induction of severe destructive Lyme arthritis in inbred LSH hamsters. Infect Immun. 1995 December; 63(12):4818-25.

Lucas, P. J. et al. Naive CD28-deficient T cells can initiate but not sustain an in vitro antigen-specific immune response. J. Immunol. 154, 5757-5768 (1995).

Matsushita, K. et al. Fas receptor and neuronal cell death after spinal cord ischemia. J. Neurosci. 20, 6879-6887 (2000).

Medema, J. P. et al. FLICE is activated by association with the CD95 death-inducing signaling complex (DISC). EMBO J. 16, 2794-2804 (1997).

Mock B A, Liu L, LePaslier D, Huang S. The B-lymphocyte maturation promoting transcription factor BLIMP1/PRDI-BF1 maps to D6S447 on human chromosome 6q21-q22.1 and the syntenic region of mouse chromosome 10. Genomics 1996; 37:24-28.

Nagata, S. Apoptosis by death factor. Cell 88, 355-365 (1997).

Needham-VanDevanter DR, Hurley L H, Reynolds V L, Theriault N Y, Krueger W C, Wierenga W. Characterization of an adduct between CC-1065 and a defined oligodeoxynucleotide duplex. Nucleic Acids Res. 1984 Aug. 10; 12(15):6159-68.

Ng C Y, Madsen J C, Rosengard B R, Allan J S. Immunosuppression for lung transplantation. Front Biosci. 2009 Jan. 1; 14:1627-41.

Okwor I, Uzonna J. Vaccines and vaccination strategies against human cutaneous leishmaniasis. Hum Vaccin. 2009 May 12; 5(5).

Oosterwegel, M. A., Greenwald, R. J., Mandelbrot, D. A., Lorsbach, R. B. & Sharpe, A. H. CTLA-4 and T cell activation. Curr. Opin. Immunol. 11, 294-300 (1999).

Quezada S A, Jarvinen L Z, Lind E F, Noelle R J. CD40/CD154 interactions at the interface of tolerance and immunity. Annu Rev Immunol 2004; 22:307-28.

Raoul, C. et al. Motoneuron death triggered by a specific pathway downstream of Fas. Potentiation by ALS-linked SOD1 mutations. Neuron 35, 1067-1083 (2002).

Raoul, C., Henderson, C. E. & Pettmann, B. Programmed cell death of embryonic motoneurons triggered through the Fas death receptor. J. Cell Biol. 147, 1049-1062 (1999).

Renshaw B R, Fanslow W C III, Armitage R J, et al. Humoral immune responses in CD40 ligand-deficient mice. J Exp Med 1994; 180:1889-900.

Ridge J P, Di Rosa F, Matzinger P. A conditioned dendritic cell can be a temporal bridge between a CD4+ T-helper and a T-killer cell. Nature 1998; 393:474-8.

Sakaguchi S. Prospects for preventative vaccines against prion diseases. Protein Pept Lett. 2009; 16(3):260-70.

Salomon, B. & Bluestone, J. A. Complexities of CD28/B7: CTLA-4 costimulatory pathways in autoimmunity and transplantation. Annu. Rev. Immunol. 19, 225-252 (2001).

Sambrook & Russell, Molecular Cloning, A Laboratory Manual (3rd Ed, 2001).

Sansom, D. M. CD28, CTLA-4 and their ligands: who does what and to whom? Immunology 101, 169-177 (2000).

Schoenberger S P, Toes R E, van der Voort E I, Offringa R, Melief C J. T-cell help for cytotoxic T lymphocytes is mediated by CD40-40L interactions. Nature 1998; 393: 480-3.

Shahinian, A. et al. Differential T cell costimulatory requirements in CD28-deficient mice. Science 261, 609-612 (1993).

Shinohara, H., Yagita, H., Ikawa, Y. & Oyaizu, N. Fas drives cell cycle progression in glioma cells via extracellular signal-regulated kinase. Cancer Res. 60, 1766-1772 (2000).

Sperling, A. I. et al. CD28/B7 interactions deliver a unique signal to naive T cells that regulates cell survival but not early proliferation. J. Immunol. 157, 3909-3917 (1996).

Suntharalingam G, Perry M R, Ward S, Brett S J, Castello-Cortes A, Brunner M D, Panoskaltsis N. Cytokine storm in a phase 1 trial of the anti-CD28 monoclonal antibody TGN1412. N Engl J Med. 2006; 355:1018-1028.

Szabo S J, Kim S T, Costa G L, Zhang X, Fathman C G, Glimcher L H. A novel transcription factor, T-bet, directs Rhl lineage commitment. Cell. 2000 Mar. 17; 100(6):655-69.

Targett G A, Greenwood B M. Malaria vaccines and their potential role in the elimination of malaria. Malar J. 2008 Dec. 11; 7 Suppl 1:S10.

Thompson, C. B. et al. CD28 activation pathway regulates the production of multiple T-cell-derived lymphokines/cytokines. Proc. Natl Acad. Sci. USA 86, 1333-1337 (1989).

Trauth, B. C. et al. Monoclonal antibody-mediated tumor regression by induction of apoptosis. Science 245, 301-305 (1989).

Van Assche G, Vermeire S, Rutgeerts P. Immunosuppression in inflammatory bowel diseases: traditional, biological or both? Curr Opin Gastroenterol. 2009 May 5.

van Kooten C, Banchereau J. CD40-40 ligand. J Leukoc Biol 2000; 67:2-17.

Wallace R B, Johnson M J, Suggs S V, Miyoshi K, Bhatt R, Itakura K. A set of synthetic oligodeoxyribonucleotide primers for DNA sequencing in the plasmid vector pBR322. Gene 1981 December; 16(1-3):21-6

Watts T H. TNF/TNFR family members in costimulation of T cell responses. Annu Rev Immunol. 2005; 23:23-68.

Wisniewski T, Konietzko U. Amyloid-beta immunisation for Alzheimer's disease. Lancet Neurol. 2008 September; 7(9):805-11.

Xu J, Foy T M, Laman J D, et al. Mice deficient for the CD40 ligand. Immunity 1994; 1:423-31.

Yokochi, T., Holly, R. D. & Clark, E. A. Lymphoblastoid antigen (BB-1) expressed on Epstein—Barr virus-activated B cell blasts, B lymphoblastoid lines, and Burkitt's lymphomas. J. Immunol. 128, 823-827 (1982).

Yonehara, S., Ishii, A. & Yonehara, M. A cell-killing monoclonal antibody (anti-Fas) to a cell surface antigen co-downregulated with the receptor of tumor necrosis factor. J. Exp. Med. 169, 1747-1756 (1989).

Yoshida T, Yoshida R, Ma B Y., Mikolajczak S, Kelvin D J., and A. Ochi. A novel mitogen fusion protein against $CD40^+$ cells with potent vaccine adjuvant properties. Vaccine. 2010; 28(21):3688-3695. Epub 2010 Mar. 30.

Young L S, Eliopoulos A G, Gallagher N J, Dawson C W. CD40 and epithelial cells: across the great divide. Immunol Today 1998; 19:502-6.

FIELD OF THE INVENTION

The invention generally relates to methods and compositions, which promote or repress antigen-specific immunity. The described polypeptide and DNA constructs are used as either immune adjuvants or suppressants for treating various chronic diseases including cancer, infectious diseases, autoimmune diseases, allergies and inflammatory diseases.

BACKGROUND OF THE INVENTION

Affording to Current Understanding of Molecular Mechanisms of Diseases, Reagents that Modulate Immune Responses are in Great Demand.

The body's defense system against microbes and other chronic diseases is mediated by the two main components of the immune system: the innate immune system and adaptive immune system. Recent advances in the study of the molecular and cellular mechanism of various diseases indicated that both innate and adaptive immune systems are targeted for the prevention and cure of various types of diseases. Innate immunity involves mechanisms that recognize structures, which are characteristic to microbial pathogens but are not present on mammalian cells. Examples of such structures include bacterial liposaccharides (LPS), viral double stranded DNA, and unmethylated CpG DNA nucleotides. The effector cells of the innate immune response system comprise neutrophils, macrophages, and natural killer cells (NK cells). In adaptive immunity, the body's immunological defense systems are stimulated by exposure to infectious agents and these responses increase in magnitude and effectiveness with each successive exposure to that particular antigen. There are two types of adaptive immune responses: (i) humoral immunity, which involves the production of pathogen-specific antibodies by B lymphocytes (B cells), and (ii) cell-mediated immunity, which is regulated by T lymphocytes (T cells). Immune effector cells in the innate and adaptive phases of immune responses can be directly or indirectly involved in the cause of some diseases, and are thus potentially important targets for therapeutics against these diseases. Recently, there has been an increasing number of vaccine strategies used against a variety of disease conditions. Infectious diseases caused by viruses, bacteria and parasites [Targett and Greenwood Malar J. 7 Suppl 1:S10 (2008); Okwor and Uzonna Hum Vaccin. May 12; 5 (2009)] are areas of on-going research using vaccines. Unexpectedly, vaccine strategies may also be effective against diseases such as Alzheimer's and prion diseases, in which the scavenger functions of immune response cells against pathogenic metabolic deposits is ineffective [Wisniewski and Konietzko, Lancet Neurol. 7:805 (2008); Sakaguchi, Protein Pept Lett., 16:260 (2009)]. Autoimmune diseases are also an area in which immune responses against the host self-components could potentially be inhibited at pathogenic level by using vaccine strategies to specific self-reactive T cells and B cells. As the list of diseases that are potential targets for treatment by immunological approaches increases, modulators for the immune competent cells are in greater demand. Improved methods for increasing or repressing immune responses, while following safe guidelines for use in humans, represent a major unmet demand in modern medicine.

B Cell- and APC-Targeting Immunotherapies

The cell surface molecule CD40 is a member of the tumor necrosis factor receptor superfamily and is broadly expressed by immune, hematopoietic, vascular, epithelial, and other cells, including a wide range of tumor cells. CD40 itself lacks intrinsic kinase or other signal transduction activity, but rather mediates its diverse effects via an intricate series of downstream adapter molecules that differentially alter gene expression depending on cell type and microenvironment. As a potential target for novel cancer therapy, CD40 may mediate tumor regression through both an indirect effect of immune activation and a direct cytotoxic effect on the CD40-expressing tumor.

CD40 is best known as a critical regulator of cellular and humoral immunity via its expression on B lymphocytes, dendritic cells, and monocytes [Grewal and Flavell, Annu Rev Immunol., 16:111 (1998); van Kooten and Banchereau, J Leukoc Biol., 67:2 (2000)].

CD40 is also expressed on the cell surface of many other non-immune cells, including endothelial cells, fibroblasts, hematopoietic progenitors, platelets and basal epithelial cells [Grewal and Flavell, Annu Rev Immunol., 16:111 (1998); van Kooten and Banchereau, J Leukoc Biol., 67:2 (2000); Young et al., Immunol Today, 9:502(1998); Quezada et al., Annu Rev Immunol., 22:307 (2004)]. The CD40 ligand (CD40L), also known as CD154, is the chief ligand described for CD40 and is expressed primarily by activated T lymphocytes and platelets [van Kooten and Banchereau, J Leukoc Biol., 67:2 (2000); Armitage et al., Nature, 357:80 (1992)]. Atherosclerosis, graft rejection, coagulation, infection control, and autoimmunity are all regulated by CD40-CD40L interactions [Grewal and Flavell, Annu Rev Immunol., 16:111 (1998); van Kooten and Banchereau, J Leukoc Biol., 67:2 (2000)]. Many tumor cells also express CD40, including nearly 100% of B-cell malignancies and up to 70% of solid tumors.

Physiologically, CD40-induced signal transduction represents a major component of a process known as T-cell "help." Ligation of CD40 on dendritic cells, for example, induces cellular maturation and activation as manifested by increased surface expression of co-stimulatory and MHC molecules, production of proinflammatory cytokines such as interleukin 12, and enhanced T-cell activation [van Kooten and Banchereau, J Leukoc Biol., 67:2 (2000); Quezada et al., Annu Rev Immunol., 22:307 (2004)]. CD40 ligation of resting B cells also increases antigen-presenting function and, in addition, induces proliferation and immunoglobulin class switching [van Kooten and Banchereau, J Leukoc Biol., 67:2 (2000); Quezada et al., Annu Rev Immunol., 22:307 (2004)]. Patients with germ line mutations in either CD40 or CD40L are markedly immunosuppressed, susceptible to opportunistic infections, and have deficient T-cell-dependent immune reactions, including IgG production, germinal center formation, and memory B-cell induction [Allen et al., Science, 259:990 (1993); Ferrari et al., Proc Natl Acad Sci USA, 98:12614 (2001); Etzioni A, Ochs H D. Pediatr Res., 56:519 (2004)]. Similar immunophenotypes are observed in mice deficient in CD40 or CD40L [Castigli et al., Proc Natl Acad Sci USA, 91:12135 (1994); Kawabe et al., Immunity, 1:167 (1994); Renshaw et al., J Exp Med., 180:1889 (1994); Xu et al., Immunity, 1:423 (1994)]. Agonistic CD40 antibodies have been shown to mimic the signal of CD40L and substitute for the function of $CD4^+$ T lymphocytes in murine models of T-cell-mediated immunity [Bennett et al., Nature, 393:478 (1998); Ridge et al., Nature, 393:474 (1998); Schoenberger et al., Nature, 393:480 (1998)]. A key mechanism of this effect is thought to be CD40/CD40L-mediated activation of host dendritic cells. Growing evidence shows that stimulating APC with soluble CD40L or an agonistic anti-CD40 antibody can, at least in part, replace the need for T helper cells and generate antigen presenting cells (APCs) that are capable of priming cytotoxic T lymphocytes (CTL). To develop pharmacotherapeutic reagents targeting the CD40/CD40L pathway, series of soluble CD40L fusion proteins were disclosed. In one invention, CD40L was joined to antigens to deliver CD40-costimulation signal and antigens together to B cells and APCs (WO/2003/063899). In another invention, the conjugate of CD40L and a Toll-like receptor ligand, Flagellin, was created to trigger a synergistic activation signaling between CD40 and TLR5 in B cells and APCs (WO/2007/103048). All these innovations aimed to use CD40L fusion proteins as vaccines by stimulating antigen-specific B cell and APCs in vivo.

T Cell Targeting Immunotherapies

Two types of major T lymphocytes have been described, $CD8^+$ cytotoxic lymphocytes (CTLs) and $CD4^+$ helper cells (Th cells). $CD8^+$ T cells are effector cells that, via the T cell receptor (TCR), recognize foreign antigens presented by class I major histocompatibility complex (MEW) molecules on, for instance, virally or bacterially infected cells. T helper cells are involved in both humoral and cell-mediated forms of effector immune responses. With respect to the humoral or antibody immune response, antibodies are produced by B lymphocytes through interactions with Th cells. Specifically, extracellular antigens, such as circulating microbes, are taken up by specialized APCs, processed, and presented in association with class II MEW molecules to $CD4^+$ Th cells. These Th cells in turn activate B lymphocytes, resulting in antibody production. In contrast, the cell-mediated immune response functions to neutralize microbes that inhabit intracellular locations after infection of a target cell.

According to the two-signal model, optimal activation of antigen-specific T lymphocytes requires specific antigen recognition by lymphocytes ('signal 1') and additional signals (called 'signal 2' or co-stimulatory signals). In the absence of signal 2, lymphocytes fail to respond effectively and are rendered anergic. Signal 1 is provided by the interaction of the peptide-antigen-MHC complex with the TCR. Signal 2 is delivered to T cells by co-stimulatory cell surface molecules expressed on APCs. The process of co-stimulation is of therapeutic interest because the manipulation of co-stimulatory signals might provide a means either to enhance or to terminate immune responses.

The B7-1/B7-2-CD28/CTLA-4 pathway is the best-characterized T-cell co-stimulatory pathway and is crucial in T-cell activation and tolerance [Karandikar et al., J. Neuroimmunol. 89:10 (1998); Oosterwegel et al., Curr. Opin. Immunol. 11:294 (1999); Salomon and Bluestone, Annu. Rev. Immunol. 19:225 (2001); Sansom, Immunology, 101:169 (2000); Chambers et al., Annu. Rev. Immunol., 19:565 (2001)]. The B7-1/B7-2-CD28/CTLA-4 pathway includes two B7 family members, B7-1 (CD80) [Freeman et al., J. Exp. Med. 174:625 (1991); Freedman et al., J. Immunol. 137:3260 (1987); Yokochi et al., J. Immunol. 128:823 (1982)] and B7-2 (CD86) [Freeman et al., Science 262:909 (1993); Freeman, et al., J. Exp. Med. 178:2185 (1993); Azuma, et al. Nature 366:76 (1993)], that have dual specificity for two CD28 family members, the stimulatory receptor CD28 antigen-receptor signaling [Aruffo and Seed, Proc. Natl Acad. Sci. USA 84:8573 (1987); Gross et al., J. Immunol., 144:3201 (1990)], by promoting T-cell survival and thereby enabling cytokines to initiate T-cell clonal expansion and differentiation [Thompsonet et al., Proc. Natl. Acad. Sci. USA 86:1333 (1989); Lucas et al., J. Immunol., 154:5757 (1995); Shahinian et al., Science 261:609 (1993); Sperling et al., J. Immunol., 157:3909 (1996); Boise et al., Immunity 3:87 (1995)]. CD28 also optimizes the responses of previously activated T cells, promoting interleukin 2 (IL-2) production and T-cell survival.

Several members of the tumor necrosis factor receptor (TNFR) family function as co-stimulatory receptors after initial T cell activation. These include CD27, 4-1BB (CD137), OX40 (CD134), HVEM, CD30 and GITR [reviewed in Watts, Annu Rev Immunol., 23:23 (2005)].

To develop immunotherapeutic reagents targeting T cells, soluble co-stimulatory receptor extracellular fragments, soluble ligand extracellular fragments, fusion proteins or agonistic antibodies against receptors or specific ligands have been studied. Alternatively, un-agonistic soluble ligands or un-agonistic antibodies have been used to block co-stimulatory receptor signaling. Either by increasing or reducing the extent of T cell costimulation, the use of ligand-fusion proteins or antibodies has shown pharmaceutical benefits to diseases including autoimmune diseases, proliferative disorders such as cancer, or infectious diseases.

Death Receptor "Fas" and Disease Therapy

Fas (CD95), a member of the tumour-necrosis factor receptor (TNFR) superfamily, was originally described as a lymphocyte receptor that can induce apoptosis [Yonehara et al., J. Exp. Med., 169:1747 (1989); Trauth et al., Science, 245:301 (1989)]. Fas is expressed in many types of tissue including glia cells, neurons and neuronal cell lines [Shinohara et al., Cancer Res., 60:1766 (2000); Gomez et al., J. Neurosci. Res., 63:421 (2001); Becher et al., Neurosciences, 84:627 (1998); Raoul et al., J. Cell Biol. 147:1049 (1999); Raoul et al., Neuron, 35:1067 (2002); Matsushita et al. J. Neurosci. 20:6879 (2000); Cheema et al., J. Neurosci., 19:1754 (1999)]. The interaction between CD95 (Fas) and its ligand (Fas-ligand, or FasL) functions to limit the duration of the immune response and/or life-span of activated lymphocytes. Apoptosis induced by Fas-FasL binding serves to clear activated self-reactive lymphocytes. Problems caused by altering this pathway have been demonstrated in animals with defects in Fas↔Fas-ligand interactions. Mice having mutations, which inactivate Fas or FasL, develop numerous disorders including autoimmune pathology resembling that seen in patients with rheumatoid arthritis or systemic lupus. It has been demonstrated that injection of FasL-expressing virus into the joints of mice with collagen-induced-arthritis, results in apoptosis of synovial cells and relief of arthritis symptoms [Zhang et al., in J. Clin. Invest., 100:1951 (1997)]. Expression of the Fas ligand reduces the number of activated inflammatory cells, which play a role in the pathogenesis of autoimmune disease. Therefore, a gene therapy strategy for introducing FasL into the joints of rheumatoid arthritis patients could function to improve disease pathology by leading to destruction of the infiltrating mononuclear cells.

Soluble Fas ligand and receptor have also been shown to be associated with tissue damage and other adverse effects. Administering an agonistic anti-Fas antibody resulted in organ damage to mice [Galle et al., J. Exp. Med. 182:1223 (1995)]. Mice injected intraperitoneally with the agonistic antibody died within several hours, and analyses revealed that severe liver damage by apoptosis was the most likely cause of death.

Fas engagement by FasL, or by antibodies against Fas, initiates binding of the intracellular death domain of Fas to an adaptor protein, the Fas-associated death domain (FADD), which couples Fas to the caspase cascade. Caspase 8 (also known as FADD-like interleukin-1 converting enzyme; FLICE) is the most upstream caspase in the apoptosis pathway, and its cleavage is a hallmark of Fas-induced death [Nagata, Cell 88: 355 (1997); Medema et al. EMBO J. 16:2794 (1997)]. Fas-mediated death signals can be inhibited by the FLICE inhibitory protein (FLIP), which blocks caspase 8 binding to FADD [Irmler et al. Nature 388:190 (1997)]. The activation of a cascade of successive caspase cleavages finally results in the activation of endonucleases that catalyse DNA breakdown into nucleosome-sized fragments, a characteristic feature of apoptosis [Nagata, Cell 88:355 (1997)].

In addition to apoptosis, Fas has been reported to mediate diverse proliferative and regenerative functions, including co-stimulatory signalling during T-cell activation [Alderson et al. J. Exp. Med., 178:2231 (1993); Alderson et al. Int. Immunol. 6:1799 (1994); Desbarats et al. Proc. Natl. Acad. Sci. USA 96:8104 (1999)], induction of angiogenesis [Biancone et al. J. Exp. Med. 186:147 (1997)], and liver regeneration after partial hepatectomy [Desbarats and Newell, Nature Med. 6:920 (2000)].

In contrast to the well-characterized apoptotic pathway, relatively little is known about the signalling pathways involved in Fas-mediated growth induction, although Fas has been shown to activate the extracellular-signal regulated kinase (ERK) pathway [Trauth et al., Science 245:301 (1989)]. ERK, a serine/threonine kinase activated by mitogen-activated protein kinase (MAPK)/ERK kinase (MEK1), mediates the cellular response to many different growth and differentiation factors [reviewed in Fukunaga and Miyamoto, Mol. Neurobiol., 16:79 (1998)]. Notably, activation of ERK prevents Fas-induced apoptosis and, conversely, inhibition of ERK prevents Fas-induced proliferation, suggesting that the MEK1/ERK pathway is involved in the transduction of Fas-mediated growth signals [Trauth et al., Science 245:301 (1989); Holmstrom et al., EMBO J., 19:5418 (2000); Kataoka, et al. Curr. Biol., 10:640 (2000)]. At present, it is not clear how Fas engagement in T-cell co-stimulation, and in the regeneration of liver and nerves, bypasses an apoptotic signal and promotes a regenerative or co-stimulation signal.

Soluble Fas-ligands has been useful reagents to induce pathological cell-specific cell death. For example, a fusion protein that connected interleukin-2-IgFc-FasL was used to kill auto-reactive T cells in autoimmune disease therapy [Bulfone-Paus et al., Transplantation. 69:1386 (2000)]. In a similar approach, the fusion protein of CD40 extracellular domain and FasL extracellular domain, CD40-FasL, showed that cell death is contingent on the binding of CD40 to CD40L expressed on target cells [Siegmund et al., J Mol Med. 84:785(2006)]. A fusion construct comprised of VEGF and FasL was found to effectively kill cancer cells by a synergistic effect between VEGF signaling and Fas signaling (WO/2007/022273). Additionally, a fusion protein containing a DC20-specific antibody fragment and soluble FasL, ScFvRit:sFasL [Bremer et al., Cancer Res., 68:597 (2008)], was applied to non-Hodgkin lymphoma and B cell chronic lymphocytic leukemia. This fusion protein efficiently activated CD20 signaling and Fas cell death signaling, resulting in a far superior proapoptotic activity, compared with co-treatment with anti-CD20 antibody (rituximab) and soluble FasL. Therefore Fas ligand-based fusion proteins have shown promising results in the field of autoimmune diseases and cancer therapy by stimulating Fas-induced death signaling in pathological cells. Fas-associated regenerative or co-stimulation signaling has not been exploited for target cell specific therapy.

Immune Suppressive Molecules

Traditionally, various steroids and inhibitors that block the cell activation and growth signaling, such as FK506 or Rapamycin, are broadly used. Some drawbacks to the use of these reagents are that they are not specific to lymphocytes and their use is often accompanied by serious side effects. The first therapeutic agents (immune suppressors) were mostly non-specific and inhibited cellular proliferation [Van Assche et al., Curr Opin Gastroenterol. May 5 (2009); Arias et al., Transplant Rev (Orlando) 23:94 (2009); Ng et al., Front Biosci., 14:1627 (2009)]. These treatments generally led to serious side effects due to intrinsic lack of pharmacospecificity. Later, cyclosporin A (CsA) was the first of a new generation of immunosuppressants with a 'site-specific' mode of action. Mechanistically, CsA mediates its in vivo effects by repressing lymphocyte activation at an early stage. Due to a low degree of myelotoxicity, CsA was considered as an attractive therapeutic drug in clinical transplantation for inhibiting lymphocytic activities without affecting either phagocytosis or migration of the reticulo-endothelial system. In 1978, CsA was tested clinically and due to its strong efficacy was used worldwide in a majority of the transplant centers to maintain graft survival post surgery [Goumenos, Expert Opin Pharmacother. 9:1695 (2008); Beauchesne, Drug Dev Ind Pharm. 33:211 (2007)]. In the meantime, much work has been put into the design of new therapeutic strategies that would present lower side effects but retain substantial efficacy. Based on research on the antigen specific T cell activation by TCR and in the recent application of the non-stimulatory CD3-specific humanized antibody (Alegre et al., J. Immunol., 155:1544 (1995), blockade of co-stimulatory receptors (i.e. CD28) with CTLA4-Ig and CD40 with anti-CD40L antibody has been attempted. Human-specific humanized non-activating anti-CD3 antibody (teplizumab) was FDA approved to prevent the T cell response that causes T cell immune deficiencies in human.

Thus far, inhibition of co-stimulatory receptors or T cell receptors (by non-activating anti-CD3 antibody) has been partially effective in inducing antigen-specific immunological tolerance.

APCs and T cells, or between T cells and B cells are tightly regulated by cell surface receptors and their counter-receptors (ligands). Therefore various techniques and reagents to facilitate or repress major receptor interactions and their signaling mechanisms have been developed for disease therapeutic purposes. Receptor agonistic or blocking antibodies, soluble extracellular domain of ligand fusion proteins, soluble death receptor ligand fusion proteins and mitogenic or immunosuppressive substances of bacterial or plant origin as described supra showed levels of efficacy beneficial to the disease therapy, although the toxic side effects are often accompanied by strong pharmacotherapeutic efficacy.

The present invention provides methods to develop powerful target cell-specific immune-stimulating fusion proteins, which could lead to the effective immunotherapy of various diseases.

SUMMARY OF THE INVENTION

This invention is based on the discovery that nucleic acid constructs that encode a minimum of (i) one functional moiety of the extracellular domain of the TNF/TNF receptor (TNFR) family agonist or the extracellular domain of the immunoglobulin family agonist or cytokine family, (ii) a second functional moiety of the extracellular domain of the TNF/TNFR family agonist or a functional moiety of the extracellular domain of the immunoglobulin family agonist or cytokine family, (iii) an immunoglobulin Fc domain (designated as IgGFc or IgFc in the text) (optional) and (iv) an antigen and the corresponding polypeptide, which the corresponding soluble fusion peptides expressed thereby (optional). A construct containing these components, when cultured with immune cells, will elicit a de novo effect to cause cell activation (i.e. cell proliferation, cytokine expression or immunoglobulin production in T cells and B cells).

This invention is also based on the discovery that the nucleic acid constructs or the expressed soluble fusion polypeptide, when administered to a host, elicits a de novo effect on immunity (i.e. increased or repressed B cell immunity and T cell immunity responses).

The function of the nucleic acids or soluble fusion protein is termed as a "synergistic" de novo effect on immunity. Specifically, the intended effect of the nucleic acid or soluble fusion protein construct is a significantly increased immune response relative to when either of the respective agonistic polypeptides contained therein are administered alone.

Particularly, this invention provides nucleic acid constructs containing genes encoding soluble fusion proteins which comprises (i) a CD40 ligand, a Fas ligand extracellular domain and an immunoglobulin IgG Fc domain [Yoshida et al., Vaccine 28: 3688 (2010)], (ii) a CD28 ligand (B7-2), a Fas ligand extracellular domain and an immunoglobulin IgG Fc domain, (iii) a OX40 ligand, a 4-1BB ligand extracellular domain and an immunoglobulin IgG Fc domain, (iv) a CD40 ligand, a ICOS extracellular domain and an immunoglobulin IgG Fc domain, (v) a NGFβ ligand, a Fas ligand extracellular domain and an immunoglobulin IgG Fc domain, (vi) an IL-2 ligand, a Fas ligand extracellular domain and an immunoglobulin IgG Fc domain. The fusion proteins will preferably elicit a de novo effect to cause immune cell activation relative to when any of the respective agonistic polypeptides contained therein are administered alone.

As described in detail infra, these nucleic acid constructs or the corresponding encoded fusion polypeptides may be administered to a host in need of such treatment as a means of:

generating enhanced (significantly greater) primary and memory B cell responses relative to immunization with antigen alone generating enhanced (significantly greater) primary and memory $CD4^+$ and/or $CD8^+$ T cell responses relative to immunization with antigen alone inducing repressed (significantly lower) antigen-specific B cell and/or T cell responses relative to immunization with antigen alone These nucleic acid constructs or the corresponding encoded fusion polypeptides may be used in treating any disease or condition in which the above-identified enhanced or repressed humoral and cellular immune responses are required therapeutically. This applies specifically to infectious diseases, proliferative disorders such as cancer, allergies, inflammatory disorders, and other chronic diseases where enhanced cellular immunity is required. Alternatively, these reagents can be used in cases where repressed cellular immunity is required, such as organ transplant rejection, autoimmune disorders and graft versus host response.

As described in detail infra, DNA constructs may comprise linear DNA, a bacterial plasmid, a viral vector such as adenoviral, baculovirus, or other viral vectors commonly used for gene therapy. Additionally, as described infra these DNA constructs or fusion polypeptides may comprise extracellular domains of other TNF/TNFR family member agonists, immunoglobulin family member agonists and cytokines. Examples of TNF/TNFR family member agonists include Fas, Fas ligand, CD27, CD30 ligand, HVEM, TROY, RELT, TNF-alpha, TNF-beta, CD70, RANK ligand, LT-alpha, LT-beta, GITR ligand and LIGHT. Examples of immunoglobulin family member agonists include B7-1, B7-2, CD28, CTLA4, ICOS and ICOS-ligand. Further, these DNA constructs may comprise genes encoding antigens of bacterial/viral pathogens and tumor specific proteins. Examples of bacterial and viral antigens include human immunodeficiency virus-1 (HIV-1)env, HIV-lpol, HIV-lgag. Examples of tumor-specific antigens include human melanoma-associated glycoprotein p9'7, MART-1 and Her2/neu breast cancer antigen.

Various other features and advantages of the present invention should become readily apparent with reference to the following description, definitions, examples, claims and appended Figures. In several places throughout the specification guidance is provided through lists of examples. In each instance, the recited list serves only as a representative group and should not be interpreted as an exclusive list.

BRIEF DESCRIPTION OF THE DRAWINGS

FIG. 2A-C. Registered sequence of CD40 ligand of human origin (SEQ ID NO: 1).

FIG. 3A-C. Registered sequence of oncostatin M of human origin (SEQ ID NO: 3).

FIG. 4A, B. Registered sequence of IgG1 Fc of human origin (SEQ ID NO: 5).

FIG. 5A-C. Nucleotide sequence and amino acid sequence of the CD40L-IgFc fusion protein (SEQ ID NO: 7).

FIG. 6A-C. Registered sequence of Fas ligand of human origin (SEQ ID NO: 9).

FIG. 7A-C. Nucleotide sequence and amino acid sequence of the FasL-IgFc fusion protein (SEQ ID NO: 11).

FIG. 8A-D. Nucleotide sequence and amino acid sequence of the CD40L-FasL-IgFc fusion protein (SEQ ID NO: 13).

FIG. 9. Western blotting analysis of CD40L-FasL-IgFc. A: anti-human IgG, B: anti-human FasL.

FIG. 10. Study of Fas binding by CD40L-FasL-IgFc.

FIG. 11. Proliferation of human PBMC induced with CD40L-FasL-IgFc.

FIG. 12. Non-T cell-specific stimulation by CD40L-FasL-IgFc.

FIG. 13. Effects of Polymixin B pre-absorption on the stimulation by CD40L-FasL-IgFc.

FIG. 14. Reduction of CD40L-FasL-IgFc-induced activation by signaling inhibitors.

FIG. 15. Induction of IgG secretion in PBL cells stimulated with CD40L-FasL-IgFc.

FIG. 16. The expression of PRDI-BF1 in response to CD40L-FasL-IgFc stimulation.

FIG. 17. Adjuvant activity of CD40L-FasL-IgFc in mice against OVA.

FIG. 18. Adjuvant activity of CD40L-FasL-IgFc in mice against Influenza hemaglutinin.

FIG. 19. Adjuvant activity of Plasmid DNA of CD40L-FasL-IgFc in mice against Influenza hemaglutinin.

FIG. 20. Adjuvant activity of CD40L-FasL-IgFc in mice against Influenza hemaglutinin-specific T cell response. A: total T cell response; B: $CD8^+$ T cell response.

FIG. 21A-C. Registered sequence of B7-2 of human origin (SEQ ID NO: 15).

FIG. 22A-D. Nucleotide sequence and amino acid sequence of the B7-2-FasL-IgFc fusion protein (SEQ ID NO: 17).

FIG. 23A-C. Nucleotide sequence and amino acid sequence of the B7-2-IgFc fusion protein (SEQ ID NO: 19).

FIG. 24. Western blotting analysis of B7-2-FasL-IgFc. A: anti-human IgG, B: anti-human FasL.

FIG. 25. Study of Fas binding by B7-2-FasL-IgFc.

FIG. 26. Activation of $CD4^+$ and $CD8^+$ T cells by B7-1-FasL-IgFc.

FIG. 27. B7-2-FasL-IgFc stimulates IL-2 production of T cells.

FIG. 28. Induction of T-bet by B7-2-FasL-IgFc activation.

FIG. 29. Reduction of B7-2-FasL-IgFc-induced activation by signaling inhibitors.

FIG. 30. Immunosuppressant activity of B7-2-FasL-IgFc in mice against Influenza hemaglutinin.

FIG. 31. Suppressant activity of plasmid DNA of B7-2-FasL-IgFc in mice against Influenza hemaglutinin.

Figure 1:
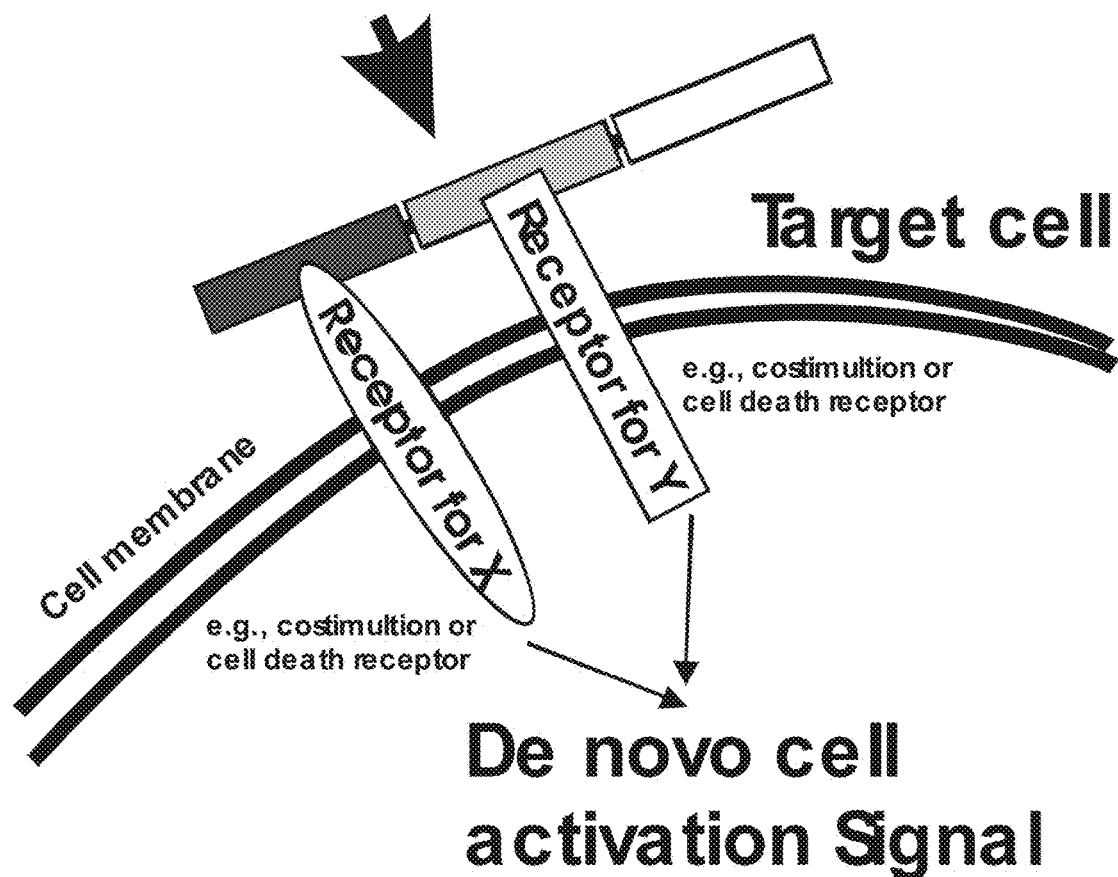
FIG. 1. Schematic diagram of the presumed structure of the multi-ligand fusion protein and the interaction with target cells to induce cell activation.

FIG. 32. Immunosuppressant activity of B7-2-FasL-IgFc in mice against Influenza hemaglutinin-specific T cell response. A: total T cell response; B: $CD8^+$ T cell response.

FIG. 33. The repression of SEB-induced splenomegaly by co-administrated Plasmid DNA of B7-2-FasL-IgFc.

FIG. 34A-C. Registered sequence of the OX40 ligand of human origin (SEQ ID NO: 21).

FIG. 35A-C. Registered sequence of the 4-1BB ligand of human origin (SEQ ID NO: 23).

FIG. 36A-D. Nucleotide sequence and amino acid sequence of the OX40L-4-1BBL-IgFc (SEQ ID NO: 25).

FIG. 37A-C. Nucleotide sequence and amino acid sequence of the OX40L-IgFc (SEQ ID NO: 27).

FIG. 38A-C. Nucleotide sequence and amino acid sequence of the 4-1BBL-IgFc (SEQ ID NO: 29).

FIG. 39. Western blotting analysis of OX40L-4-1BBL-IgFc. A: anti-human IgG, B: anti-human FasL.

FIG. 40. Activation of PBMCs by OX40L-4-1BBL-IgFc.

FIG. 41. Adjuvant activity of OX40L-4-1BBL-IgFc/PCI-neo in mice against Influenza hemaglutinin.

FIG. 42. Adjuvant activity of OX40L-4-1BBL-IgFc in mice against Influenza hemaglutinin-specific T cell response. A: total T cell response; B: $CD8^+$ T cell response.

FIG. 43A-C. Registered sequence of ICOS of human origin (SEQ ID NO: 31).

FIG. 44A-D. Nucleotide sequence and amino acid sequence of CD40L-ICOS-IgFc (SEQ ID NO: 33).

FIG. 45. Western blotting analysis of CD40L-ICOS-IgFc. A: anti-human IgG, B: anti-human FasL.

FIG. 46. Adjuvant activity of Plasmid DNA of CD40L-ICOS-IgFc in mice against Influenza hemaglutinin.

FIG. 47. Adjuvant activity of CD40L-ICOS-IgFc/PCIneo in mice against Influenza hemaglutinin-specific T cell response. A: total T cell response; B: $CD8^+$ T cell response.

FIG. 48A, B. Registered sequences of NGFβ of human origin (SEQ ID NO: 35).

FIG. 49A-C. Nucleotide sequence and amino acid sequence of the NGFβ-FasL-IgFc fusion protein (SEQ ID NO: 37).

FIG. 50. Western blotting analysis of NGFβ-FasL-IgFc. A: anti-human IgG, B: anti-human FasL.

FIG. 51. Adjuvant activity of Plasmid DNA of NGFβ-FasL-IgFc in mice against Influenza hemaglutinin.

FIG. 52. Adjuvant activity of NGFβ-FasL-IgFc/PCIneo in mice against Influenza hemaglutinin-specific T cell response. A: total T cell response; B: $CD8^+$ T cell response.

FIG. 53A, B. Registered sequence of IL-2 of human origin (SEQ ID NO: 39).

FIG. 54A-D. Nucleotide sequence and amino acid sequence of IL-2-FasL-IgFc (SEQ ID NO: 41).

FIG. 55. Western blotting analysis of IL-2-FasL-IgFc. A: anti-human IgG, B: anti-human FasL.

FIG. 56. Adjuvant activity of Plasmid DNA of IL-2-FasL-IgFc in mice against Influenza hemaglutinin.

FIG. 57. Suppressant activity of IL-2-FasL-IgFc/PCIneo in mice against Influenza hemaglutinin-specific T cell response.

DETAILED DESCRIPTION OF THE INVENTION

The present invention is based on the discovery that the soluble protein expression products of fusion cDNA constructs, composed of a co-stimulation ligand extracellular domain linked with a Fas death receptor ligand extracellular domain and immunoglobulin Fc domain, stimulates human lymphocytes to proliferate and produce cytokines rather than inducing cell death or cell co-stimulation.

One embodiment of the invention provides cDNA constructs encoding a novel synergistic agonistic polypeptide combination comprising (i) a cDNA encoding a specific TNF family agonistic extracellular domain polypeptide (i.e. CD40 ligand extracellular domain) and (ii) a cDNA encoding a different TNF family agonistic extracellular domain specific to Fas agonist (Fas ligand extracellular domain). Optional components of these constructs include (iii) cDNA encoding an immunoglobulin Fc domain and (iv) the cDNA encoding the desired antigen polypeptide. The soluble expression products of these gene constructs, designated as CD40 ligand (L)-Fas ligand (L)-IgFc (SEQ ID NO: 13), when cultured with a host cells stimulate CD40 expressing cells, inducing cell proliferation and cytokine production. These DNA constructs, either the vectors themselves or the purified protein they encode, when administered to a host may be used to generate enhanced humoral and cellular antigen-specific immune responses.

The present invention provides expression vectors and host cells containing a cDNA construct encoding this novel synergistic agonistic polypeptide combination comprising (i) a cDNA encoding a specific TNF family agonistic extracellular domain polypeptide (i.e. CD40 ligand extracellular domain) and (ii) a cDNA encoding a different TNF family agonistic extracellular domain specific to Fas (Fas ligand extracellular domain). Optional components of these constructs include (iii) cDNA encoding an immunoglobulin Fc domain and (iv) cDNA encoding the desired antigen against which enhanced antigen specific cellular immune response is a desirable outcome.

Another embodiment of the present invention provides DNA constructs encoding a novel synergistic agonistic polypeptide combination comprising (i) a cDNA encoding a specific immunoglobulin family agonistic extracellular domain polypeptide, preferably a CD28 agonist (i.e. B7-2 extracellular domain), and (ii) a cDNA encoding a different agonistic TNF family polypeptide extracellular domain of Fas agonist (Fas ligand extracellular domain). Optional components of these constructs include (iii) a cDNA encoding an immunoglobulin Fc domain and (iv) a cDNA encoding the desired antigen to which desired antigen-specific cellular immune response are elicited. The expression products of these gene constructs, designated as B7-2-FasL-IgFc (SEQ ID NO: 17), stimulate CD28 expressing cells resulting in the induction of cell proliferation and cytokine production. These DNA constructs, vectors containing or the expression product of these DNA constructs, when administered to a host, may be used to generate enhanced or repressed antigen-specific humoral or cellular immune responses.

The present invention further provides expression vectors and host cells containing a cDNA construct encoding novel synergistic agonistic polypeptide combination comprising (i) a cDNA encoding a specific immunoglobulin gene family agonistic extracellular domain polypeptide, preferably a CD28 agonist (B7-2 extracellular domain) and (ii) a cDNA encoding a different agonistic TNF family polypeptide extracellular domain of Fas agonist (Fas ligand extracellular domain). Optional components of these constructs include. Optional components of these constructs include (iii) cDNA encoding an immunoglobulin Fc domain and (iv) cDNA encoding the desired antigen against which repressed antigen specific cellular immune response are desirable outcome.

Another embodiment of the present invention provides cDNA constructs encoding a novel synergistic agonistic polypeptide combination comprising (i) a cDNA encoding a specific TNF family agonistic extracellular domain polypeptide, preferably a OX40 agonist (OX40 ligand extracellular domain) and (ii) a cDNA encoding a different TNF family agonistic extracellular domain of 4-1BB agonist (4-1BB ligand extracellular domain). Optional components of these constructs include (iii) cDNA encoding an immunoglobulin Fc domain and (iv) cDNA encoding the desired antigen. The expression products of these gene constructs, designated as OX40L-4-1BBL-IgFc (SEQ ID NO: 25), when cultured with a host cell, stimulate OX40 and 4-1BB expressing cells resulting in activation of T cells and regulatory T cells inducing cell proliferation and cytokine productions. These cDNA constructs, vectors containing or the protein expression product of these constructs, when administered to a host, may be used to generate enhanced antigen-specific humoral and cellular immune responses.

The present invention further provides expression vectors and host cells containing a cDNA construct encoding novel synergistic agonistic polypeptide combination comprising (i) a cDNA encoding a specific TNF family agonistic extracellular domain polypeptide, preferably a OX40 agonist (OX40 ligand extracellular domain) and (ii) a cDNA encoding a different TNF family agonistic extracellular domain of 4-1BB agonist (4-1BB ligand extracellular domain). Optional components of these constructs include (iii) cDNA encoding an immunoglobulin Fc domain and (iv) desired antigen to which enhanced antigen-specific cellular immune response is a desirable outcome.

Another embodiment of the present invention provides DNA constructs encoding a novel synergistic agonistic polypeptide combination comprising (i) a cDNA encoding a specific TNF family agonistic extracellular domain of specific CD40 agonist (CD40 ligand extracellular domain), and (ii) a cDNA encoding a specific immunoglobulin family receptor extracellular domain polypeptide, preferably a ICOS (i.e. ICOS extracellular domain). Optional components of these constructs include (iii) a cDNA encoding an immunoglobulin Fc domain and (iv) a cDNA encoding the desired antigen to which desired antigen-specific cellular immune response are elicited. The expression products of these gene constructs, designated as CD40L-ICOS-IgFc (SEQ ID NO: 33), stimulate ICOS ligand expressing cells resulting in the induction of cell proliferation and cytokine production. These DNA constructs, vectors containing or the expression product of these DNA constructs, when administered to a host, may be used to generate enhanced or repressed antigen-specific humoral or cellular immune responses.

The present invention further provides expression vectors and host cells containing a cDNA construct encoding novel synergistic agonistic polypeptide combination comprising (i) a cDNA encoding a specific different TNF family agonistic extracellular domain polypeptide of specific CD40 agonist (CD40 ligand extracellular domain), and (ii) a cDNA encoding a specific immunoglobulin family receptor extracellular domain polypeptide, preferably a ICOS (i.e. ICOS extracellular domain). Optional components of these constructs include (iii) a cDNA encoding a immunoglobulin Fc domain and (iv) a cDNA encoding the desired antigen against which repressed antigen specific cellular immune response are desirable outcome.

Another embodiment of the present invention provides cDNA constructs encoding a novel synergistic agonistic polypeptide combination comprising (i) a cDNA encoding a specific, neuro growth factor (NGF) family polypeptide, preferably NGFβ and (ii) a cDNA encoding a specific TNF family agonistic extracellular domain polypeptide of Fas agonist (Fas ligand extracellular domain). Optional components of these constructs include (iii) cDNA encoding an immunoglobulin Fc domain and (iv) cDNA encoding the desired antigen to which enhanced antigen-specific cellular immune responses are a desired outcome. The expression products of these gene constructs, designated as NGF-FasL-IgFc (SEQ ID NO: 37), when cultured with a host cells in vitro preferably, stimulate NGF receptor expressing cells (i.e. neuronal cells and B cells) resulting in the induction of cell proliferation, cell differentiation and cytokine production. These cDNA constructs, vectors containing or the expression product of these DNA constructs, when administered to a host may be used to generate (i) growth promotion of nerve cells and (ii) enhanced antigen-specific humoral and cellular immune responses.

The present invention further provides expression vectors and host cells containing a cDNA construct encoding novel synergistic agonistic polypeptide combination comprising (i) a cDNA encoding a specific NGF family polypeptide, preferably NGFβ and (ii) a cDNA encoding a specific TNF family agonistic extracellular domain polypeptide of Fas agonist (Fas ligand extracellular domain). Optional components of the constructs include (iii) cDNA encoding an immunoglobulin Fc domain and (iv) cDNA encoding the desired antigen to which enhanced antigen specific cellular immune response are targeted.

Another embodiment of the present invention provides cDNA constructs encoding a novel synergistic agonistic polypeptide combination comprising (i) a cDNA encoding a specific interleukin 2 family agonistic polypeptide, preferably a interleukin 2 and (ii) a cDNA encoding a specific TNF family agonistic extracellular domain polypeptide of Fas agonist (Fas ligand extracellular domain). Optional components of these constructs include (iii) cDNA encoding an immunoglobulin Fc domain and (iv) desired antigen to which enhanced antigen-specific cellular immune response are desirable outcome. The protein expression products of these gene constructs, designated as IL-2-FasL-IgFc (SEQ ID NO: 41) when cultured with a host cells in vitro stimulate IL-2 receptor expressing cells resulting in activated T cells and B cells and the induction of cell proliferation and cytokine production. These cDNA constructs, vectors containing or the expression product of these cDNA constructs, when administered to a host, may be used to generate enhanced antigen-specific humoral and repressed cellular immune responses.

The present invention further provides expression vectors and host cells containing a cDNA construct encoding novel synergistic agonistic polypeptide combination comprising (i) a cDNA encoding a specific interleukin 2 family agonistic polypeptide (i.e. interleukin 2 itself) and (ii) a cDNA encoding a specific TNF family agonistic extracellular domain polypeptide of Fas agonist (Fas ligand extracellular domain). Optional components of these constructs also include (iii) cDNA encoding an immunoglobulin Fc domain and (iv) cDNA encoding the desired antigen to which enhanced antigen-specific cellular immune responses are a desirable outcome.

In addition, the invention provides methods of using vectors and host cells to produce a composition containing the novel synergistic conjugates (i) CD40 ligand/Fas ligand [Yoshida et al., Vaccine 28: 3688 (2010)], (ii) B7-2/Fas ligand, (iii) OX40 ligand/4-1BB ligand, (iv) CD40 ligand/ICOS, (v) NGFβ/Fas ligand or (vi) IL-2/Fas ligand. In each of the 6 vectors described, there is an option to link to an Fc/antigen polypeptide conjugate.

Further, the invention provides methods of administering the DNA or fusion proteins into a host in which an antigen-specific immune response is required to be elicited or repressed. For example, administration of these reagents to a subject with a chronic disease such as cancer, an infectious or autoimmune disease, or an allergic disorder, may be beneficial.

The invention also provides compositions comprising novel synergistic fusion constructs containing antigen polypeptide conjugates, which are suitable for administration to a host in order to elicit an enhanced antigen-specific humoral or cellular immune response.

The invention provides novel methods of immunotherapy comprising the administration of said novel synergistic fusion constructs of agonists-antigen polypeptide conjugate or a cDNA encoding said fusion protein polypeptide to a host in need of such treatment in order to elicit an enhanced antigen-specific humoral and cellular immune response. In preferred embodiments, these compositions and conjugates will be administered to a subject with or at risk of developing a cancer, an infection, particularly a chronic infectious diseases (i.e. involving a virus, bacteria or parasite) or an autoimmune, inflammatory or allergic condition. As an example, in the preferred embodiment described infra, the invention is used to elicit antigen-specific cellular immune responses against chronic viral infections such as type A Influenza virus and human immunodeficiency virus HIV-1. HIV-1 infection is a well-recognized example of a disease where protective immunity almost certainly will require the generation of potent and long-lived cellular immune responses against the virus.

Further, the invention provides novel methods of immunotherapy comprising the administration of said novel synergistic fusion proteins encoding agonists-antigen polypeptide conjugates or cDNA constructs encoding said fusion protein polypeptide to a host in need of such treatment in order to elicit a repressed antigen specific humoral and cellular immune response. In preferred embodiments, these compositions and conjugates will be administered to a subject with or at risk of developing an organ rejection reaction against transplanted allo or xeno organs (i.e. kidney, heart, liver) or autoimmune, inflammatory or allergic conditions.

As used herein the following terms shall have the meanings set forth. Otherwise all terms shall have the meaning they would normally be accorded by a person skilled in the relevant art.

The term "agonist" refers to a compound that in combination with a receptor can produce a cellular response. An agonist may be a ligand that directly binds to the receptor. Alternatively an agonist may combine with a receptor indirectly by for example (a) forming a complex with another molecule that directly binds to the receptor, or (b) otherwise resulting in the modification of another compound so that the other compound directly binds to the receptor. An agonist herein will typically refer to a TNF family agonist, TNFR family agonist, an immunoglobulin family agonist or a cytokine family agonist.

The term "antigen" herein refers to any substance that is capable of being the target of an immune response. An antigen may be the target, for example, of a cell-mediated and/or humoral immune response (i.e. immune cell maturation, production of cytokines, production of antibodies, etc.) when contacted with immune cells. Examples of antigens include bacterial, viral, fungal polypeptides, autoantigens, allergens, and the like.

The term "synergy" and variations thereof refers to activity such as immunostimulatory activity achieved when administering a combination of active agents that is greater than the additive activity of the active agents administered individually.

The term "conjugate" herein refers to a single molecule, typically a DNA fusion or polypeptide fusion that contains a plurality of agonists or genes encoding and optionally an antigen or gene encoding wherein each are directly or indirectly attached to one another, e.g., by the use of linkers, and wherein these agonists and antigen, if present, may be in any order relative to one another in the conjugate.

Herein "(i) CD40 ligand (CD40L), (ii) Fas ligand (FasL), (iii) B7-2, (iv) IL-2, (v) NGFβ, (vi) OX40 ligand (OX40L), (vii) 4-1BB ligand (4-1BBL) and (viii) ICOS" includes any polypeptide or protein that specifically recognizes and activates the (i) CD40 receptor, (ii) Fas receptor, (iii) CD28 receptor, (iv) IL-2 receptor, (v) NGF receptor, (vi) OX40 receptor, (vii) 4-1BB receptor and (viii) ICOS ligand respectively, and activates its biological activity. Preferably they are human corresponding proteins or derivatives or polymers or fragments thereof. Particularly the invention embraces CD40L, FasL, B7-2, IL-2, NGF, OX40L, 4-1BBL and ICOS proteins and fragments possessing at least 75-80% identity, more preferably at least 90%-95% sequence identity or more to the native polypeptide or a fragment thereof which recognize and activate the specific receptors. The amino acid sequence and corresponding nucleic acid sequence of each polypeptide is disclosed; CD40L in U.S. Pat. Nos. 6,410,711 and 5,962,406; FasL in U.S. Pat. No. 6,046,310, WIPO Patent No. WO/1997/033617, WO/1995/013293 and; B7-2 in U.S. Pat. No. 5,942,607; OX40L in U.S. Pat. No. 5,457,035; 4-1BBL in U.S. Pat. No. 6,838,262; IL-2 in Genbank No. NM_000586; NGFβ in GenBank No. NM_002506 and ICOS in GenBank No. NM_012092 all incorporated by reference in their entirety herein.

"TNF/TNFR" refers to a member of the tumor necrosis factor superfamily or the tumor necrosis factor receptor superfamily. Examples thereof include CD40, CD40L, 4-1BB, 4-IBBL, CD27, CD70, CD30, CD30 ligand (CD153), OX40, OX-40L, Fas, FasL, TNF-alpha, TNF-beta, TNFR2, RANK, LT-beta, LT-alpha, HVEM. GITR, TROY, RELT, of any species and allelic variants and derivatives thereof.

The term "cytokine" is understood to mean any protein or peptide, analog or functional fragment thereof, which is capable of stimulating or inducing a pro survival effect against a pre-selected cell-type, for example, a lymphocyte or a monocyte, in a mammal. Accordingly, it is contemplated that a variety of cytokines can be incorporated into the cytokines of the invention. Useful cytokines include, for example, tumor necrosis factors (TNFs), interleukins (ILs), lymphokines (Ls), colony stimulating factors (CSFs), interferons (IFNs) including species variants, truncated analogs thereof which are capable of stimulating or inducing such pro survival responses. Useful neuro growth factors include, for example, NGFβ. Useful lymphokines include, for example, LT. Useful colony stimulating factors include, for example, GM-CSF and M-CSF. Useful interleukins include, for example, IL-2, IL-4, IL-5, IL-7, IL-12, IL-15 and IL-18. Useful interferons, include, for example, IFN-α, IFN-β and IFN-γ.

The terms "treatment" and "therapeutic method" refer to both therapeutic treatment and prophylactic/preventative measures. Those in need of treatment may include individuals already having a particular medical disorder as well as those who may ultimately acquire the disorder (i.e., those needing preventative measures).

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

The term "co-stimulate" with reference to activated immune cells includes the ability of a co-stimulatory molecule to provide a second, non-activating receptor mediated signal (a "costimulatory signal") that induces proliferation or effector function. For example, a co-stimulatory signal can result in cytokine secretion (i.e. in a T cell that has received a T cell-receptor-mediated signal).

As used herein the term "co-stimulatory molecule" includes molecules, which are present on (i) antigen presenting cells (i.e. B7-1, B7-2, B7RP-1, ICOSL, OX40L, 4-1BBL and/or related molecules that bind to co-stimulatory receptors (i.e., CD28, CTLA4, ICOS, OX40, 4-1BB and/or related molecules) on T cells, and (ii) T cells (i.e. CD40L, ICOS and/or related molecules that bind to costimulatory receptors (i.e. CD40, ICOSL and/or related molecules) on antigen presenting cells and B cells.

The term "soluble" includes molecules, such as co-stimulatory molecules, which are not cell associated. Soluble co-stimulatory molecules retain the function of the cell-associated molecules from which they are derived in that they are capable of binding to their cognate ligands on T cells and mediating signal transduction via (i) CD28, CTLA4, OX40, 4-1BB and/or related molecules on a T cell, and (ii) CD40, ICOSL and/or related molecules on antigen presenting cells and B cells, however, they are in soluble form (i.e. they are not membrane bound).

The term "fusion" or "fusion protein" as used herein refers to the combination of amino acid sequences in one polypeptide chain, preferably by in frame fusion of corresponding coding nucleotide sequences. In nature, the X and Y entities normally exist in separate proteins, which are brought together in the fusion protein of the invention. In the fusion protein of the present invention, the coding sequence of the first polypeptide (X) is fused in frame with the coding sequence of the second polypeptide (Y) either directly or through a linker. By "fused in frame", it is meant that the expression of the fused coding sequences results in the fusion protein comprising both the first and the second polypeptides. This means, for example, that there is no translational terminator between the reading frames of the X and Y polypeptides. Even through the fusion between the X and Y entities can take place internally at any site, the Y entity is preferably fused to either the COOH or the NH2 terminus of the X entity (resulting in a fusion of the formula X—Y and Y—X respectively). As used herein, the term "directly" refers to a fusion of the polypeptides X and Y without a peptide linker in between (i.e. the codons encoding the X entity are contiguous with the codons encoding the Y entity). In addition, the fusion protein may also include further elements (Z) apart from X, Y and a linker, such as an initiator methionine, a signal peptide, an anchor polypeptide (e.g., immunoglobulin Fc domain) and an antigen polypeptide. Fusion proteins essentially consisting of X and Y, Z (optional) and a linker (optional) are preferred embodiments in the context of the present invention.

The fusion proteins encompassed by the present invention are not limited by the particular identity of X and Y, nor by the number of X and/or Y entities employed in the fusion protein. The X and the Y polypeptides are different (i.e. heterologous with respect to one another). The difference may be in terms of structure (i.e. below 40% identity between their respective amino acid sequences) and/or in terms of their respective biological activity (i.e. X and Y are involved in different pathways of the immune system). The X and Y entities involved in the fusion protein of the invention may individually originate (be obtained, isolated) from human or animal origin (i.e. canine, avian, bovine, murine, ovine, porcine, feline, simian and the like). The fusion protein may also comprise X and Y entities of diverse origins (i.e. X of human origin and Y of animal origin).

The current invention is based on the discovery in that the immunoglobulin IgG Fc domain-conjugated fusion protein comprising an extracellular domain of B7-2 (the ligand of CD28 T cell co-stimulation receptor, Fas antigen), and an extracellular domain of Fas-ligand (the ligand of cell death receptor), did not induce cell death in human Fas-apoptosis-sensitive Jurkat T cell line or human peripheral blood T lymphocytes. The net effect of this fusion protein, designated as B7-2-FasL-IgFc (SEQ ID NO: 17), was a strong activation of proliferation in peripheral blood T lymphocytes. The observed activation was comparable to that induced by the well-known T cell mitogen PHA. The binding of B7-2 with the CD28 co-stimulation receptor alone does not cause T cell proliferation or cytokine production, while treatment with Fas-ligand alone renders T lymphocytes highly susceptible to cell death. According to understanding, the strong cell activation by simultaneous stimulation of a co-stimulation receptor and another death receptor is not a predictable outcome. Indeed, the additive stimulation of Fas and CD28 by Fas- and CD28-specific specific monoclonal antibodies does not cause T cell activation. Similarly, the T cell activation was caused only by the B7-2-FasL-IgFc fusion protein and not by treatment with a mixture of the B7-2-IgFc (SEQ ID NO: 19) and FasL-IgFc (SEQ ID NO: 11) fusion proteins. A possible explanation for the strong activation in $CD28^+/Fas^+$ T cells is that B7-2 and FasL must be located in the close proximity to each other, as is the case when linked together in the B7-2-FasL-IgFc fusion protein. Interestingly, although B7-2-FasL-IgFc polypeptide induced a mitogenic response in T cells cultured in vitro, the administration of the polypeptide or the plasmid DNA in vivo resulted in the severe repression of humoral and cellular immune responses.

Since Fas is expressed in almost the entire population of lymphocytes, the specificity of B7-2-FasL-IgFc to T cells is presumed to be determined by the binding of the B7-2 domain CD28 on T cells. To investigate this further, the inventor asked if the replacement of B7-2 extracellular domain with an extracellular domain of the B cell costimulatory ligand (a CD40 ligand), could change the specificity of the resulting CD40L-FasL-IgFc fusion protein. Indeed, the treatment with this fusion protein, designated CD40L-FasL-IgFc, did not activate T lymphocytes but resulted in a strong mitogenic activity against B cells.

The experiments described supra demonstrated that a fusion protein, which conjugates “X” (an extracellular domain of a co-stimulatory receptor ligand) with “Y” (a Fas ligand extracellular domain) and “Z” (IgFc domain) possesses de novo mitogenic activity. This formula to create the mitogen fusion protein was further exploited by testing if both X and Y portions could be replaced with extracellular domains of other costimulation receptors (FIG. 1). When the ligand of T cell OX40 costimulatory receptor, and the ligand of 4-1BB T cell costimulatory receptor were used as the “X” and “Y” respectively, the resulting fusion protein (OX40L-4-1BBL-IgFc, SEQ ID NO: 25) acquired a strong mitogen activity in human peripheral blood mono nuclear cells. When stimulated by either OX40L-IgFc (SEQ ID NO: 27) or 4-BBL-IgFc (SEQ ID NO: 29) alone, however, no significant mitogen activity was observed.

In further studies, the fusion protein which conjugates “X” (the extracellular domain of CD40L with “Y” (the extracellular domain of ICOS, a costimulatory receptor of activated T cells) was constructed and designated CD40L-ICOS-IgFc (SEQ ID NO: 33). By replacing the Fas ligand with immunoglobulin family polypeptide, ICOS, the resulting fusion protein was expected to target B cells, which express both CD40 and ICOS ligand. When injected into mice along with influenza hemaglutinin (HA) antigens, the CD40L-ICOS-IgFc gene construct (SEQ ID NO: 33) caused a significantly increased HA-specific antibody response. The reason for this was that the CD40L-ICOS-IgFc plasmid DNA functioned as a DNA adjuvant. These results demonstrated that it is possible to create various functional fusion proteins with different target cell specificity by changing the combination of the “X” and “Y” components.

In another expansion, the fusion protein comprising NGFβ as “X” and FasL as “Y” was generated. This fusion protein, designated NGFβ-FasL-IgFc (SEQ ID NO: 37), was expected to target nerve cells and B cells as in previous reports showed that NGF0 could promote B cell growth. As expected, the fusion protein caused a strong B cell antibody response in vivo when the expression plasmid was co-administrated with influenza HA antigens. This fusion protein gene construct also induced a strong HA-specific $CD8^+$ T cell response in mice co-administrated with the HA antigens.

Another fusion protein, in which interleukin 2 (IL-2) was inserted to the domain “X”, was designated IL-2-FasL-IgFc (SEQ ID NO: 41). Based on the properties of its conjugated proteins, IL-2-FasL-IgFc was expected to stimulate IL-2 receptor-positive T cells and B cell. Our data indicates that IL-2-FasL-IgFc treatment resulted in a repressive effect on cellular responses against the co-administrated influenza HA antigens in mice. Interestingly, the in vivo function of IL-2-FasL-IgFc was similar to that shown by B7-FasL-IgFc administration in that is also targeted T cells.

It has been long established that many receptors and their contra-receptors (ligands) expressed trigger bi-directional signaling. Thus receptor extracellular domains become ligands to the contra-receptors during receptor/contra-receptor-mediated cell-cell communication. Accordingly, many receptor extracellular domains would be available for “X” or “Y” in the fusion protein constructs described herein to create target cell-specific mitogens.

The provided examples of fusion proteins and their functions demonstrate the robust potential of the fusion proteins generated based on the construct of “X”-“Y”-IgFc paradigm. Moreover, IgG Fc could be replaced with other domains of immunoglobulins such as IgM Fc domain, which would result in the formation of pentamers of the fusion protein.

The beneficial characteristics of the fusion proteins in the current invention would include:

i) The fusion protein comprises the polypeptides derived from extracellular domains of co-stimulation receptors, death receptors and their ligands to activate T cells, B cells or antigen presenting cells. This will allow lymphocytes still capable of recognizing antigens by T cell antigen receptors or B cell immunoglobulin receptors during the activation by fusion protein mitogens.

ii) Following the recipe "X"-"Y"-IgFc, the target specific mitogens could be customized for any target molecule by choosing target cell-specific co-stimulatory or death receptor ligands.

iii) Following the recipe "X"-"Y"-IgFc, the desirable function could be designed as a single molecule stimulation fusion protein by choosing specific receptor ligands.

As described by example in the study of B7-2-FasL-IgFc and IL-2-FasL-IgFc, the administration of the fusion protein or expression plasmid DNA represses the in vivo immune response against co-administrated antigens. This feature of the fusion protein would be applicable to the disease therapies, in which there is a need to apply immunosuppressive treatment.

The fusion protein, B7-2-FasL-IgFc, could be used as is to cause adjuvant activity or repressant activity to the immune response in vivo against the co-administrated antigens.

The fusion protein, B7-2-FasL-IgFc, could be conjugated with antigen polypeptides by recombinant DNA techniques to create single molecule adjuvant-antigen vaccines or single molecule immunorepressant-antigen tolerance inducers.

The plasmid DNA consisting of the fusion protein, B7-2-FasL-IgFc, could be used as DNA adjuvant or DNA suppressant by in vivo administration.

These characteristics make the described the fusion protein, B7-2-FasL-IgFc, excellent immunological adjuvant or suppressant candidates, which would satisfy unmet demands in broad areas of medicine.

Some of the innovations aimed to apply the soluble death receptor ligand extracellular domain fusion proteins to target the death receptor of pathological cells, such as cancer cells or auto-reactive immune cells. In other instances, co-stimulatory receptor ligands were used to block the co-stimulatory receptor signaling. In addition, co-stimulatory receptor-specific monoclonal antibodies were often used to enhance the activation of T cells, B cells or antigen presenting cells as to cause adjuvant effects. In some cases, Fas ligand was conjugated with other functional molecules such as interleukin-2 or VEGF, in order to navigate the fusion protein to specific target cells and increase their sensitivity to cell death. In these examples, Fas ligand domains in the fusion constructs are carefully positioned to the C-terminal ends of the polypeptides to cause cell death in target cells following ligation with the endogenous Fas receptor. The current invention should be construed as unique because the manner in which Fas ligand domain is integrated does not result in cell death in $Fas^r$ cells.

The in vivo repressor function by some fusion proteins and their plasmid DNAs could be valuable for the immune-suppressive therapy against both organ transplant rejection and autoimmune diseases. For example, B7-2-FasL-IgFc is an outstanding candidate for the induction of antigen-specific immunological tolerance in vivo—a function which no known current medicine can fulfill. Other than plant lectins (i.e. Con A and PHA) or bacterial enterotoxins (i.e. SEB and SEA), only few molecules are known to be T cell mitogens. Specific potential example is superagonistic anti-CD28 antibody [Beyersdorf et al., Ann Rheum Dis. 64:91 (2005)]. Recent studies of superagonistic anti-CD28 antibody (WO/2006/050949) showed the potential of desirable effects in vivo by increasing the activity of T regulatory cells, which repressed disease symptoms in animal autoimmune disease models [Beyersdorf et al., Ann Rheum Dis. 64:91 (2005)]. The administration of superagonistic anti-CD28 antibody to humans, however, resulted in serious toxic side effects in clinical trials [Suntharalingam et al., N Engl J Med., 355: 1018 (2006)]. Thus antigen-specific T lymphocyte repressants remain in great demand. The B7-2-FasL-IgFc of the current invention could ease the shortage of the T lymphocyte mitogens usable to induce antigen-specific tolerance in vivo.

Immune adjuvant effects in vivo by fusion proteins and their plasmid DNAs of the current invention will be highly useful in the development of effective vaccines. Until now, the development of vaccine adjuvants has heavily weighed on the ligands for the Toll like receptor (TLR) family receptors. The stimulation of the TLR family receptors expressed by antigen presenting cells causes increased expression of ligands and cytokines in turn causing increased the T cell and B cell co-stimulation signaling. This co-stimulation signaling is crucial for the efficient vaccination by inducing T cell differentiation, T cell memory development, B cell differentiation and B cell antibody-affinity maturation. Therefore the TLR ligands indirectly facilitate the events essential for the efficient vaccination. The fusion proteins and their plasmid DNAs of the current invention will become very effective adjuvants by directly stimulating co-stimulation signaling in B cells and antigen presenting cells, thereby enhancing the $CD8^+$ T cell memory and B cell immunoglobulin affinity maturation to a great extent.

Exemplification of the Invention with Model Fusion Proteins

Example 1

Methods and Materials

1. General Recombinant DNA Methods

Unless otherwise indicated, for generating nucleic acids encoding the fusion proteins of the present invention and for expression of the fusion proteins, routine techniques in the field of recombinant genetics were employed. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al, eds., 1994-2009).

For proteins, sizes are given in kilodaltons (kDa) or number of amino acid residues. Proteins sizes are estimated from gel electrophoresis, protein sequencing, amino acid sequences deduced from cDNA, or from published protein sequences.

Oligonucleotides that are not commercially available can be chemically synthesized according to the solid phase phosphoramidite triester [Beaucage and Caruthers, Tetrahedron Letts. 22:1859-1862 (1981)], using an automated synthesizer [Van Devanter et al, Nucleic Acids Res. 12:6159 (1984)]. Purification of oligonucleotides is performed by either native acrylamide gel electrophoresis or by anion-exchange HPLC [Pearson and Reanier, J. Chrom. 255:137 (1983)]. The sequence of the cloned genes and synthetic oligonucleotides can be verified after cloning using the chain termination method for sequencing double-stranded templates [Wallace et al, Gene 16:21 (1981)].

2. Western Blotting

Antibodies against the extracellular domain of Fas ligand (sc-957), OX40 ligand (sc-11404), CD40 ligand (sc-978)

and horse raddish peroxidase (HRP)-conjugated human IgG (sc-2923) were purchased from Santa Cruz Biotechnology. The ligand-specific antibodies were used for Western blotting at a final concentration of 1.0 µg/ml. The secondary antibodies used were goat anti-rabbit IgG horse HRP-conjugated antibody (sc-2054, Santa Cruz Biotechnology). Both secondary antibodies were used at a final concentration of 0.4 µg/ml. Bands were visualized using chemiluminescence (ECL reagents from Amersham).

3. Proliferation and ELISA Assays

Human lymphocytes were stimulated for 3 days in 96 U-bottom well plates with various concentrations of recombinant fusion proteins. In some experiments, a NF-κB inhibitor (SN50, 18 µM, Calbiochem, San Diego, Calif., USA) and a MEK1/2 inhibitor (PD98059, 1 µg/ml, Calbiochem) were added to the cell culture media. Cell proliferation was assessed by thymidine uptake assays. Cultured cells were pulsed with 1 µCi/well of [$^3$H]thymidine (ICN, Costa Mesa, Calif., USA) for 18 hours and then harvested onto glass fiber filters. [$^3$H]thymidine incorporation was measured by standard liquid scintillation counting techniques. In some experiments, HA antigen-specific cell proliferation response was assayed by the MTT assay [van de Loosdrecht et al., J. Immunol. Methods, 174:311(1994)], which is a direct measure of cell viability.

The relative concentrations of TNP-specific human IgG and IgM in supernatants from 4 day cultures were determined by ELISA assays. TNP$_{22}$-BSA (1 µg/ml) was used to coat assay plates, and alkaline phosphatase-conjugated anti-human IgG (Fab-specific) (Sigma) or anti-human IgM (µ-chain-specific) (Sigma) were used as the detection reagents. The concentration of IL-2 in fusion protein-stimulated culture supernatants was measured by human-IL-2-specific ELISA kit (Roche, Laval, QC, Canada). The lower limit of detection was 30 pg/ml in IL-2 assay.

4. Assay for PRDI-BF1, T-Bet and GATA3 RNAs Concentration

Using specific primers, PRDI-BF1 RNA was amplified by RT-PCR (20 cycles) from cytoplasmic RNA derived from PBL cells stimulated for three days with fusion proteins (0.1 µM). T-bet and GATA3 RNAs were amplified by RT-PCR (25 cycles) from cytoplasmic RNA derived from CD4$^+$ T cells stimulated for five days with fusion proteins (0.1 µM). Each sample was subjected to electrophoresis on agarose gels and stained with ethidium bromide (EtBr) to detect amplified fragments: 594 bp for PRDI-BF1, 206 bp for T-bet and 131 bp for GATA3.

5. Vaccination of Mice

Balb/c mice (4-6 wks of age) were primed intra peritoneal (i.p.) route with 0.1 ml of protein antigens, OVA albumin (Sigma) or GSK VAXIGRIP (GlaxoSmithKline, Mississauga, Ontario, Canada), in the presence and absence of fusion protein or cDNA harboring plasmid. Serum samples were collected from lateral tail vain at time points indicated in the Figures. To determine the antigen-specific IgG titer in the serum of the individual mouse, ELISA were performed using 0.1 µg/ml antigen-coated assay plates (Maxisorp, Nunc 44-2404-21) following the standard procedure.

Example 2 [Yoshida et al., Vaccine 28: 3688 (2010)]

Construction of X:TNF-Family Extracellular Domain Polypeptide and Y: TNF-Family Extracellular Domain Polypeptide Fusion Protein.

Construction of CD40L-FasL-IgFc Plasmid DNA

To prepare the CD40$^+$ B cell-specific CD40L-FasL-IgFc fusion protein mitogen gene construct, cDNAs encoding the extracellular domain of human CD40 ligand, extracellular domain of human Fas ligand, signaling sequence of oncostain M and CH2-CH3 domain of human IgG1 was generated by reverse transcriptase polymerase chain reaction (RT-PCR).

The extracellular domain of human CD40L [NM_000074, *Homo sapiens* CD40 ligand (CD40LG)] (amino acid residues 46-261) was amplified from human thymic RNA (Clontech B-D, Palo Alto, Calif., USA) using the following primers: forward 5'-CTTCATAGAAGGTTGGA-CAAGATA-3' (SEQ ID NO: 43) and reverse 5'-GAGTTT-GAGTAAGCC AAAGGACGT-3' (SEQ ID NO: 44). The registered human CD40L message sequence is shown in FIG. 2 (SEQ ID NO: 1).

The signal peptide of Oncostatin M [NM_020530, *Homo sapiens* oncostatin M (OSM)] (amino acid residues 1-25) was amplified using the following primers: forward 5'-ATGGGGGTACTGCTCACACAGAGG-3' (SEQ ID NO: 45) and reverse 5'-CATGCTCGCCATGCTTG GAAACAG-3' (SEQ ID NO: 46). The registered human Oncostatin M message sequence is shown in FIG. 3 (SEQ ID NO: 3). These PCR products were subsequently utilized in a second round of PCR. Primers encoding the 3' sequence of the Oncostatin M fragment and the 5' portion of human CD40L were designed to overlap; annealing of the PCR products yielded a hybrid template. The template encoding the chimeric construct was selectively amplified using external primers specific for the 5' region of Oncostatin M and the 3' region of human CD40L. Each primer containing appropriate restriction sites (Nhe I/Xho I) for subcloning into the mammalian expression vector PCIneo (Promega, Madison, Wis.). The resulting PCR fragment was ligated into the PCIneo vector (OncoM-hCD40L/PCIneo), and transfected into *E. coli* competent cells, which were selected on an ampicillin-containing agar plate.

The hinge region, consisting of CH2 and CH3 domains (amino acid residues 219-447) of human IgG1, was amplified by RT-PCR from total human peripheral lymphocytes RNA, using the following primers: forward 5'-AAA CTCGAGAAATCT TGTGACAAAACTCACACATGC-CCACCGTG-3' (SEQ ID NO: 47) and reverse 5'-CG TCTAGATCATTTACCCGGAGACAGGG AGAG-3' (SEQ ID NO: 48), introducing the Xho I and Xba I sites, respectively (sites are underlined). The registered human IgG1 message sequence is shown in FIG. 4 (SEQ ID NO: 5). This PCR product was cloned into OncoM-hCD40L/PCIneo after digestion and purification (the resultant product coded as OncoM-CD40L-IgFc/PCIneo). The cDNA sequence of OncoM-CD40L-IgFc is shown in FIG. 5 (SEQ ID NO: 7). This fusion protein was a ~50 kDa molecular mass in reduced SDS-PAGE and was designated as CD40L-IgFc in the text.

Chimeric Ig molecules expressing the extracellular portion of the human FasL gene and the human IgG1 constant domains were created as follows: the extracellular domain of human FasL (amino acid residues 108-281) was amplified by RT-PCR from total RNA of human thymus, using the following primers: forward 5'-CCG CTCGAGCAGCTCTTCC ACCTACAG-3' (SEQ ID NO: 49) and reverse 5'-GGC CTCGAGCTTATATAAGCCGAAAAACGTC-3' (SEQ ID NO: 50), including the Xho I sites, respectively (sites are underlined). The registered human FasL message sequence is shown in FIG. 6 (SEQ ID NO: 9). External primers encoding the 5' portion and the 3' portion of Oncostatin M, FasL and IgG1 were used to amplify the OncoM-hCD40L-hFasL-IgFc/PCIneo. Each primer contained appropriate restriction sites for subcloning into the PCIneo vector, yielding OncoM-hFasL-IgFc/PCIneo. This fusion protein was a ~40 kDa molecular mass in reduced SDS-PAGE and was designated as FasL-IgFc in text. The cDNA sequence of OncoM-FasL-IgFc is shown in FIG. 7 (SEQ ID NO:

The extracellular domain of human FasL (amino acid residues 108-281) was cloned in frame at the 3' end of the hCD40L in the OncoM-hCD40L-IgFc/PCIneo (the resultant product coded as CD40L-FasL-IgFc/PCIneo). This fusion protein was detected as a ~70 kDa molecular mass in reduced SDS-PAGE and was designated as CD40L-FasL-IgFc in the text. All constructs were confirmed by DNA sequencing. The cDNA sequence of OncoM-CD40L-FasL-IgFc is shown in FIG. 8 (SEQ ID NO: 13). Plasmid DNA was purified by cesium chloride gradient ultracentrifugation.

Expression of CD40L-FasL-IgFc in Mammalian Cell Lines and Protein Purification from the Cell Culture Supernatants of Transfected Cells.

The pCI-neo harboring CD40L-FasL-IgFc cDNA construct, CD40L-FasL-IgFc/PCIneo was transfected in Chinese hamster ovarian fibroblastic cell (CHO cell) by electroporation technique. CHO cells (ATCC, CRL-9606) were maintained in Dulbecco's modified MEM (Invitrogen) supplemented with 1× Penicillin and Streptomycin (100× stock solution, Invitrogen), 1×L-glutamine (100× stock solution, Invitrogen) and 5% fetal bovine serum (FBS, Invitrogen). CHO cells were maintained in Culture flasks (Falcon 175 $cm^2$) in 5% CO2 at 37° C. Cells were passaged weekly by 1/10 into a new flask. To split CHO cells to a new flask, medium was discarded from flask and replaced 3 ml 0.25% trypsin-EDTA medium (Invitrogen). After a 5 minute incubation at 37° C., cells were agitated by 5 ml pipette (Becton-Dickinson, Falcon) and harvested as a single cell suspension. Cells were pelleted by centrifuge (Sorvall RT 6000 Series tabletop centrifuge, 900 rpm for 6 minutes), resuspended to 1ml of DMEM, and then 0.1 ml of cell suspension was seeded to new flask with 20 ml of culture medium.

To transfect CD40L-FasL-IgFc/PCIneo expression vector to CHO cells, CHO cells were harvested by trypsin on day 4 after the split, washed once, then resuspended at a density of $10^7$ cells/ml in Na-phosphate buffered 0.9% NaCl solution. Expression plasmid (5 μg) was added to 0.5 ml of cell suspension in electroporation cuvette (Bio-Rad, 165-2081). The cuvette was chilled on ice 5 minutes prior to electroporation with a Gene-Pulser (Bio-Rad) at 250V, 975 μF. The cuvette was chilled again on ice for 30 minutes. The cells were washed once, resuspended with 10 mL DMEM tissue culture medium containing 5% FBS and then distributed to a 96 well flat bottom tissue culture plate at 100 μl/well. Twenty-four hours later, 100 μl of tissue culture medium containing 1 mg/ml of G418-sulfate (Geneticin, Invitrogen) was added to each well to select G418 resistant (positively transfected) cells. In 10 days, G418-resistant cells formed colonies detectable by microscopy. Supernatants were screened for the presence of the fusion protein by human immunoglobulin G Fc-specific ELISA, which detects the secreted fusion proteins. Cells expressing the fusion proteins were expanded in culture and harvested spent medium for protein purification. To obtain cell culture spent medium of the CD40L-FasL-IgFc CHO transfectant cell, cells were maintained in flasks (Falcon 300 $cm^2$) with 300 ml of DMEM supplemented with 5% FBS.

Fusion proteins secreted in the spent medium of the CHO transfected cells were purified by Protein G column (Hi-Trap™ Protein G HP Columns GE Healthcare). Protein G columns (1 ml bed volume) were loaded with 500 ml of spent medium at flow rate 0.5 ml/min using chromatography pump (P500, Pharmacia) at 4° C. The column was washed with 20 ml of phosphate buffered saline (PBS) then, CD40L-FasL-IgFc was eluted with 2 ml of pH 2.7, 0.2 M Glycine-HCl. The eluate was neutralized with 0.2 ml of pH 9.0, 1.0 M potassium phosphate buffer, then dialyzed against 0.01M Sodium phosphate buffer (pH 7.2) for two days before filtered with 0.22 μm Millipore syringe filter (EW-29950-30) to make sterile fusion protein stock suitable for downstream cellular and biochemical analysis. The protein concentrations were measured using Pierce BCA protein assay kit (Thermo Scientific, 23225).

Purified CD40L-FasL-IgFc was First Analysed by the Western Blotting Analysis.

Two μg of protein was subjected to SDS-PAGE under reduced conditions and probed by human IgG specific Western blotting. Twelve well precast gels, 10% Nu-PAGE (Invitrogen) were used with a MOPS-based running buffer. Thirteen μl of protein solution, 5 μl of loading buffer and 2 μl of 0.5 M DTT were mixed in 1.5 ml micro centrifuge tube, heated at 75° C. for 10 minutes before loading to each well of the Nu-PAGE Gel. The reduced protein samples were resolved for 50 minutes at 200 V in 1×MOPS running buffer (Invitrogen). Separated proteins were then transferred to PVDF membranes using transfer buffer containing 10% Methanol (Sigma). The PVDF membranes were blocked with 3% fat free milk in 0.1% Tween 20 (Sigma)-PBS for an hour at room temperature, then incubated with goat anti-human IgG HRP or rabbit anti-human FasL over night. The membrane was washed with 0.1% Tween 20 PBS and developed using chemiluminescence substrate [ECL detection buffer (Pierce)] and exposed to X-ray film (Kodak).

A dominant band at ~75 kDa was observed and determined to be glycosylated CD40L-FasL-IgFc (FIG. 9A). The predicted molecular weight of the CD40L-FasL-IgFc is 70.6 kDa without glycosylation. The same protein sample was also subjected to SDS-PAGE under reduced conditions and probed by human FasL specific Western blotting. In paralleled experiment to FIG. 9A, the PVDF membrane was probed with rabbit anti-human FasL antibody overnight, washed with 0.1% Tween 20-PBS and then probed with anti-Rabbit IgG-HRP for 1 hour at room temperature. The results obtained from chemiluminescence and exposure of the membrane to X-ray film showed a similar picture of the protein bands as observed in the human IgG-specific Western blotting (FIG. 9B). The data indicate that the 70 kDa protein is most likely the protein band representing the monomer of the fusion protein CD40L-FasL-IgFc.

FIG. 9. Western Blotting Analysis of CD40L-FasL-IgFc.

CD40L-FasL-IgFc was subjected to SDS-PAGE under reduced conditions, probed by human IgG specific (A) or human FasL specific (B) western blotting. The dominant band at ~75 kDa and corresponds to glycosylated CD40L-FasL-IgFc. The control is the fraction derived from the protein G column and contains non-specifically proteins (confirmed by Coomassie staining).

Study of Fas Binding by CD40L-FasL-IgFc.

Previous studies have not tested Fas-containing fusion protein constructs in which Fas ligand is located in the middle of two different polypeptide domains like CD40L-FasL-IgFc. Thus, it is important to test if CD40L-FasL-IgFc can bind to the cell surface Fas antigen. We tested the binding of CD40L-FasL-IgFc to the CD40 negative/Fas positive mouse T cell line EL4 (ATCC# TIB39). EL4 cells ($5\times10^6$) were incubated with 2 μg of CD40L-FasL-IgFc in 0.5 ml of DMEM on ice for 1 hour. Cells were washed with PBS and lysed by 0.5 ml of ice cold 1% NP-40 lysis buffer (50 mM Tris-buffer pH7.4, 250 mM NaCl, 5 mM EDTA, 0.1% NP-40, plus protease inhibitors). After removing the insoluble cell debris by micro centrifugation (11500 rpm for 1 hour at 4° C.), CD40L-FasL-IgFc was precipitated by Protein A/G agarose beads (Santa Cruz # sc-2003) overnight. The beads were washed with PBS, resuspended with 40 μl loading buffer containing DTT, heated for 10 minutes at 75° C. and then resolved by 10% Nu-PAGE with MOPS running buffer. PVDF membrane-transferred protein blots were probed with a mouse Fas-specific rat monoclonal antibody (Jo2 Becton Dickinson #554254), washed and subsequently probed with anti-mouse IgG-HRP detection antibody (Promega).

FIG. 10. Study of Fas Binding by CD40L-FasL-IgFc.

For a positive control (in the left-end lane), Fas molecule of EL4 cell lysate was immunoprecipitated with mouse Fas-specific rat monoclonal antibody (Jo2). For another control (in the middle lane) a fusion protein, CD40L-IgFc, was used instead of CD40L-FasL-IgFc for the incubation with EL4 before cell lysate preparation.

Analysis of the Function of CD40L-FasL-IgFc In Vitro.

CD40L-FasL-IgFc Fusion Protein Activates B Cells and Macrophages.

We found that following treatment with our fusion protein, the target human B lymphoma cells (Raji ATCC, CCL 86 and Daudi ATCC, CCL213) did not undergo cell death, while an antibody against human Fas (14G5) effectively killed B lymphomas in our study. In light of this result, we wished to examine the precise function associated with this fusion protein. We cultured human PBMCs and mouse spleen cells in the presence of CD40L-FasL-IgFc. Whole blood, obtained from a healthy donor, was twice diluted with Na-PBS (pH 7.2) and peripheral blood mononuclear cells (PBMCs) were separated by Ficoll density gradients (Ficoll-Paque Plus, Amarsham Biotech) by centrifugation (Sorvall RT 6000, 1500 rpm for 15 minutes at room temperature). The peripheral blood mononuclear cells were collected from the interphase between the PBS top layer and Ficoll plus bottom layer, washed with PBS and subjected to cell proliferation assays. After measuring the concentration of the cells using a hemocytometer, the cells were diluted in proliferation assay medium (RPMI1640, $5\times10^{-5}$ M 2-mercaptoethanol, 1×L-glutamine, supplemented with 10% FBS). Human lymphocytes were stimulated for 3 days in 96 U bottom plates with various concentrations of recombinant fusion proteins. A $^3$H-Thymidine label was used to measure the uptake by the proliferating cells. Surprisingly, the cultures exhibited significant cell activation when viewed under a microscope, even at low concentration of fusion protein (0.1-0.01 μg/ml) (FIG. 11).

FIG. 11. Proliferation of Human PBMC Induced with CD40L-FasL-IgFc.

PBMCs were stimulated with various fusion proteins for three days prior to proliferation assay. Data indicate the means and standard deviations of triplicate samples. The data represent the five experiments with similar results. ■: CD40L-IgFc, ●: FasL-IgFc, □: CD40L-IgFc+FasL-IgFc, ◆: IgFc, ○: CD40L-FasL-IgFc.

In these experiments, the control protein used (FasL-IgFc) did not induce detectable cytotoxic activity in either the Raji human B cell line or the Fas apoptosis-sensitive Jurkat human T cell line. Culturing with FasL-IgFc also resulted in a small but increase in human PBL primary cultured cells. It was evident that our design of FasL fusion protein failed to create Fas apoptosis-inducing ligands. Another control protein, the CD40L-IgFc fusion protein, induced a mitogenic response. When the CD40L-IgFc and FasL-IgFc proteins were added as a mixture to PBMC cultures an additive effect of proliferation was observed. Overall, the CD40L-FasL-IgFc fusion protein greatly exceeded the mitogenic response induced by the co-stimulation with CD40L-IgFc and FasL-IgFc, and indeed the cell activation by CD40L-FasL-IgFc was specific for the non-T cell subsets, which contain CD40$^+$ cells (FIG. 12). Additionally, in the study of the phenotype of CD40L-FasL-IgFc activated cells, we observed the activation in B cell (CD19$^+$), and monocyte (CD14$^+$) fractions increased by 30% and 15%, respectively in cultures stimulated for 5 days with CD40L-FasL-IgFc. The results suggest a novel activation mechanism of B-cell/monocyte induced by the co-clustering Fas and CD40 by CD40L-FasL-IgFc.

FIG. 12. Non-T Cell-Specific Stimulation by CD40L-FasL-IgFc.

PBL-T cells and PBL-non-T cells were stimulated with CD40L-FasL-IgFc (0.1 μM) for three days prior to proliferation assay. Data indicate the means and standard deviations of triplicate samples. The data represent the three experiments with similar results. C: control response, S: response against CD40L-FasL-IgFc.

This effect was not due to inadvertent contamination with endotoxin, as adsorption with Polymixin B did not attenuate the mitogenic activity of this fusion protein (FIG. 13).

FIG. 13. Effects of Polymixin B Pre-Absorption on the Stimulation by CD40L-FasL-IgFc.

CD40L-FasL-IgFc was pre-absorbed with Polymixin B-coated beads (Sigma). PBMCs were stimulated with this Polymixin-B pre-absorbed or unabsorbed CD40L-FasL-IgFc for three days prior to proliferation assays. Filled columns show responses against absorbed CD40L-FasL-IgFc. Open columns show responses against CD40L-FasL-IgFc prior to absorption. Data indicate the means and standard deviations of triplicate samples.

The CD40L-FasL Fusion Protein Activates the NF-κB Pathway and MEK1/2 ERK Pathway.

Besides activating Caspase-dependent apoptotic pathways, Fas stimulates the NF-κB and ERK pathways. CD40 is also linked to stimulation of similar signaling pathways. Therefore, we hypothesized that the synergistic effect of Fas/CD40 activation is due to a convergence of signals at the level of the NF-κB and MEK1/2 ERK pathways. To test this, we assessed the effects of inhibitors specific for NF-κB or MEK1/2 on CD40L-FasL-IgFc-induced stimulation of PBL cells. We found that both inhibitors partially suppressed CD40L-FasL-IgFc-induced cell proliferation. Therefore the results pointed to a mechanism of activation by our fusion protein that involves both NF-κB and MEK1/2 activation (FIG. 14).

FIG. 14. Reduction of CD40L-FasL-IgFc-Induced Activation by Signaling Inhibitors.

PBMCs were stimulated with CD40L-FasL-IgFc for three days in the presence of NF-κB inhibitor (SN50) and MEK1/2 inhibitor (PD98059). Data indicate the means and standard deviations of triplicate samples. The data represent the three experiments with similar results.

CD40L-FasL Fusion Protein Induces B-Cell Differentiation In Vitro.

We next assessed the effect on IgG secretion by fusion protein-induced co-clustering of CD40 and Fas in B cells. PBL-B cells were incubated with CD40L-FasL-IgFc for four days and the supernatants were assayed for IgG- and IgM-specific trinitrophenyl (TNP) hapten [Galanaud et al., Cell. Immunol., 106:234 (1987)]. We found anti-TNP IgG was significantly increased in CD40L-FasL-IgFc-stimulated cultures, whereas cultures with either CD40L-IgFc or FasL-IgFc alone did not show significant changes in IgG secretion (FIG. 15).

FIG. 15. Induction of IgG Secretion in PBL Cells Stimulated with CD40L-FasL-IgFc.

PBMCs were stimulated with fusion proteins for four days. The relative concentrations of TNP-specific human IgG and IgM in supernatants were determined by ELISA assays. Data indicate the means and standard deviations of triplicate samples. The data represent the three experiments with similar results.

Moreover, we found an increased expression of PRDI-BF1 RNA, which indicates terminal B cell differentiation [Mock et al., Genomics, 37:24 (1996)] in cultures stimulated with CD40L-FasL-IgFc (FIG. 16). Taken together, the data suggests that co-clustering of CD40 and Fas by CD40L-FasL-IgFc induces B-cell differentiation in vitro.

FIG. 16. The Expression of PRDI-BF1 in Response to CD40L-FasL-IgFc Stimulation.

PBMCs were stimulated with fusion proteins (0.1 µM) for three days. The total RNA was assayed for the message of PRDI-BF1 by RT-PCR. Each sample was electrophoresed on agarose gels and stained with ethidium bromide (EtBr) to detect amplified fragments. The data represent the results from three experiments with similar results.

Study for the Function of CD40L-FasL-IgFc In Vivo.

The CD40L-FasL Fusion Protein Boosts IgG Response In Vivo Against Antigens Administrated Simultaneously.

Stimulation of CD40$^+$ cells by the CD40L-FasL-IgFc could allow this molecule to function as an adjuvant in vivo, by enhancing the activity of B cells and APCs. Many ligands specific for TLR family receptors act as adjuvants in experimental animals. These adjuvants augment the antibody and T cell responses against the co-injected vaccines such as type A influenza virus antigens. To determine if our fusion protein can behave as an adjuvant, we tested CD40L-FasL-IgFc in mice to see if it increases the immune response against co-injected protein antigens.

Anti-OVA Albumin (OVA) Immune Response.

Following immunization with a small dose of OVA (0.2 µs) by itself, a significant primary antibody production was not observed (FIG. 17). In contrast, the immunizations with a mixture of CD40L-FasL-IgFc and the OVA, resulted in the mice producing high titers of OVA-specific IgG antibodies, and this response was increased markedly following a boost by 0.2 µg OVA.

FIG. 17. Adjuvant Activity of CD40L-FasL-IgFc in Mice Against OVA.

Balb/c mice were immunized i.p. with 0.2 µg of OVA and 5 µg of CD40L-FasL-IgFc (indicated as Primed). On Day 14, blood samples were harvested and subsequently mice were injected with 0.2 µg of OVA (indicated as Boosted). Sera from day 14 and day 21 were analysed by ELISA for the IgG activity against OVA. The titer was calculated based on the dilutions and ELISA reader readings that first showed larger than twice of pre-immune sera readings at the same dilutions. Squares indicate mice immunized with OVA alone. Circles indicate mice immunized with both OVA and CD40L-FasL-IgFc. Numbers in squares and circles indicate individual mouse. The anti-HA activity of pre-immune serum from each mouse was equally low at less than 50 in titer.

Anti-Influenza Vaccine Response.

In the study similar to the OVA immunizations, in vivo adjuvant activity of CD40L-FasL-IgFc was investigated in mice using a specific human influenza vaccine as an antigen (FIG. 18). The vaccine, GSK VAXIGRIP, contains HA antigens of H1N1, H3N2 but the preparation is adjuvant-free. The vaccine dose (3 µg/mouse) used to prime was sufficient to induce a primary response detectable by vaccine-specific anti-IgG ELISA. The addition of CD40L-FasL-IgFc significantly increased the antibody response detected by ELISAs. Secondary responses following boosts were also far greater in groups primed with CD40L-FasL-IgFc than in the mice primed with vaccine only. Therefore this study demonstrated that the influenza HA antigen-specific immune response was augmented by CD40L-FasL-IgFc.

FIG. 18. Adjuvant Activity of CD40L-FasL-IgFc in Mice Against Influenza Hemaglutinin.

Balb/c mice were immunized i.p. with 3 µg of HA and 5 µg of CD40L-FasL-IgFc (indicated as Primed). On Day 14, blood samples were harvested from tail vain and subsequently mice were injected with 3 µg of HA (indicated as Boosted). Sera from day 14 and day 24 (for the study of secondary response) were analysed by ELISA for the IgG activity against HA. The titer was calculated based on the dilutions and ELISA reader readings that first showed larger than twice of pre-immune sera readings at the same dilutions. Squares indicate mice immunized with HA alone. Circles indicate mice immunized with HA and CD40L-FasL-IgFc. Numbers in squares and circles indicate individual mouse. The anti-HA activity of pre-immune serum from each mouse was equally low at less than 50 in titer.

The Plasmid DNA of CD40L-FasL-IgFc increases Anti-Influenza HA Immune Response In Vivo.

Recently, attempts have been made to elicit pathogen-specific antibody and T cell responses using Plasmid DNAs. These Plasmid DNAs encode pathogen antigens that are to be used as vaccine reagents. In carrying out these experiments, immunizations were often performed in combination with adjuvants such as Alum or TLR ligands (i.e. CpG) [Daubenberger Curr Opin Mol Ther. 9:45(2007)]. Since we have demonstrated that our CD40L-FasL-IgFc possesses potent adjuvant effects against co-administrated protein antigens, we wished to test if the plasmid encoding the CD40L-FasL-IgFc would function as a DNA-adjuvant. Indeed, we observed an increased influenza vaccine-specific IgG response following the administration of the pCI-neo-CD40L-FasL-IgFc plasmid (CeCl2-purified) in conjunction with influenza vaccine (FIG. 19).

FIG. 19. Adjuvant Activity of Plasmid DNA of CD40L-FasL-IgFc in Mice Against Influenza Hemaglutinin.

Balb/c mice were immunized i.p. with 3 µg of HA and 3 µg of CD40L-FasL-IgFc/PCIneo (indicated as Primed). On Day 14, blood samples were harvested from tail vain and subsequently mice were injected with 3 µg of HA (indicated as Boosted). Sera from day 14 and day 24 (for the study of secondary response) were analysed by ELISA for the IgG activity against HA. The titer was calculated as descried in FIG. 18. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Adjuvant Activity of CD40L-FasL-IgFc on T Cell Responses Against Influenza Hemaglutinin.

Both the helper T cell response and the cytotoxic CD8$^+$ T cell response are vital for the vaccine antigen-specific immune responses. Therefore this study was aimed at investigating the regulation of the HA-specific T cell response following CD40L-FasL-IgFc injection. Balb/c mice were immunized i.p. with 3 µg of HA and 3 µg of CD40L-FasL-IgFc. On Day 14, mice were injected with 3 µg of HA. Spleen cells harvested on day 60 (for the study of memory response) were analysed by proliferation assays against HA. Under sterile conditions, harvested spleens were minced in between a pair of slide glasses and red blood cells were removed by Gey's solution-treatment for 1 minute on ice. The prepared spleen cells ($10^6$/ml) were stimulated in 96 well U bottom plates ($10^5$/well) with 0.1 µg/ml HA for 48 hours in RPMI1640, 1×L-Glutamine (Invitrogen), $5×10^{-5}$ M 2-mercaptoethanol (Sigma) and 10% FBS (Invitrogen). The results showed the percent viabilities of cells measured by MTT assay performed by standard procedures. To measure the activity of $CD8^+$ cytotoxic T cell response, monoclonal anti-L3T4 (anti-CD4) antibody (GK1.5, Pharmingen, 553726, 1 µg/ml) and monoclonal anti-class II MHC antibody (anti-I-E 14-4-4, Pharmingen, 558734, 1 µg/ml) were added in the culture medium. The presence of these antibodies blocks the CD4 T cell response as reported [Lim et al., Infect Immun., 63:4818 (1995)].

Interestingly, the addition of CD40L-FasL-IgFc lowered the HA-specific response by total T cells compared with HA only immunized spleen cells. In contrast to the response by total T cells, the $CD8^+$ T cell response was only detectable in spleen cells immunized with CD40L-FasL-IgFc and not in mouse cells immunized with HA alone. The data showed strong adjuvant activity by CD40L-FasL-IgFc to antigen-specific $CD8^+$ T cell responses in vivo.

FIG. 20. Adjuvant Activity of CD40L-FasL-IgFc in Mice Against Influenza Hemaglutinin-Specific T Cell Response.

A indicates total T cell response; B indicates $CD8^+$ T cell response.

Percent viability is calculated based on the comparison with the non-stimulated cells (100%). The data shows the average and standard deviation derived from the triplicate sample. Not immunized: normal mice, Immunized: mice were immunized with HA only.

Example 3

Construction of a Fusion Protein Comprised of X: Immunoglobulin-Family Receptor Ligand Extracellular Domain Polypeptide, Y: TNF-Family Extracellular Domain Polypeptide Fusion Protein.

The B7-1(CD80)/B7-2(CD86)-CD28 pathway is the best-characterized T-cell co-stimulatory pathway. B7-1 and B7-2 are cell surface immunoglobulin family proteins expressed on macrophages and B cells. The CD28 signaling induced by B7-1 and B7-2 does not induce cell proliferation or cytokine secretion. It does, however, promote greatly enhanced activation events when T cells are simultaneously stimulated with T cell receptors. To determine if Fas signaling incorporate with CD28 signaling to elicit T cell proliferation, we constructed a B7-2-FasL-IgFc fusion protein. The result from the study of B7-2-FasL-IgFc was expected to address whether the conjugation of an immunoglobulin family co-stimulatory receptor ligand with a TNFR family death receptor ligand in the fusion protein mitogen formula ("X"-"Y"-IgFc) results in a novel mitogen.

Construction of B7-2-FasL-IgFc Plasmid DNA.

Registered message and amino acid sequence for human B7-2 is shown in FIG. 21 (SEQ ID NO: 15).

The extracellular domain of human B7-2 (amino acid residues: 24-247) was amplified by RT-PCR, from total RNA derived from Raji cells, using the following primers: forward 5'-GGA CTCGAGGCTCCTCTGAAGATTCAAGC-3' (SEQ ID NO: 51) and reverse 5'-AATCTCGAGA GGAATGTG-GTCTGGGGGAG-3' (SEQ ID NO: 52). The primers introduced Xho I sites useful for DNA subcloning (underlined). The PCR product was cloned in frame at the 3' end of the hFasL in the OncoM-hFasL-IgGFc/PCIneo (the resultant product coded as OncoM-hB7-2-hFasL-IgGFc/PCIneo). The cDNA sequence and predicted amino acid sequence for this fusion construct is shown in FIG. 22 (SEQ ID NO: 17).

Chimeric Ig molecules expressing the extracellular protein of the human B7-2 gene and human IgG1 constant domains were created as follows: external primers encoding the 5' portion and the 3' portion of Oncostatin M, B7-2 and IgG1 were used to amplify the OncoM-hB7-2-IgGFc/PCIneo. Each primer contained appropriate restriction sites for subcloning into the PCIneo vector, yielding OncoM-B7-2-IgGFc/PCIneo (cDNA sequence and predicted amino acid sequence for this fusion construct is shown in FIG. 23, (SEQ ID NO: 19). This fusion protein, designated as B7-2-IgFc, was a ~40 kDa molecular mass when subjected to SDS-PAGE under reduced conditions.

The transfection of B7-2-FasL-IgFc/PCIneo into CHO cell and the establishment of the stable transfectant cells were performed as described in the Example 2.

The Western blotting analysis for the Protein G column-purified B7-2-FasL-IgFc fusion protein was performed as described in the Example 2.

This fusion protein designated as B7-2-FasL-IgFc was detected as a ~75 kDa molecular mass when subjected to SDS-PAGE under reduced conditions (FIG. 24).

The data indicated that the 75 kDa protein corresponds to the protein band representing the monomer of the fusion protein B7-2-FasL-IgFc.

FIG. 24. Western Blotting Analysis of B7-2-FasL-IgFc.

B7-2-FasL-IgFc was subjected to SDS-PAGE under reduced conditions, probed by human IgG specific (A) or human FasL specific (B) western blotting. The dominant band (~75 kDa) corresponds to glycosylated B7-2-FasL-IgFc. The predicted molecular weight of the B7-2-FasL-IgFc is 72.5 kDa without glycosylation. The control is the fraction derived from the protein G column and contains non-specific proteins (confirmed by Coomassie staining).

Study of Fas Binding by B7-2-FasL-IgFc.

To test if B7-2-FasL-IgFc binds to the cell surface Fas antigen, the binding of B7-2-FasL-IgFc to Fas positive mouse T cell line EL4 was tested using a similar approach described in Example 2.

FIG. 25. Study of Fas Binding by B7-2-FasL-IgFc.

For positive control (in the left end lane), Fas molecule of EL4 cell lysate was immunoprecipitated. In another control (in the middle lane) a fusion protein, CD40L-IgFc was used instead of B7-2-FasL-IgFc for the incubation with EL4 prior to cell lysate preparation.

Study for the Function of B7-2-FasL-IgFc In Vitro.

B7-2-FasL-IgFc Fusion Protein Activated T Cells.

PBMCs derived from normal healthy human adults were separated from whole blood using Ficoll-Paque Plus. Peripheral blood lymphocyte (PBL)-T cells, PBL-B cells, $CD4^+$ T cells, $CD8^+$ T cells were purified by negative selection using RosetteSep (StemCell Tec. Vancouver, BC, Canada), while non-T cells were purified by negative selection using pan-T magnet beads (M-450, Dynal, Lake Success, N Y, USA). The purity of human PBL-T cells was greater than 97% as determined by CD3 staining and flow cytometry. The residual T cell in non-T cell subsets was observed to be less than 5%. CD4+ and CD8+ T cells were purified to greater than 90% positive for CD4 and CD8, respectively as determined by flow cytometry studies.

Strikingly, when tested in primarily cells, the B7-2-FasL-IgFc fusion protein induced a strong T cell-specific mitogenic response (FIG. 26).

FIG. 26. Activation of CD4+ and CD8+ T Cells by B7-1-FasL-IgFc.

Total T cells, CD4+ T cells and CD8+ T cells were stimulated with either B7-2-FasL-IgFc or control fusion proteins. CD4+ T cells and CD8+ T cells were stimulated with various fusion proteins. After 72 hours in culture, cell proliferation was assessed. Data indicates the average and standard deviation of quadruplicate samples. The data represent the three experiments with similar results.

●: B7-2-FasL-IgFc, ▼: phytohemagglutinin, ▲: B7-2-IgFc, v: FasL-IgFc, ◇: OKT3 and Δ: B7-2-IgFc+FasL-IgFc.

In top panel ■ indicates the response by B cells against B7-2-FasL-IgFc (5 µg/ml).

The magnitude of proliferation induced by B7-2-FasL-IgFc was comparable to phytohemagglutinin-induced T cell mitogenesis, while neither B7-2-IgFc nor FasL-IgFc showed observable mitogenic effects in T cells. The proliferation of both CD4+ and CD8+ T cells increased by stimulation with B7-2-FasL-IgFc, but CD8+ T cells required greater than a 20 fold dose to achieve similar levels of proliferation to CD4+ T cells. The stimulation of T cells resulted in the secretion of IL-2 (FIG. 27).

FIG. 27. B7-2-FasL-IgFc Stimulates IL-2 Production of T Cells.

T cells were stimulated by B7-2-FasL-IgFc (1 µg/ml) or phytohemagglutinin (5 µg/ml) for 3 days. The concentration of IL-2 in culture supernatants was measured by ELISA assays. The lower limit of detection was 30 pg/ml in IL-2 assay. The data represent the three experiments with similar results.

Moreover, five days of culture with B7-2-FasL-IgFc showed a significant increase in the T-bet transcription factor RNA, but not that of GATA3 in cells (FIG. 28).

FIG. 28. Induction of T-Bet by B7-2-FasL-IgFc Activation.

CD4+ T cells were stimulated by B7-2-FasL-IgFc (0.1 µM) for 5 days before total RNA was harvested and tested for increased mRNA expression of T-bet (for Th1 differentiation) and GATA-3 (for Th2 differentiation) by RT-PCR. Each sample was electrophoresed on agarose gels and stained with ethidium bromide (EtBr) to detect amplified fragments: 206 bp for T-bet and 131 bp for GATA3. The data represent the three experiments with similar results.

These results indicated that B7-2-FasL-IgFc stimulated differentiation of CD4+ T cells in vitro by skewing towards Th1 subsets [Szabo et al., Cell. 100:655 (2000)]. As was observed in CD40L-FasL-IgFc-induced stimulation of B cells, the inhibitors for NF-κB pathway and ERK pathway attenuated T cell activation by B7-2-FasL-IgFc (FIG. 29).

FIG. 29. Reduction of B7-2-FasL-IgFc-Induced Activation by Signaling Inhibitors.

PBMCs were stimulated with B7-2-FasL-IgFc (0.1 µM) for three days in the presence of SN50 and PD98059. Data indicate the means and standard deviations of triplicate samples. The data represent the three experiments with similar results.

Study for the Function of B7-2-FasL-IgFc In Vivo.

B7-2-FasL-IgFc fusion protein represses the IgG response in vivo against antigens administrated simultaneously.

In reasons analogous to CD40L-FasL-IgFc, the stimulation of CD28+ T cells by B7-2-FasL-IgFc fusion protein could indicate that this fusion protein could function as an adjuvant in vivo by enhancing the activity of T cells. To determine if the fusion protein behaves as an adjuvant, we tested B7-2-FasL-IgFc in mice to see if it increases the immune response against co-injected HA antigens.

Anti-Influenza Vaccine Response.

The potential in vivo adjuvant activity of B7-2-FasL-IgFc fusion protein was investigated in mice using a specific human influenza vaccine as an antigen (FIG. 30). The vaccine dose (3 μg/mouse) used to prime was sufficient to induce a primary response detectable by HA-specific anti-IgG ELISAs. To our surprise, the administration of B7-2-FasL-IgFc repressed the antibody response detected by ELISAs. Secondary responses following boosts were also far lower in groups primed with vaccine only. Therefore this study demonstrated that the influenza HA antigen-specific immune response was repressed by B7-2-FasL-IgFc fusion protein.

FIG. 30. Immunosuppressant Activity of B7-2-FasL-IgFc in Mice Against Influenza Hemaglutinin.

Balb/c mice were immunized i.p. with 3 μg of HA and 5 μg of B7-2-FasL-IgFc (indicated as Primed). On Day 14, blood samples were harvested from tail vain and mice were subsequently injected with 3 μg HA (indicated as Boosted). Sera from day 14 and day 24 (for the study of secondary response) were analysed by ELISA for the IgG activity against HA. The titer was calculated based on the dilutions and ELISA readings that first showed larger than twice of pre-immune sera readings at the same dilutions. Squares indicate mice immunized with HA alone. Circles indicate mice immunized with HA with B7-2-FasL-IgFc. Numbers in squares and circles indicate individual mouse. The anti-HA activity of pre-immune serum from each mouse was equally low at less than 50 in titer.

The plasmid DNA of B7-2-FasL-Fusion Protein Represses Anti-Influenza HA Immune Response In Vivo.

As an extension from the fusion protein result shown in FIG. 30, we tested if the plasmid DNA encoding the B7-2-FasL-IgFc/PCIneo could function as DNA-suppressant to the immune response against co-administrated vaccine antigen. Indeed, it was observed that a heavily repressed influenza vaccine-specific IgG response occurred following the administration of the B7-2-FasL-IgFc/PCIneo plasmid in conjunction with influenza vaccine (FIG. 31).

FIG. 31. Suppressant Activity of Plasmid DNA of B7-2-FasL-IgFc in Mice Against Influenza Hemaglutinin.

Balb/c mice were immunized i.p. with 3 μg of HA and 3 μg of B7-2-FasL-IgFc plasmid (indicated as Primed). On Day 14, blood samples were harvested from tail vain and mice were subsequently injected with 3 μg of HA (indicated as Boosted). Sera from day 14 and day 24 (for the study of secondary response) were analysed by ELISA for the IgG activity against HA. The titer was calculated as described in Example 2. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Suppressant Activity of B7-2-FasL-IgFc on T Cell Responses Against Influenza Hemaglutinin.

The results from the study of the antibody response in HA antigen and B7-FasL-IgFc administrated mice could indicate that T cell response to HA antigen is also suppressed in the mice. The study of B7-2-FasL-IgFc, therefore, investigated how the Influenza hemaglutinin-specific T cell response is regulated following B7-2-FasL-IgFc injection. As we expected, the addition of B7-2-FasL-IgFc suppressed the HA-specific response by total T cells compared with spleen cells from mice immunized with HA alone (FIG. 32 A). The CD8+ T cell response was also undetectable in spleen cells from mice immunized with B7-2-FasL-IgFc (FIG. 32B). The data showed the strong immunosuppressant activity by B7-2-FasL-IgFc to antigen-specific T cell responses in vivo.

FIG. 32. Immunosuppressant Activity of B7-2-FasL-IgFc in Mice Against Influenza Hemaglutinin-Specific T Cell Response.

Balb/c mice were immunized i.p. with 3 μg of HA and 5 μg of B7-2-FasL-IgFc. On Day 14, mice were injected with an additional 3 μg HA. Spleen cells from day 60 were analysed by proliferation assay against HA. Spleen cells stimulated for 48 hours with HA and were analysed for viability by MTT assay as described in the Example 2. A indicates total T cell response; B indicates CD8+ T cell response.

Percent viability is calculated based on the comparison with the non-stimulated cells (100%). The data shows the average and standard deviation derived from the triplicate samples. Not immunized: normal mice, Immunized: mice were immunized with HA alone.

Repression of Staphyloccocal enterotoxin B (SEB) induced splenomegaly by plasmid DNA of B7-2-FasL-IgFc.

Staphylococcal enterotoxins (SEA, SEB, SEC etc.) are a group of bacterial toxins, which activate T cells upon combining with class II MEW antigens on B cells or antigen presenting cells [Kotzin et al., Adv Immunol., 54:99 (1993)]. Those toxins are called "superantigens" and are known to activate T cells in vivo. Resulting from the in vivo activation of T cells, the injection of a superantigen such as SEB into mice causes splenomegaly within 48 hours. To characterize the repressor effect against T cell by plasmid DNA of B7-2FasL-IgFc, Balb/c mice (6 weeks of age) were intraperitonealy injected with 20 μg of SEB and 3 μg of B7-2-FasL-IgFc/PCIneo. Two days later, spleens were harvested aseptically and the weight of the spleen was measured by analytical balance (Mettler). The data indicated in FIG. 33 showed a strong repression of SEB-induced splenomegaly by plasmid DNA of B7-2-FasL-IgFc.

FIG. 33. The Repression of SEB-Induced Splenomegaly by Co-Administrated Plasmid DNA of B7-2-FasL-IgFc.

Three mice were used to each group. The data indicates the spleen weight average of three and the standard deviation. The spleen weight* indicates the weight at milligram order.

The data strongly suggests that the B7-2-FasL-IgFc construct could be used as the DNA suppressant in vivo and showed a potential of this fusion protein to apply to the diseases where in the immune suppression is necessary, such as autoimmune diseases and transplant rejection reaction.

Example 4

Construction of a Fusion Protein Comprising X: TNF-Family Extracellular Domain Polypeptide and Y: TNF-Family Extracellular Domain Polypeptide Fusion Protein.

Both CD40L-FasL-IgFc in Example 2 and B7-2-FasL-IgFc in Example 3 employed the death receptor ligand (FasL) extracellular domain as the domain "Y". To further our understanding about the combination of the "Y" domain and "X" domain, which render the fusion protein mitogenic to target cells, a new set of T cell co-stimulatory receptor ligands were chosen. In the new gene construct, "X" is OX40 ligand (OX40L) extracellular domain and "Y" is 4-1BB ligand (4-1BBL) extracellular domain. Both OX40L and 4-1BBL are the TNF family ligands for TNFR family T cell co-stimulatory receptor OX40 and 4-1BB respectively. OX40 signal has a critical role in the T cell maintenance of an immune response to generate an antigen-specific memory response due to its ability to promote survival. 4-1BB signal contributes to the clonal expansion, survival, and development of T cells. 4-1BB can also enhance T cell apoptosis induced by TCR/CD3 triggered activation, and regulate CD28 co-stimulation to promote IL-2/interferon-γ producing Th1 cell responses.

Construction of OX40L-4-1BBL-IgFc Plasmid DNA.

Registered messages and amino acid sequences for human OX40L and 4-1BBL is shown in FIG. 34 (SEQ ID NO: 21) and FIG. 35 (SEQ ID NO: 23) respectively.

The extracellular domain of human OX40L [HUMGP34M, *Homo sapiens* mRNA for glycoprotein 34, complete cds] (amino acid residues: 51-183) was amplified by RT-PCR from human monocyte cell line THP-1, using the following primers: forward 5'-GGA CTCGAGCAGGTATCACATCGGTATCC-3' (SEQ ID NO: 53) including the Xho I site and reverse 5'-GGA ACGCGTAAGGACACAGAATTCACCAG-3' (SEQ ID NO: 54), including the Mlu I sites, respectively (sites are underlined). The PCR product was cloned in frame at the Xho I-Mlu I site of PCIneo.

The extracellular domain of human 4-1BBL (NP_003802, *Homo sapiens* tumor necrosis factor (ligand) superfamily, member 9) (amino acid residues: 49-254) was first amplified by RT-PCR from human monocyte cell line THP-1, using the following primers: forward 5'-GGA ACGCGTGCCTGCCCTGGCCGTGTCCG-3' (SEQ ID NO: 55) inducing the Mlu I site and reverse 5'-AAT CTCGAGTTCCGACCTCGGTGAAGGGA-3' (SEQ ID NO: 56), including the Kpn I sites, respectively (sites are underlined). The PCR product was cloned in frame at the Mlu I-Kpn I site of PCIneo.

Xba I fragment of IgFc was inserted in frame into Xba I site of PCIneo.

hOncoM fragment with Nhe I/Xho I restriction sites was the same as used to generate OncoM-B7-2-IgFc and inserted into the Nhe I-Xho I restriction site of PCIneo.

OX40L-IgFc/PCIneo or 4-1BB-IgFc/PCIneo was prepared by removing 4-1BBL or OX40L from OncoM-OX40L-4-1BBL-IgFc/PCIneo (designated as OX40L-4-1BBL-IgFc/PCIneo described previously in the text.

The cDNA sequence for of the fusion constructs, OX40L-4-1BBL-IgFc/PCIneo, OX40L-IgFc/PCIneo and 4-1BB-IgFc/PCIneo are shown in FIG. 36 (SEQ ID NO: 25), 37 (SEQ ID NO: 27) and 38 (SEQ ID NO: 29) respectively.

The transfection of OX40L-4-1BBL-IgFc/PCIneo into CHO cell and the establishment of the stable transfectant cells were performed as described in the Example 2.

The Western blotting analysis for the Protein G column purified OX40L-4-1BBL-IgFc fusion protein was performed as described in the Example 2

This fusion protein designated as OX40L-4-1BBL-IgFc was detected as a ~70 kDa molecular mass in reduced SDS-PAGE (FIG. 39). The data indicate that the 70 kDa protein corresponds to the protein band representing the monomer of the fusion protein OX40L-4-1BBL-IgFc.

FIG. 39. Western Blotting Analysis of OX40L-4-1BBL-IgFc.

The OX40L-4-1BBL-IgFc fusion protein was subjected to SDS-PAGE under reduced conditions and probed by human IgG specific (A) or human OX40 ligand specific (B)

western blotting. The dominant band at ~70 kDa corresponds to glycosylated OX40L-4-1BBL-IgFc protein. The presumed molecular weight of OX40L-4-1BBL-IgFc is 66.4 kDa without post-translational modification.

Study for the Function of OX40L-4-1BBL-IgFc In Vitro. OX40L-4-1BBL-IgFc Fusion Protein Activated PBMCs.

Peripheral blood mononuclear cells from normal healthy human adults were separated from whole blood using Ficoll-Paque Plus. Unexpectedly, when tested in PBMCs, the mixture of OX40L-IgFc and 4-1BBL-IgFc induced a mitogenic response. The OX40L-4-1BBL-IgFc fusion protein, however, induced a far greater mitogenic response (FIG. 40).

FIG. 40. Activation of PBMCs by OX40L-4-1BBL-IgFc.

PBMCs were stimulated with OX40L-4-1BBL-IgFc (1 µg/ml) and control fusion proteins: OX40L-IgFc (1 µg/ml), 4-1BBL-IgFc (1 µg/ml) and OX40L-IgFc (0.5 µm/ml)+4-1BBL-IgFc (0.5 µm/ml). Cell proliferation was assessed following 72 hours in culture. Data indicates the average and standard deviation of quadruplicate samples.

The Plasmid DNA of OX40L-4-1BBL-IgFc Fusion Protein Increases Anti-Influenza Hemaglutinin Immune Response In Vivo.

We next tested if the plasmid encoding the OX40L-4-1BBL-IgFc fusion protein would function as DNA-adjuvant. Significantly, we observed an increased influenza vaccine-specific IgG response following the administration of the OX40L-4-1BBL-IgFc/PCIneo plasmid in conjunction with influenza vaccine in mice (FIG. 41).

FIG. 41. Adjuvant Activity of OX40L-4-1BBL-IgFc/PCIneo in Mice Against Influenza Hemaglutinin.

Balb/c mice were immunized i.p. with 3 µg of HA and 3 µg of OX40L-4-1BBL-IgFc/PCIneo plasmid (indicated as Primed). On Day 14, blood samples were harvested and mice were subsequently injected with 3 µg of HA (indicated as Boosted). Sera from day 14 and day 24 were analysed by ELISA for the IgG activity against HA. The titer was calculated as described in Example 2. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Poor Activity of OX40L-4-1BBL-IgFc/PCIneo on T Cell Responses Against Influenza Hemaglutinin.

The study of OX40L-4-1BBL-IgFc was extended to investigate how the Influenza hemaglutinin-specific T cell response is regulated following OX40L-4-1BBL-IgFc/PCIneo injection (FIG. 42). Interestingly, the addition of OX40L-4-1BBL-IgFc/PCIneo repressed the HA-specific response by total T cells compared with spleens from mice immunized with HA alone. The response by total T cells and CD8$^+$ T cell response was undetectable in spleen cells from mice immunized with HA and OX40L-4-1BBL-IgFc/PCIneo and it was nearly identical to cells from mice immunized with HA alone. The data showed poor adjuvant activity by OX40L-4-1BBL-IgFc/PCIneo to antigen-specific T cell responses in vivo, which contrasted to the strong adjuvant activity to antibody response by B cells.

FIG. 42. Adjuvant Activity of OX40L-4-1BBL-IgFc in Mice Against Influenza Hemaglutinin-Specific T Cell Response.

Balb/c mice were immunized intraperioneally with 3 µg of HA and 3 µg of OX40L-4-1BBL-IgFc/PCIneo plasmid. On Day 14, mice were injected with and additional 3 µg of HA. Spleen cells from day 60 were analysed by proliferation assay against HA. Spleen cells stimulated for 48 hours with HA and were analysed for viability by MTT assay as described in the Example 2. A indicates total T cell response; B indicates the CD8$^+$ T cell response.

Percent viability is calculated based on the comparison with the non-stimulated cells (100%). The data shows the average and standard deviation derived from the triplicate samples. Not immunized: normal mice; Immunized: mice were immunized with HA only.

Example 5

Construction of a Fusion Protein Comprising X: TNF-Family Ligand Extracellular Domain Polypeptide and Y: Immunoglobulin-Family Receptor Extracellular Domain Polypeptide Fusion Protein.

In the additional combination of "X" and "Y" of the X—Y-IgFc fusion protein mitogens, "X" the extracellular domain of CD40L and "Y" the extracellular domain of ICOS were chosen. ICOS is an inducible co-stimulatory molecule on T cells and its expression depends on the activation state of T cells. ICOS, a member of CD28/CTLA4 family, is not categorized as the ligand but is a receptor of which the ligand (ICOS ligand) is expressed on B cells and antigen presenting cells. Like the CD40/CD40L interaction and many other receptor/cell surface-expressed contra-receptor (ligand) interaction, the interaction between ICOS and ICOS ligand is known to stimulate bi-directional signaling, which co-stimulates both T cell (by ICOS signaling) and B cell (by ICOS ligand signaling). Accordingly, the CD40L-ICOS-IgFc could stimulate both B cells and antigen presenting cells. The purpose of developing this fusion protein was to test if the extracellular domain of the immunoglobulin family co-stimulation receptor can be used as the domain "Y" of a fusion protein mitogen.

Construction of CD40L-ICOS-IgFc Plasmid DNA.

Registered RNA message and predicted amino acid sequence for human ICOS is shown in FIG. 43 (SEQ ID NO: 31).

The extracellular domain of human ICOS [NM_012092, *Homo sapiens* inducible T-cell co-stimulator (ICOS)] (amino acid residues: 20-141) was first amplified by RT-PCR from total RNA of PHA-stimulated human PBMCs, using the following primers: forward 5'-GGA <u>CTCGAG</u>GGAGAAATCAATGGTTCTGC-3' (SEQ ID NO: 57) and reverse 5'-AAT<u>CTCGAG</u> AACTTCAGCTG-GCAACAAA-3' (SEQ ID NO: 58), including the Xho I sites, respectively (sites are underlined). The PCR product was cloned in frame at the 3' end of the hCD40L in the OncoMCD40L-IgGFc/PCIneo. The resultant product, OncoM-hCD40L-hICOS-IgGFc/PCIneo was designated as CD40L-ICOS-IgFc/PCIneo.

The cDNA sequence for this fusion construct is shown in FIG. 44 (SEQ ID NO: 33).

CHO cells were transfected with CD40L-ICOS-IgFc/PCIneo as described in Example 2. The CD40L-ICOSL-IgFc protein secreted in the culture supernatant of the stable CHO transfectant was purified by protein G column. Purified CD40L-ICOSL-IgFc was analysed by SDS-PAGE Western blotting specific for human IgG and human CD40 ligand (FIG. 45).

FIG. 45. Western Blotting Analysis of CD40L-ICOS-IgFc.

Purified CD40L-ICOS-IgFc was subjected to SDS-PAGE under reduced conditions, probed by human IgG specific (A) or human CD40L specific (B) western blotting. The dominant band at ~70 kDa corresponds to glycosylated CD40L-ICOS-IgFc. The predicted molecular weight of the CD40L-

ICOS-IgFc is 64.4 kDa without post-translational modification. The data indicate that the ~70 kDa protein is the protein band representing the monomer of the fusion protein CD40L-ICOS-IgFc.

Study for the Function of CD40L-ICOS-IgFc/PCIneo In Vivo.

The Plasmid DNA of CD40L-ICOS-IgFc-Fusion Protein Increases Anti-Influenza Hemaglutinin Immune Response In Vivo.

We tested if the plasmid DNA encoding the CD40L-ICOS-IgFc fusion protein would function as a DNA-adjuvant similar to CD40L-FasL-IgFc in Example 2. Indeed, increased influenza vaccine-specific IgG response was observed following the administration of the CD40L-ICOS-IgFc/PCIneo plasmid in conjunction with influenza vaccine (FIG. 46).

FIG. 46. Adjuvant Activity of Plasmid DNA of CD40L-ICOS-IgFc in Mice Against Influenza Hemaglutinin.

Balb/c mice were immunized i.p. with 3 µg of HA and 3 µg of CD40L-ICOS-IgFc plasmid. On Day 14, mice were injected with an additional 3 µg HA. Sera from day 14 and day 24 were analysed by ELISA for the IgG activity against HA. The titer was calculated as descried in Example 2. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Effect of Plasmid DNA of CD40L-ICOS-IgFc on T Cell Responses Against Influenza Hemaglutinin.

The study of CD40L-ICOS-IgFc was furthered by investigating how the Influenza hemaglutinin-specific T cell response is regulated following CD40L-ICOS-IgFc/PCIneo injection (FIG. 47). Interestingly, the addition of CD40L-ICOS-IgFc/PCIneo lowered the HA-specific response by total T cells compared with spleen cells derived from mice immunized with HA alone. In contrast to the response by total T cells, the CD8$^+$ T cell response was only detectable in spleen cells from mice immunized with HA and CD40L-ICOS-IgFc/PCIneo whereas it was not detected in spleen cells from mice immunized with HA alone. The data showed the adjuvant activity by CD40L-ICOS-IgFc/PCIneo to antigen-specific CD8$^+$ T cell responses in vivo. The activation of CD8$^+$ T cells, however, was lower than that observed by CD40L-FasL-IgFc treated mice spleen cells.

FIG. 47. Adjuvant Activity of CD40L-ICOS-IgFc/PCIneo in Mice Against Influenza Hemaglutinin-Specific T Cell Response.

Balb/c mice were immunized i.p. with 3 µg of HA and 3 µg of CD40L-ICOS-IgFc/PCIneo plasmid. On Day 14, mice were injected with an additional 3 µg of HA. Spleen cells from day 60 were analysed by proliferation assay against HA. Spleen cells stimulated for 48 hours with HA and were analysed for viability by MTT assay as described in the Example 2. A indicates total T cell response; B indicates CD8$^+$ T cell response. Percent viability is calculated based on the comparison with the non-stimulated cells (100%). The data shows the average and standard deviation derived from the triplicate samples. Not immunized: normal mice; Immunized: mice were immunized with HA only.

The results indicated that the extracellular domain of immunoglobulin family co-stimulation receptor, but not the ligand itself, is also usable to create a novel fusion protein mitogen.

Example 6

Construction of a Fusion Protein Comprised of X: NGFβ-Family Cytokine, Y: TNF Family Extracellular Domain Polypeptide Fusion Protein.

In another variation of "X" and "Y" of the X—Y-IgFc fusion protein mitogens, "X" nerve growth factor (NGFβ) and "Y" the extracellular domain of FasL were chosen. NGFβ is a NGFβ family cytokine and an important factor for the survival, differentiation and maintenance of the sensory and sympathetic neurons. Like other members of NGFβ family cytokines, NGFβ possesses various functions, one of which is to promote B cell growth [Brodie and Gelfand, J Immunol. 148:3492 (1992)]. Accordingly, the NGFβ-FasL-IgFc could stimulate B cells and antigen presenting cells, which will promote the antibody response by B cells in vivo. This fusion protein will also tested to see whether the NGF-family cytokine can be used as the domain of a fusion protein mitogen.

Construction of NGFβ-FasL-IgFc Plasmid DNA.

Registered RNA message and amino acid sequence for human NGFβ is shown in FIG. 48 (SEQ ID NO: 35).

The human NGFβ (NM_002506, *Homo sapiens* nerve growth factor (beta polypeptide)) (amino acid residues: 122-241) was first amplified by RT-PCR from total RNA of PHA-stimulated human PBMCs, using the following primers: forward 5'-GGA<u>CTCGAG</u>TCA TCATCCCATC-CCATCTT-3' (SEQ ID NO: 59) and reverse 5'-AAT <u>CTCGAG</u> GGCTCTTCTCACAGCC TTCC-3' (SEQ ID NO: 60), including the Xho I sites, respectively (sites are underlined). The PCR product was cloned in frame at the 5' end of the hFasL in the OncoMFasL-IgGFc/PCIneo. The resultant product OncoM-hNGFβ-hFasL-IgGFc/PCIneo was designated as NGFβ-FasL-IgFc/PCIneo.

The cDNA sequence for this fusion construct is shown in FIG. 49 (SEQ ID NO: 37).

CHO cells were transfected with NGFβ-FasL-IgFc/PCIneo as described in Example 2. The NGFβ-FasL-IgFc protein secreted in the culture supernatant of the stable CHO transfectant was purified by protein G column. Purified NGFβ-FasL-IgFc was analysed by SDS-PAGE Western blotting specific for human IgG and human Fas ligand (FIG. 50).

FIG. 50. Western Blotting Analysis of NGFβ-FasL-IgFc.

Purified NGFβ-FasL-IgFc was subjected to SDS-PAGE under reduced conditions, and probed by human IgG specific (A) or human FasL specific (B) western blotting. The dominant band at ~65 kDa corresponds to glycosylated NGFβ-FasL-IgFc protein. The predicted molecular weight of the NGFβ-FasL-IgFc is 60.5 kDa without post-translational modification. The data indicate that the ~65 kDa protein the protein band representing the monomer of the fusion protein NGFβ-FasL-IgFc.

Study for the Function of NGFβ-FasL-IgFc/PCIneo In Vivo.

The Plasmid DNA of the NGFβ-FasL-IgFc Fusion Protein Increases Anti-Influenza HA Immune Response In Vivo.

We tested if the plasmid DNA encoding the NGFβ-FasL-IgFc fusion protein would function as DNA-adjuvant in a manner similar to the CD40L-FasL-IgFc fusion protein described in Example 2. Indeed, a largely increased influenza vaccine-specific IgG response was observed following the administration of the NGFβ-FasL-IgFc/PCIneo plasmid in conjunction with influenza vaccine (FIG. 51).

FIG. 51. Adjuvant Activity of Plasmid DNA of NGFβ-FasL-IgFc in Mice Against Influenza Hemaglutinin.

Balb/c mice were immunized i.p. with 3 µg of HA and 3 µg of NGFβ-FasL-IgFc plasmid (indicated as Primed). On Day 14, blood samples were harvested from tail vain and mice were injected with and additional 3 µg HA (indicated as Boosted). Sera from day 14 and day 24 were analysed by ELISA for the IgG activity against HA. The titer was calculated as described in Example 2. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Effect of Plasmid DNA of NGFβ-FasL-IgFc on T Cell Responses Against Influenza Hemaglutinin.

The study of NGFβ-FasL-IgFc investigated how the HA-specific T cell response is regulated following NGFβ-FasL-IgFc/PCIneo injection (FIG. 52). Similarly to results observed following CD40L-FasL-IgFc injection, the addition of NGFβ-FasL-IgFc/PCIneo lowered the HA-specific response by total T cells compared with spleen cells derived from mice immunized with HA alone. In contrast to the response by total T cells, CD8+ T cell response was increased to the level nearly equal to that observed by CD40L-FasL-IgFc-treated mouse cells and only detectable in spleen cells immunized HA and NGFβ-FasL-IgFc/PCIneo. The data showed significant adjuvant activity by NGFβ-FasL-IgFc/PCIneo to HA-specific CD8+ T cell responses in vivo.

FIG. 52. Adjuvant Activity of NGFβ-FasL-IgFc/PCIneo in Mice Against Influenza Hemaglutinin-Specific T Cell Response.

Balb/c mice were immunized i.p. with 3 µg of HA and 3 µg of NGFβ-FasL-IgFc/PCIneo plasmid. On Day 14, mice were injected with an additional 3 µg of HA. Spleen cells from day 60 were analysed by proliferation assay against HA. Spleen cells stimulated for 48 hours and were analysed for viability by MTT assay as described in the Example 2. A indicates total T cell response; B indicates CD8+ T cell response. Percent viability is calculated based on the comparison with the non-stimulated cells (100%). The data shows the average and standard deviation derived from the triplicate samples. Not immunized: normal mice, Immunized: mice were immunized with HA only.

Example 7

Construction of a X: Interleukin 2-Family Cytokine, Y: TNF Family Extracellular Domain Polypeptide Fusion Protein.

In another variation of "X" and "Y" of the X-Y-IgFc fusion protein mitogens, "X" interleukin-2 (IL-2) and "Y" the extracellular domain of FasL were chosen. IL-2 is an IL-2 family cytokine and an important factor for the growth of T cells and the survival of T cells and B cells. Both T cells and B cells express receptors for IL-2 and it is possible both T and B cells would both be stimulated by the fusion protein IL-2-FasL-IgFc administration in vivo. This study also tested if the IL-2-family cytokines (IL-2, IL-4, IL-7, IL-9, IL-15, and IL-21) can be used as the domain of a fusion protein mitogen.

Construction of IL-2-FasL-IgFc Plasmid DNA.

Registered RNA message and amino acid sequence for human IL-2 is shown in FIG. 53 (SEQ ID NO: 39).

The human IL-2 (NM_000586, Homo sapiens interleukin-2) (amino acid residues: 21-154) was amplified by RT-PCR from amplified by RT-PCR from total RNA of PHA-stimulated human PBMCs, using the following primers: forward 5'-GGAGAATTCGCA CCTACTTCAAGTTC-TAC-3' (SEQ ID NO: 61). and reverse 5'-AAT ACGCGTAGTCAGTGTTGAGAT GCTGCT-3' (SEQ ID NO: 62), including the EcoRI and Mlu I sites, respectively (sites are underlined). The PCR product was cloned in frame at the 5' end of the hFasL by replacing the EcoR I/Mlu I fragment of hB7-2 of OncoM-hB7-2-hFasL-IgGFc/PCIneo following the double digestion with EcoRI and Mlu I. The resultant product OncoM-hIL-2-hFasL-IgGFc/PCIneo was designated as IL-2-FasL-IgFc/PCIneo.

The cDNA sequence for this fusion construct is shown in FIG. 54 (SEQ ID NO: 41).

CHO cells were transfected with IL-2-FasL-IgFc/PCIneo as described in Example 2. The IL-2-FasL-IgFc/PCIneo protein secreted in the culture supernatant of the stable CHO transfectant was purified by protein G column. Purified IL-2-FasL-IgFc/PCIneo was analysed by SDS-PAGE Western blotting specific for human IgG and human Fas ligand (FIG. 55).

FIG. 55. Western Blotting Analysis of IL-2-FasL-IgFc.

Purified IL-2-FasL-IgFc was subjected to SDS-PAGE under reduced conditions and probed by human IgG specific (A) or human FasL specific (B) western blotting. The dominant band at ~70 kDa corresponds to glycosylated IL-2-FasL-IgFc protein. The predicted molecular weight of IL-2-FasL-IgFc protein is 65.4 kDa without post-translational modification. The data indicate that the ~70 kDa protein is the protein band representing the monomer of the fusion protein IL-2-FasL-IgFc.

Study for the Function of IL-2-FasL-IgFc/PCIneo In Vivo.

The plasmid DNA of the IL-2-FasL-IgFc Fusion Protein Increases Anti-Influenza Hemaglutinin Immune Response In Vivo.

We tested if the plasmid DNA encoding the IL-2-FasL-IgFc fusion protein would function as a DNA-adjuvant similar to that observed with the CD40L-FasL-IgFc fusion protein outlined in Example 2. Indeed, increased influenza vaccine-specific IgG responses were observed following the administration of the IL-2-FasL-IgFc/PCIneo plasmid in conjunction with influenza vaccine (FIG. 56).

FIG. 56. Adjuvant Activity of Plasmid DNA of IL-2-FasL-IgFc in Mice Against Influenza Hemaglutinin.

Balb/c mice were immunized i.p. with 3 µg of HA and 3 µg of IL-2-FasL-IgFc plasmid (indicated as Primed). On Day 14, blood samples were harvested from tail vain and mice were injected with an additional 3 µg HA (indicated as Boosted). Sera from day 14 and day 24 were analysed by ELISA for the IgG activity against HA. The titer was calculated as described in Example 2. Squares indicate mice immunized with HA alone. Circles indicate mice immunized with HA with plasmid. Numbers in squares and circles indicate individual mouse. The anti-HA activity of pre-immune serum from each mouse was equally low at less than 20 in titer.

Effect of Plasmid DNA of IL-2-FasL-IgFc on T Cell Responses Against Influenza Hemaglutinin.

The inventor investigated how the Influenza hemaglutinin-specific T cell response is regulated following IL-2-FasL-IgFc/PCIneo injection in mice (FIG. 57). Interestingly, the addition of IL-2-FasL-IgFc/PCIneo repressed the HA-specific response by total T cells compared with spleen cells derived from mice immunized with HA alone. The CD8+ T cell response was not increased significantly but still a little higher than that observed by treatment of mice with B7-2-FasL-IgFc described earlier. The data showed that the adjuvant activity by IL-2-FasL-IgFc/PCIneo to antigen-specific T cell response in vivo is marginal.

FIG. 57. Suppressant Activity of IL-2-FasL-IgFc/PCIneo in Mice Against Influenza Hemaglutinin-Specific T Cell Response.

Balb/c mice were immunized i.p. with 3 µg of HA and 3 µg of IL-2-FasL-IgFc/PCIneo plasmid. On Day 14, mice were injected with an additional 3 µg of HA. Spleen cells from day 60 were analysed by proliferation assay against HA. Spleen cells stimulated for 48 hours with HA and were analysed for viability by MTT assay as described in the Example 2. A indicates total T cell response; B indicates CD8$^+$ T cell response.

Percent viability is calculated based on the comparison with the non-stimulated cells (100%). The data shows the average and standard deviation derived from the triplicate samples. Not immunized: normal mice, Immunized: mice were immunized with HA only.

The Examples presented supra indicate that the current invention can generate a variety of fusion protein mitogens, which acquire different functions. Some of the fusion proteins possessed unique characteristics, which could be beneficial in the treatment of various human diseases. It is also anticipated that, based on these examples, the present invention will provide novel methods of treatment of diseases that either enhance or repress cellular and humoral immunity. Diseases or conditions that are viable targets for this mode of treatment include chronic and debilitating human diseases such as cancer and other proliferative diseases, infectious diseases, autoimmunity, allergic conditions, inflammatory conditions such as arteriosclerosis and organ transplant rejection. The invention broadly encompasses the use of the fusion proteins and plasmid DNAs for treatment or prevention of diseases wherein enhanced or reduced antigen specific cellular immunity is desirable.

It is to be understood that the invention is not limited to the embodiments listed above and the right is reserved to the illustrated embodiments and all modifications coming within the scope of the following claims.

The various references to journals, patents, and other publications which are cited herein comprise the state of the art and are incorporated by reference as though fully set forth.

The invention claimed is:

1. An immunostimulatory fusion polypeptide comprising in N-terminal to C-terminal direction a polypeptide comprising the receptor binding domain of nerve growth factor beta, a polypeptide comprising the receptor binding domain of Fas ligand, and a polypeptide comprising the human immunoglobulin Fc domain.

2. A recombinant nucleic acid (cDNA) comprising a polynucleotide sequence that encodes the fusion polypeptide of claim 1.

3. A cDNA expression vector containing a fusion polynucleotide sequence according to claim 2.

4. A cDNA expression vector of claim 3, which is selected from a plasmid, recombinant virus, and episomal vector.

5. A cell line that comprises the cDNA expression vector of claim 3.

6. The immunostimulatory fusion polypeptide of claim 1, which is substantially pure.

* * * * *